US010308615B2

(12) United States Patent
Casimiro-Garcia et al.

(10) Patent No.: US 10,308,615 B2
(45) Date of Patent: Jun. 4, 2019

(54) HETEROCYCLIC COMPOUNDS AS INHIBITORS OF VANIN-1 ENZYME

(71) Applicant: Pfizer Inc., New York, NY (US)

(72) Inventors: Agustin Casimiro-Garcia, Concord, MA (US); Jeffrey Scott Condon, Melrose, MA (US); Andrew Christopher Flick, East Lyme, CT (US); Ariamala Gopalsamy, Lexington, MA (US); Steven J. Kirincich, Concord, MA (US); John Paul Mathias, Concord, MA (US); Joseph Walter Strobach, Wentzville, MO (US); Jason Shaoyun Xiang, Winchester, MA (US); Li Huang Xing, Lexington, MA (US); Xiaolun Wang, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/574,625

(22) PCT Filed: May 16, 2016

(86) PCT No.: PCT/IB2016/052825
§ 371 (c)(1),
(2) Date: Nov. 16, 2017

(87) PCT Pub. No.: WO2016/193844
PCT Pub. Date: Dec. 8, 2016

(65) Prior Publication Data

US 2018/0148420 A1 May 31, 2018

Related U.S. Application Data

(60) Provisional application No. 62/167,962, filed on May 29, 2015, provisional application No. 62/195,005, filed on Jul. 21, 2015.

(51) Int. Cl.

| | |
|---|---|
| *C07D 239/42* | (2006.01) |
| *C07D 401/12* | (2006.01) |
| *C07D 403/12* | (2006.01) |
| *A61K 31/505* | (2006.01) |
| *C07D 239/28* | (2006.01) |
| *C07D 241/14* | (2006.01) |
| *A61P 1/00* | (2006.01) |
| *A61P 1/04* | (2006.01) |
| *A61P 35/00* | (2006.01) |
| *C07D 405/10* | (2006.01) |

(52) U.S. Cl.
CPC .......... *C07D 239/42* (2013.01); *A61K 31/505* (2013.01); *A61P 1/00* (2018.01); *A61P 1/04* (2018.01); *A61P 35/00* (2018.01); *C07D 239/28* (2013.01); *C07D 241/14* (2013.01); *C07D 401/12* (2013.01); *C07D 403/12* (2013.01); *C07D 405/10* (2013.01)

(58) Field of Classification Search
CPC ............................ C07D 401/12; C07D 403/12
See application file for complete search history.

(56) References Cited

FOREIGN PATENT DOCUMENTS

| | | |
|---|---|---|
| EP | 2565182 | 3/2013 |
| WO | 2008/063888 | 5/2008 |
| WO | 2009/143018 | 11/2009 |
| WO | 2011/133888 | 10/2011 |
| WO | 2011/133920 | 10/2011 |
| WO | 2012/158957 | 11/2012 |
| WO | 2013/019621 | 2/2013 |
| WO | 2013/151938 | 10/2013 |
| WO | 2014/048547 | 4/2014 |

OTHER PUBLICATIONS

Kaskow et al., "Diverse biological activities of the vascular non-inflammatory molecules The Vanin pantetheinases", Biochemical and Biophysical Reasearch Communications, vol. 417(2), pp. 653-658 (2012).

*Primary Examiner* — Brian E McDowell
(74) *Attorney, Agent, or Firm* — James T. Wasicak

(57) ABSTRACT

Compounds, pharmaceutically acceptable salts thereof, are disclosed wherein the compounds have the structure of Formula I

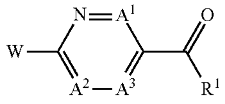

as defined in the specification. Corresponding pharmaceutical compositions, methods of treatment, methods of synthesis, and intermediates are also disclosed.

8 Claims, 3 Drawing Sheets

HETEROCYCLIC COMPOUNDS AS INHIBITORS OF VANIN-1 ENZYME

This application is a 35 U.S.C. 371 National Stage of International Application No. PCT/IB2016/052825 filed May 16, 2016, which claims the benefit of U.S. Provisional Application No. 62/195,005 filed Jul. 21, 2015, and claims benefit of 62/167,962 filed May 29, 2015, each of which is herein incorporated by reference in their entirety.

FIELD

The present invention relates to novel heterocyclic compounds, or pharmaceutically acceptable salts thereof, and pharmaceutical compositions comprising the same. The present invention also relates to methods of treating a subject by administering a therapeutically effective amount of these compounds, or salts thereof, to a subject. In general, these compounds act as inhibitors of vanin-1 enzyme.

BACKGROUND

Vanin-1 is a cell surface associated, glycosylphosphatidyl inositol (GPI)—anchored protein which is expressed at high levels in kidney, liver and the small intestine. Vanin-1 expression can be up-regulated in multiple cell types under various inflammatory and oxidative stress conditions. Soluble Vanin-1 is found in serum of mice and humans indicating that Vanin-1 can be shed of the cell surface (Rommelaere S, et al. PPARalpha regulates the production of serum Vanin-1 by liver. FEBS Lett. 2013 Nov. 15; 587(22):3742-8). Three Vanin family members have been described in humans (Vanin-1, Vanin-2 and Vanin-3) and these are classified as members of the biotinidase branch of the nitrilase superfamily (Kaskow B J, et al. Diverse biological activities of the vascular non-inflammatory molecules—the Vanin pantetheinases. Biochem Biophys Res Commun. 2012 Jan. 13; 417(2):653-8).

To date the only known substrate for Vanin-1 is pantetheine and it is believed that Vanin-1 acts as the predominant pantetheinase in vivo catalyzing its hydrolysis to produce pantothenic acid (vitamin B5) and cysteamine (Pitari G, et al. Pantetheinase activity of membrane-bound vanin-1: lack of free cysteamine in tissues of vanin-1 deficient mice. FEBS Lett. 2000; 483:149-154). These products impact diverse biological processes. Panthothenic acid is a necessary factor in the synthesis of Coenzyme A (CoA), a cofactor involved in many metabolic processes such as fatty acid synthesis and oxidation of pyruvate. The amino-thiol cysteamine, the second product of Vanin-1 enzymatic reaction, impacts the cellular redox status (Kaskow B J, et al. Diverse biological activities of the vascular non-inflammatory molecules—the Vanin pantetheinases. Biochem Biophys Res Commun. 2012 Jan. 13; 417(2):653-8 and Nitto T, Onodera K. The Linkage between coenzyme A metabolism and inflammation: roles of Pantetheinase. Journal of pharmacological sciences 2013:123: 1-8).

Vanin-1-deficient mice show no developmental defects nor do they show obvious spontaneous phenotype. However, diverse Vanin-1-dependent phenotypes are revealed in situations of metabolic challenge and/or oxidative stress and tissue damage. Vanin-1-deficient mice exhibit resistance to oxidative tissue injury caused by γ-irradiation or by the administration of paraquat which is correlated with significantly increased glutathione levels (Berruyer C, et al. Vanin-1−/− mice exhibit a glutathione mediated tissue resistance to oxidative stress. Mol Cell Biol. 2004; 24:7214-7224). Vanin-1 deficient animals are also protected against multiple mouse models of IBD including DSS (dextran sulfate) and TNBS (trinitrobenzene sulfonate) colitis as evidenced by preserved mucosal barrier and reduced inflammatory infiltrate (Berruyer C, et al. Vanin-1 licenses inflammatory mediator production by gut epithelial cells and controls colitis by antagonizing peroxisome proliferator-activated receptor g activity. J Exp Med. 2006; 203:2817-2827 and et al. Vanin-1−/− mice show decreased NSAID- and *Schistosoma*-induced intestinal inflammation associated with higher glutathione stores. J Clin Invest. 2004; 113:591-597). In humans, Vanin-1 expression is significantly increased in the colonic mucosa from IBD patients and functional polymorphisms in the regulatory regions of the Vanin-1 gene are associated with susceptibility to inflammatory bowel diseases (Gensollen T, et. al. Functional polymorphisms in the regulatory regions of the VNN1 gene are associated with susceptibility to inflammatory bowel diseases. Inflamm Bowel Dis. 2013 October; 19(11):2315-25). In addition, patients with ulcerative colitis have an increased risk of developing colorectal cancer and Vanin-1 knock-out mice exhibit drastically reduced incidence of tumors in colitis associated cancer model (Pouyet L, et al. Epithelial vanin-1 controls inflammation-driven carcinogenesis in the colitis-associated colon cancer model. Inflamm Bowel Dis. 2010 January; 16(1):96-104).

Vanin-1 is a key activator for hepatic gluconeogenesis (Chen S, et al. Vanin-1 is a key activator for hepatic gluconeogenesis. Diabetes. 2014 June; 63(6):2073-85. doi: 10.2337/db13-0788. Epub 2014 Feb. 18). Vanin-1 regulates the activation of smooth muscle cells in vitro and development of neointimal hyperplasia in response to carotid artery ligation in vivo. Polymorphysims in VNN1 gene are associated with blood pressure and HDL levels further supporting Vanin-1's role in cardiovascular diseases. Vanin-1 deficiency prevents mice from the development of adrenocortical neoplasia in Sf-1 transgenic mice suggesting a role for Vanin-1 in certain cancers. In the context of infection, Vanin-1 deficiency reduces granuloma formation and tissue damage against *Coxiella burnetii*, a bacterium that causes 0 fever. Vanin-1 is highly up-regulated in psoriatic skin lesions compared with normal individuals. Vnn-1 gene is also up-regulated in whole blood of patients with pediatric immune thrombocytopenia (ITP) where overexpression of VNN1, is associated with progression to chronic ITP. In addition, elevated Vanin-1 has been detected in urines of patients with multiple renal disorders including systemic lupus erythematosus, nephrotoxicant-induced renal injury and type 2-diabetes (Rommelaere S, et al. PPARalpha regulates the production of serum Vanin-1 by liver. FEBS Lett. 2013 Nov. 15; 587(22):3742-8).

There is a need for novel and potent small molecule compounds which act as inhibitors of vanin-1 enzyme.

SUMMARY

This invention relates to a compound of Formula I, Embodiment (1):

Formula I

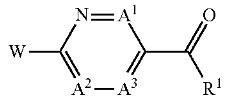

or a pharmaceutically acceptable salt thereof, wherein $A^1$ is N, $A^2$ is $C(R^3)$ and $A^3$ is $C(R^3)$;

$A^1$ is $C(R^3)$, $A^2$ is N and $A^3$ is $C(R^3)$;

$A^1$ is $C(R^3)$, $A^2$ is $C(R^3)$ and $A^3$ is N;

$A^1$ is N, $A^2$ is N and $A^3$ is $C(R^3)$; or $A^1$ is $C(R^3)$, $A^2$ is N and $A^3$ is N;

$R^1$ is selected from the group consisting of:

(i) 6 to 10 membered aryl optionally substituted with one, two, three or four E; and (ii) 5 to 11 membered heteroaryl optionally substituted with one, two, three or four E, wherein said 5 to 11 membered heteroaryl (a) comprises one, two or three heteroatoms independently selected for each occurrence from the group consisting of —N═, —N(J)-, —O—, and —S— and (b) is not bound to the carbonyl of Formula (I) through a nitrogen;

W is selected from the group consisting of:

(i) $—NHCG_2-R^2$;

(ii) $—NHCG_2CG_2-R^2$;

(iii) $—OCG_2-R^2$;

(iv) $—OCG_2CG_2-R^2$;

$R^2$ is selected from the group consisting of:

(i) phenyl optionally substituted with one, two, three or four E;

(ii) 5 to 6 membered heteroaryl optionally substituted with one, two, three or four E, wherein said 5 to 6 membered heteroaryl comprises one or two heteroatoms independently selected for each occurrence from the group consisting of —N═, —N(J)-, —O—, and —S—;

(iii) $—C_3-C_7$ carbocyclyl optionally substituted with one, two, three, four, five or six E;

(iv) 4 to 7 membered heterocyclyl optionally substituted with one, two, three, four, five or six E, wherein said 4 to 7 membered heterocyclyl comprises one or two heteroatoms independently selected for each occurrence from the group consisting of —N(J)-, —O— and —S—; and (v) 4 to 7 membered heterocyclyl optionally substituted with one, two, three, four, five or six E, wherein said 4 to 7 membered heterocyclyl is (i) bound to W through a first heterocyclyl ring heteroatom —N— and (ii) which optionally comprises a second ring heteroatom independently selected from the group consisting of —N(J)-, —O—, and —S—;

$R^3$ is independently selected for each occurrence from the group consisting of —H, —F, —Cl, —CN, $—CH_3$, $—CH_2CH_3$, $—CH_2F$, $—CHF_2$, $—CF_3$, $—CF_2CF_3$, $—OCH_3$, $—OCH_2F$, $—OCHF_2$, $—OCF_3$, $—SCH_3$, $—SCH_2F$, $—SCHF_2$, and $—SCF_3$;

E is independently selected for each occurrence from the group consisting of:

(i) —H;

(ii) —halo;

(iii) —CN;

(iv) —OH;

(v) $—CO_2H$;

(vi) $—C_1-C_6$alkyl optionally substituted with one, two, three, four, five or six K;

(vii) $—OC_1-C_6$alkyl optionally substituted with one, two, three, four, five or six K;

(viii) $—SC_1-C_6$alkyl optionally substituted with one, two, three, four, five or six K;

(ix) $—C_3-C_5$cycloalkyl optionally substituted with one, two, three, four, five or six K;

(x) $—OC_3-C_5$cycloalkyl optionally substituted with one, two, three, four, five or six K;

(xi) $—SC_3—C_5$ cycloalkyl optionally substituted with one, two, three, four, five or six K;

(xii) $—C_1-C_6$alkyl($C_3-C_5$cycloalkyl) optionally substituted with one, two, three, four, five or six K;

(xiii) 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—;

(xiv) $—NH_2$;

(xv) —NH($C_1-C_6$alkyl), which $C_1-C_6$alkyl is optionally substituted with one, two, three, four, five or six K;

(xvi) —N($C_1-C_6$alkyl$)_2$, which $C_1-C_6$alkyl is, independently for each occurrence, optionally substituted with one, two, three, four, five or six K;

(xvii) $—C(O)NH_2$;

(xviii) —C(O)NH($C_1-C_6$alkyl), which $C_1-C_6$alkyl is optionally substituted with one, two, three, four, five or six K;

(xix) —C(O)N($C_1-C_6$alkyl$)_2$, which $C_1-C_6$alkyl is, independently for each occurrence, optionally substituted with one, two, three, four, five or six K;

(xx) —NHC(O)($C_1-C_6$alkyl), which $C_1-C_6$alkyl is optionally substituted with one, two, three, four, five or six K;

(xxi) —N($C_1-C_6$alkyl)C(O)($C_1-C_6$alkyl), which $C_1-C_6$alkyl is, independently for each occurrence, optionally substituted with one, two, three, four, five or six K;

(xxii) $—SO_2$($C_1-C_6$alkyl), which $C_1-C_6$alkyl is optionally substituted with one, two, three, four, five or six K;

(xxiii) $—SO_2NH_2$;

(xxiv) $—SO_2NH$($C_1-C_6$alkyl), which $C_1-C_6$alkyl is optionally substituted with one, two, three, four, five or six K;

(xxv) $—SO_2N$($C_1-C_6$alkyl$)_2$, which $C_1-C_6$alkyl is, independently for each occurrence optionally substituted with one, two, three, four, five or six K;

(xxvi) $—NHSO_2$($C_1-C_6$alkyl), which $C_1-C_6$alkyl is optionally substituted with one, two, three, four, five or six K; and (xxvii) —N($C_1-C_6$alkyl)$SO_2$($C_1-C_6$alkyl), which $C_1-C_6$alkyl is, independently for each occurrence, optionally substituted with one, two, three, four, five or six K;

G is independently selected for each occurrence from the group consisting of:

(i) —H;

(ii) —halo;

(iii) —OH;

(iv) $—C_1-C_6$alkyl optionally substituted optionally substituted with one, two, three, four, five or six K;

(v) $—OC_1-C_6$alkyl optionally substituted with one, two, three, four, five or six K;

(vi) $—SC_1-C_6$alkyl optionally substituted with one, two, three, four, five or six K;

(vii) —NH($C_1-C_6$alkyl), which $C_1-C_6$alkyl is optionally substituted with one, two, three, four, five or six K;

(viii) —N($C_1-C_6$alkyl$)_2$, which $C_1-C_6$alkyl is, independently for each occurrence, optionally substituted with one, two, three, four, five or six K;

(ix) $—C_3-C_5$cycloalkyl optionally substituted with one, two, three, four, five or six K; and (x) 4 to 5 membered heterocyclyl optionally substituted with one, two, three, four, five or six K, which said 4 to 5 membered heterocyclyl comprises one or two heteroatoms independently selected for each occurrence from the group consisting of —N(J)-, —O— or —S—;

or two geminal G may, together with the carbon to which they are bound, form a —$C_3$-$C_5$cycloalkylene optionally substituted with one, two, three, four, five or six K or a 4 to 5 membered heterocyclylene optionally substituted with one, two, three, four, five or six K, wherein said 4 to 5 membered heterocyclylene comprises one heteroatom independently selected from the group consisting of —N(J)-, —O—, or —S—;

J is independently selected, for each occurrence, from the group consisting of:

(i) —H;

(ii) —$C_1$-$C_6$alkyl optionally substituted with one, two, three, four, five or six K;

(iii) —C(O)$NH_2$;

(iv) —C(O)NH($C_1$-$C_6$alkyl), which $C_1$-$C_6$alkyl is optionally substituted with one, two, three, four, five or six K;

(v) —C(O)N($C_1$-$C_6$alkyl)$_2$, which $C_1$-$C_6$alkyl is, independently for each occurrence, optionally substituted with one, two, three, four, five or six K; and (vi) —$SO_2$($C_1$-$C_6$alkyl), which $C_1$-$C_6$alkyl is optionally substituted with one, two, three, four, five or six halo; and K is independently selected, for each occurrence, from the group consisting of —H, —F, —Cl, —OH, —CN, —$CO_2H$, —$CH_3$, —$CH_2CH_3$, —$CH_2F$, —$CHF_2$, —$CF_3$, —$CF_2CF_3$, —$OCH_3$, —$OCH_2F$, —$OCHF_2$, —$OCF_3$, —$SCH_3$, —$SCH_2F$, —$SCHF_2$, —$SCF_3$—$NH_2$, —NH($CH_3$), —N($CH_3$)$_2$, and —$CONH_2$.

In another Embodiment (3), the invention provides a compound of Formula (I), or a pharmaceutically acceptable salt thereof, according to any preceding Embodiment, wherein $A^1$ is N, $A^2$ is C($R^3$) and $A^3$ is C($R^3$).

In another Embodiment (3.1), the invention provides a compound of Formula (I), or a pharmaceutically acceptable salt thereof, according to any preceding Embodiment, wherein $A^1$ is N, $A^2$ is CH and $A^3$ is C($R^3$).

In another Embodiment (3.2), the invention provides a compound of Formula (I), or a pharmaceutically acceptable salt thereof, according to any preceding Embodiment, wherein $A^1$ is N, $A^2$ is C($R^3$) and $A^3$ is CH.

In another Embodiment (3.3), the invention provides a compound of Formula (I), or a pharmaceutically acceptable salt thereof, according to any preceding Embodiment, wherein $A^1$ is N, $A^2$ is CH and $A^3$ is CH.

In another Embodiment (4), the invention provides a compound of Formula (I), or a pharmaceutically acceptable salt thereof, according to Embodiment (1), wherein $A^1$ is C($R^3$), $A^2$ is N and $A^3$ is C($R^3$).

In another Embodiment (4.1), the invention provides a compound of Formula (I), or a pharmaceutically acceptable salt thereof, according to Embodiment (1) or Embodiment (4), wherein $A^1$ is CH, $A^2$ is N and $A^3$ is C($R^3$).

In another Embodiment (4.2), the invention provides a compound of Formula (I), or a pharmaceutically acceptable salt thereof, according to Embodiment (1), Embodiment (4), or Embodiment (4.1), wherein $A^1$ is C($R^3$), $A^2$ is N and $A^3$ is CH.

In another Embodiment (4.3), the invention provides a compound of Formula (I), or a pharmaceutically acceptable salt thereof, according to Embodiment (1), Embodiment (4), Embodiment (4.1), or Embodiment (4.2) wherein $A^1$ is CH, $A^2$ is N and $A^3$ is CH.

In another Embodiment (5), the invention provides a compound of Formula (I), or a pharmaceutically acceptable salt thereof, according to Embodiment (1) or wherein $A^1$ is C($R^3$), $A^2$ is C($R^3$) and $A^3$ is N.

In another Embodiment (5.1), the invention provides a compound of Formula (I), or a pharmaceutically acceptable salt thereof, according to Embodiment (1), or Embodiment (5), wherein $A^1$ is CH, $A^2$ is C($R^3$) and $A^3$ is N.

In another Embodiment (5.2), the invention provides a compound of Formula (I), or a pharmaceutically acceptable salt thereof, according to Embodiment (1), Embodiment (5), or Embodiment (5.1), wherein $A^1$ is CH, $A^2$ is CH and $A^3$ is N.

In another Embodiment (6), the invention provides a compound of Formula (I), or a pharmaceutically acceptable salt thereof, according to any preceding Embodiment, wherein $R^3$ is —H, —F, —$CH_3$, —$CH_2F$, —$CHF_2$, —$CF_3$, —$OCH_3$, —$OCH_2F$, —$OCHF_2$, and —$OCF_3$.

In another Embodiment (6.1), the invention provides a compound of Formula (I), or a pharmaceutically acceptable salt thereof, according to any preceding Embodiment, wherein $R^3$ is —H.

In another Embodiment (7), the invention provides a compound of Formula (I), or a pharmaceutically acceptable salt thereof, according to any preceding Embodiment, wherein $R^1$ is a 6 to 10 membered aryl, for example phenyl, which $R^1$ is optionally substituted as defined for a compound of Formula (I).

In another Embodiment (7.1), the invention provides a compound of Formula (I), or a pharmaceutically acceptable salt thereof, according to any preceding Embodiment, wherein $R^1$ is phenyl, which phenyl is optionally substituted as defined for a compound of Formula (I).

In another Embodiment (8), the invention provides a compound of Formula (I), or a pharmaceutically acceptable salt thereof, according to any preceding Embodiment, wherein $R^1$ is a 5 to 11 membered heteroaryl, wherein said 5 to 11 membered heteroaryl (a) comprises one, two or three heteroatoms independently selected for each occurrence from the group consisting of —N=, —N(J)-, —O—, and —S— and (b) is not bound to the carbonyl of Formula (I) through a nitrogen, for example thiophenyl, 1,4-dioxochromanyl, quinolinyl, pyrazolyl, indazolyl, pyridinyl, N-methyl-indazolyl or N-methyl-pyrazolyl, which $R^1$ is optionally substituted as defined for a compound of Formula (I).

In another Embodiment (8.1), the invention provides a compound of Formula (I), or a pharmaceutically acceptable salt thereof, according to any preceding Embodiment, wherein $R^1$ is selected from the group consisting of pyrrolyl, furanyl, pyrrolinyl, thiophenyl, pyrazolyl, N-methyl-pyrazolyl, imidazolyl, oxazolyl, isoxazolyl, pyrazolinyl, imidazolinyl, thiazolyl, isothiazolyl, triazolyl, tetrazolyl, pyridinyl, pyranyl, pyridazinyl, pyrazinyl, triazinyl, pyrimidinyl, quinolinyl, indazolyl, N-methyl-indazolyl, and 1,4-dioxochromanyl, which $R^1$ is not bound to the carbonyl of Formula (I) through a nitrogen, and which $R^1$ is optionally substituted as defined for a compound of Formula (I).

In another Embodiment (8.2), the invention provides a compound of Formula (I), or a pharmaceutically acceptable salt thereof, according to any preceding Embodiment, wherein $R^1$ is selected from the group consisting of thiophenyl, 1,4-dioxochromanyl, quinolinyl, pyrazolyl, indazolyl, pyridinyl, N-methyl-indazolyl and N-methyl-pyrazolyl which $R^1$ is optionally substituted as defined for a compound of Formula (I), and, when $R^1$ is quinolinyl, pyrazolyl, indazolyl, or pyridinyl, said quinolinyl, pyrazolyl, indazolyl, or pyridinyl is not bound to the carbonyl of Formula (I) through a nitrogen.

In another Embodiment (9), the invention provides a compound of Formula (I), or a pharmaceutically acceptable salt thereof, according to any preceding Embodiment, wherein W is —$NHCG_2$-$R^2$.

In another Embodiment (9.1), the invention provides a compound of Formula (I), or a pharmaceutically acceptable salt thereof, according to any preceding Embodiment, wherein W is —$NHCG_2CG_2$-$R^2$.

In another Embodiment (9.2), the invention provides a compound of Formula (I), or a pharmaceutically acceptable salt thereof, according to any preceding Embodiment, wherein W is —$OCG_2$-$R^2$.

In another Embodiment (9.3), the invention provides a compound of Formula (I), or a pharmaceutically acceptable salt thereof, according to any preceding Embodiment, wherein W is —$OCG_2CG_2$-$R^2$.

In another Embodiment (10), the invention provides a compound of Formula (I), or a pharmaceutically acceptable salt thereof, according to any preceding Embodiment, wherein G is independently selected for each occurrence from the group consisting of —H; —$C_1$-$C_6$alkyl, for example methyl; —$OC_1$-$C_6$alkyl; —$C_3$-$C_5$cycloalkyl; or two geminal G may, together with the carbon to which they are bound, form a —$C_3$-$C_5$cycloalkylene, for example cyclopropylene or cyclobutylene, which G is optionally substituted as defined for a compound of Formula (I).

In another Embodiment (10.1), the invention provides a compound of Formula (I), or a pharmaceutically acceptable salt thereof, according to any preceding Embodiment, wherein G is independently selected for each occurrence from the group consisting of —H; —$C_1$-$C_6$alkyl, for example methyl; or two geminal G may, together with the carbon to which they are bound, form a —$C_3$-$C_5$cycloalkylene, for example cyclopropylene or cyclobutylene, which G is optionally substituted as defined for a compound of Formula (I).

In another Embodiment (11), the invention provides a compound of Formula (I), or a pharmaceutically acceptable salt thereof, according to any preceding Embodiment, wherein W is —$NHCG_2$-$R^2$ and wherein G is independently selected for each occurrence from the group consisting of —H; —$C_1$-$C_6$alkyl, for example methyl, which —$C_1$-$C_6$alkyl, is optionally substituted as defined for a compound Formula (I); or two geminal G may be taken together with the carbon to which they are bound to form a —$C_3$-$C_5$cycloalkylene, for example cyclopropylene or cyclobutylene, which —$C_3$-$C_5$cycloalkylene is optionally substituted as defined for a compound of Formula (I).

In another Embodiment (11.1), the invention provides a compound of Formula (I), or a pharmaceutically acceptable salt thereof, according to any preceding Embodiment, wherein W is —$NHCG_2$-$R^2$ and wherein G is independently selected for each occurrence from the group consisting of —H; —$CH_3$; and where two geminal G may be taken together with the carbon to which they are bound to form cyclopropylene or cyclobutylene.

In another Embodiment (11.2), the invention provides a compound of Formula (I), or a pharmaceutically acceptable salt thereof, according to any preceding Embodiment, wherein W is selected from the group consisting of —$NHCH_2$—$R^2$; —$NHC(CH_3)H$—$R^2$; —$NHC(CH_3)_2$—$R^2$;

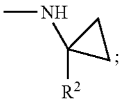; and 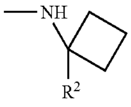.

In another Embodiment (11.3), the invention provides a compound of Formula (I), or a pharmaceutically acceptable salt thereof, according to any preceding Embodiment, wherein W is —$OCG_2$-$R^2$ and wherein G is independently selected for each occurrence from the group consisting of —H; —$C_1$-$C_6$alkyl, for example methyl, which —$C_1$-$C_6$alkyl, is optionally substituted as defined for a compound Formula (I); or two geminal G may be taken together with the carbon to which they are bound to form a —$C_3$-$C_5$cycloalkylene, for example cyclopropylene or cyclobutylene, which —$C_3$-$C_5$cycloalkylene is optionally substituted as defined for a compound of Formula (I).

In another Embodiment (11.4), the invention provides a compound of Formula (I), or a pharmaceutically acceptable salt thereof, according to any preceding Embodiment, wherein W is —$OCG_2$-$R^2$ and wherein G is independently selected for each occurrence from the group consisting of —H; —$CH_3$; and where two geminal G may be taken together with the carbon to which they are bound to form cyclopropylene or cyclobutylene.

In another Embodiment (11.5), the invention provides a compound of Formula (I), or a pharmaceutically acceptable salt thereof, according to any preceding Embodiment, wherein W is selected from the group consisting of —$OCH_2$—$R^2$; —$OC(CH_3)H$—$R^2$; —$OC(CH_3)_2$—$R^2$;

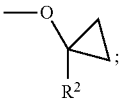; and 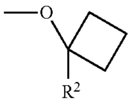.

In another Embodiment (11.6), the invention provides a compound of Formula (I), or a pharmaceutically acceptable salt thereof, according to any preceding Embodiment, wherein W is —$OCH_2$—$R^2$.

In another Embodiment (12), the invention provides a compound of Formula (I), or a pharmaceutically acceptable salt thereof, according to any preceding Embodiment, wherein $R^2$ is phenyl, which $R^2$ is optionally substituted as defined for a compound of Formula (I).

In another Embodiment (13), the invention provides a compound of Formula (I), or a pharmaceutically acceptable salt thereof, according to any preceding Embodiment, wherein $R^2$ is 5 to 6 membered heteroaryl, wherein said 5 to 6 membered heteroaryl comprises one or two heteroatoms independently selected for each occurrence from the group consisting of —N═, —N(J)-, —O—, and —S—, for example pyrazinyl, pyrimidinyl, pyridinyl or pyridazinyl, and which $R^2$ is optionally substituted as defined for a compound of Formula (I).

In another Embodiment (13.1), the invention provides a compound of Formula (I), or a pharmaceutically acceptable salt thereof, according to any preceding Embodiment, wherein $R^2$ is selected from the group consisting of pyrrolyl, furanyl, pyrrolinyl, thiophenyl, pyrazolyl, N-methyl-pyrazolyl, imidazolyl, oxazolyl, isoxazolyl, pyrazolinyl, imidazolinyl, thiazolyl, isothiazolyl, triazolyl, tetrazolyl, pyridinyl, pyranyl, pyridazinyl, pyrazinyl, triazinyl and pyrimidinyl, and which $R^2$ is optionally substituted as defined for a compound of Formula (I).

In another Embodiment (13.2), the invention provides a compound of Formula (I), or a pharmaceutically acceptable salt thereof, according to any preceding Embodiment, wherein $R^2$ is selected from the group consisting of pyrazinyl, pyrimidinyl, pyridinyl or pyridazinyl, and which $R^2$ is optionally substituted as defined for a compound of Formula (I).

In another Embodiment (13.3), the invention provides a compound of Formula (I), or a pharmaceutically acceptable salt thereof, according to any preceding Embodiment, wherein $R^2$ is —$C_3$-$C_7$ carbocyclyl optionally substituted with one, two, three, four, five or six E, for example cyclopropyl, cyclobutyl, cyclopentyl or cyclohexyl, which $R^2$ is optionally substituted with E as defined in Formula (I).

In another Embodiment (13.4), the invention provides a compound of Formula (I), or a pharmaceutically acceptable salt thereof, according to any preceding Embodiment, wherein $R^2$ is selected from the group consisting of cyclopropyl, cyclobutyl, cyclopentyl and cyclohexyl, which $R^2$ is optionally substituted with E as defined in Formula (I).

In another Embodiment (13.5), the invention provides a compound of Formula (I), or a pharmaceutically acceptable salt thereof, according to any preceding Embodiment, wherein $R^2$ is cyclohexyl, which $R^2$ is optionally substituted with E as defined in Formula (I).

In another Embodiment (13.6), the invention provides a compound of Formula (I), or a pharmaceutically acceptable salt thereof, according to any preceding Embodiment, wherein $R^2$ is 4 to 7 membered heterocyclyl wherein said 4 to 7 membered heterocyclyl comprises one or two heteroatoms independently selected for each occurrence from the group consisting of —N(J)-, —O— and —S—, for example azetidinyl; oxetanyl; thietanyl; pyrrolidinyl; tetrahydrofuranyl; tetrahydrothiophenyl; pyrazolidinyl; imidazolidinyl; dioxolanyl; thiazolidinyl; isoxazolidinyl; tetrahydropyranyl; piperidinyl; piperazinyl; morpholinyl; dioxanyl or thiomorpholinyl; wherein when $R^2$ is a heterocyclyl which comprises a heteroatom —N(J)-, J is defined as in Formula (I); and which $R^2$ is optionally substituted with E as defined in Formula (I).

In another Embodiment (13.7), the invention provides a compound of Formula (I), or a pharmaceutically acceptable salt thereof, according to any preceding Embodiment, wherein $R^2$ is selected from the group consisting of azetidinyl; oxetanyl; thietanyl; pyrrolidinyl; tetrahydrofuranyl; tetrahydrothiophenyl; pyrazolidinyl; imidazolidinyl; dioxolanyl; thiazolidinyl; isoxazolidinyl; tetrahydropyranyl; piperidinyl; piperazinyl; morpholinyl; dioxanyl and thiomorpholinyl; wherein when $R^2$ is a heterocyclyl which comprises a heteroatom —N(J)-, J is defined as in Formula (I); and which $R^2$ is optionally substituted with E as defined in Formula (I).

In another Embodiment (13.8), the invention provides a compound of Formula (I), or a pharmaceutically acceptable salt thereof, according to any preceding Embodiment, wherein $R^2$ is selected from the group consisting of pyrrolidinyl; tetrahydropyranyl; and piperidinyl, which pyrrolidinyl and piperidinyl are substituted on the ring nitrogen with J as defined in Formula (I), and which $R^2$ is optionally substituted with E as defined in Formula (I).

In another Embodiment (13.9), the invention provides a compound of Formula (I), or a pharmaceutically acceptable salt thereof, according to any preceding Embodiment, wherein $R^2$ is selected from the group consisting of pyrrolidinyl; tetrahydropyranyl; and piperidinyl, which pyrrolidinyl; and piperidinyl are substituted on the ring N with J, which J is —$C_1$-$C_6$alkyl, for example —$CH_3$, or —$CH_2CH_3$, to form, for example N-methyl piperidinyl or N-ethyl pyrrolidinyl, and which $R^2$ is further substituted with E as defined in Formula (I).

In another Embodiment (13.10), the invention provides a compound of Formula (I), or a pharmaceutically acceptable salt thereof, according to any preceding Embodiment, wherein $R^2$ is selected from the group consisting of N-methyl piperidinyl; N-ethyl pyrrolidinyl; and tetrahydropyranyl; which $R^2$ is further substituted with E as defined in Formula (I).

In another Embodiment (13.11), the invention provides a compound of Formula (I), or a pharmaceutically acceptable salt thereof, according to any preceding Embodiment, wherein $R^2$ is a 4 to 7 membered heterocyclyl optionally substituted with one, two, three, four, five or six E, wherein said 4 to 7 membered heterocyclyl is (i) bound to W through a first heterocyclyl ring heteroatom —N— and (ii) which optionally comprises a second ring heteroatom independently selected from the group consisting of —N(J)-, —O—, and —S—, for example azetidinyl; pyrrolidinyl; pyrazolidinyl; imiidazolidinyl; thiazolidinyl; piperidinyl; piperazinyl; mopholidinyl or thiomorpholidinyl, and wherein when $R^2$ is a heterocyclyl which comprises a second ring heteroatom —N(J)-, J is defined as in Formula (I), and which $R^2$ is optionally substituted with E as defined in Formula (I). In another Embodiment (14), the invention provides a compound of Formula (I), or a pharmaceutically acceptable salt thereof, according to any preceding Embodiment, wherein E is selected, independently for each occurrence, from the group consisting of —H; -halo, for example —F or —Cl; —CN; —OH; —$CO_2H$; —$C_1$-$C_6$alkyl, for example —$CH_3$, which —$C_1$-$C_6$alkyl is optionally substituted with one, two, three, four, five or six K to form, for example, —$CF_3$, or —$CH_2CO_2H$; —$OC_1$-$C_6$alkyl, for example —$OCH_3$, which —$OC_1$-$C_6$alkyl is optionally substituted with one, two, three, four, five or six K to form, for example, —$OCF_3$; 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—, for example N-methyl piperidinyl; —$NH_2$; —NH($C_1$-$C_6$alkyl), which $C_1$-$C_6$alkyl is optionally substituted with one, two, three, four, five or six K; —N($C_1$-$C_6$alkyl)$_2$, which $C_1$-$C_6$alkyl is, independently for each occurrence, optionally substituted with one, two, three, four, five or six K; —C(O)$NH_2$; —C(O)NH($C_1$-$C_6$alkyl), which $C_1$-$C_6$alkyl is optionally substituted with one, two, three, four, five or six K; —C(O)N($C_1$-$C_6$alkyl)$_2$, which $C_1$-$C_6$alkyl is, independently for each occurrence, optionally substituted with one, two, three, four, five or six K; and —$SO_2$($C_1$-$C_6$alkyl), which $C_1$-$C_6$alkyl is optionally substituted with one, two, three, four, five or six K, for example —$SO_2CH_3$.

In another Embodiment (14.1), the invention provides a compound of Formula (I), or a pharmaceutically acceptable salt thereof, according to any preceding Embodiment, wherein E is selected, independently for each occurrence, from the group consisting of —H; -halo, for example —F or —Cl; —CN; —OH; —$CO_2H$; —$C_1$-$C_6$alkyl, for example —$CH_3$, which —$C_1$-$C_6$alkyl is optionally substituted with one, two, three, four, five or six K to form, for example, —$CF_3$ or —$CH_2CO_2H$; —$OC_1$-$C_6$alkyl, for example —$OCH_3$, which —$OC_1$-$C_6$alkyl is optionally substituted with one, two, three, four, five or six K to form, for example, —$OCF_3$; 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—, for example N-methyl piperidinyl; $—NH_2$; $—C(O)NH_2$; and $—SO_2(C_1-C_6alkyl)$, which $C_1-C_6alkyl$ is optionally substituted with one, two, three, four, five or six K, for example $—SO_2CH_3$.

In another Embodiment (14.2), the invention provides a compound of Formula (I), or a pharmaceutically acceptable salt thereof, according to any preceding Embodiment, wherein E is selected, independently for each occurrence, from the group consisting of —H; —F; —Cl; —CN; —OH; $—CO_2H$; $—CH_3$; $—CF_3$; $—CH_2CO_2H$; $—OCH_3$; $—OCF_3$; N-methyl piperidinyl; $—NH_2$; $—C(O)NH_2$; and $—SO_2CH_3$.

In another Embodiment (15), the invention provides a compound of Formula (I), or a pharmaceutically acceptable salt thereof, according to any preceding Embodiment, wherein $R^1$ is selected from the group consisting of phenyl, thiophenyl, 1,4-dioxochromanyl, quinolinyl, pyrazolyl, indazolyl, pyridinyl, N-methyl-indazolyl and N-methyl-pyrazolyl, which $R^1$ is optionally substituted with one, two, three or four E, which E is independently selected for each occurrence from the group consisting of —H; —F; —Cl; —CN; —OH; $—CO_2H$; $—CH_3$; $—CF_3$; $—CH_2CO_2H$; $—OCH_3$; $—OCF_3$; N-methyl piperidinyl; $—NH_2$; $—C(O)NH_2$; and $—SO_2CH_3$.

In another Embodiment (15.1), the invention provides a compound of Formula (I), or a pharmaceutically acceptable salt thereof, according to any preceding Embodiment, wherein $R^1$ is selected from the group consisting of phenyl, thiophenyl, 1,4-dioxochromanyl, quinolinyl, pyrazolyl, indazolyl, pyridinyl, N-methyl-indazolyl and N-methyl-pyrazolyl, which $R^1$ is optionally substituted with one, two, three or four E, which E are independently selected for each occurrence from the group consisting of —H; —F; —Cl; —CN; $—CO_2H$; $—CH_3$; $—CF_3$; $—CH_2CO_2H$; $—OCH_3$; $—C(O)NH_2$; and $—SO_2CH_3$.

In another Embodiment (15.2), the invention provides a compound of Formula (I), or a pharmaceutically acceptable salt thereof, according to any preceding Embodiment, wherein $R^1$ is selected from the group consisting of unsubstituted phenyl; phenyl substituted with one E, which E is selected from the group consisting of —F, —Cl, CN, $—CO_2H$, $CH_3$, $—CF_3$, $—CH_2CO_2H$, $—OCH_3$, $—C(O)NH_2$, and $SO_2CH_3$; and phenyl substituted with two E, which E is selected independently for each occurrence from the group consisting of —F, —Cl, —CN, $—CH_3$, $—CF_3$ and $—OCH_3$.

In another Embodiment (15.3), the invention provides a compound of Formula (I), or a pharmaceutically acceptable salt thereof, according to any preceding Embodiment, wherein $R^1$ is selected from the group consisting of unsubstituted thiophenyl; unsubstituted 1,4-dioxochromanyl; quinolinyl which quinolinyl is substituted with one E, which E is $—CH_3$; N-methyl-pyrazolyl; N-methyl-indazolyl, and pyridinyl, which pyridinyl is substituted with one E, which E is $—CF_3$.

In another Embodiment (16), the invention provides a compound of Formula (I), or a pharmaceutically acceptable salt thereof, according to any preceding Embodiment, wherein $R^2$ is selected from the group consisting of phenyl, pyrazinyl, pyrimidinyl, pyridinyl and pyridazinyl, which $R^2$ is optionally substituted with one, two, three or four E, which E is independently selected for each occurrence from the group consisting of —H; —F; —Cl; —CN; —OH; $—CO_2H$; $—CH_3$; $—CF_3$; $—CH_2CO_2H$; $—OCH_3$; $—OCF_3$; N-methyl piperidinyl; $—NH_2$; $—C(O)NH_2$; and $—SO_2CH_3$.

In another Embodiment (16.1), the invention provides a compound of Formula (I), or a pharmaceutically acceptable salt thereof, according to any preceding Embodiment, wherein $R^2$ is selected from the group consisting of phenyl, pyrazinyl, pyrimidinyl, pyridinyl and pyridazinyl, which $R^2$ is optionally substituted with one, two, three or four E, which E is independently selected for each occurrence from the group consisting of —H; —F; —Cl; —CN; —OH; $—CO_2H$; $—CH_3$; $—CF_3$; $—OCH_3$; $—OCF_3$; —N-methyl piperidinyl; $—NH_2$; and $—C(O)NH_2$.

In another Embodiment (16.2), the invention provides a compound of Formula (I), or a pharmaceutically acceptable salt thereof, according to any preceding Embodiment, wherein $R^2$ is selected from the group consisting of unsubstituted phenyl; phenyl substituted with one E, which E is selected from the group consisting of —F, —Cl, —CN, $—CO_2H$, $—OCH_3$, $—OCF_3$, —N-methyl piperidinyl, and $—C(O)NH_2$; and phenyl substituted with two E, which E is, independently for each occurrence, selected from the group consisting of —F and —Cl.

In another Embodiment (16.3), the invention provides a compound of Formula (I), or a pharmaceutically acceptable salt thereof, according to any preceding Embodiment, wherein $R^2$ is selected from the group consisting of unsubstituted pyrazinyl; pyrazinyl substituted with one E, which E is selected from the group consisting of —CN and $—NH_2$; unsubstituted pyrimidinyl; pyrimidinyl substituted with one E, which E is selected from the group consisting of —CN; unsubstituted pyridinyl; pyridinyl substituted with one E, which E is selected from the group consisting of —CN, —OH, $—CH_3$, $—CF_3$, $—NH_2$, and $—C(O)NH_2$; and unsubstituted pyridazinyl.

In another Embodiment (16.4), the invention provides a compound of Formula (I), or a pharmaceutically acceptable salt thereof, according to any preceding Embodiment, wherein $R^2$ is cyclohexyl which cyclohexyl substituted with one E, which E is selected from the group consisting of —H; —F; —Cl; —CN; —OH; $—CO_2H$; $—CH_3$; $—CF_3$; $—CH_2CO_2H$; $—OCH_3$; $—OCF_3$; N-methyl piperidinyl; $—NH_2$; $—C(O)NH_2$; and $—SO_2CH_3$.

In another Embodiment (16.5), the invention provides a compound of Formula (I), or a pharmaceutically acceptable salt thereof, according to any preceding Embodiment, wherein $R^2$ is cyclohexyl which cyclohexyl substituted with one E which E is —OH.

In another Embodiment (16.6), the invention provides a compound of Formula (I), or a pharmaceutically acceptable salt thereof, according to any preceding Embodiment, wherein $R^2$ is selected from the group consisting of N-methyl piperidinyl; N-ethyl pyrrolidinyl; and tetrahydropyranyl; which $R^2$ is optionally substituted with one E, which E is selected from the group consisting of —H; —F; —Cl; —CN; —OH; $—CO_2H$; $—CH_3$; $—CF_3$; $—CH_2CO_2H$; $—OCH_3$; $—OCF_3$; N-methyl piperidinyl; $—NH_2$; $—C(O)NH_2$; and $—SO_2CH_3$.

In another Embodiment (16.7), the invention provides a compound of Formula (I), or a pharmaceutically acceptable salt thereof, according to any preceding Embodiment, wherein $R^2$ is selected from the group consisting of N-methyl piperidinyl; N-ethyl pyrrolidinyl; and tetrahydropyranyl.

In another Embodiment (17), the invention provides a compound of Formula (I), or a pharmaceutically acceptable salt thereof, according to any preceding Embodiment, wherein J is, independently for each occurrence, selected from the group consisting of —H and —$C_1$-$C_6$alkyl, for example —$CH_3$.

In another Embodiment (18), the invention provides a compound of Formula (I), or a pharmaceutically acceptable salt thereof, according to any preceding Embodiment, wherein K is, independently for each occurrence, selected from the group consisting of —H, —F, —Cl, —OH, —CN, —$CH_3$, —$CH_2F$, —$CHF_2$, —$CF_3$, —$OCH_3$, —$OCH_2F$, —$OCHF_2$, —$OCF_3$, —$NH_2$, —$NH(CH_3)$, and —$N(CH_3)_2$.

The present invention also relates to a pharmaceutical composition comprising a compound of Formula (I), or a pharmaceutically acceptable salt thereof, and a pharmaceutically acceptable excipient.

The present invention also relates to a method of treating a disease or a disorder in a patient, comprising administering to a patient in need thereof a therapeutically effective amount of a compound of Formula (I), or a pharmaceutically acceptable salt thereof or a pharmaceutical composition comprising a therapeutically effective amount of a compound of Formula (I), or a pharmaceutically acceptable salt thereof.

In another embodiment, the present invention further provides a method of inhibiting vanin-1 enzyme in a cell, comprising contacting the cell with a therapeutically effective amount of a compound of Formula (I), or a pharmaceutically acceptable salt thereof, or a pharmaceutical composition comprising a therapeutically effective amount of a compound of Formula (I), or a pharmaceutically acceptable salt thereof.

In another embodiment, the present invention further provides a method of inhibiting vanin-1 enzyme, comprising contacting the enzyme with a therapeutically effective amount of a compound of Formula (I), or a pharmaceutically acceptable salt thereof, or a pharmaceutical composition comprising a therapeutically effective amount of a compound of Formula (I), or a pharmaceutically acceptable salt thereof.

In another embodiment, the present invention relates to a method of treating a disease or disorder mediated by, or otherwise associated with, inhibition of the vanin-1 enzyme, comprising administering to a patient in need thereof a therapeutically effective amount of a compound of Formula (I), or a pharmaceutically acceptable salt thereof, or a pharmaceutical composition comprising a therapeutically effective amount of a compound of Formula (I), or a pharmaceutically acceptable salt thereof.

This invention also relates to a compound of Formula II, Embodiment (20):

Formula II

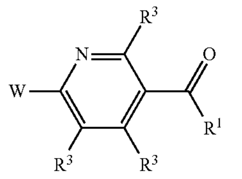

or a pharmaceutically acceptable salt thereof, wherein $R^1$ is selected from the group consisting of:

(i) 6 to 10 membered aryl optionally substituted with one, two, three or four E; and (ii) 5 to 6 membered heteroaryl optionally substituted with one, two, three or four E, wherein said 5 to 6 membered heteroaryl (a) comprises one, two or three heteroatoms independently selected for each occurrence from the group consisting of —N═, —N(J)-, —O—, and —S— and (b) is not bound to the carbonyl of Formula (I) through a nitrogen;

W is selected from the group consisting of:

(i) —$NHCG_2$-$R^2$;

(ii) —$NHCG_2CG_2$-$R^2$;

(iii) —$OCG_2$-$R^2$;

(iv) —$OCG_2CG_2$-$R^2$;

$R^2$ is selected from the group consisting of:

(i) phenyl optionally substituted with one, two, three or four E;

(ii) 5 to 6 membered heteroaryl optionally substituted with one, two, three or four E, wherein said 5 to 6 membered heteroaryl comprises one or two heteroatoms independently selected for each occurrence from the group consisting of —N═, —N(J)-, —O—, and —S—; and (iii) —$C_3$-$C_7$ carbocyclyl optionally substituted with one, two, three, four, five or six E;

$R^3$ is independently selected for each occurrence from the group consisting of —H, —F, —Cl, —CN, —$CH_3$, —$CH_2CH_3$, —$CH_2F$, —$CHF_2$, —$CF_3$, —$CF_2CF_3$, —$OCH_3$, —$OCH_2F$, —$OCHF_2$, —$OCF_3$, —$SCH_3$, —$SCH_2F$, —$SCHF_2$, and —$SCF_3$;

E is independently selected for each occurrence from the group consisting of:

(i) —H;

(ii) —halo;

(iii) —CN;

(iv) —OH;

(v) —$CO_2H$;

(vi) —$C_1$-$C_6$alkyl optionally substituted with one, two, three, four, five or six K;

(vii) —$OC_1$-$C_6$alkyl optionally substituted with one, two, three, four, five or six K;

(viii) —$SC_1$-$C_6$alkyl optionally substituted with one, two, three, four, five or six K;

(ix) —$C_3$-$C_5$cycloalkyl optionally substituted with one, two, three, four, five or six K;

(x) —$OC_3$-$C_5$cycloalkyl optionally substituted with one, two, three, four, five or six K;

(xi) —$SC_3$—$C_5$cycloakyl optionally substituted with one, two, three, four, five or six K;

(xii) —$C_1$-$C_6$alkyl($C_3$-$C_5$cycloalkyl) optionally substituted with one, two, three, four, five or six K;

(xiii) 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—;

(xiv) —$NH_2$;

(xv) —NH($C_1$-$C_6$alkyl), which $C_1$-$C_6$alkyl is optionally substituted with one, two, three, four, five or six K;

(xvi) —N($C_1$-$C_6$alkyl)$_2$, which $C_1$-$C_6$alkyl is, independently for each occurrence, optionally substituted with one, two, three, four, five or six K;

(xvii) —C(O)$NH_2$;

(xviii) —C(O)NH($C_1$-$C_6$alkyl), which $C_1$-$C_6$alkyl is optionally substituted with one, two, three, four, five or six K;

(xix) —C(O)N($C_1$-$C_6$alkyl)$_2$, which $C_1$-$C_6$alkyl is, independently for each occurrence, optionally substituted with one, two, three, four, five or six K;

(xx) —NHC(O)($C_1$-$C_6$alkyl), which $C_1$-$C_6$alkyl is optionally substituted with one, two, three, four, five or six K;

(xxi) —N($C_1$-$C_6$alkyl)C(O)($C_1$-$C_6$alkyl), which $C_1$-$C_6$alkyl is, independently for each occurrence, optionally substituted with one, two, three, four, five or six K;
(xxii) —$SO_2$($C_1$-$C_6$alkyl), which $C_1$-$C_6$alkyl is optionally substituted with one, two, three, four, five or six K;
(xxiii) —$SO_2NH_2$;
(xxiv) —$SO_2$NH($C_1$-$C_6$alkyl), which $C_1$-$C_6$alkyl is optionally substituted with one, two, three, four, five or six K;
(xxv) —$SO_2$N($C_1$-$C_6$alkyl)$_2$, which $C_1$-$C_6$alkyl is, independently for each occurrence optionally substituted with one, two, three, four, five or six K;
(xxvi) —$NHSO_2$($C_1$-$C_6$alkyl), which $C_1$-$C_6$alkyl is optionally substituted with one, two, three, four, five or six K; and
(xxvii) —N($C_1$-$C_6$alkyl)$SO_2$($C_1$-$C_6$alkyl), which $C_1$-$C_6$alkyl is, independently for each occurrence, optionally substituted with one, two, three, four, five or six K;

G is independently selected for each occurrence from the group consisting of:
(i) —H;
(ii) —halo;
(iii) —OH;
(iv) —$C_1$-$C_6$alkyl optionally substituted optionally substituted with one, two, three, four, five or six K;
(v) —$OC_1$-$C_6$alkyl optionally substituted with one, two, three, four, five or six K;
(vi) —$SC_1$-$C_6$alkyl optionally substituted with one, two, three, four, five or six K;
(vii) —NH($C_1$-$C_6$alkyl), which $C_1$-$C_6$alkyl is optionally substituted with one, two, three, four, five or six K;
(viii) —N($C_1$-$C_6$alkyl)$_2$, which $C_1$-$C_6$alkyl is, independently for each occurrence, optionally substituted with one, two, three, four, five or six K;
(ix) —$C_3$-$C_5$cycloalkyl optionally substituted with one, two, three, four, five or six K; and
(x) 4 to 5 membered heterocyclyl optionally substituted with one, two, three, four, five or six K, which said 4 to 5 membered heterocyclyl comprises one or two heteroatoms independently selected for each occurrence from the group consisting of —N(J)-, —O— or —S—;
or two geminal G may, together with the carbon to which they are bound, form a —$C_3$-$C_5$cycloalkylene optionally substituted with one, two, three, four, five or six K or a 4 to 5 membered heterocyclylene optionally substituted with one, two, three, four, five or six K, wherein said 4 to 5 membered heterocyclylene comprises one heteroatom independently selected from the group consisting of —N(J)-, —O—, or —S—;

J is independently selected, for each occurrence, from the group consisting of:
(i) —H;
(ii) —$C_1$-$C_6$alkyl optionally substituted with one, two, three, four, five or six K;
(iii) —C(O)$NH_2$;
(iv) —C(O)NH($C_1$-$C_6$alkyl), which $C_1$-$C_6$alkyl is optionally substituted with one, two, three, four, five or six K;
(v) —C(O)N($C_1$-$C_6$alkyl)$_2$, which $C_1$-$C_6$alkyl is, independently for each occurrence, optionally substituted with one, two, three, four, five or six K; and
(vi) —$SO_2$($C_1$-$C_6$alkyl), which $C_1$-$C_6$alkyl is optionally substituted with one, two, three, four, five or six halo; and K is independently selected, for each occurrence, from the group consisting of —H, —F, —Cl, —OH, —CN, —$CO_2$H, —$CH_3$, —$CH_2CH_3$, —$CH_2$F, —$CHF_2$, —$CF_3$, —$CF_2CF_3$, —$OCH_3$, —$OCH_2$F, —$OCHF_2$, —$OCF_3$, —$SCH_3$, —$SCH_2$F, —$SCHF_2$, —$SCF_3$—$NH_2$, —NH($CH_3$), —N($CH_3$)$_2$, and —CON$H_2$.

In another Embodiment (21), this invention provides a compound of Formula (II):

Formula II

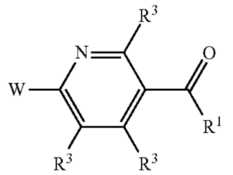

or a pharmaceutically acceptable salt thereof, wherein $R^1$ is selected from the group consisting of:
(i) 6 to 10 membered aryl optionally substituted with one, two, three or four E; and
(ii) 5 to 6 membered heteroaryl optionally substituted with one, two, three or four E, wherein said 5 to 6 membered heteroaryl (a) comprises one, two or three heteroatoms independently selected for each occurrence from the group consisting of —N═, —N(J)-, —O—, and —S— and (b) is not bound to the carbonyl of Formula (I) through a nitrogen;

W is selected from the group consisting of:
(i) —NHC$G_2$-$R^2$;
(ii) —NHC$G_2$C$G_2$-$R^2$;
(iii) —OC$G_2$-$R^2$;
(iv) —OC$G_2$C$G_2$-$R^2$;

$R^2$ is selected from the group consisting of:
(i) phenyl optionally substituted with one, two, three or four E;
(ii) 5 to 6 membered heteroaryl optionally substituted with one, two, three or four E, wherein said 5 to 6 membered heteroaryl comprises one or two heteroatoms independently selected for each occurrence from the group consisting of —N═, —N(J)-, —O—, and —S—; and
(iii) —$C_3$-$C_7$ carbocyclyl optionally substituted with one, two, three, four, five or six E;

$R^3$ is independently selected for each occurrence from the group consisting of —H, —F, —Cl, —CN, —$CH_3$, —$CH_2CH_3$, —$CH_2$F, —$CHF_2$, —$CF_3$, —$CF_2CF_3$, —$OCH_3$, —$OCH_2$F, —$OCHF_2$, —$OCF_3$, —$SCH_3$, —$SCH_2$F, —$SCHF_2$, and —$SCF_3$;

E is independently selected for each occurrence from the group consisting of:
(i) —H;
(ii) —halo;
(iii) —CN;
(iv) —OH;
(v) —$CO_2$H;
(vi) —$C_1$-$C_6$alkyl optionally substituted with one, two, three, four, five or six K;
(vii) —$OC_1$-$C_6$alkyl optionally substituted with one, two, three, four, five or six K;
(viii) —$SC_1$-$C_6$alkyl optionally substituted with one, two, three, four, five or six K;
(ix) —$C_3$-$C_5$cycloalkyl optionally substituted with one, two, three, four, five or six K;

(x) —$OC_3$-$C_5$cycloalkyl optionally substituted with one, two, three, four, five or six K;
(xi) —$SC_3$-$C_5$cycloalkyl optionally substituted with one, two, three, four, five or six K;
(xii) —$C_1$-$C_6$alkyl($C_3$-$C_5$cycloalkyl) optionally substituted with one, two, three, four, five or six K;
(xiii) 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—;
(xiv) —$NH_2$;
(xv) —NH($C_1$-$C_6$alkyl), which $C_1$-$C_6$alkyl is optionally substituted with one, two, three, four, five or six K;
(xvi) —N($C_1$-$C_6$alkyl)$_2$, which $C_1$-$C_6$alkyl is, independently for each occurrence, optionally substituted with one, two, three, four, five or six K;
(xvii) —C(O)$NH_2$;
(xviii) —C(O)NH($C_1$-$C_6$alkyl), which $C_1$-$C_6$alkyl is optionally substituted with one, two, three, four, five or six K;
(xix) —C(O)N($C_1$-$C_6$alkyl)$_2$, which $C_1$-$C_6$alkyl is, independently for each occurrence, optionally substituted with one, two, three, four, five or six K;
(xx) —NHC(O)($C_1$-$C_6$alkyl), which $C_1$-$C_6$alkyl is optionally substituted with one, two, three, four, five or six K;
(xxi) —N($C_1$-$C_6$alkyl)C(O)($C_1$-$C_6$alkyl), which $C_1$-$C_6$alkyl is, independently for each occurrence, optionally substituted with one, two, three, four, five or six K;
(xxii) —$SO_2$($C_1$-$C_6$alkyl), which $C_1$-$C_6$alkyl is optionally substituted with one, two, three, four, five or six K;
(xxiii) —$SO_2NH_2$;
(xxiv) —$SO_2$NH($C_1$-$C_6$alkyl), which $C_1$-$C_6$alkyl is optionally substituted with one, two, three, four, five or six K;
(xxv) —$SO_2$N($C_1$-$C_6$alkyl)$_2$, which $C_1$-$C_6$alkyl is, independently for each occurrence optionally substituted with one, two, three, four, five or six K;
(xxvi) —$NHSO_2$($C_1$-$C_6$alkyl), which $C_1$-$C_6$alkyl is optionally substituted with one, two, three, four, five or six K; and
(xxvii) —N($C_1$-$C_6$alkyl)$SO_2$($C_1$-$C_6$alkyl), which $C_1$-$C_6$alkyl is, independently for each occurrence, optionally substituted with one, two, three, four, five or six K;

G is independently selected for each occurrence from the group consisting of:
(i) —H;
(ii) —halo;
(iii) —OH;
(iv) —$C_1$-$C_6$alkyl optionally substituted optionally substituted with one, two, three, four, five or six K;
(v) —$OC_1$-$C_6$alkyl optionally substituted with one, two, three, four, five or six K;
(vi) —$SC_1$-$C_6$alkyl optionally substituted with one, two, three, four, five or six K;
(vii) —NH($C_1$-$C_6$alkyl), which $C_1$-$C_6$alkyl is optionally substituted with one, two, three, four, five or six K;
(viii) —N($C_1$-$C_6$alkyl)$_2$, which $C_1$-$C_6$alkyl is, independently for each occurrence, optionally substituted with one, two, three, four, five or six K;
(ix) —$C_3$-$C_5$cycloalkyl optionally substituted with one, two, three, four, five or six K; and
(x) 4 to 5 membered heterocyclyl optionally substituted with one, two, three, four, five or six K, which said 4 to 5 membered heterocyclyl comprises one or two heteroatoms independently selected for each occurrence from the group consisting of —N(J)-, —O— or —S—;

or two geminal G may, together with the carbon to which they are bound, form a —$C_3$-$C_5$cycloalkylene optionally substituted with one, two, three, four, five or six K or a 4 to 5 membered heterocyclylene optionally substituted with one, two, three, four, five or six K, wherein said 4 to 5 membered heterocyclylene comprises one heteroatom independently selected from the group consisting of —N(J)-, —O—, or —S—;

J is independently selected, for each occurrence, from the group consisting of:
(i) —H;
(ii) —$C_1$-$C_6$alkyl optionally substituted with one, two, three, four, five or six K;
(iii) —C(O)$NH_2$;
(iv) —C(O)NH($C_1$-$C_6$alkyl), which $C_1$-$C_6$alkyl is optionally substituted with one, two, three, four, five or six K;
(v) —C(O)N($C_1$-$C_6$alkyl)$_2$, which $C_1$-$C_6$alkyl is, independently for each occurrence, optionally substituted with one, two, three, four, five or six K; and
(vi) —$SO_2$($C_1$-$C_6$alkyl), which $C_1$-$C_6$alkyl is optionally substituted with one, two, three, four, five or six halo; and K is independently selected, for each occurrence, from the group consisting of —H, —F, —Cl, —OH, —CN, —$CO_2H$, —$CH_3$, —$CH_2CH_3$, —$CH_2F$, —$CHF_2$, —$CF_3$, —$CF_2CF_3$, —$OCH_3$, —$OCH_2F$, —$OCHF_2$, —$OCF_3$, —$SCH_3$, —$SCH_2F$, —$SCHF_2$, —$SCF_3$—$NH_2$, —NH($CH_3$), —N($CH_3$)$_2$, and —$CONH_2$;

with the proviso that when $R^1$ is phenyl, that $R^2$ can not also be phenyl; and with the proviso that when $R^1$ is phenyl and W is —$OCG_2CG_2$-$R^2$, that $R^2$ can not be thiophenyl.

In another Embodiment (22), the invention provides a compound of Formula (II), or a pharmaceutically acceptable salt thereof, according to any preceding Embodiment, wherein $R^3$ is —H, —F, —$CH_3$, —$CH_2F$, —$CHF_2$, —$CF_3$, —$OCH_3$, —$OCH_2F$, —$OCHF_2$, and —$OCF_3$.

In another Embodiment (22.1), the invention provides a compound of Formula (II), or a pharmaceutically acceptable salt thereof, according to any preceding Embodiment, wherein $R^3$ is —H.

In another Embodiment (23), the invention provides a compound of Formula (II), or a pharmaceutically acceptable salt thereof, according to any preceding Embodiment, wherein $R^1$ is a 6 to 10 membered aryl, for example phenyl, which $R^1$ is optionally substituted as defined for a compound of Formula (II).

In another Embodiment (23.1), the invention provides a compound of Formula (II), or a pharmaceutically acceptable salt thereof, according to any preceding Embodiment, wherein $R^1$ is phenyl, which phenyl is optionally substituted as defined for a compound of Formula (II).

In another Embodiment (24), the invention provides a compound of Formula (II), or a pharmaceutically acceptable salt thereof, according to Embodiment (20), Embodiment (21), Embodiment (22), or Embodiment (22.1), wherein $R^1$ is a 5 to 6 membered heteroaryl, wherein said 5 to 6 membered heteroaryl (a) comprises one, two or three heteroatoms independently selected for each occurrence from the group consisting of —N═, —N(J)-, —O—, and —S— and (b) is not bound to the carbonyl of Formula (I) through a nitrogen, for example thiophenyl, pyrazolyl, pyridinyl, or N-methyl-pyrazolyl, which $R^1$ is optionally substituted as defined for a compound of Formula (II).

In another Embodiment (24.2), the invention provides a compound of Formula (II), or a pharmaceutically acceptable salt thereof, according to Embodiment (20), Embodiment (21), Embodiment (22), Embodiment (22.1), or Embodiment (24) wherein $R^1$ is selected from the group consisting of thiophenyl, pyrazolyl, pyridinyl, and N-methyl-pyrazolyl which $R^1$ is optionally substituted as defined for a compound of Formula (II), and, when $R^1$ is pyrazolyl, or pyridinyl, said pyrazolyl, or pyridinyl is not bound to the carbonyl of Formula (II) through a nitrogen.

In another Embodiment (25), the invention provides a compound of Formula (II), or a pharmaceutically acceptable salt thereof, according to any preceding Embodiment, wherein W is $—NHCG_2-R^2$.

In another Embodiment (25.1), the invention provides a compound of Formula (II), or a pharmaceutically acceptable salt thereof, according to any preceding Embodiment, wherein W is $—NHCG_2CG_2-R^2$.

In another Embodiment (25.2), the invention provides a compound of Formula (II), or a pharmaceutically acceptable salt thereof, according to any preceding Embodiment, wherein W is $—OCG_2-R^2$.

In another Embodiment (25.3), the invention provides a compound of Formula (II), or a pharmaceutically acceptable salt thereof, according to any preceding Embodiment, wherein W is $—OCG_2CG_2-R^2$.

In another Embodiment (26), the invention provides a compound of Formula (II), or a pharmaceutically acceptable salt thereof, according to any preceding Embodiment, wherein G is independently selected for each occurrence from the group consisting of —H; $—C_1-C_6$alkyl, for example methyl; $—OC_1-C_6$alkyl; $—C_3-C_5$cycloalkyl; or two geminal G may, together with the carbon to which they are bound, form a $—C_3-C_5$cycloalkylene, for example cyclopropylene or cyclobutylene, which G is optionally substituted as defined for a compound of Formula (II).

In another Embodiment (26.1), the invention provides a compound of Formula (II), or a pharmaceutically acceptable salt thereof, according to any preceding Embodiment, wherein G is independently selected for each occurrence from the group consisting of —H; $—C_1-C_6$alkyl, for example methyl; or two geminal G may, together with the carbon to which they are bound, form a $—C_3-C_5$cycloalkylene, for example cyclopropylene or cyclobutylene, which G is optionally substituted as defined for a compound of Formula (II).

In another Embodiment (26.2), the invention provides a compound of Formula (II), or a pharmaceutically acceptable salt thereof, according to any preceding Embodiment, wherein G is independently selected for each occurrence from the group consisting of —H; and $—C_1-C_6$alkyl, for example methyl.

In another Embodiment (27), the invention provides a compound of Formula (II), or a pharmaceutically acceptable salt thereof, according to any preceding Embodiment, wherein W is $—NHCG_2-R^2$ and wherein G is independently selected for each occurrence from the group consisting of —H; $—C_1-C_6$alkyl, for example methyl, which $—C_1-C_6$alkyl, is optionally substituted as defined for a compound Formula (II); or two geminal G may be taken together with the carbon to which they are bound to form a $—C_3-C_5$cycloalkylene, for example cyclopropylene or cyclobutylene, which $—C_3-C_5$cycloalkylene is optionally substituted as defined for a compound of Formula (II).

In another Embodiment (27.1), the invention provides a compound of Formula (II), or a pharmaceutically acceptable salt thereof, according to any preceding Embodiment, wherein W is $—NHCG_2-R^2$ and wherein G is independently selected for each occurrence from the group consisting of —H; $—CH_3$; and where two geminal G may be taken together with the carbon to which they are bound to form cyclopropylene or cyclobutylene.

In another Embodiment (27.2), the invention provides a compound of Formula (II), or a pharmaceutically acceptable salt thereof, according to any preceding Embodiment, wherein W is selected from the group consisting of $—NHCH_2—R^2$; $—NHC(CH_3)H—R^2$; $—NHC(CH_3)_2—R^2$;

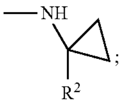
; and
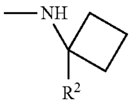
.

In another Embodiment (27.3), the invention provides a compound of Formula (II), or a pharmaceutically acceptable salt thereof, according to any preceding Embodiment, wherein W is selected from the group consisting of $—NHCH_2—R^2$; and $—NHC(CH_3)H—R^2$.

In another Embodiment (27.4), the invention provides a compound of Formula (II), or a pharmaceutically acceptable salt thereof, according to any preceding Embodiment, wherein W is $—OCG_2-R^2$ and wherein G is independently selected for each occurrence from the group consisting of —H; $—C_1-C_6$alkyl, for example methyl, which $—C_1-C_6$alkyl, is optionally substituted as defined for a compound Formula (II); or two geminal G may be taken together with the carbon to which they are bound to form a $—C_3-C_5$cycloalkylene, for example cyclopropylene or cyclobutylene, which $—C_3-C_5$cycloalkylene is optionally substituted as defined for a compound of Formula (II).

In another Embodiment (27.5), the invention provides a compound of Formula (II), or a pharmaceutically acceptable salt thereof, according to any preceding Embodiment, wherein W is $—OCG_2-R^2$ and wherein G is independently selected for each occurrence from the group consisting of —H; $—CH_3$; and where two geminal G may be taken together with the carbon to which they are bound to form cyclopropylene or cyclobutylene.

In another Embodiment (27.6), the invention provides a compound of Formula (II), or a pharmaceutically acceptable salt thereof, according to any preceding Embodiment, wherein W is selected from the group consisting of $—OCH_2—R^2$; $—OC(CH_3)H—R^2$; $—OC(CH_3)_2—R^2$;

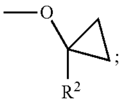
; and
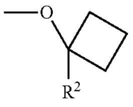
.

In another Embodiment (27.7), the invention provides a compound of Formula (II), or a pharmaceutically acceptable salt thereof, according to any preceding Embodiment, wherein W is $—OCH_2—R^2$.

In another Embodiment (28), the invention provides a compound of Formula (II), or a pharmaceutically acceptable salt thereof, according to any preceding Embodiment, wherein $R^2$ is phenyl, which $R^2$ is optionally substituted as defined for a compound of Formula (II).

In another Embodiment (29), the invention provides a compound of Formula (II), or a pharmaceutically acceptable salt thereof, according to any preceding Embodiment, wherein $R^2$ is 5 to 6 membered heteroaryl, wherein said 5 to 6 membered heteroaryl comprises one or two heteroatoms independently selected for each occurrence from the group consisting of —N═, —N(J)-, —O—, and —S—, for example pyrazinyl, pyrimidinyl, pyridinyl or pyridazinyl, and which $R^2$ is optionally substituted as defined for a compound of Formula (II).

In another Embodiment (29.1), the invention provides a compound of Formula (II), or a pharmaceutically acceptable salt thereof, according to any preceding Embodiment, wherein $R^2$ is selected from the group consisting of pyrrolyl, furanyl, pyrrolinyl, thiophenyl, pyrazolyl, N-methyl-pyrazolyl, imidazolyl, oxazolyl, isoxazolyl, pyrazolinyl, imidazolinyl, thiazolyl, isothiazolyl, triazolyl, tetrazolyl, pyridinyl, pyranyl, pyridazinyl, pyrazinyl, triazinyl and pyrimidinyl, and which $R^2$ is optionally substituted as defined for a compound of Formula (II).

In another Embodiment (29.2), the invention provides a compound of Formula (II), or a pharmaceutically acceptable salt thereof, according to any preceding Embodiment, wherein $R^2$ is selected from the group consisting of pyrazinyl, pyrimidinyl, pyridinyl or pyridazinyl, and which $R^2$ is optionally substituted as defined for a compound of Formula (II).

In another Embodiment (29.3), the invention provides a compound of Formula (II), or a pharmaceutically acceptable salt thereof, according to any preceding Embodiment, wherein $R^2$ is pyrimidinyl which pyrimidinyl is optionally substituted as defined for a compound of Formula (II).

In another Embodiment (29.4), the invention provides a compound of Formula (II), or a pharmaceutically acceptable salt thereof, according to any preceding Embodiment, wherein $R^2$ is —$C_3$-$C_7$ carbocyclyl optionally substituted with one, two, three, four, five or six E, for example cyclopropyl, cyclobutyl, cyclopentyl or cyclohexyl, which $R^2$ is optionally substituted as defined in Formula (II).

In another Embodiment (29.5), the invention provides a compound of Formula (II), or a pharmaceutically acceptable salt thereof, according to any preceding Embodiment, wherein $R^2$ is selected from the group consisting of cyclopropyl, cyclobutyl, cyclopentyl and cyclohexyl, which $R^2$ is optionally substituted as defined in Formula (II).

In another Embodiment (29.6), the invention provides a compound of Formula (II), or a pharmaceutically acceptable salt thereof, according to any preceding Embodiment, wherein $R^2$ is cyclohexyl, which $R^2$ is optionally substituted as defined in Formula (II).

In another Embodiment (30), the invention provides a compound of Formula (II), or a pharmaceutically acceptable salt thereof, according to any preceding Embodiment, wherein E is selected, independently for each occurrence, from the group consisting of —H; -halo, for example —F or —Cl; —CN; —OH; —$CO_2$H; —$C_1$-$C_6$alkyl, for example —$CH_3$, which —$C_1$-$C_6$alkyl is optionally substituted with one, two, three, four, five or six K to form, for example, —$CF_3$, or —$CH_2CO_2H$; —O$C_1$-$C_6$alkyl, for example —$OCH_3$, which —O$C_1$-$C_6$alkyl is optionally substituted with one, two, three, four, five or six K to form, for example, —$OCF_3$; 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—, for example N-methyl piperidinyl; —$NH_2$; —NH($C_1$-$C_6$alkyl), which $C_1$-$C_6$alkyl is optionally substituted with one, two, three, four, five or six K; —N($C_1$-$C_6$alkyl)$_2$, which $C_1$-$C_6$alkyl is, independently for each occurrence, optionally substituted with one, two, three, four, five or six K; —C(O)$NH_2$; —C(O)NH($C_1$-$C_6$alkyl), which $C_1$-$C_6$alkyl is optionally substituted with one, two, three, four, five or six K; —C(O)N($C_1$-$C_6$alkyl)$_2$, which $C_1$-$C_6$alkyl is, independently for each occurrence, optionally substituted with one, two, three, four, five or six K; and —$SO_2$($C_1$-$C_6$alkyl), which $C_1$-$C_6$alkyl is optionally substituted with one, two, three, four, five or six K, for example —$SO_2CH_3$.

In another Embodiment (30.1), the invention provides a compound of Formula (II), or a pharmaceutically acceptable salt thereof, according to any preceding Embodiment, wherein E is selected, independently for each occurrence, from the group consisting of —H; -halo, for example —F or —Cl; —CN; —OH; —$CO_2$H; —$C_1$-$C_6$alkyl, for example —$CH_3$, which —$C_1$-$C_6$alkyl is optionally substituted with one, two, three, four, five or six K to form, for example, —$CF_3$ or —$CH_2CO_2H$; —O$C_1$-$C_6$alkyl, for example —$OCH_3$, which —O$C_1$-$C_6$alkyl is optionally substituted with one, two, three, four, five or six K to form, for example, —$OCF_3$; 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—, for example N-methyl piperidinyl; —$NH_2$; —C(O)$NH_2$; and —$SO_2$($C_1$-$C_6$alkyl), which $C_1$-$C_6$alkyl is optionally substituted with one, two, three, four, five or six K, for example —$SO_2CH_3$.

In another Embodiment (30.2), the invention provides a compound of Formula (II), or a pharmaceutically acceptable salt thereof, according to any preceding Embodiment, wherein E is selected, independently for each occurrence, from the group consisting of —H; —F; —Cl; —CN; —OH; —$CO_2$H; —$CH_3$; —$CF_3$; —$CH_2CO_2H$; —$OCH_3$; —$OCF_3$; N-methyl piperidinyl; —$NH_2$; —C(O)$NH_2$; and —$SO_2CH_3$.

In another Embodiment (30.3), the invention provides a compound of Formula (II), or a pharmaceutically acceptable salt thereof, according to any preceding Embodiment, wherein E is selected, independently for each occurrence, from the group consisting of —H; —CN; —$CF_3$; and —$SO_2CH_3$.

In another Embodiment (31), the invention provides a compound of Formula (II), or a pharmaceutically acceptable salt thereof, according to any preceding Embodiment, wherein $R^1$ is selected from the group consisting of phenyl, thiophenyl, pyrazolyl, pyridinyl, and N-methyl-pyrazolyl, which $R^1$ is optionally substituted with one, two, three or four E, which E is independently selected for each occurrence from the group consisting of —H; —F; —Cl; —CN; —OH; —$CO_2$H; —$CH_3$; —$CF_3$; —$CH_2CO_2H$; —$OCH_3$; —$OCF_3$; N-methyl piperidinyl; —$NH_2$; —C(O)$NH_2$; and —$SO_2CH_3$.

In another Embodiment (31.1), the invention provides a compound of Formula (II), or a pharmaceutically acceptable salt thereof, according to any preceding Embodiment, wherein $R^1$ is selected from the group consisting of phenyl, thiophenyl, pyrazolyl, pyridinyl, and N-methyl-pyrazolyl, which $R^1$ is optionally substituted with one, two, three or four E, which E are independently selected for each occurrence from the group consisting of —H; —F; —Cl; —CN; —$CH_3$; —$OF_3$; -00$H_3$; —$OCF_3$; —C(O)$NH_2$; and —$SO_2CH_3$.

In another Embodiment (31.2), the invention provides a compound of Formula (II), or a pharmaceutically acceptable salt thereof, according to any preceding Embodiment, wherein $R^1$ is selected from the group consisting of unsubstituted phenyl; phenyl substituted with one E, which E is selected from the group consisting of —F, —Cl, —CN, —$CO_2H$, —$CH_3$, —$CF_3$, —$CH_2CO_2H$, —$OCH_3$, —C(O)$NH_2$, and $SO_2CH_3$; and phenyl substituted with two E, which E is selected independently for each occurrence from the group consisting of —F, —Cl, CN, $CH_3$, —$CF_3$, and —$OCH_3$.

In another Embodiment (31.3), the invention provides a compound of Formula (II), or a pharmaceutically acceptable salt thereof, according to any preceding Embodiment, wherein $R^1$ is selected from the group consisting of unsubstituted phenyl; phenyl substituted with one E, which E is selected from the group consisting of —CN, —$CF_3$, and $SO_2CH_3$.

In another Embodiment (31.4), the invention provides a compound of Formula (II), or a pharmaceutically acceptable salt thereof, according to any preceding Embodiment, wherein $R^1$ is selected from the group consisting of unsubstituted thiophenyl; N-methyl-pyrazolyl; and pyridinyl, which pyridinyl is substituted with one E, which E is —$CF_3$.

In another Embodiment (32), the invention provides a compound of Formula (II), or a pharmaceutically acceptable salt thereof, according to any preceding Embodiment, wherein $R^2$ is selected from the group consisting of phenyl, pyrazinyl, pyrimidinyl, pyridinyl and pyridazinyl, which $R^2$ is optionally substituted with one, two, three or four E, which E is independently selected for each occurrence from the group consisting of —H; —F; —Cl; —CN; —OH; —$CO_2H$; —$CH_3$; —$CF_3$; —$CH_2CO_2H$; —$OCH_3$; —$OCF_3$; N-methyl piperidinyl; —$NH_2$; —C(O)$NH_2$; and —$SO_2CH_3$.

In another Embodiment (32.1), the invention provides a compound of Formula (II), or a pharmaceutically acceptable salt thereof, according to any preceding Embodiment, wherein $R^2$ is selected from the group consisting of phenyl, pyrazinyl, pyrimidinyl, pyridinyl and pyridazinyl, which $R^2$ is optionally substituted with one, two, three or four E, which E is independently selected for each occurrence from the group consisting of —H; —F; —Cl; —CN; —OH; —$CO_2H$; —$CH_3$; —$CF_3$; —$OCH_3$; —$OCF_3$; —N-methyl piperidinyl; —$NH_2$; and —C(O)$NH_2$.

In another Embodiment (32.2), the invention provides a compound of Formula (II), or a pharmaceutically acceptable salt thereof, according to any preceding Embodiment, wherein $R^2$ is selected from the group consisting of unsubstituted phenyl; phenyl substituted with one E, which E is selected from the group consisting of —F, —Cl, —CN, —$CO_2H$, —$OCH_3$, —$OCF_3$, —N-methyl piperidinyl, and —C(O)$NH_2$; and phenyl substituted with two E, which E is, independently for each occurrence, selected from the group consisting of —F and —Cl.

In another Embodiment (32.3), the invention provides a compound of Formula (I), or a pharmaceutically acceptable salt thereof, according to any preceding Embodiment wherein $R^2$ is selected from the group consisting of unsubstituted pyrazinyl; pyrazinyl substituted with one E, which E is selected from the group consisting of —CN and —$NH_2$; unsubstituted pyrimidinyl; pyrimidinyl substituted with one E, which E is selected from the group consisting of —CN; unsubstituted pyridinyl; pyridinyl substituted with one E, which E is selected from the group consisting of —CN, —OH, —$CH_3$, —$CF_3$, —$NH_2$, and —C(O)$NH_2$; and unsubstituted pyridazinyl.

In another Embodiment (32.4), the invention provides a compound of Formula (I), or a pharmaceutically acceptable salt thereof, according to any preceding Embodiment, wherein $R^2$ is unsubstituted pyrimidinyl.

In another Embodiment (32.5), the invention provides a compound of Formula (II), or a pharmaceutically acceptable salt thereof, according to any preceding Embodiment, wherein $R^2$ is cyclohexyl which cyclohexyl substituted with one E, which E is selected from the group consisting of —H; —F; —Cl; —CN; —OH; —$CO_2H$; —$CH_3$; —$CF_3$; —$CH_2CO_2H$; —$OCH_3$; —$OCF_3$; N-methyl piperidinyl; —$NH_2$; —C(O)$NH_2$; and —$SO_2CH_3$.

In another Embodiment (32.6), the invention provides a compound of Formula (II), or a pharmaceutically acceptable salt thereof, according to any preceding Embodiment, wherein $R^2$ is cyclohexyl which cyclohexyl substituted with one E which E is —OH.

In another Embodiment (33), the invention provides a compound of Formula (I), or a pharmaceutically acceptable salt thereof, according to any preceding Embodiment, wherein J is, independently for each occurrence, selected from the group consisting of —H and —$C_1$-$C_6$alkyl, for example —$CH_3$.

In another Embodiment (34), the invention provides a compound of Formula (I), or a pharmaceutically acceptable salt thereof, according to any preceding Embodiment, wherein K is, independently for each occurrence, selected from the group consisting of —H, —F, —Cl, —OH, —CN, —$CH_3$, —$CH_2F$, —$CHF_2$, —$CF_3$, —$OCH_3$, —$OCH_2F$, —$OCHF_2$, —$OCF_3$, —$NH_2$, —$NH(CH_3)$, and —$N(CH_3)_2$.

The present invention also relates to a pharmaceutical composition comprising a compound of Formula (II), or a pharmaceutically acceptable salt thereof, and a pharmaceutically acceptable excipient.

The present invention also relates to a method of treating a disease or a disorder in a patient, comprising administering to a patient in need thereof a therapeutically effective amount of a compound of Formula (II), or a pharmaceutically acceptable salt thereof or a pharmaceutical composition comprising a therapeutically effective amount of a compound of Formula (II), or a pharmaceutically acceptable salt thereof.

In another embodiment, the present invention further provides a method of inhibiting vanin-1 enzyme in a cell, comprising contacting the cell with a therapeutically effective amount of a compound of Formula (II), or a pharmaceutically acceptable salt thereof, or a pharmaceutical composition comprising a therapeutically effective amount of a compound of Formula (II), or a pharmaceutically acceptable salt thereof.

In another embodiment, the present invention further provides a method of inhibiting vanin-1 enzyme, comprising contacting the enzyme with a therapeutically effective amount of a compound of Formula (II), or a pharmaceutically acceptable salt thereof, or a pharmaceutical composition comprising a therapeutically effective amount of a compound of Formula (II), or a pharmaceutically acceptable salt thereof.

In another embodiment, the present invention relates to a method of treating a disease or disorder mediated by, or otherwise associated with, inhibition of the vanin-1 enzyme, comprising administering to a patient in need thereof a therapeutically effective amount of a compound of Formula (II), or a pharmaceutically acceptable salt thereof, or a pharmaceutical composition comprising a therapeutically effective amount of a compound of Formula (II), or a pharmaceutically acceptable salt thereof.

This invention also relates to a compound of Formula III, Embodiment (50):

Formula III

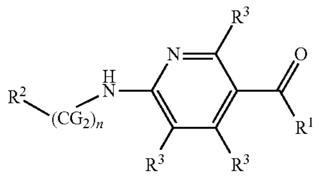

or a pharmaceutically acceptable salt thereof, wherein $R^1$ is selected from the group consisting of:

(i) 6 to 10 membered aryl optionally substituted with one, two, three or four E; and (ii) 5 to 6 membered heteroaryl optionally substituted with one, two, three or four E, wherein said 5 to 6 membered heteroaryl (a) comprises one, two or three heteroatoms independently selected for each occurrence from the group consisting of —N═, —N(J)-, —O—, and —S— and (b) is not bound to the carbonyl of Formula (I) through a nitrogen;

$R^2$ is selected from the group consisting of:

(i) 4 to 7 membered heterocyclyl optionally substituted with one, two, three, four, five or six E, wherein said 4 to 7 membered heterocyclyl comprises one or two heteroatoms independently selected for each occurrence from the group consisting of —N(J)-, —O— and —S—; and (ii) 4 to 7 membered heterocyclyl optionally substituted with one, two, three, four, five or six E, wherein said 4 to 7 membered heterocyclyl is (i) bound to —NH—$(CG_2)_n$- through a first heterocyclyl ring heteroatom —N— and (ii) which optionally comprises a second ring heteroatom independently selected from the group consisting of —N(J)-, —O—, and —S—;

n is selected from the group consisting of 1 and 2;

$R^3$ is independently selected for each occurrence from the group consisting of —H, —F, —Cl, —CN, —$CH_3$, —$CH_2CH_3$, —$CH_2F$, —$CHF_2$, —$CF_3$, —$CF_2CF_3$, —$OCH_3$, —$OCH_2F$, —$OCHF_2$, —$OCF_3$, —$SCH_3$, —$SCH_2F$, —$SCHF_2$, and —$SCF_3$;

E is independently selected for each occurrence from the group consisting of:

(i) —H;

(ii) —halo;

(iii) —CN;

(iv) —OH;

(v) —$CO_2H$;

(vi) —$C_1$-$C_6$alkyl optionally substituted with one, two, three, four, five or six K;

(vii) —O$C_1$-$C_6$alkyl optionally substituted with one, two, three, four, five or six K;

(viii) —S$C_1$-$C_6$alkyl optionally substituted with one, two, three, four, five or six K;

(ix) —$C_3$-$C_5$cycloalkyl optionally substituted with one, two, three, four, five or six K;

(x) —O$C_3$-$C_5$cycloalkyl optionally substituted with one, two, three, four, five or six K;

(xi) —S$C_3$-$C_5$cycloalkyl optionally substituted with one, two, three, four, five or six K;

(xii) —$C_1$-$C_6$alkyl($C_3$-$C_5$cycloalkyl) optionally substituted with one, two, three, four, five or six K;

(xiii) 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—;

(xiv) —$NH_2$;

(xv) —NH($C_1$-$C_6$alkyl), which $C_1$-$C_6$alkyl is optionally substituted with one, two, three, four, five or six K;

(xvi) —N($C_1$-$C_6$alkyl)$_2$, which $C_1$-$C_6$alkyl is, independently for each occurrence, optionally substituted with one, two, three, four, five or six K;

(xvii) —C(O)$NH_2$;

(xviii) —C(O)NH($C_1$-$C_6$alkyl), which $C_1$-$C_6$alkyl is optionally substituted with one, two, three, four, five or six K;

(xix) —C(O)N($C_1$-$C_6$alkyl)$_2$, which $C_1$-$C_6$alkyl is, independently for each occurrence, optionally substituted with one, two, three, four, five or six K;

(xx) —NHC(O)($C_1$-$C_6$alkyl), which $C_1$-$C_6$alkyl is optionally substituted with one, two, three, four, five or six K;

(xxi) —N($C_1$-$C_6$alkyl)C(O)($C_1$-$C_6$alkyl), which $C_1$-$C_6$alkyl is, independently for each occurrence, optionally substituted with one, two, three, four, five or six K;

(xxii) —$SO_2$($C_1$-$C_6$alkyl), which $C_1$-$C_6$alkyl is optionally substituted with one, two, three, four, five or six K;

(xxiii) —$SO_2NH_2$;

(xxiv) —$SO_2$NH($C_1$-$C_6$alkyl), which $C_1$-$C_6$alkyl is optionally substituted with one, two, three, four, five or six K;

(xxv) —$SO_2$N($C_1$-$C_6$alkyl)$_2$, which $C_1$-$C_6$alkyl is, independently for each occurrence optionally substituted with one, two, three, four, five or six K;

(xxvi) —NH$SO_2$($C_1$-$C_6$alkyl), which $C_1$-$C_6$alkyl is optionally substituted with one, two, three, four, five or six K; and (xxvii) —N($C_1$-$C_6$alkyl)$SO_2$($C_1$-$C_6$alkyl), which $C_1$-$C_6$alkyl is, independently for each occurrence, optionally substituted with one, two, three, four, five or six K;

G is independently selected for each occurrence from the group consisting of:

(i) —H;

(ii) —halo;

(iii) —OH;

(iv) —$C_1$-$C_6$alkyl optionally substituted optionally substituted with one, two, three, four, five or six K;

(v) —O$C_1$-$C_6$alkyl optionally substituted with one, two, three, four, five or six K;

(vi) —S$C_1$-$C_6$alkyl optionally substituted with one, two, three, four, five or six K;

(vii) —NH($C_1$-$C_6$alkyl), which $C_1$-$C_6$alkyl is optionally substituted with one, two, three, four, five or six K;

(viii) —N($C_1$-$C_6$alkyl)$_2$, which $C_1$-$C_6$alkyl is, independently for each occurrence, optionally substituted with one, two, three, four, five or six K;

(ix) —$C_3$-$C_5$cycloalkyl optionally substituted with one, two, three, four, five or six K; and (x) 4 to 5 membered heterocyclyl optionally substituted with one, two, three, four, five or six K, which said 4 to 5 membered heterocyclyl comprises one or two heteroatoms independently selected for each occurrence from the group consisting of —N(J)-, —O— or —S—;

or two geminal G may, together with the carbon to which they are bound, form a —$C_3$-$C_5$cycloalkylene optionally substituted with one, two, three, four, five or six K or a 4 to 5 membered heterocyclylene optionally substituted with one, two, three, four, five or six K, wherein said 4 to 5 membered heterocyclylene comprises one heteroatom independently selected from the group consisting of —N(J)-, —O—, or —S—;

J is independently selected, for each occurrence, from the group consisting of:

(i) —H;

(ii) —$C_1$-$C_6$alkyl optionally substituted with one, two, three, four, five or six K;

(iii) —C(O)$NH_2$;

(iv) —C(O)NH($C_1$-$C_6$alkyl), which $C_1$-$C_6$alkyl is optionally substituted with one, two, three, four, five or six K;

(v) —C(O)N($C_1$-$C_6$alkyl)$_2$, which $C_1$-$C_6$alkyl is, independently for each occurrence, optionally substituted with one, two, three, four, five or six K; and (vi) —$SO_2$($C_1$-$C_6$alkyl), which $C_1$-$C_6$alkyl is optionally substituted with one, two, three, four, five or six halo; and K is independently selected, for each occurrence, from the group consisting of —H, —F, —Cl, —OH, —CN, —$CO_2$H, —$CH_3$, —$CH_2CH_3$, —$CH_2F$, —$CHF_2$, —$CF_3$, —$CF_2CF_3$, —$OCH_3$, —$OCH_2F$, —$OCHF_2$, —$OCF_3$, —$SCH_3$, —$SCH_2F$, —$SCHF_2$, —$SCF_3$—$NH_2$, —NH($CH_3$), —N($CH_3$)$_2$, and —$CONH_2$.

In another Embodiment (51), the invention provides a compound of Formula (III), or a pharmaceutically acceptable salt thereof, according to any preceding Embodiment, wherein $R^3$ is —H, —F, —$CH_3$, —$CH_2F$, —$CHF_2$, —$CF_3$, —$OCH_3$, —$OCH_2F$, —$OCHF_2$, and —$OCF_3$.

In another Embodiment (51.1), the invention provides a compound of Formula (III), or a pharmaceutically acceptable salt thereof, according to any preceding Embodiment, wherein $R^3$ is —H.

In another Embodiment (52), the invention provides a compound of Formula (III), or a pharmaceutically acceptable salt thereof, according to any preceding Embodiment, wherein $R^1$ is a 6 to 10 membered aryl, for example phenyl, which $R^1$ is optionally substituted as defined for a compound of Formula (III).

In another Embodiment (52.1), the invention provides a compound of Formula (III), or a pharmaceutically acceptable salt thereof, according to any preceding Embodiment, wherein $R^1$ is phenyl, which phenyl is optionally substituted as defined for a compound of Formula (III).

In another Embodiment (53), the invention provides a compound of Formula (III), or a pharmaceutically acceptable salt thereof, according to any preceding Embodiment, wherein $R^1$ is a 5 to 6 membered heteroaryl, wherein said 5 to 6 membered heteroaryl (a) comprises one, two or three heteroatoms independently selected for each occurrence from the group consisting of —N═, —N(J)-, —O—, and —S— and (b) is not bound to the carbonyl of Formula (III) through a nitrogen, for example thiophenyl, pyrazolyl, pyridinyl, or N-methyl-pyrazolyl, which $R^1$ is optionally substituted as defined for a compound of Formula (III).

In another Embodiment (53.1), the invention provides a compound of Formula (III), or a pharmaceutically acceptable salt thereof, according to any preceding Embodiment, wherein $R^1$ is selected from the group consisting of thiophenyl, pyrazolyl, pyridinyl, and N-methyl-pyrazolyl, which $R^1$ is optionally substituted as defined for a compound of Formula (II), and, when $R^1$ is pyrazolyl, or pyridinyl, said pyrazolyl, or pyridinyl is not bound to the carbonyl of Formula (II) through a nitrogen.

In another Embodiment (54), the invention provides a compound of Formula (III), or a pharmaceutically acceptable salt thereof, according to any preceding Embodiment, wherein n is 1.

In another Embodiment (55), the invention provides a compound of Formula (III), or a pharmaceutically acceptable salt thereof, according to any preceding Embodiment, wherein n is 2.

In another Embodiment (56), the invention provides a compound of Formula (III), or a pharmaceutically acceptable salt thereof, according to any preceding Embodiment, wherein G is independently selected for each occurrence from the group consisting of —H; —$C_1$-$C_6$alkyl, for example methyl; —O$C_1$-$C_6$alkyl; —$C_3$-$C_5$cycloalkyl; or two geminal G may, together with the carbon to which they are bound, form a —$C_3$-$C_5$cycloalkylene, for example cyclopropylene or cyclobutylene, which G is optionally substituted as defined for a compound of Formula (III).

In another Embodiment (56.1), the invention provides a compound of Formula (III), or a pharmaceutically acceptable salt thereof, according to any preceding Embodiment, wherein G is independently selected for each occurrence from the group consisting of —H; —$C_1$-$C_6$alkyl, for example methyl; or two geminal G may, together with the carbon to which they are bound, form a —$C_3$-$C_5$cycloalkylene, for example cyclopropylene or cyclobutylene, which G is optionally substituted as defined for a compound of Formula (III).

In another Embodiment (57), the invention provides a compound of Formula (III), or a pharmaceutically acceptable salt thereof, according to any preceding Embodiment, wherein n is 1 and wherein G is independently selected for each occurrence from the group consisting of —H; —$C_1$-$C_6$alkyl, for example methyl, which —$C_1$-$C_6$alkyl, is optionally substituted as defined for a compound Formula (III); or two geminal G may be taken together with the carbon to which they are bound to form a —$C_3$-$C_5$cycloalkylene, for example cyclopropylene or cyclobutylene, which —$C_3$-$C_5$cycloalkylene is optionally substituted as defined for a compound of Formula (III).

In another Embodiment (57.1), the invention provides a compound of Formula (III), or a pharmaceutically acceptable salt thereof, according to any preceding Embodiment, wherein n is 1 and wherein G is independently selected for each occurrence from the group consisting of —H; —$CH_3$; and where two geminal G may be taken together with the carbon to which they are bound to form cyclopropylene or cyclobutylene, to form, for example —NH$CH_2$—$R^2$; —NHC($CH_3$)H—$R^2$; —NHC($CH_3$)$_2$—$R^2$;

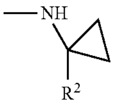
; and
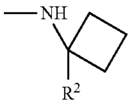
.

In another Embodiment (58), the invention provides a compound of Formula (III), or a pharmaceutically acceptable salt thereof, according to any preceding Embodiment, wherein $R^2$ is 4 to 7 membered heterocyclyl wherein said 4 to 7 membered heterocyclyl comprises one or two heteroatoms independently selected for each occurrence from the group consisting of —N(J)-, —O— and —S—, for example azetidinyl; oxetanyl; thietanyl; pyrrolidinyl; tetrahydrofuranyl; tetrahydrothiophenyl; pyrazolidinyl; imidazolidinyl; dioxolanyl; thiazolidinyl; isoxazolidinyl; tetrahydropyranyl;

piperidinyl; piperazinyl; morpholinyl; dioxanyl or thiomorpholinyl; wherein when $R^2$ is a heterocycylyl which comprises a heteroatom —N(J)-, J is defined as in Formula (III); and which $R^2$ is optionally substituted as defined in Formula (III).

In another Embodiment (58.1), the invention provides a compound of Formula (III), or a pharmaceutically acceptable salt thereof, according to any preceding Embodiment, wherein $R^2$ is selected from the group consisting of azetidinyl; oxetanyl; thietanyl; pyrrolidinyl; tetrahydrofuranyl; tetrahydrothiophenyl; pyrazolidinyl; imidazolidinyl; dioxolanyl; thiazolidinyl; isoxazolidinyl; tetrahydropyranyl; piperidinyl; piperazinyl; morpholinyl; dioxanyl and thiomorpholinyl; wherein when $R^2$ is a heterocycylyl which comprises a heteroatom —N(J)-, J is defined as in Formula (III); and which $R^2$ is optionally substituted as defined in Formula (III).

In another Embodiment (58.2), the invention provides a compound of Formula (III), or a pharmaceutically acceptable salt thereof, according to any preceding Embodiment, wherein $R^2$ is selected from the group consisting of pyrrolidinyl; tetrahydropyranyl; and piperidinyl, which pyrrolidingyl and piperidinyl are substituted on the ring nitrogen with J as defined in Formula (III), and which $R^2$ is optionally substituted as defined in Formula (III).

In another Embodiment (58.3), the invention provides a compound of Formula (III), or a pharmaceutically acceptable salt thereof, according to any preceding Embodiment, wherein $R^2$ is selected from the group consisting of pyrrolidinyl, tetrahydropyranyl, and piperidinyl; which pyrrolidinyl; and piperidinyl are substituted on the ring N with J, which J is —$C_1$-$C_6$alkyl, for example —$CH_3$, or —$CH_2CH_3$, to form, for example N-methyl piperidinyl or N-ethyl pyrrolidinyl; and which $R^2$ is further substituted with E as defined in Formula (III).

In another Embodiment (58.4), the invention provides a compound of Formula (III), or a pharmaceutically acceptable salt thereof, according to any preceding Embodiment, wherein $R^2$ is selected from the group consisting of N-methyl piperidinyl; N-ethyl pyrrolidinyl; and tetrahydropyranyl; which $R^2$ is further substituted with E as defined in Formula (III).

In another Embodiment (59), the invention provides a compound of Formula (III), or a pharmaceutically acceptable salt thereof, according to any preceding Embodiment, wherein $R^2$ is a 4 to 7 membered heterocyclyl wherein said 4 to 7 membered heterocyclyl is (i) bound to —NH—$(CG_2)_n$- through a first heterocyclyl ring heteroatom —N— and (ii) which optionally comprises a second ring heteroatom independently selected from the group consisting of —N(J)-, —O—, and —S—, for example azetidinyl; pyrrolidinyl; pyrazolidinyl; imidazoliidinyl; thiazolidinyl; piperidinyl; piperazinyl; mopholidinyl or thiomorpholidinyl, and wherein when $R^2$ is heterocyclyl which comprises a second ring heteroatom —N(J)-, J is defined as in Formula (III); and which $R^2$ is optionally substituted as defined in Formula (III).

In another Embodiment (60), the invention provides a compound of Formula (III), or a pharmaceutically acceptable salt thereof, according to any preceding Embodiment, wherein E is selected, independently for each occurrence, from the group consisting of —H; -halo, for example —F or —Cl; —CN; —OH; —$CO_2H$; —$C_1$-$C_6$alkyl, for example —$CH_3$, which —$C_1$-$C_6$alkyl is optionally substituted with one, two, three, four, five or six K to form, for example, —$CF_3$, or —$CH_2CO_2H$; —$OC_1$-$C_6$alkyl, for example —$OCH_3$, which —$OC_1$-$C_6$alkyl is optionally substituted with one, two, three, four, five or six K to form, for example, —$OCF_3$; 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—, for example N-methyl piperidinyl; —$NH_2$; —NH($C_1$-$C_6$alkyl), which $C_1$-$C_6$alkyl is optionally substituted with one, two, three, four, five or six K; —N($C_1$-$C_6$alkyl)$_2$, which $C_1$-$C_6$alkyl is, independently for each occurrence, optionally substituted with one, two, three, four, five or six K; —C(O)$NH_2$; —C(O)NH($C_1$-$C_6$alkyl), which $C_1$-$C_6$alkyl is optionally substituted with one, two, three, four, five or six K; —C(O)N($C_1$-$C_6$alkyl)$_2$, which $C_1$-$C_6$alkyl is, independently for each occurrence, optionally substituted with one, two, three, four, five or six K; and —$SO_2$($C_1$-$C_6$alkyl), which $C_1$-$C_6$alkyl is optionally substituted with one, two, three, four, five or six K, for example —$SO_2CH_3$.

In another Embodiment (60.1), the invention provides a compound of Formula (III), or a pharmaceutically acceptable salt thereof, according to any preceding Embodiment, wherein E is selected, independently for each occurrence, from the group consisting of —H; -halo, for example —F or —Cl; —CN; —OH; —$CO_2H$; —$C_1$-$C_6$alkyl, for example —$CH_3$, which —$C_1$-$C_6$alkyl is optionally substituted with one, two, three, four, five or six K to form, for example, —$CF_3$ or —$CH_2CO_2H$; —$OC_1$-$C_6$alkyl, for example —$OCH_3$, which —$OC_1$-$C_6$alkyl is optionally substituted with one, two, three, four, five or six K to form, for example, —$OCF_3$; 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—, for example N-methyl piperidinyl; —$NH_2$; —C(O)$NH_2$; and —$SO_2$($C_1$-$C_6$alkyl), which $C_1$-$C_6$alkyl is optionally substituted with one, two, three, four, five or six K, for example —$SO_2CH_3$.

In another Embodiment (60.2), the invention provides a compound of Formula (III), or a pharmaceutically acceptable salt thereof, according to any preceding Embodiment, wherein E is selected, independently for each occurrence, from the group consisting of —H; —F; —Cl; —CN; —OH; —$CO_2H$; —$CH_3$; —$CF_3$; —$CH_2CO_2H$; —$OCH_3$; —$OCF_3$; N-methyl piperidinyl; —$NH_2$; —C(O)$NH_2$; and —$SO_2CH_3$.

In another Embodiment (61), the invention provides a compound of Formula (III), or a pharmaceutically acceptable salt thereof, according to any preceding Embodiment, wherein $R^1$ is selected from the group consisting of phenyl, thiophenyl, pyrazolyl, pyridinyl, and N-methyl-pyrazolyl, which $R^1$ is optionally substituted with one, two, three or four E, which E is independently selected for each occurrence from the group consisting of —H; —F; —Cl; —CN; —OH; —$CO_2H$; —$CH_3$; —$CF_3$; —$CH_2CO_2H$; —$OCH_3$; —$OCF_3$; N-methyl piperidinyl; —$NH_2$; —C(O)$NH_2$; and —$SO_2CH_3$.

In another Embodiment (61.1), the invention provides a compound of Formula (III), or a pharmaceutically acceptable salt thereof, according to any preceding Embodiment, wherein $R^1$ is selected from the group consisting of phenyl, thiophenyl, pyrazolyl, pyridinyl, and N-methyl-pyrazolyl, which $R^1$ is optionally substituted with one, two, three or four E, which E are independently selected for each occurrence from the group consisting of —H; —F; —Cl; —CN; —$CO_2H$; —$CH_3$; —$CF_3$; —$CH_2CO_2H$; —$OCH_3$; —C(O)$NH_2$; and —$SO_2CH_3$.

In another Embodiment (61.2), the invention provides a compound of Formula (III), or a pharmaceutically acceptable salt thereof, according to any preceding Embodiment, wherein $R^1$ is selected from the group consisting of unsubstituted phenyl; phenyl substituted with one E, which E is selected from the group consisting of —F, —Cl, CN, —$CO_2H$, $CH_3$, —$CF_3$, —$CH_2CO_2H$, —$OCH_3$, —C(O)$NH_2$, and $SO_2CH_3$; and phenyl substituted with two E, which E is selected independently for each occurrence from the group consisting of —F, —Cl, —CN, —$CH_3$, —$CF_3$ and —$OCH_3$.

In another Embodiment (61.3), the invention provides a compound of Formula (III), or a pharmaceutically acceptable salt thereof, according to any preceding Embodiment, wherein $R^1$ is selected from the group consisting of unsubstituted thiophenyl; N-methyl-pyrazolyl; and pyridinyl, which pyridinyl is substituted with one E, which E is —$CF_3$.

In another Embodiment (62), the invention provides a compound of Formula (III), or a pharmaceutically acceptable salt thereof, according to any preceding Embodiment, wherein $R^2$ is selected from the group consisting of N-methyl piperidinyl; N-ethyl pyrrolidinyl; and tetrahydropyranyl; which $R^2$ is optionally substituted with one E, which E is selected from the group consisting of —H; —F; —Cl; —CN; —OH; —$CO_2H$; —$CH_3$; —$CF_3$; —$CH_2CO_2H$; —$OCH_3$; —$OCF_3$; N-methyl piperidinyl; —$NH_2$; —C(O)$NH_2$; and —$SO_2CH_3$.

In another Embodiment (62.1), the invention provides a compound of Formula (III), or a pharmaceutically acceptable salt thereof, according to any preceding Embodiment, wherein $R^2$ is selected from the group consisting of N-methyl piperidinyl; N-ethyl pyrrolidinyl; and tetrahydropyranyl.

In another Embodiment (63), the invention provides a compound of Formula (III), or a pharmaceutically acceptable salt thereof, according to any preceding Embodiment, wherein J is, independently for each occurrence, selected from the group consisting of —H and —$C_1$-$C_6$alkyl, for example —$CH_3$.

In another Embodiment (64), the invention provides a compound of Formula (III), or a pharmaceutically acceptable salt thereof, according to any preceding Embodiment, wherein K is, independently for each occurrence, selected from the group consisting of —H, —F, —Cl, —OH, —CN, —$CH_3$, —$CH_2F$, —$CHF_2$, —$CF_3$, —$OCH_3$, —$OCH_2F$, —$OCHF_2$, —$OCF_3$, —$NH_2$, —NH($CH_3$), and —N$(CH_3)_2$.

The present invention also relates to a pharmaceutical composition comprising a compound of Formula (III), or a pharmaceutically acceptable salt thereof, and a pharmaceutically acceptable excipient.

The present invention also relates to a method of treating a disease or a disorder in a patient, comprising administering to a patient in need thereof a therapeutically effective amount of a compound of Formula (III), or a pharmaceutically acceptable salt thereof or a pharmaceutical composition comprising a therapeutically effective amount of a compound of Formula (III), or a pharmaceutically acceptable salt thereof.

In another embodiment, the present invention further provides a method of inhibiting vanin-1 enzyme in a cell, comprising contacting the cell with a therapeutically effective amount of a compound of Formula (III), or a pharmaceutically acceptable salt thereof, or a pharmaceutical composition comprising a therapeutically effective amount of a compound of Formula (III), or a pharmaceutically acceptable salt thereof.

In another embodiment, the present invention further provides a method of inhibiting vanin-1 enzyme, comprising contacting the enzyme with a therapeutically effective amount of a compound of Formula (III), or a pharmaceutically acceptable salt thereof, or a pharmaceutical composition comprising a therapeutically effective amount of a compound of Formula (III), or a pharmaceutically acceptable salt thereof.

In another embodiment, the present invention relates to a method of treating a disease or disorder treating mediated by, or otherwise associated with, inhibition of the vanin-1 enzyme, comprising administering to a patient in need thereof a therapeutically effective amount of a compound of Formula (III), or a pharmaceutically acceptable salt thereof, or a pharmaceutical composition comprising a therapeutically effective amount of a compound of Formula (III), or a pharmaceutically acceptable salt thereof.

DETAILED DESCRIPTION

Figure 1:
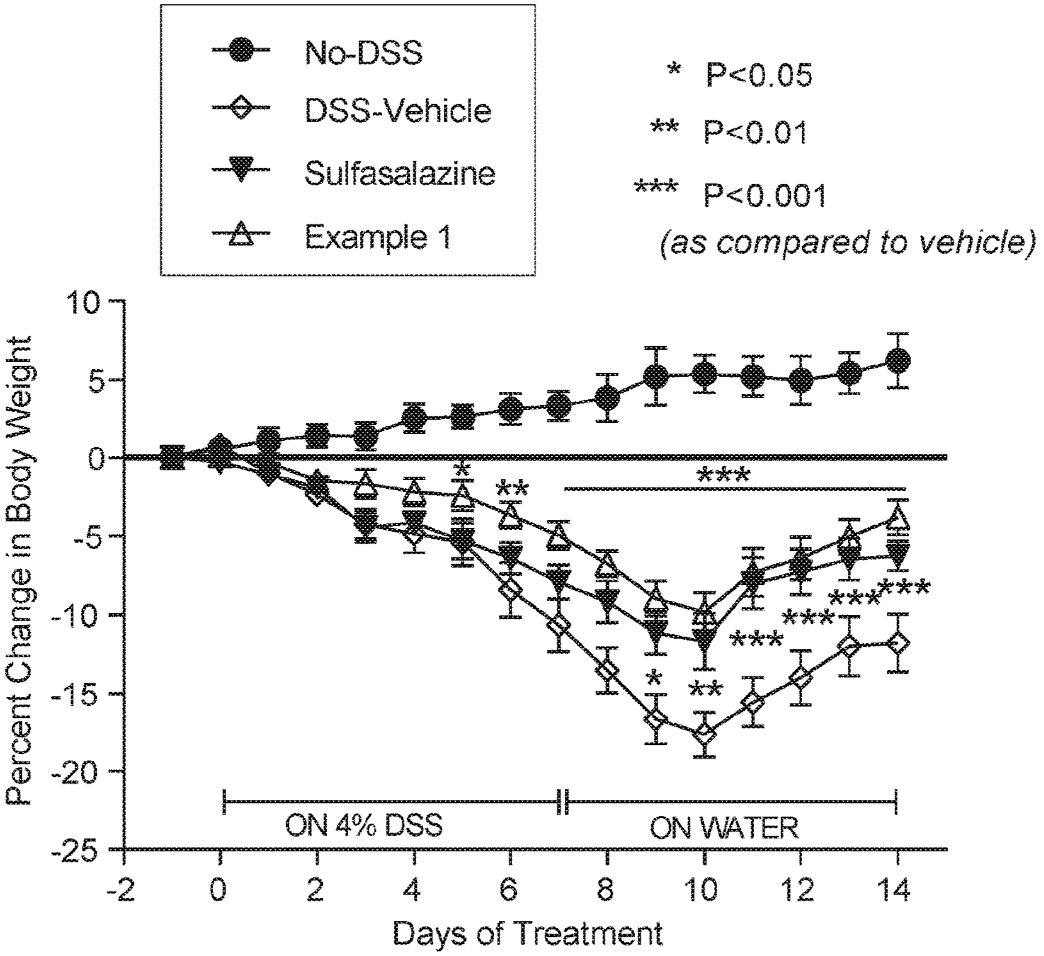
FIG. 1 shows the percentage change in body weight of the mice in the induced colitis mouse model of Inflammatory Bowel Disease following exposure to 4% dextran sulfate sodium, including results obtained with the test compound.

The present invention relates to novel heterocyclic compounds of the invention which, in general, inhibit vanin-1 enzyme.

Compounds reported as having vanin activity include those disclosed in WO 2014/048547, published on 3 Apr. 2014.

Compounds reported as having vanin activity are earlier disclosed in U.S. provisional application 62/167,962, which application was filed on 29 May 2015 and which is incorporated herein by reference in its entirety.

Throughout this application, it should be noted that, as used in this specification and the appended claims, the singular form “a”, “an” and “the” include plural references unless the context clearly dictates otherwise. Thus, for example, reference to “a compound” includes a plurality of compounds.

Unless defined otherwise, all technical and scientific terms used herein have the same meaning as commonly understood by one of ordinary skill in the art to which this invention is related. The following terms are defined for purposes of the invention as described herein.

As used herein, unless otherwise noted, “alkyl” whether used alone or as part of a substituent group refers to a saturated straight or branched hydrocarbon chain (ie a substituent obtained from a hydrocarbon by removal of a hydrogen) having from one to twenty carbon atoms or any number within this range, for example, from one to six carbon atoms, from one to four carbon atoms or from one to three carbon atoms. Designated numbers of carbon atoms (e.g. $C_{1-6}$) shall refer independently to the number of carbon atoms in an alkyl moiety or to the alkyl portion of a larger alkyl-containing substituent. Examples of alkyl groups include, but are not limited to, methyl, ethyl, n-propyl, iso-propyl, n-butyl, sec-butyl, iso-butyl, tert-butyl, pentyl, isoamyl, hexyl and the like. Where so indicated, alkyl groups can be optionally substituted. In substituent groups with multiple alkyl groups such as $N(C_1\text{-}C_6alkyl)_2$, the alkyl groups may be the same or different.

As used herein, unless otherwise noted, "alkoxy" refers to groups of formula —Oalkyl, wherein "alkyl" is as defined herein. Designated numbers of carbon atoms (e.g. $—OC_1—C_6$) shall refer independently to the number of carbon atoms in the alkyl moiety of the alkoxy group, for example, but not limited to, from one to six carbon atoms or from one to three carbon atoms. Examples of alkoxy groups include, but are not limited to, methoxy, ethoxy, n-propoxy, iso-propoxy, n-butoxy, sec-butoxy, iso-butoxy, tert-butoxy, and the like. Where so indicated, alkoxy groups can be optionally substituted.

As used herein, unless otherwise noted, "aryl" whether used alone or part of another group refers to a carbocyclic fully unsaturated or partially unsaturated single or fused ring system. If the rings are fused, one of the rings must be fully unsaturated or partially unsaturated and the fused ring(s) may be fully saturated, partially unsaturated or fully unsaturated. The aryl group may be optionally substituted as defined herein. The term "aryl" embraces aromatic radicals such as phenyl, naphthyl, tetrahydronaphthyl, indanyl, biphenyl, benzo[b][1,4]oxazin-3(4H)-onyl, 2,3-dihydro-1H indenyl and 1,2,3,4-tetrahydronaphthalenyl.

As used herein, unless otherwise noted, "cycloalkyl" whether used alone or as part of another group, refers to a fully saturated hydrocarbon ring having from three to fourteen ring carbon atoms, for example, from four to seven; or from three to seven; or from three to six; or from three to five ring carbon atoms. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Where so indicated, cycloalkyl rings can be optionally substituted. Examples of cycloalkyl groups include, but are not limited to, cyclopropyl, cyclobutyl, cyclopentyl, cyclohexyl, cycloheptyl, cyclooctanyl, decalinyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, unless otherwise noted, the terms "haloalkyl" and "haloalkoxy" are intended to include both branched and straight-chain saturated aliphatic "alkyl" or "alkoxy" groups respectively, wherein "alkyl" and "alkoxy" are as defined herein, having the specified number of carbon atoms and in which at least one hydrogen is replaced with a halogen atom. As used herein, the term "halogen atom" refers to F, Cl, Br and I. Haloalkyl groups include perhaloalkyl groups, wherein all hydrogens of an alkyl group have been replaced with halogens (e.g., $—CF_3$, $—CF_2CF_3$). In certain embodiments in which two or more hydrogen atoms are replaced by halogen atoms, the halogen atoms can be the same (e.g., $CHF_2$, $—CF_3$) or different (e.g., $CF_2Cl$). Where so indicated, haloalkyl or haloalkoxy groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

As used herein, unless otherwise noted, the terms "heterocyclyl" and "heterocycloalkyl" are used interchangeably and, whether used alone or as part of another group, are defined herein as referring to a group having one or more rings (e.g., 1, 2 or 3 rings) and having from 3 to 11 ring atoms (e.g. 3 to 6 ring atoms, 4 to 7 ring atoms, 4 to 5 ring atoms) wherein at least one ring atom, alternatively 1 to 5 ring atoms, alternatively 1 to 4 ring atoms, alternatively 1 to 3 ring atoms, alternatively one ring atom, alternatively two ring atoms, is a heteroatom, independently selected, unless indicated otherwise, from the group consisting of nitrogen (N), oxygen (O), and sulfur (S), and wherein the ring that includes the heteroatom is fully saturated. Exemplary heterocyclyl groups have from 3 to 11 ring atoms, alternatively 4 to 7 ring atoms, alternatively 4 to 5 ring atoms, alternatively 3 to 6 ring atoms, of which, where chemically possible, from 1 to 5, alternatively 1 to 4, alternatively 1 to 3, alternatively 4, alternatively 3, alternatively 2, alternatively 1 ring atom, is a heteroatoms independently selected in each instance from, unless indicated otherwise, the group consisting of nitrogen (N), oxygen (O), or sulfur (S). In a group that has a heterocyclyl substituent, unless otherwise stated, the ring atom of the heterocyclyl substituent that is bound to the group may be one of the heteroatoms, or it may be a ring carbon atom, where the ring carbon atom may be in the same ring as the heteroatom(s), or the ring carbon may be in a different ring from the heteroatom(s). Where so indicated, the heterocyclyl substituent can be optionally further substituted with one or more group(s) or substituent(s), which group(s) or substituent(s) may be bound to the heteroatom(s) or may be bound to the ring carbon atom, where the ring carbon atom may be in the same ring as the at least one heteroatom or where the ring carbon atom may be in a different ring from the heteroatom(s). Examples of monocyclic heterocyclyl groups include, but are not limited to, oxetanyl, diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline.

As used herein, unless otherwise noted, the term "heteroaryl" whether used alone or as part of another group, is defined herein as a single or fused ring system having from five to eleven ring atoms (e.g. from five to ten ring atoms of from five to six ring atoms) wherein at least one ring atom, alternatively 2 ring atoms, alternatively 3 ring atoms, alternatively 4 ring atoms, in at least one ring is a heteroatom independently selected in each instance from, unless otherwise indicated, the group consisting of nitrogen (N), oxygen (O), and sulfur (S), and wherein further at least one of the rings comprising a heteroatom is fully unsaturated or partially unsaturated. In heteroaryl groups that include 2 or more fused rings, additional rings may bear one or more heteroatoms, may be a carbocycle (e.g., 6,7-Dihydro-5H-cyclopentapyrimidine) or may be aryl (e.g., benzofuranyl, benzo-thiophenyl, indolyl, indolinyl, tetrahydroquinolinyl, chromanyl, 1,4-dioxochromanyl). In a group that has a heteroaryl substituent, unless otherwise indicated, the ring atom of the heteroaryl substituent that is bound to the group may be the at least one heteroatom, or it may be a ring carbon atom, where the ring carbon atom may be in the same ring as the at least one heteroatom or where the ring carbon may be in a different ring from the at least one heteroatom. Where so indicated, heteroaryl groups can be substituted. If the heteroaryl substituent is substituted with a group or substituent, the group or substituent may be bound to the heteroatom, or it may be bound to a ring carbon atom, where the ring carbon atom may be in the same ring as the heteroatom(s), or where the ring carbon atom may be in a different ring from the heteroatom(s). Examples of monocyclic heteroaryl rings include, but are not limited to, 1,2,3,4-tetrazolyl, [1,2,3]triazolyl, [1,2,4]triazolyl, triazinyl, thiazol-2-yl, thiazol-4-yl, imidazol-1-yl, 1H-imidazol-2-yl, 1H-imidazol-4-yl, oxazolyl, isoxazolin-5-yl, furan-2-yl, furan-3-yl, thiophen-2-yl, thiophen-4-yl, pyrimidin-2-yl, pyrimidin-4-yl, pyrimidin-5-yl, pyridazinyl, pyrazinyl, pyridin-2-yl, pyridin-3-yl, and pyridin-4-yl pyridinyl. Examples of heteroaryl rings containing 2 or more fused rings include, but are not limited to, benzofuranyl, benzothiophenyl, benzoxazolyl, benzthiazolyl, benztriazolyl, cinnolinyl, naphthyridinyl, benzimidazolyl, aza-indolyl, aza-benzimidazolyl, phenanthridinyl, 7H-purinyl, 9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, and isoquinolinyl. The term "heteroaryl" also includes pyridyl N-oxides and groups containing a pyridine N-oxide ring.

As used herein, unless otherwise stated, the term "amino" refers to —$NH_2$.

As used herein, unless otherwise stated, the term "alkylamino" refers to —N(H)alkyl, the term "alkyl" having already been defined herein. Examples of alkylamino substituents include, but are not limited to, methylamino, ethylamino, and propylamino.

As used herein, unless otherwise stated, the term "dialkylamino" refers to —$N(alkyl)_2$ where the two alkyls may be the same or different and where the term "alkyl" has already been defined herein. Examples of dialkylamino substituents include, but are not limited to, dimethylamino, diethylamino, ethylmethylamino, and dipropylamino.

As used herein, unless otherwise stated, the term "amido" refers to —C(=O)$NH_2$.

As used herein, unless otherwise stated, the term "halogen" or "halogen atom" refers to the group consisting of fluorine (which may be depicted as —F), chlorine (which may be depicted as —Cl), bromine (which may be depicted as —Br), or iodine (which may be depicted as —I).

As used herein, unless otherwise stated, the terms "hydroxy" and "hydroxyl" are used interchangeably and as used herein mean an —OH group. As used herein, unless otherwise noted, the terms "hydroxyalkyl" and "hydroxyalkoxy" are intended to include both branched and straight-chain saturated aliphatic "alkyl" or "alkoxy" groups respectively, wherein "alkyl" and "alkoxy" are as defined herein, having the specified number of carbon atoms and in which at least one hydrogen is replaced with a —OH group. Where so indicated, hydroxyalkyl and hydroxyalkoxy groups can optionally be substituted with one or more substituents in addition to —OH. Examples of hydroxyalkyl groups include, but are not limited to, $CH_2OH$, $CH_2CH_2OH$, $CH_2(OH)CH_2OH$.

As used herein, unless otherwise stated, the term "oxo" or "carbonyl" refers to =O.

As used herein, unless otherwise stated, the term "carboxy" refers to —$CO_2H$.

As used herein, unless otherwise stated, the term sulfonyl refers to —$SO_2$—.

As used herein, the term "substituted" is used throughout the specification. The term "substituted" is defined herein as a moiety, whether acyclic or cyclic, which has one or more (e.g. 1-10) hydrogen atoms replaced by a substituent as defined herein below. Substituents include those that are capable of replacing one or two hydrogen atoms of a single moiety at a time, and also those that can replace two hydrogen atoms on two adjacent carbons to form said substituent. For example, substituents that replace single hydrogen atoms include, but are not limited to, halogen, hydroxy, and the like. A two hydrogen atom replacement includes, but is not limited to, carbonyl, oximino, and the like. Substituents that replace two hydrogen atoms from adjacent carbon atoms include, but are not limited to, epoxy, and the like. When a moiety is described as "substituted" any number of its hydrogen atoms can be replaced, as described above. For example, difluoromethyl is a substituted $C_1$ alkyl; trifluoromethyl is a substituted $C_1$ alkyl; 4-hydroxyphenyl is a substituted aryl ring; (N,N-dimethyl-5-amino)octanyl is a substituted $C_8$ alkyl; 3-guanidinopropyl is a substituted $C_3$ alkyl; and 2-carboxy-3-fluoropyridinyl is a substituted heteroaryl.

A multi-moiety substituent is bound through the atom indicated by "-". To illustrate this the term "—$OC_1$-$C_3$hydroxyalkyl" is an $OC_1$-$C_3$alkyl group substituted by a hydroxy group. Further, any carbon number pre-fix attached to a multi-moiety substituent only applies to the moiety it immediately precedes. To illustrate, the term "cycloalkyl($C_1$-$C_4$)alkyl" contains two moieties: alkyl and cycloalkyl. The ($C_1$-$C_4$) pre-fix on the cycloalkyl($C_1$-$C_4$)alkyl means that the alkyl moiety of the alkylcycloalkyl contains from 1 to 4 carbon atoms, the ($C_1$-$C_4$) pre-fix does not describe the cycloalkyl moiety.

If a group of substituents are collectively described as being optionally substituted by one or more of a list of substituents, the group may include (1) unsubstitutable substituents, (2) substitutable substituents that are not substituted by the optional substituents, and/or (3) substitutable substituents that are substituted by one or more of the optional substituents.

If a substituent is described such that it "may be substituted" or as being "optionally substituted" with up to a particular number of non-hydrogen substituents, that substituent may be either (1) not substituted; or (2) substituted by up to that particular number of non-hydrogen substituents or by up to the maximum number of substitutable positions on the substituents, whichever is less. Thus, for example, if a substituent is described as a heteroaryl optionally substituted with one, two or three substituents, then any heteroaryl with less than three substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent.

At various places in the present specification, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$—$C_5$, $C_3$-$C_4$, $C_4$-$C_6$, $C_4$-$C_5$, and $C_5$-$C_6$ alkyl. For example, the term "$C_{1-3}$ alkyl" is specifically intended to individually disclose $C_1$, $C_2$, $C_3$, $C_1$-$C_3$, $C_1$-$C_2$, and $C_2$-$C_3$ alkyl.

As used herein, the term "compounds of the invention" means, unless otherwise stated, compounds of Formula (I) or compounds of Embodiment (1), Embodiment (3), Embodiment (3.1), Embodiment (3.2), Embodiment (3.3), Embodiment (4), Embodiment (4.1), Embodiment (4.2), Embodiment (4.3), Embodiment (5), Embodiment (5.1), Embodiment (5.2), Embodiment (6), Embodiment (6.1), Embodiment (7), Embodiment (7.1), Embodiment (8), Embodiment (8.1), Embodiment (8.2), Embodiment (9), Embodiment (9.1), Embodiment (9.2), Embodiment (9.3), Embodiment (10), Embodiment (10.1), Embodiment (11), Embodiment (11.1), Embodiment (11.2), Embodiment (11.3), Embodiment (11.4), Embodiment (11.5), Embodiment (11.6), Embodiment (12), Embodiment (13), Embodiment (13.1), Embodiment (13.2), Embodiment (13.3), Embodiment (13.4), Embodiment (13.5), Embodiment (13.6), Embodiment (13.7), Embodiment (13.8), Embodiment (13.9), Embodiment (13.10), Embodiment (13.11), Embodiment (14), Embodiment (14.1), Embodiment (14.2), Embodiment (15), Embodiment (15.1), Embodiment (15.2), Embodiment (15.3), Embodiment (16), Embodiment (16.1), Embodiment (16.2), Embodiment (16.3), Embodiment (16.4), Embodiment (16.5), Embodiment (16.6), Embodiment (16.7), Embodiment (17), Embodiment (18), compounds of Formula (II), Embodiment (20), Embodiment (21), Embodiment (22), Embodiment (22.1), Embodiment (23), Embodiment (23.1), Embodiment (24), Embodiment (24.2), Embodiment (25), Embodiment (25.1), Embodiment (25.2), Embodiment (25.3), Embodiment (26), Embodiment (26.1), Embodiment (26.2), Embodiment (27), Embodiment (27.1), Embodiment (27.2), Embodiment (27.3), Embodiment (27.4), Embodiment (27.5), Embodiment (27.6), Embodiment (27.7), Embodiment (28), Embodiment (29), Embodiment (29.1), Embodiment (29.2), Embodiment (29.3), Embodiment (29.4), Embodiment (29.5), Embodiment (29.6), Embodiment (30), Embodiment (30.1), Embodiment (30.2), Embodiment (30.3), Embodiment (31), Embodiment (31.1), Embodiment (31.2), Embodiment (31.3), Embodiment (31.4), Embodiment (32), Embodiment (32.1), Embodiment (32.2), Embodiment (32.3), Embodiment (32.4), Embodiment (32.5), Embodiment (32.6), Embodiment (33), Embodiment (34), compounds of Formula (III), Embodiment (50), Embodiment (51), Embodiment (51.1), Embodiment (52), Embodiment (52.1), Embodiment (53), Embodiment (53.1), Embodiment (54), Embodiment (55), Embodiment (56), Embodiment (56.1), Embodiment (57), Embodiment (57.1), Embodiment (58), Embodiment (58.1), Embodiment (58.2), Embodiment (58.3), Embodiment (58.4), Embodiment (59), Embodiment (60), Embodiment (60.1), Embodiment (60.2), Embodiment (61), Embodiment (61.1), Embodiment (61.2), Embodiment (61.3), Embodiment (62), Embodiment (62.1), Embodiment (63), Embodiment (64), or a pharmaceutically acceptable salt of such compounds.

As used herein, the term "compounds of Formula (I)" means, unless otherwise stated, compounds of Formula (I), or compounds of Embodiment (1), Embodiment (3), Embodiment (3.1), Embodiment (3.2), Embodiment (3.3), Embodiment (4), Embodiment (4.1), Embodiment (4.2), Embodiment (4.3), Embodiment (5), Embodiment (5.1), Embodiment (5.2), Embodiment (6), Embodiment (6.1), Embodiment (7), Embodiment (7.1), Embodiment (8), Embodiment (8.1), Embodiment (8.2), Embodiment (9), Embodiment (9.1), Embodiment (9.2), Embodiment (9.3), Embodiment (10), Embodiment (10.1), Embodiment (11), Embodiment (11.1), Embodiment (11.2), Embodiment (11.3), Embodiment (11.4), Embodiment (11.5), Embodiment (11.6), Embodiment (12), Embodiment (13), Embodiment (13.1), Embodiment (13.2), Embodiment (13.3), Embodiment (13.4), Embodiment (13.5), Embodiment (13.6), Embodiment (13.7), Embodiment (13.8), Embodiment (13.9), Embodiment (13.10), Embodiment (13.11), Embodiment (14), Embodiment (14.1), Embodiment (14.2), Embodiment (15), Embodiment (15.1), Embodiment (15.2), Embodiment (15.3), Embodiment (16), Embodiment (16.1), Embodiment (16.2), Embodiment (16.3), Embodiment (16.4), Embodiment (16.5), Embodiment (16.6), Embodiment (16.7), Embodiment (17), Embodiment (18), or a pharmaceutically acceptable salt of such compounds.

As used herein, the term "compounds of Formula (II)" means, unless otherwise stated, compounds of Formula (II), Embodiment (20), Embodiment (21), Embodiment (22), Embodiment (22.1), Embodiment (23), Embodiment (23.1), Embodiment (24), Embodiment (24.2), Embodiment (25), Embodiment (25.1), Embodiment (25.2), Embodiment (25.3), Embodiment (26), Embodiment (26.1), Embodiment (26.2), Embodiment (27), Embodiment (27.1), Embodiment (27.2), Embodiment (27.3), Embodiment (27.4), Embodiment (27.5), Embodiment (27.6), Embodiment (27.7), Embodiment (28), Embodiment (29), Embodiment (29.1), Embodiment (29.2), Embodiment (29.3), Embodiment (29.4), Embodiment (29.5), Embodiment (29.6), Embodiment (30), Embodiment (30.1), Embodiment (30.2), Embodiment (30.3), Embodiment (31), Embodiment (31.1), Embodiment (31.2), Embodiment (31.3), Embodiment (31.4), Embodiment (32), Embodiment (32.1), Embodiment (32.2), Embodiment (32.3), Embodiment (32.4), Embodiment (32.5), Embodiment (32.6), Embodiment (33), Embodiment (34), or a pharmaceutically acceptable salt of such compounds.

As used herein, the term "compounds of Formula (III)" means, unless otherwise stated, compounds of Formula (III), Embodiment (50), Embodiment (51), Embodiment (51.1), Embodiment (52), Embodiment (52.1), Embodiment (53), Embodiment (53.1), Embodiment (54), Embodiment (55), Embodiment (56), Embodiment (56.1), Embodiment (57), Embodiment (57.1), Embodiment (58), Embodiment (58.1), Embodiment (58.2), Embodiment (58.3), Embodiment (58.4), Embodiment (59), Embodiment (60), Embodiment (60.1), Embodiment (60.2), Embodiment (61), Embodiment (61.1), Embodiment (61.2), Embodiment (61.3), Embodiment (62), Embodiment (62.1), Embodiment (63), Embodiment (64), or a pharmaceutically acceptable salt of such compounds.

In certain embodiments, the compounds of Formula (I) include the Examples exemplified herein, or a pharmaceutically acceptable salt thereof.

The compounds of the invention not only include compounds as hereinbefore defined, but also all forms of the compounds of the invention, including isomers (including optical, geometric and tautomeric isomers), hydrates, solvates, complexes, salts (including solvates and complexes thereof) crystalline and non-crystalline forms, isomorphs, polymorphs, isotopically-labeled derivatives, metabolites and prodrugs (including tautomeric forms of such prodrugs) thereof.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to for example, chiral chromatography, diastereomeric salt formation, kinetic resolution, and asymmetric synthesis. The present invention also includes cis and trans or E/Z isomers of compounds of the invention containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of the invention may exist in both unsolvated and solvated forms. The term "solvate" as used herein means a physical association of a compound with one or more solvent molecules, whether organic or inorganic, including water ('hydrate'). As noted above, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the invention (e.g. a compound of Formula (I)) with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, .beta.-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-benzylethylenediamine, chloroprocaine, choline, diethanolamine, ethylenediamine, meglumine (N-methylglucamine), and procaine. Basic nitrogen-containing groups may be quaternized with agents such as lower alkyl (C.sub.1-C.sub.6) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $_{15}O$, $^{17}O$ and $^{18}O$, phosphorus, such as $^{32}P$, and sulphur, such as $^{35}S$. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, and $^{125}$I are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996), incorporated herein by reference. Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

In some embodiments, compounds described herein could be prepared as prodrugs. A "prodrug" refers to an agent that is converted (e.g., either spontaneous or enzymatic) within the target physiological system into the parent drug in vivo. Prodrugs are designed to overcome problems associated with stability, toxicity, lack of specificity, or limited bioavailability. In some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985). Prodrugs may be designed as reversible drug derivatives, for use as modifiers to enhance drug transport to site-specific tissues. See, e.g., Fedorak et al., Am. J. Physiol., 269:G210-218 (1995); McLoed et al., Gastroenterol, 106: 405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

Some preferred prodrugs are variations or derivatives of compounds that have groups cleavable under metabolic conditions. Common prodrugs include acid derivatives such as esters, such as carboxylic esters (eg ethyl esters) and phosphate esters prepared by reaction of parent acids with a suitable alcohol (e.g., a lower alkanol), or of parent alcohols with a suitable acid (e.g. phosphate esters of hydroxyl groups); amides prepared by reaction of the parent acid compound with an amine, or basic groups reacted to form an acylated base derivative (e.g., a lower alkylamide).

In one Embodiment, the invention relates to prodrugs of compounds of Formula (I) or (II), or pharmaceutically acceptable salts thereof.

The present invention also relates to a pharmaceutical composition comprising a compound of Formula (I), or a pharmaceutically acceptable salt thereof, and a pharmaceutically acceptable excipient.

Methods of formulation are well known in the art and are disclosed, for example, in Remington: *The Science and Practice of Pharmacy*, Mack Publishing Company, Easton, Pa., 21st Edition (2005), incorporated herein by reference.

Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent.

In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Formulations comprising crystalline forms of the compositions described herein for slow absorption from subcutaneous or intramuscular injection are provided herein. Additionally, delayed absorption of a parenterally administered drug form may be accomplished by dissolving or suspending the compounds in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients ass lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The compounds described herein can also be in micro-encapsulated form with one or more excipients as noted above. The solid dosage forms of tablets, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

Compositions of the invention may also be formulated for delivery as a liquid aerosol or inhalable dry powder. Liquid aerosol formulations may be nebulized predominantly into particle sizes that can be delivered to the terminal and respiratory bronchioles.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. A physiologically acceptable carrier should not cause significant irritation to an organism and does not abrogate the biological activity and properties of the administered compound.

An “excipient” refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

Compounds of the invention, or pharmaceutically acceptable salts thereof, may inhibit the vanin-1 enzyme. Such compounds may therefore be useful for treating diseases or disorders that are mediated by, or otherwise associated with, inhibition of the vanin-1 enzyme, the method comprising administering to a subject in need thereof, an effective amount of a compound of the invention.

The present invention also relates to a method of treating a disease or a disorder in a patient, comprising administering to a patient in need thereof a therapeutically effective amount of a compound of Formula (I) or (II), or a pharmaceutically acceptable salt thereof, or a pharmaceutical composition comprising a therapeutically effective amount of a compound of Formula (I) or (II), or a pharmaceutically acceptable salt thereof.

In another embodiment, the present invention further provides a method of inhibiting vanin-1 enzyme in a cell, comprising contacting the cell with a therapeutically effective amount of a compound of Formula (I) or (II), or a pharmaceutically acceptable salt thereof, or a pharmaceutical composition comprising a therapeutically effective amount of a compound of Formula (I) or (II), or a pharmaceutically acceptable salt thereof In another embodiment, the present invention relates to a method of treating a disease or disorder treating mediated by, or otherwise associated with, inhibition of the vanin-1 enzyme, comprising administering to a patient in need thereof a therapeutically effective amount of a compound of Formula (I) or (II), or a pharmaceutically acceptable salt thereof, or a pharmaceutical composition comprising a therapeutically effective amount of a compound of Formula (I) or (II), or a pharmaceutically acceptable salt thereof.

In another embodiment, the present invention relates to a compound of Formula (I) or (II), or a pharmaceutically acceptable salt thereof, for use as a medicament.

In another embodiment, the present invention relates to a compound of Formula (I) or (II), or a pharmaceutically acceptable salt thereof, for use in the treatment of a disease or disorder mediated by, or otherwise associated with, inhibition of the vanin-1 enzyme.

In another embodiment, the present invention relates to the use of a compound of Formula (I) or (II), or a pharmaceutically acceptable salt thereof, for the manufacture of a medicament to treat a disease or disorder mediated by, or otherwise associated with, inhibition of the vanin-1 enzyme.

In yet another embodiment, the present invention relates to a pharmaceutical composition for use in the treatment of a disease or disorder mediated by, or otherwise associated with, inhibition of the vanin-1 enzyme, which composition comprises a compound of Formula (I), or a pharmaceutically acceptable salt thereof, and a pharmaceutically acceptable excipient.

In yet another embodiment, the present invention relates to a pharmaceutical composition for use in the treatment of a disease or disorder mediated by, or otherwise associated with, inhibition of the vanin-1 enzyme, which composition comprises a compound of Formula (II), or a pharmaceutically acceptable salt thereof, and a pharmaceutically acceptable excipient.

In another Embodiment, the present invention relates to a method of treating a disease or a disorder in a patient, which disease or disorder is selected from the group consisting of auto-immune diseases, inflammatory diseases, allergic diseases, metabolic diseases, infection-based diseases, trauma or tissue-injury based diseases, fibrotic diseases, genetic diseases, cardiovascular diseases, vascular diseases, heart diseases, neurological diseases, neurodegenerative diseases, respiratory diseases, pulmonary diseases, airways diseases, renal diseases, skin and/or dermatological diseases, liver diseases, gastrointestinal diseases, oral diseases, pain and sensory diseases, hematopoietic diseases, joint diseases, muscle diseases, and bone diseases, comprising administering to a patient in need thereof a therapeutically effective amount of a compound of Formula (I), or a pharmaceutically acceptable salt thereof, or a pharmaceutical composition comprising a therapeutically effective amount of a compound of Formula (I), or a pharmaceutically acceptable salt thereof.

In another Embodiment, the present invention relates to a method of treating a disease or a disorder in a patient, which disease or disorder is selected from the group consisting of auto-immune diseases, inflammatory diseases, allergic diseases, metabolic diseases, infection-based diseases, trauma or tissue-injury based diseases, fibrotic diseases, genetic diseases, cardiovascular diseases, vascular diseases, heart diseases, neurological diseases, neurodegenerative diseases, respiratory diseases, pulmonary diseases, airways diseases, renal diseases, skin and/or dermatological diseases, liver diseases, gastrointestinal diseases, oral diseases, pain and sensory diseases, hematopoietic diseases, joint diseases, muscle diseases, and bone diseases, comprising administering to a patient in need thereof a therapeutically effective amount of a compound of Formula (II), or a pharmaceutically acceptable salt thereof, or a pharmaceutical composition comprising a therapeutically effective amount of a compound of Formula (II), or a pharmaceutically acceptable salt thereof.

In another embodiment, the present invention relates to a compound of Formula (I) or (II), or a pharmaceutically acceptable salt thereof, for use in the treatment of a disease or disorder, which disease or disorder is selected from the group consisting of auto-immune diseases, inflammatory diseases, allergic diseases, metabolic diseases, infection-based diseases, trauma or tissue-injury based diseases, fibrotic diseases, genetic diseases, cardiovascular diseases, vascular diseases, heart diseases, neurological diseases, neurodegenerative diseases, respiratory diseases, pulmonary diseases, airways diseases, renal diseases, skin and/or dermatological diseases, liver diseases, gastrointestinal diseases, oral diseases, pain and sensory diseases, hematopoietic diseases, joint diseases, muscle diseases, and bone diseases.

In another embodiment, the present invention relates to the use of a compound of Formula (I) or (II), or a pharmaceutically acceptable salt thereof, for the manufacture of a medicament to treat a disease or disorder, which disease or disorder is selected from the group consisting of auto-immune diseases, inflammatory diseases, allergic diseases, metabolic diseases, infection-based diseases, trauma or tissue-injury based diseases, fibrotic diseases, genetic diseases, cardiovascular diseases, vascular diseases, heart diseases, neurological diseases, neurodegenerative diseases, respiratory diseases, pulmonary diseases, airways diseases, renal diseases, skin and/or dermatological diseases, liver diseases, gastrointestinal diseases, oral diseases, pain and sensory diseases, hematopoietic diseases, joint diseases, muscle diseases, and bone diseases.

In another Embodiment, the present invention relates to a method of treating a disease or a disorder in a patient, which disease or disorder is selected from the group consisting of disease or disorder is selected from the group consisting of inflammatory bowel disease, ulcerative colitis, Crohn's disease, colorectal cancer, and gastritis, comprising administering to a patient in need thereof a therapeutically effective amount of a compound of Formula (I) or (II), or a pharmaceutically acceptable salt thereof, or a pharmaceutical composition comprising a therapeutically effective amount of a compound of Formula (I) or (II), or a pharmaceutically acceptable salt thereof.

In another Embodiment, the present invention relates to a method of treating a disease or a disorder in a patient, which disease or disorder is selected from the group consisting of disease or disorder is selected from the group consisting of inflammatory bowel disease, ulcerative colitis, Crohn's disease, colorectal cancer, and gastritis, comprising administering to a patient in need thereof a therapeutically effective amount of a compound of Formula (II), or a pharmaceutically acceptable salt thereof, or a pharmaceutical composition comprising a therapeutically effective amount of a compound of Formula (II), or a pharmaceutically acceptable salt thereof.

In another embodiment, the present invention relates to a compound of Formula (I) or (II), or a pharmaceutically acceptable salt thereof, for use in the treatment of a disease or disorder, which the disease or disorder is selected from the group consisting of disease or disorder is selected from the group consisting of inflammatory bowel disease, ulcerative colitis, Crohn's disease, colorectal cancer, and gastritis.

In another embodiment, the present invention relates to the use of a compound of Formula (I) or (II), or a pharmaceutically acceptable salt thereof, for the manufacture of a medicament to treat a disease or disorder, which disease or disorder is selected from the group consisting of disease or disorder is selected from the group consisting of inflammatory bowel disease, ulcerative colitis, Crohn's disease, colorectal cancer, and gastritis.

As used herein, the terms "treat" and "treating," as used herein, refer to partially or completely alleviating, inhibiting, ameliorating and/or relieving a condition from which a patient is suspected to suffer.

As used herein, the term "therapeutically effective" refers to a substance or an amount that elicits a desirable biological activity or effect.

The term "therapeutically effective amount" as used herein, refers to that amount of the therapeutic agent sufficient to result in amelioration of one or more symptoms of a disorder, or prevent advancement of a disorder, or cause regression of the disorder. For example, with respect to the treatment of asthma, a therapeutically effective amount preferably refers to the amount of a therapeutic agent that increases peak air flow by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.%. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

The term "abnormal cell growth" as used herein, unless otherwise indicated, refers to cell growth that is independent of normal regulatory mechanisms (e.g., loss of contact inhibition). Abnormal cell growth may be benign (not cancerous), or malignant (cancerous).

As used herein "cancer" refers to any malignant and/or invasive growth or tumor caused by abnormal cell growth. As used herein "cancer" refers to solid tumors named for the type of cells that form them, or cancers of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

As used herein, except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, but are not limited to for example, conventional work-ups to determine risk factors that may be associated with the targeted or suspected disease or condition. These and other routine methods allow the clinician to select patients in need of therapy using the methods and compounds of the present invention.

As used herein, the term "inhibitor(s) of vanin-1 enzyme" refers to a compound that binds to the vanin-1 enzyme and decreases the resulting enzymatic activity.

As used herein, the term "mammal" as used herein, refers to a human, a non-human primate, canine, feline, bovine, ovine, porcine, murine, or other veterinary or laboratory mammal. Those skilled in the art recognize that a therapy which reduces the severity of pathology in one species of mammal can be predictive of the effect of the therapy on another species of mammal.

As used herein, the term "modulate" as used herein, refers to encompasses either a decrease or an increase in activity or expression depending on the target molecule.

As used herein, the term "other therapeutic agents" as used herein, refers to any therapeutic agent that has been used, is currently used or is known to be useful for treating a disease or a disorder encompassed by the present invention.

A "pharmaceutically/therapeutically effective amount" means an amount which is capable of providing a therapeutic and/or prophylactic effect. The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 20 mg/kg and ideally from about 0.1 mg/kg to about 10 mg/kg. Factors such as clearance rate, half-life and maximum tolerated dose (MTD) have yet to be determined but one of ordinary skill in the art can determine these using standard procedures.

As used herein, the term "$IC_{50}$" refers to an amount, concentration or dosage of a particular test compound that achieves a 50% inhibition of a maximal response in an assay that measures such response. The value depends on the assay used.

Inhibitors of vanin-1 enzyme may be used in the treatment of a variety of diseases or disorders related to systemic or tissue inflammation, inflammatory responses to infection or hypoxia, cellular activation and proliferation, lipid metabolism, fibrosis and in the treatment of viral infections.

The disease may be, but not limited to, one of the following classes: auto-immune diseases, inflammatory diseases, allergic diseases, metabolic diseases, infection-based diseases, trauma or tissue-injury based diseases, fibrotic diseases, genetic diseases, cardiovascular diseases, vascular diseases, heart diseases, neurological diseases, neurodegenerative diseases, respiratory diseases, pulmonary diseases, airways diseases, renal diseases, skin and/or dermatological diseases, liver diseases, gastrointestinal diseases, oral diseases, pain and sensory diseases, hematopoietic diseases, joint diseases, muscle diseases, and bone diseases.

Specific autoimmune diseases include, but are not limited to: rheumatoid arthritis, osteoarthritis, psoriasis, allergic dermatitis, systemic lupus erythematosus (and resulting complications), Sjögren's syndrome, multiple sclerosis, asthma, glomerular nephritis, irritable bowel syndrome, inflammatory bowel disease, Crohn's disease, ankylosing spondylitis, Behçet's disease, lupus nephritis, scleroderma, systemic scleroderma, type 1 or juvenile on-set diabetes, alopecia universalis, acute disseminated encephalomyelitis, Addison's disease, antiphospholipid antibody syndrome, atrophic gastritis of pernicious anemia, autoimmune alopecia, autoimmune hemolytic anemia, autoimmune hepatitis, autoimmune encephalomyelitis, autoimmune thrombocytopenia, Bullous pemphigoid, Chagas disease, Celiac disease, chronic hepatitis, Cogan's syndrome, dermatomyositis, endometriosis, Goodpasture's syndrome, Graves' disease, Guillain-Barré syndrome, Hashimoto's disease (or Hashimoto's thyroiditis), hemolytic anemia, hidradentitis suppurativa, idiopathic thrombocytopenia purpura, interstitial cystitis, membranous glomerulopathy, morphea, mystenia gravis, narcolepsy, pemphigus, pernicous anemia, polyarteritis *nodosa*, polymyositis, primary biliary cirrhosis, Reiter's syndrome, schizophrenia, symphathetic opthalmia, systemic sclerosis, temporal arteritis, thyroiditis, vasculitis, vitiglio, vulvodynia, Wegner's granulomatosis, palmoplantar keratoderma, systemic-onset Juvenile Idiopathic Arthritis (SJIA), or an indication listed in a separate category herein.

Specific inflammatory diseases include, but are not limited to: chronic obstructive pulmonary diseases, airway hyper-responsiveness, cystic fibrosis, acute respiratory distress syndrome, sinusitis, rhinitis, gingivitis, atherosclerosis, chronic prostatitis, glomerular nephritis, ulcerative colitis, uveitis, periodontal disease, or an indication listed in a separate category herein.

Specific pain conditions include, but are not limited to: inflammatory pain, surgical pain, visceral pain, dental pain, premenstrual pain, central pain, pain due to burns, migraine or cluster headaches, nerve injury, interstitial cystitis, cancer pain, viral, parasitic or bacterial infection, post-traumatic injury, pain associated with irritable bowel syndrome, gout, pain associated with any of the other indications listed within this specification, or an indication listed in a separate category herein.

Specific respiratory, airway and pulmonary conditions include, but are not limited to: asthma (which may encompass chronic, late, bronchial, allergic, intrinsic, extrinsic or dust), chronic obstructive pulmonary disease, idiopathic pulmonary fibrosis, pulmonary arterial hypertension, cystic fibrosis, interstitial lung disease, acute lung injury, sarcoidosis, allergic rhinitis, chronic cough, bronchitis, recurrent airway obstruction, emphysema, or bronchospasm, or an indication listed in a separate disease category herein.

Specific gastrointestinal (GI) disorders include, but are not limited to: Irritable Bowel Syndrome (IBS), Inflammatory Bowel Disease (IBD), biliary colic and other biliary disorders, renal colic, diarrhea-dominant IBS, pain associated with GI distension, ulcerative colitis, Crohn's Disease, irritable bowel syndrome, Celiac disease, proctitis, eosinophilic gastroenteritis, mastocytosis, or an indication listed in a separate disease category herein.

Specific allergic diseases include, but are not limited to: anaphylaxis, allergic rhinitis, allergic dermatitis, allergic urticaria, angioedema, allergic asthma, allergic reactions to: food, drugs, insect bites, pollen; or an indication listed in a separate disease category herein.

Specific infection-based diseases include, but are not limited to: sepsis, septic shock, viral diseases, malaria, Lyme disease, ocular infections, conjunctivitis, Whipple Disease, or an indication listed in a separate disease category herein.

Specific trauma and tissue injury-based conditions include, but are not limited to: Renal glomerular damage, reperfusion injury (for example to heart, kidney, lung), spinal cord injury, tissue scarring, tissue adhesion, tissue repair, transplant rejection (for examples to heart, lung, bone marrow, cartilage, cornea, kidney, limb, liver, muscle, myoblast, pancreas, pancreatic islet, skin, nerve, small intestine, trachea), hypersensitivities, or an indication listed in a separate disease category herein.

Specific fibrotic diseases include, but are not limited to: Idiopathic pulmonary fibrosis, liver fibrosis, renal fibrosis, or an indication listed in a separate disease category herein.

Specific joint, muscle and bone disorders include, but are not limited to: osteoarthritis, osteoporosis, rheumatoid arthritis, juvenile arthritis, psoriatic arthritis, erosive osteoarthritis of the hand, arthrofibrosis/traumatic knee injury, anterior cruciate knee ligament tear, relapsing polychondritis, recurrent multifocal osteomyelitis, Majeed Syndrome, ankylosing spondylitis, gout of the lumbar spine, antisynthetase syndrome, idiopathic inflammatory myopathies, articular chondrocalcinosis, systemic-onset Juvenile Idiopathic Arthritis (SJIA), gout and pyrophosphate crystal arthritis, or an indication listed in a separate disease category herein.

Specific skin/dermatological diseases include, but are not limited to: psoriasis, atopic dermatitis, cutaneous lupus, acne, dermatomyositis, eczema, pruritus, scleroderma, Sweet Syndrome/neutrophilic dermatosis, neutrophilic panniculitis, acrodermatitis (form of pustular psoriasis), or an indication listed in a separate disease category herein.

Specific renal diseases include, but are not limited to: acute kidney injury (AKI) (sepsis-AKI, coronary artery bypass graft-AKI, cardiac surgery-AKI, non-cardiac surgery-AKI, transplant surgery-AKI cisplatin-AKI, contrast/imaging agent induced-AKI), glomerulonephritis, IgA nephropathy, crescentic GN, lupus nephritis, HIV associated nephropathy, membraneous nephropathy, C3 glomerulopathy, Dense deposit disease, ANCA vasculitis, diabetic nephropathy, hemolytic-uremic syndrome, atypical Hemolytic-uremic syndrome, nephrotic syndrome, nephritic syndrome, hypertensive nephrosclerosis, ApoL1 nephropathy, focal segmental glomerulosclerosis, Alport syndrome, Fanconi, syndrome, crystal nephropathy, nephrolithiasis, nephrotic syndrome, renal transplant rejection, amyloidosis, glomerulonephritis in SJIA, or an indication listed in a separate disease category herein.

Specific hematopoietic diseases include, but are not limited to: hemolytic anemia, or an indication listed in a separate disease category herein.

Specific liver diseases include, but are not limited to: liver fibrosis, liver cirrhosis, nonalcoholic steatohepatitis (NASH), or an indication listed in a separate disease category herein.

Specific oral diseases include, but are not limited to: gingivitis, periodontal disease or an indication listed in a separate disease category herein.

Specific metabolic diseases include, but are not limited to: Type 2 diabetes (and resulting complications), gout and hyperuricemia, metabolic syndrome, insulin resistance, obesity, or an indication listed in a separate disease category herein.

Compounds of the current invention are also useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, nonsmall-cell lung carcinoma, lymphomas, Hodgkins and Non-Hodgkins, a mammary carcinoma, follicular carcinoma, undifferentiated carcinoma, papillary carcinoma, seminoma, melanoma, smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, intravascular large B-cell lymphoma), or an indication listed in a separate disease category herein.

Cardiovascular conditions include, but are not limited to coronary heart disease, acute coronary syndrome, ischaemic heart disease, first or recurrent myocardial infarction, secondary myocardial infarction, non-ST segment elevation myocardial infarction, or ST segment elevation myocardial infarction, ischemic sudden death, transient ischemic attack, peripheral occlusive arterial disease, angina, atherosclerosis, hypertension, heart failure (such as congestive heart failure), diastolic dysfunction (such as left ventricular diastolic dysfunction, diastolic heart failure, and impaired diastolic filling), systolic dysfunction (such as systolic heart failure with reduced ejection fraction), vasculitis, ANCA vasculitis, post-myocardial infarction cardiac remodeling atrial fibrillation, arrhythmia (ventricular), ischemia, hypertrophic cardiomyopathy, sudden cardiac death, myocardial and vascular fibrosis, impaired arterial compliance, myocardial necrotic lesions, vascular damage, left ventricular hypertrophy, decreased ejection fraction, cardiac lesions, vascular wall hypertrophy, endothelial thickening, fibrinoid necrosis of coronary arteries, adverse remodeling, stroke, and the like, or an indication listed in a separate disease category herein. Also, included are venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty).

Cardiovascular complications of type 2 diabetes are associated with inflammation, accordingly, the compounds of the present invention may be used to treat diabetes and diabetic complications such as macrovascular disease, hyperglycemia, metabolic syndrome, impaired glucose tolerance, hyperuricemia, glucosuria, cataracts, diabetic neuropathy, diabetic nephropathy, diabetic retinopathy, obesity, dyslipidemia, hypertension, hyperinsulinemia, and insulin resistance syndrome, or an indication listed in a separate disease category herein.

Linkage of innate immunity, oxidative stress and inflammation to disease has been demonstrated in neuroinflammatory and neurodegenerative conditions. Therefore, the compounds of the present invention are particularly indicated for use in the treatment of neuroinflammatory and neurodegenerative conditions (i.e., disorders or diseases) in mammals including humans such as multiple sclerosis, migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); mental deficiency (including Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism), myotrophic lateral sclerosis, chronic fatigue syndrome, or an indication listed in a separate disease category herein.

In one embodiment the acute or chronic autoimmune and/or inflammatory condition is a disorder of lipid metabolism via the regulation of APO-A1 such as hypercholesterolemia, atherosclerosis and Alzheimer's disease.

In another embodiment the acute or chronic autoimmune and/or inflammatory condition are respiratory disorders such as asthma, chronic obstructive pulmonary disease, pulmonary arterial hypertension or idiopathic pulmonary fibrosis.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis, scleroderma or inflammatory bowel disease (Crohn's disease and Ulcerative colitis).

In another embodiment the acute or chronic autoimmune and/or inflammatory condition is multiple sclerosis.

In a further embodiment the acute or chronic autoimmune and/or inflammatory condition is Type I diabetes.

In certain embodiments, the present invention relates to any of the aforementioned embodiments, wherein the disease or disorder is selected from the group consisting of Parkinson disease, Alzheimer disease, multiple sclerosis, schizophrenia, dementia, Huntington's disease, arthritis, diabetes, osteoarthritis, cataract, macular degeneration, prostate problems, prostate cancer, breast cancer, lung cancer, colorectal cancer, bladder cancer, uterine cancer, ovarian cancer, lymphoma, skin cancer, stomach cancer, liver cancer, wasting disease, toxic hepatitis, viral hepatitis (A, B, C), chronic hepatitis, cirrhosis, asthma, emphysema, pneumonia, bronchitis (chronic and acute), cystic fibroses, pulmonary fibroses, chronic obstructive pulmonary disease (COPD), adult respiratory distress syndrome (ARDS), arteriosclerosis & its consequences, heart failure, heart attack, kidney failure, high blood pressure, stroke, impaired circulation, heart disease, cholesterol and plaque formation, reperfusion injury, inflammatory bowel disease, ulcerative colitis, Crohn's disease, gastritis, stomach cancer, pancreatitis, peptic ulcer, kidney failure, renal toxicity, oxidative stress from dialysis, viral infection including, but not limited to, HIV and AIDS, toxic Hepatitis & cirrhosis, viral hepatitis (type A, B, & C), herpes, common cold, bacterial infection, chronic fatigue syndrome, psoriases, eczema, SLE (lupus), vasculitis, polymyositis, mycosis fungoides, scleroderma, pemhigoid, atopic dermatitis, contact dermatitis, sebborrheic dermatitis, dermatitis herpetiformis, acne conglobate, acne vularis, UV radiation skin damage, glaucoma, hearing loss, ear infection, sinusitis, periodontal (gum) disease, and nose, mouth & throat (upper respiratory tract) disease.

In certain embodiments, the present invention relates to any of the aforementioned embodiments, wherein the disease or disorder is selected from the group consisting of inflammatory bowel disease, ulcerative colitis, Crohn's disease, colorectal cancer, and gastritis.

The compounds described herein may be administered to humans and other animals orally, parenterally, sublingually, by aerosolization or inhalation spray, intranasal spray or via dry powder inhalation, rectally, intracisternally, intravaginally, intraperitoneally, bucally, intrathecally or topically in dosage unit formulations containing conventional nontoxic pharmaceutically acceptable carriers, adjuvants, and vehicles as desired. The term parenteral as used herein includes subcutaneous injection, intravenous injection, intramuscular injection, intrasternal injection, or infusion techniques. Topical administration may also involve the use of transdermal administration such as transdermal patches or ionophoresis devices.

Effective amounts of the compounds of the invention generally include any amount sufficient to detectably modulate vanin-1 activity, and in one embodiment inhibit vanin-1 enzyme, or to alleviate symptoms of diseases associated with vanin-1 activity, and in one embodiment those associated with inhibition of vanin-1 enzyme, or susceptible to vanin-1 activity modulation, in one embodiment inhibition of vanin-1 enzyme.

The amount of active ingredient that may be combined with the carrier materials to produce a single dosage form will vary depending upon the host treated and the particular mode of administration. It will be understood, however, that the specific dose level for any particular subject will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

In certain embodiments, the present invention relates to any of the aforementioned embodiments, wherein the treatment of a disease or disorder treating mediated by, or otherwise associated with, inhibition of the vanin-1 enzyme comprises administering an additional therapeutic agent.

In one embodiment, the invention relates to a combination of a compound of Formula (I), or a pharmaceutically acceptable salt thereof, and a second pharmaceutically active ingredient, or pharmaceutically acceptable salt thereof.

In one embodiment, the invention relates to a combination of a compound of Formula (II), or a pharmaceutically acceptable salt thereof, and a second pharmaceutically active ingredient, or pharmaceutically acceptable salt thereof.

As used herein, the terms "co-administration", "co-administered", "a combination of" or "in combination with", refers to a combination of a compound of the invention and one or more other pharmaceutically active ingredient, or a pharmaceutically acceptable salt thereof, includes the following:

a. simultaneous administration of such a combination of a compound of the invention and a further pharmaceutically active agent to a patient in need of treatment, when such components are formulated together into a single dosage form which releases said components at substantially the same time to said patient, b. substantially simultaneous administration of such a combination of a compound of the invention and a further pharmaceutically active agent to a patient in need of treatment, when such components are formulated apart from each other into separate dosage forms which are taken at substantially the same time by said patient, whereupon said components are released at substantially the same time to said patient, c. sequential administration of such a combination of a compound of the invention and a further pharmaceutically active agent to a patient in need of treatment, when such components are formulated apart from each other into separate dosage forms which are taken at consecutive times by said patient with a significant time interval between each administration, whereupon said components are released at substantially different times to said patient; and, d. sequential administration of such a combination of a compound of the invention and a further pharmaceutically active agent to a patient in need of treatment, when such components are formulated together into a single dosage form which releases said components in a controlled manner.

In particular, it is contemplated that the compounds of the invention may be administered with the following therapeutic agents:

Non-steroidal anti-inflammatory drugs (NSAIDs), including but not limited to, non-selective COX1/2 inhibitors such as piroxicam, naproxen, flubiprofen, fenoprofen, ketoprofen, ibuprofen, etodolac (Lodine), mefanamic acid, sulindac, apazone, pyrazolones (such as phenylbutazone), salicylates (such as aspirin); selective COX2 inhibitors such as: celecoxib, rofecoxib, etoricoxib, valdecoxib, meloxicam;

Immunomodulatory and/or anti-inflammatory agents, including but not limited to, methotrexate, leflunomide, ciclesonide chloroquine, hydroxychloroquine, d-penicillamine, auranofin, sulfasalazine, sodium aurothiomalate, cyclosporine, azathioprine, cromolyn, hydroxycarbamide, retinoids, fumarates (such as monomethyl and dimethyl fumarate), glatiramer acetate, mitoxantrone, teriflunomide, suplatast tosilate, mycophenolate mofetil and cyclophosphamide, laquinimod, voclosporin, PUR-118, AMG 357, AMG 811, BCT197;

Antimalarials, including but not limited to, hydroxychloroquine (Plaquenil) and chloroquine (Aralen), cyclophosphamide (Cytoxan), methotrexate (Rheumatrex), azathioprine (Imuran), mesalamine (Asacol) and sulfasalazine (Azulfidine):

Antibiotics, including but not limited to, Flagyl or ciprofloxacin;

Anti-TNFα agents, including but not limited to, infliximab, adalimumab, certolizumab pegol, golimumab and etanercept;

Anti-CD20 agents, including but not limited to, rituximab, ocrelizumab, ofatumumab and PF-05280586;

Antidiarrheals, such as diphenoxylate (Lomotil) and loperamide (Imodium);

Bile acid binding agents, such as cholestyramine, alosetron (Lotronex) and ubiprostone (Amitiza);

Laxatives, such as Milk of Magnesia, polyethylene glycol (MiraLax), Dulcolax, Correctol and Senokot, and anticholinergics or antispasmodics such as dicyclomine (Bentyl);

T lymphocyte activation inhibitors, including but not limited to, abatacept;

Glucocorticoid receptor modulators that may be dosed orally, by inhalation, by injection, topically, rectally, by ocular delivery, including but not limited to, betamethasone, prednisone, hydrocortisone, prednisolone, flunisolide, triamcinoline acetonide, beclomethasone, dipropionate, budesonide, fluticasone propionate, ciclesonide, mometasone furoate, fluocinonide, desoximetasone, methylprednisolone or PF-04171327;

Aminosalicyic acid derivatives, including but not limited to, sulfasalazine and mesalazine;

Anti-α4 integrin agents, including but not limited to, natalizumab;

α1- or α2-adrenergic agonist agents including but not limited to: propylhexidrine, phenylephrine, phenylpropanolamine, pseudoephedrine or naphazoline hydrochloride, oxymethazoline hydrochloride, tetrahydrozoline hydrochloride, xylometazoline hydrochloride or ethylnorepinephrine hydrochloride;

β-adrenergic agonists, including but not limited to, metaproterenol, isoprotenerol, isoprenaline, albuterol, salbutamol, formoterol, salmeterol, terbutaline, orciprenaline, botolterol mesylate, pirbuterol;

Anticholinergic agents, including but not limited to, ipratropium bromide, tiotropium bromide, oxitropium bromide, aclindinium bromide, glycopyrrolate, pirenzipine or telenzepine;

Inhaled long acting beta-agonists, long acting muscarinic antagonists and long acting corticosteroids, including but not limited, to those included in the following reference: Y. Mushtaq, The COPD pipeline, *Nat Rev Drug Discov*, 2014, 13(4), 253-254. http://dx.doi.org/10.1038/nrd425;

Leukotriene pathway modulators, including but not limited to, 5-LO Inhibitors (such as zileuton), FLAP antagonists (such as veliflapon, fiboflapon), LTD4 antagonists (such as montelukast, zafirlukast or pranlukast;

H1 receptor antagonists, including but not limited to, cetirizine, loratidine, desloratidine, fexofenadine, astemizole, azelastine or chlorpheniramine;

PDE4 inhibitors, including but not limited to, apremilast, roflumilast or AN2728;

Vitamin D receptor modulators, including but not limited to, paricalcitol;

Nrf2 pathway activators, including but not limited to, fumarates, sulfurophane and bardoxolone methyl;

Modulators of the RAR-related orphan receptor (ROR) family, in particular RORg;

Modulator and/or antagonists of the chemokine receptors, including but not limited to, CCR2 antagonists (such as CCX140, BMS-741672, PF-4634817, CCX-872, NOX-E36), CCR2/5 antagonists (such as PF-4634817), CCR9 (such as vercirnon, CCX507), CCR1 modulators, CCR4 modulators, CCR5 modulators, CCR6 modulators, CXCR6 modulators, CXCR7 modulators) and CXCR2 modulators (such as danirixin, AZD5069);

Prostaglandins, including but not limited to, prostacyclin;

PDE5 inhibitors, including but not limited to, sildenafil, PF-489791, vardenafil and tadalafil;

Endothelin receptor antagonists, including but not limited to, bosentan, ambrisentan, sparsentan, atrasentan, zibotentan and macitentan;

Soluble guanylate cyclase activators, including but not limited to, riociguat;

Interferons, including but not limited to, interferon beta-la interferon beta-1b;

Sphingosine 1-phosphate receptor modulators, including but not limited to, fingolimod, ponesimod;

Inhibitors of the complement pathway, including but not limited to, C5aR antagonists (such as CCX168, PMX-53, NN8210), C5 inhibitors (such as eculizumab), inhibitors of complement factors B and D, inhibitors of MASP2 (such as OMS-721) and ARC-1905;

Inhibitors of Janus kinases (one of more of JAK1, JAK2, JAK3, TYK2), including but not limited to, decernotinib, cerdulatinib, JTE-052, ruxolitinib, tofacitnib, Baricitinib, Peficitinib, GLPG-0634, INCB-47986, INCB-039110, PF-04965842, XL-019, ABT-494, R-348, GSK-2586184, AC-410, BMS-911543 and PF-06263276;

Inhibitors of other anti-inflammatory or immunomodulatory kinases, including but not limited to, spleen tyrosine kinase (SYK) inhibitors, p38 MAP kinase inhibitors (such as PF-3715455, PH-797804, AZD-7624, AKP-001, UR-13870, FX-005, semapimod, pexmetinib, ARRY-797, RV-568, dilmapimod, ralimetinib), PI3K inhibitors (such as GSK-2126458, pilaralisib, GSK-2269557), PI3Kg and/or PI3Kd inhibitors (such as CAL-101/GS-1101, duvelisib), JNK inhibitors, ERK1 and/or 2 inhibitors, IKKb inhibitors, BTK inhibitors, ITK inhibitors, ASK1 inhibitors (such as GS-4997), PKC inhibitors (such as sotrastaurin), TrkA antagonists (such as CT-327), MEK1 inhibitors (such as E6201);

Antioxidants, including but not limited to, myeloperoxidase inhibitors (such as AZD-3241), NOX4 and other NOX enzymes (such as GKT-137831) and N-acetyl cysteine;

Inhibitors of IL5, including but not limited to, mepolizumab, reslizumab and benralizumab;

Inhibitors of IL4, including but not limited to, pascolizumab, altrakincept and pitrakinra;

Inhibitors of IL13, including but not limited to, tralokinumab, anrukinzumab and lebrikizumab;

Anti-IL6 agents, including but not limited to, tocilizumab, olokizumab, siltuximab, PF-4236921 and sirukumab;

Inhibitors/Antagonists of IL17/IL17R, including but not limited to, secukinumab, RG-7624, brodalumab and ixekizumab;

Antagonists of IL12 and/or IL23, including but not limited to, tildrakizumab, guselkumab, MEDI12070 and AMG 139;

Inhibitors of IL33, including but not limited to, AMG 282;

Inhibitors of IL9, including but not limited to, MEDI-528;

Inhibitors of GM-CSF, including but not limited to, MT203;

Anti CD4 agents, including but not limited to, tregalizumab and rigerimod;

CRTH2 antagonists, including but not limited to, AZD-1981;

Inhibitors of B lymphocyte stimulator (BLYS; also known as BAFF), a protein that is often increased in patients with SLE, including but not limited to, belimumab, tabalumab, blisibimod, and atacicept;

CD22-specific monoclonal antibodies, including but not limited to, epratuzumab;

Inhibitors of interferon-α, including but not limited to, sifalimumab and rontalizumab;

Inhibitor of type I interferon receptors, including but not limited to, MEDI-546;

FcγRIIB agonists, including but not limited to, SM-101;

Modified and/or recombinant versions of Heat Shock Protein 10 (Hsp10, also known as Chaperonin 10 or EPF), including but not limited to, INV-103;

Inhibitors of the TNF superfamily receptor 12A (TWEAK receptor), including but not limited to, BIIB-023, enavatuzumab, and RG-7212;

Inhibitors of xanthine oxidase, including but not limited to, allopurinol, benzbromarone, febuxostat, topiroxostat, tisopurine and inositols;

Inhibitors of URAT1 (also known as SLC22A12), including but not limited to, lesinurad, RDEA 3170, UR1102 and levotofispam;

Inhibitors of toll-like receptors (TLRs), including but not limited to, one or more of TLR7, TLR8, TLR9 (such as IMO-8400, IMO-3100, DV-1179), TLR2 and/or TLR 4 (such as VB-201, OPN-305);

Agonists of TLRs, including but not limited to, TLR7 (such as GSK2245035, AZD8848), TLR9 (such as AZD1419);

Activators SIRT1, including but not limited to, SRT2104;

A3 receptor agonists, including but not limited to, CF101;

Other agents of use of the treatment of psoriasis, including but not limited to, IDP-118, LAS41004, LEO 80185, LEO 90100, PH-10, WBI-1001, CNT01959, BT-061, cimzia, ustekinumab, MK-3222/SCH 900222, ACT-128800, AEBO71, alitretinoin, ASP015K, Apo805K1, BMS-582949, FP187, hectoral (doxercalciferol), LEO 22811, Ly3009104 (INCB28050), calcipotriene foam (STF 115469), tofacitinib (CP-690,550), M518101 and CycloPsorb™;

Antifibrotic agents, including but not limited to: pirfenidone, inhibitors of LOXL2 (such as Simtuzumab), FT-011, modulators of epiregulin and/or TGFβ (such as LY-3016859), modulators of TGFβ (such as LY-2382770, fresolimumab);

Prolyl hydroxylase inhibitors, including but not limited to, GSK1278863, FG-2216, ASP-1517/FG-4592, AKB-6548, JTZ-951, BAY-85-3934 and DS-1093;

Inhibitors of granulocyte macrophage colony-stimulating factor, including but not limited to, GSK3196165 (MOR103), PD-0360324 and mavrilimumab;

Inhibitors of MAdCAM and/or $\alpha 4\beta 7$ integrin, including but not limited to, PF-00547659 and MEDI7183 (abrilumab);

Inhibitors of connective tissue growth factor (CTGF), including but not limited to, PF-06473871; Inhibitors of cathepsin C, including but not limited to, GSK2793660;

Inhibitors of soluble epoxide hydrolase, including but not limited to, GSK2269557;

Inhibitors of the TNFR1 associated death domain protein, including but not limited to, GSK2862277;

Anti-CD19 agents, including but not limited to, MEDI-551 and AMG 729;

Anti-B7RP1 agents/inhibitors of ICOS ligand, including but not limited to, MEDI5872 and AMG-557;

Inhibitors of thymic stromal lymphoprotein, including but not limited to, AMG157;

Inhibitors of IL2, including but not limited to, daclizumab;

Inhibitors of Leucine rich repeat neuronal protein 6A, including but not limited to, Anti-Lingo (Biogen);

Inhibitors of integrins, including but not limited to, alpha-V/beta-6 (STX-100) and alpha-V/beta-3 (VPI-2690B);

Anti-CD40L agents, including but not limited to, CDP-7657;

Modulators of the dopamine D3 receptor, including but not limited to, ABT-614;

Inhibitors and/or modulators of galectin-3, including but not limited to, GCS-100 and GR-MD-02;

Agents for treating diabetic nephropathy, including but not limited to, DA-9801 and ASP-8232;

Agents for treating acute kidney injury, including but not limited to, THR-184, TRC-160334, NX-001, EA-230, ABT-719, CMX-2043, BB-3 and MTP-131;

Modulators of inflammasomes, including but not limited to, inhibitors of NLRP3;

Modulators of bromodomains, including but not limited to, BRD4;

Modulators of GPR43; and

Inhibitors of TRP channels, including but not limited to, TRPA1, TRPC3, TRPC5, TRPC6 and TRPC6.

Additional therapeutic agents include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, epinephrine, nitroglycerin, nitroprusside, etc.

Combination agents useful for treating vasculitis are included, for example, azathioprine, cyclophosphamide, mycophenolate, mofetil, rituximab, etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another embodiment the second agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another embodiment, the agent is at least one anti-platelet agent. Especially preferred anti-platelet agents are aspirin and clopidogrel. The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as celecoxib or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE3 inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase. Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil. Examples of suitable cardiac glycosides include *digitalis* and ouabain.

In one embodiment, a compound of the invention may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™). In another embodiment, a compound of the invention may be co-administered with a loop diuretic. In still another embodiment, the loop diuretic is selected from furosemide and torsemide. In still another embodiment, one or more compounds of the invention may be co-administered with furosemide. In still another embodiment, one or more compounds of the invention may be co-administered with torsemide which may optionally be a controlled or modified release form of torsemide.

In another embodiment, a compound of the invention may be co-administered with a thiazide-type diuretic. In still another embodiment, the thiazide-type diuretic is selected from the group consisting of chlorothiazide and hydrochlorothiazide. In still another embodiment, one or more compounds of the invention may be co-administered with chlorothiazide. In still another embodiment, one or more compounds of the invention may be co-administered with hydrochlorothiazide. In another embodiment, one or more compounds of the invention may be co-administered with a phthalimidine-type diuretic. In still another embodiment, the phthalimidine-type diuretic is chlorthalidone.

Examples of suitable combination mineralocorticoid receptor antagonists include spironolactone and eplerenone. Examples of suitable combination phosphodiesterase inhibitors include: PDE3 inhibitors (such as cilostazol); and PDE5 inhibitors (such as sildenafil).

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesteryl ester transfer protein inhibitors.

Anti-inflammatory agents also include sPLA2 and IpPLA2 inhibitors (such as darapladib), 5 LO inhibitors (such as atrelueton) and IL-1 and IL-1 r antagonists (such as canakinumab).

Other atherosclerotic agents include agents that modulate the action of PCSK9, for example, called bococizumab.

Cardiovascular complications of type 2 diabetes are associated with deleterious levels of MPO, accordingly, the compounds of the present invention may be used in combination with anti-diabetic agents, particularly type 2 antidiabetic agents. Examples of suitable anti-diabetic agents include (e.g. insulins, metfomin, DPPIV inhibitors, GLP-1 agonists, analogues and mimetics, SGLT1 and SGLT2 inhibitors) Suitable anti-diabetic agents include an acetyl-CoA carboxylase- (ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a PDE10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

The compounds of the present invention may be used in combination with neuroinflammatory and neurodegenerative agents in mammals. Examples of additional neuroinflammatory and neurodegenerative agents include antidepressants, antipsychotics, anti-pain agents, anti-Alzheimer's agents, and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, nortriptyline, protriptyline, amoxapine, desipramine and maprotiline. Examples of suitable SSRIs include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable SNRIs of use in the present invention include venlafaxine. Examples of suitable atypical anti-depressants include bupropion, lithium, trazodone and viloxazine. Examples of anti-Alzheimer's agents include NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A receptor (5-HT1A) agonists, and CRF antagonists. Suitable benzodiazepines include alprazolam, chlordiazepoxide, clonazepam, chlorazepate, diazepam, lorazepam, oxazepam, and prazepam. Suitable 5-HT1A receptor agonists include buspirone and ipsapirone. Suitable CRF antagonists include verucerfont. Suitable atypical antipsychotics include paliperidone, ziprasidone, risperidone, aripiprazole, olanzapine, and quetiapine. Suitable nicotine acetylcholine agonists include CP-601927 and varenicline. Anti-pain agents include pregabalin, gabapentin, clonidine, neostigmine, baclofen, midazolam, ketamine and ziconotide.

Inasmuch as it may be desirable to administer a combination of active compounds, for example, for the purpose of treating a particular disease or condition, it is within the scope of the present invention that two or more pharmaceutical compositions, at least one of which comprises a compound of the invention, may conveniently be combined in the form of a kit suitable for co-administration of the compositions. Representative kits include at least one compound of the present invention and a package insert or other labeling including directions.

Compounds of the present invention can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given; other process conditions can also be used unless otherwise stated. Optimum reaction conditions can vary with the particular reactants or solvent used. Those skilled in the art will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatography such as high-performance liquid chromatograpy (HPLC), gas chromatography (GC), gel-permeation chromatography (GPC), or thin layer chromatography (TLC).

Preparation of the compounds can involve protection and deprotection of various chemical groups. The chemistry of protecting groups can be found, for example, in Greene et al., *Protective Groups in Organic Synthesis,* 4th. Ed. (John Wiley & Sons, 2007), the entire disclosure of which is incorporated by reference herein for all purposes.

The reactions or the processes described herein can be carried out in suitable solvents, which can be readily selected by one skilled in the art. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art. The reagents used in the preparation of the compounds of these teachings can be either commercially obtained or can be prepared by standard procedures described in the literature. For example, compounds of the present invention can be prepared according to the methods illustrated in the following Synthetic Schemes.

Scheme 1

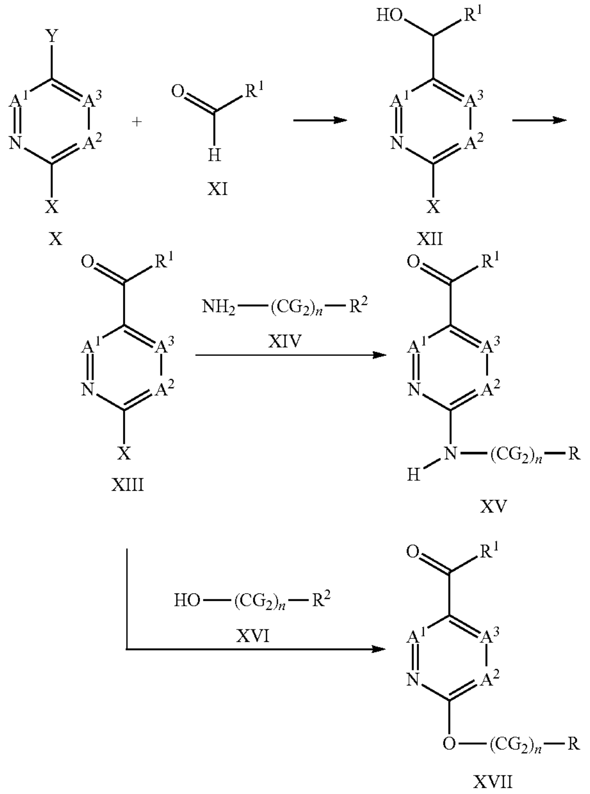

According to Scheme 1 the Formula XV compounds wherein $A^1$, $A^2$, $A^3$, G, $R^1$ and $R^2$ are defined as above and n is 1 or 2, may be prepared from the Formula X compounds, wherein $A^1$, $A^2$, and $A^3$ are defined as above and X and Y are halides, typically Y is bromo and X is chloro, by Grignard reaction, oxidation of the resulting alcohol, and aromatic nucleophilic substitution reaction with an appropriate Formula XIV compound wherein G and $R^2$ are defined as above and n is 1 or 2.

Compounds of Formula XI and XIV can be prepared by the methods described above as well as by methods known in the art. The compounds of Formula XI and XIV used in the preparation of the compounds of these teachings can be either commercially obtained or can be prepared by standard procedures described in the literature. For example, a Formula XIV compound such as 1-(pyrazin-2-yl)cyclopropanamine was prepared from 2-fluoropyrazine as described in step 1 through step 4 for Example 5.

Thus, the Formula XII compounds wherein $A^1$, $A^2$, $A^3$ and $R^1$ are defined as above and X is a halide, typically chloro, may be prepared from the appropriate Formula X and Formula XI compounds, wherein $R^1$ is defined as above, by Grignard reaction.

For example, the Formula X compound may be conveniently converted to the Grignard reagent by addition of an alkylmagnesium halide such as isopropylmagnesium chloride in an aprotic solvent such as tetrahydrofuran at a low temperature of about −78° C. to about −20° C., typically −30° C., over a period of about 10 min to about 30 min, to a solution of Formula X compound in an aprotic solvent like tetrahydrofuran at a low temperature of about −78° C. to about −20° C., typically −30° C. The resulting mixture is typically stirred at a low temperature of about −78° C. to about −20° C., typically −30° C. for about 1 h to about 30 minutes. To this mixture, the Formula XI compound is added at a low temperature of about −78° C. to about −20° C., typically −30° C. for about 2 h to about 1 h to prepare the desired Formula XII compound.

The Formula XIII compounds wherein $A^1$, $A^2$, $A^3$ and $R^1$ are defined as above and X is a halide, typically chloro may be prepared by oxidation of Formula XII compounds.

For example, the Formula XII compound is treated with an oxidizing reagent such as Dess-Martin periodinane in an aprotic solvent such as dichloromethane at ambient temperature for about 6 h to about 1 h, typically 1.5 h to prepare the desired Formula XIII compound.

The Formula XV compounds may be prepared from Formula XIII compounds by aromatic nucleophilic substitution reaction with an appropriate Formula XIV compound.

For example, the Formula XIII compound is combined with the Formula XIV compound in an aprotic solvent such as tetrahydrofuran in the presence of a base such as diisopropylethyl amine at a temperature of about 100° C. to about 50° C., typically 60° C. for about 18 h to about 4 h to prepare the Formula XV compound.

According to Scheme 1 the Formula XVII compounds wherein $A^1$, $A^2$, $A^3$, G, $R^1$ and $R^2$ are defined as above and n is 1 or 2, may be prepared from the Formula XIII compounds by aromatic nucleophilic substitution reaction with an appropriate Formula XVI compound wherein G and $R^2$ are defined as above and n is 1 or 2.

For example, the Formula XIII compound is combined with the Formula XVI compound in a polar solvent such as acetonitrile in the presence of a base such as cesium carbonate at a temperature of about 60° C. to about 25° C., typically 25° C. for about 18 h to about 2 h to prepare the Formula XVII compound.

Scheme 2

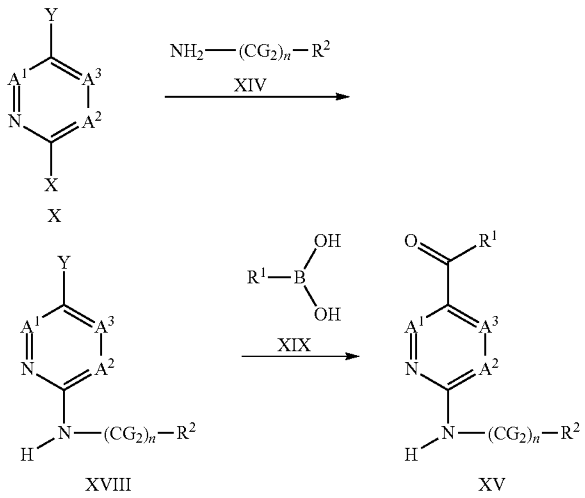

Alternatively, and according to Scheme 2, the Formula XV compounds may be prepared from the Formula X compounds by aromatic nucleophilic substitution reaction with an appropriate Formula XIV compound and carbonylative Suzuki-Miyaura coupling with an appropriate Formula XIX compound wherein $R^1$ is defined as above.

Thus, the Formula XVIII compounds wherein $A^1$, $A^2$, $A^3$, G and $R^2$ are defined as above, Y is a halide, typically bromo, and n is 1 or 2, may be prepared from the appropriate Formula X and Formula XIV compounds by aromatic nucleophilic substitution reaction.

For example, the Formula X compound is combined with the Formula XIV compound in a solvent such as isopropanol in the presence of a base such as diisopropylethyl amine under microwave irradiation at an elevated temperature of about 160° C. to about 120° C., typically 160° C. for about 2 h to about 1 h to prepare the Formula XVIII compound.

The Formula XV compounds may be prepared by carbonylative Suzuki-Miyaura coupling with an appropriate Formula XIX compound. The carbonylative Suzuki coupling has been described previously by Bjerglund et al. *Org. Lett.* 2014, 16, 1888-1891 and Jafarpour et al. *Eur J. Org. Chem.* 2011, 2128-2132.

For example, the Formula XVIII compound is combined with a phosphine ligand such as catacxium A in a solvent such as anisole-toluene combined in equal proportions and in the presence of a base such as diisopropylethylamine. The mixture is degassed with an inert gas such as argon for about 30 minutes to about 5 minutes and then sonicated for about 15 minutes to about 5 minutes. This process is repeated several times, typically three times. This mixture is combined with Formula XIX compound in the presence of molybdenum hexacarbonyl and a solution of a palladium catalyst such as palladium diacetate in a solvent such as anisole. The mixture is heated at a temperature of about 160° C. to about 100° C., typically 120° C. for about 24 h to about 12 h to prepare the Formula XV compound.

substitution reaction with an appropriate Formula XIV compound wherein G and $R^2$ are defined as above and n is 1 or 2.

Thus, the Formula XXI compounds wherein $R^1$ and $R^3$ are defined as above and X is a halide, typically chloro, may be prepared from the appropriate Formula XX and Formula XI compounds, wherein $R^1$ is defined as above, by Grignard reaction.

For example, the Formula XX compound may be conveniently converted to the Grignard reagent by addition of an alkylmagnesium halide such as isopropylmagnesium chloride in an aprotic solvent such as tetrahydrofuran at a low temperature of about −78° C. to about −20° C., typically −30° C., over a period of about 10 min to about 30 min, to a solution of Formula XX compound in an aprotic solvent like tetrahydrofuran at a low temperature of about −78° C. to about −20° C., typically −30° C. The resulting mixture is typically stirred at a low temperature of about −78° C. to about −20° C., typically −30° C. for about 1 h to about 30 minutes. To this mixture, the Formula XI compound is added at a low temperature of about −78° C. to about −20° C., typically −30° C. for about 2 h to about 1 h to prepare the desired Formula XXI compound.

The Formula XXII compound wherein $R^1$ and $R^3$ are defined as above and X is a halide, typically chloro may be prepared by oxidation of Formula XXI compound.

For example, the Formula XXI compound is treated with an oxidizing reagent such as Dess-Martin periodinane in an aprotic solvent such as dichloromethane at ambient temperature for about 6 h to about 1 h, typically 1.5 h to prepare the desired Formula XXII compound.

The Formula XXIII compound may be prepared from Formula XXII compound by aromatic nucleophilic substitution reaction with an appropriate Formula XIV compound.

For example, the Formula XXII compound is combined with the Formula XIV compound in an aprotic solvent such as tetrahydrofuran in the presence of a base such as diiso- Scheme 3

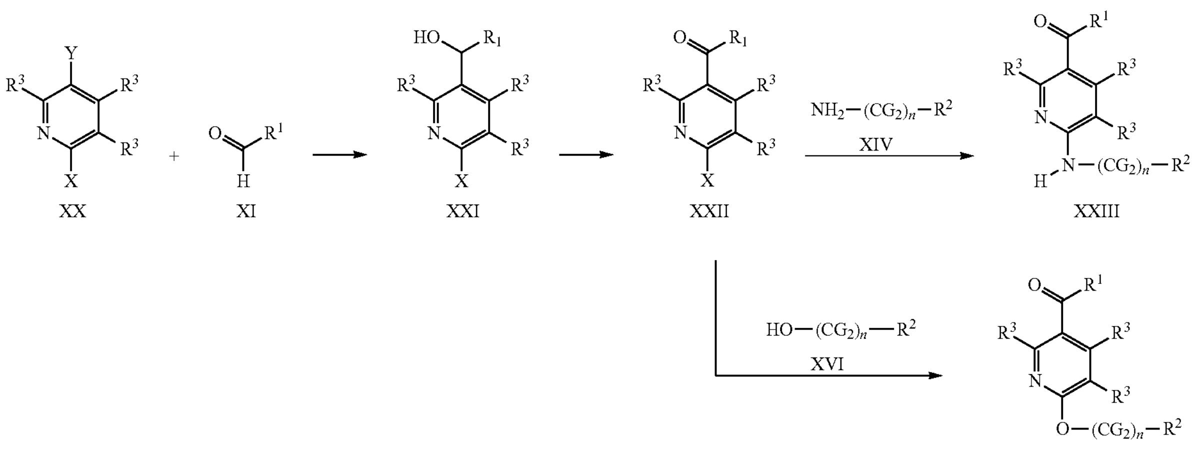

XX XI XXI XXII XXIII
XXIV

According to Scheme 3 the Formula XXIII compounds wherein G, $R^1$, $R^2$ and $R^3$ are defined as above and n is 1 or 2, may be prepared from the Formula XX compounds, wherein $R^3$ is defined as above and X and Y are halides, typically Y is bromo and X is chloro, by Grignard reaction, oxidation of the resulting alcohol, and aromatic nucleophilic propylethyl amine at a temperature of about 100° C. to about 50° C., typically 60° C. for about 18 h to about 4 h to prepare the Formula XXIII compound.

According to Scheme 3 the Formula XXIV compounds wherein G, $R^1$, and $R^3$ are defined as above and n is 1 or 2, may be prepared from the Formula XXII compounds by aromatic nucleophilic substitution reaction with an appropriate Formula XVI compound wherein G and $R^2$ are defined as above and n is 1 or 2.

For example, the Formula XXII compound is combined with the Formula XVI compound in a polar solvent such as acetonitrile in the presence of a base such as cesium carbonate at a temperature of about 60° C. to about 25° C., typically 25° C. for about 18 h to about 2 h to prepare the Formula XXIV compound.

EXAMPLES AND PREPARATIONS

In the non-limiting Examples and Preparations that are set out later in the description, and in the aforementioned Schemes, the following the abbreviations, definitions and analytical procedures may be referred to:

br.—broad peaks
° C.—degree Celsius
$CDCl_3$—deuterated chloroform
$CD_3OD$—deuterated methanol
d—doublet peak
dd—double doublet peak
DMSO-d6—perdeuterated dimethyl sulfoxide
dt—double triplet peak
g—gram(s)
GC—gas chromatography
H (e.g., 1H, 2H) —hydrogen(s)
h—hour (s)
hr—hour(s)
LC—liquid chromatography
m—multiplet
M—molarity
MeOH-d4—deuterated methanol
mg—milligram(s)
MHz—megahertz
min—minute(s)
mL—milliliter(s)
mmol—millimole(s)
mp—melting point
MS—mass spectrum
N—normality
NMR—nuclear magnetic resonance
pH—negative logarithm of hydronium ion concentration
q—quartet peak
Rf— retention factor
s—singlet peak
t—triplet peak
td—triple doublet peak
TLC—thin layer chromatography
uL—microliter Unless indicated otherwise, the following chemical formulas and acronyms have the indicated meanings:

AcOH—glacial acetic acid
DCM—dichloromethane
DIEA—diisopropylethylamine
DIPEA—N,N-Diisopropylethylamine
DMF—dimethylformamide
DMSO—dimethylsulfoxide
DPPA—diphenylphosphoryl azide
$Et_3N$—triethylamine
EtOAc—ethyl acetate
FA—formic acid
$H_2$—hydrogen gas
$H_2O_2$—hydrogen peroxide
HCl—hydrochloric acid
HPLC—high performance liquid chromatography
IPA—isopropyl alcohol
iPrMgCl—isopropylmagnesium chloride
MeCN—acetonitrile
MeOH—methanol
$Mo(CO)_6$—molybdenum hexacarbonyl
$K_2CO_3$—potassium carbonate
KHMDS—potassium bis(trimethylsilyl)amide
$Na_2SO_4$—sodium sulfate
$Na_2S_2O_3$—sodium thiosulfate
NaBr—sodium bromide
NaH—sodium hydride
$NaHCO_3$—sodium bicarbonate
NaOH—sodium hydroxide
$NH_4Cl$—ammonium chloride
$NiCl_2.6H_2O$—nickel(II) chloride hexahydrate
NMP—N-methyl-2-pyrrolidinone
Pd—C—palladium on carbon
$Pd(OAc)_2$—palladium(II) acetate
$Pd(PPh_3)_4$—tetrakis(triphenylphosphine)palladium(0)
$POCl_3$—phosphorus oxychloride
$SOCl_2$—thionyl chloride
TFA—trifluoroacetic acid
THF—tetrahydrofuran Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.).

Products were generally dried under vacuum before being carried on to further reactions or submitted for biological testing. $^1H$ Nuclear magnetic resonance (NMR) spectra were in all cases consistent with the proposed structures. Characteristic chemical shifts (6) are given in parts-per-million referenced to residual peaks from the deuterated solvents employed using conventional abbreviations for designation of major peaks: e.g. s, singlet; d, doublet; t, triplet; q, quartet; m, multiplet; br, broad. The following abbreviations have been used for common solvents: $CDCl_3$, deuterochloroform; DMSO-$d_6$, deuterodimethylsulfoxide; and MeOH-$d_4$, deuteromethanol. Where appropriate, tautomers may be recorded within the NMR data; and some exchangeable protons may not be visible. Mass spectra, MS (m/z), were recorded using either electrospray ionisation (ESI) or atmospheric pressure chemical ionisation (APCI). Where relevant and unless otherwise stated the m/z data provided are for isotopes $^{19}F$, $^{35}Cl$, $^{79}Br$ and $^{127}I$.

In general, reactions were followed by thin layer chromatography and/or liquid chromatography-mass spectrometry, and subjected to work-up when appropriate. It will be recognized by one skilled in the art that purifications may vary between experiments: in general, sorbents, solvents and the solvent ratios used for eluants/gradients were chosen to provide appropriate Rfs or retention times. It will also be recognized by one skilled in the art that HPLC purifications may be effected in a variety of ways, including the use of normal stationary phases, reverse stationary phases, chiral stationary phases, and supercritical eluants. The appropriate choices of conditions for chromatographic and HPLC purifications will be discerned by one skilled in the art.

HPLC Methods:

Method 1: Column: Waters symmetry 2.1×50 mm 5 um Mobile phase: MeCN/water (0.05% TFA); 10 to 80%; wavelength: 220 nm. 6 min run.

Method 2: Column: Gemini NX C18 50×4.6 mm, 3 um, Mobile phase: MeCN/water (0.05% formic acid); wavelength: 220 nm. 8 min run Method 3: Column: ZORBAX XDB C18 4.6×50 mm 1.8 um Mobile phase: MeCN/water (0.05% TFA): wavelength: 220 nm. 9 min run Method 4: Column: Eclipse XDB C18 150×4.6 mm 5 um, Mobile phase: MeCN/water (10 mM NH4OAc).

Method 5: Column: Luna Silica-2 (4.6×250 mm 5 u). normal phase 22 min run.

Method SP3126: HPLC column: RESTEK C18 (30×2.1) 3 u; temperature 50° C.; Mobile phase A: 0.05% formic acid in water (v/v); Mobile phase B: acetonitrile; Gradient 98% A/2% B hold for 0.74 minute, 98% A/2% B to 90% A/10% B in 0.25 minute, 90% A/10% B to 2% A/98% B in 1 minute, hold at 90% A/10% B to 2% A/98% B for 0.25 minute, 2% A/98% B to 98% A/2% B in 0.65 minute, hold at 98% A/2% B for 0.1 minute. Flow rate 1.5 mL/min.

Either IUPAC or ACD Labs have been used as naming packages, and are interchangeable throughout the Examples and Preparations.

Example 1: Preparation of 3-[(2-{[1-(pyrimidin-5-yl)cyclopropyl]amino}pyrimidin-5-yl)carbonyl]benzonitrile Step 1:

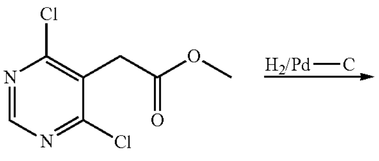

1

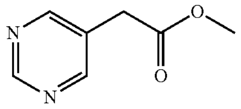

2

To a stirred solution of methyl (4,6-dichloropyrimidin-5-yl)acetate (1, 5 g, 22.62 mmol) in THF was added triethylamine (8.6 mL, 61.39 mmol) and the resulting mixture was degassed with argon. Then 5% Pd—C was added to the reaction mixture and it was subjected to hydrogenation using hydrogen balloon for 16 hours. After completion (monitored by TLC, 30% EtOAc in hexanes, Rf 0.3), it was filtered through Celite and washed with THF (3×50 mL). The filtrate was concentrated under reduced pressure and the crude residue was purified by column chromatography (100-200 mesh silica, gradient elution of 100% hexanes to 30% ethyl acetate in hexanes) to afford methyl pyrimidin-5-ylacetate (2) as light yellow liquid. Yield: 2.6 g (75.5%). $^1$H NMR (400 MHz, DMSO-$d_6$) δ 9.08 (s, 1H), 8.72 (s, 2H), 3.81 (s, 2H), 3.65 (s, 3H). LCMS [M+H]$^+$: 153.0

Step 2:

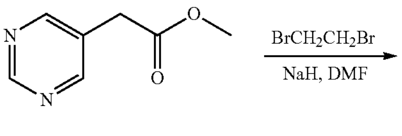

2

-continued

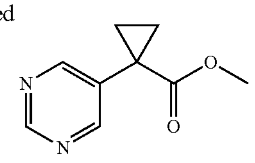

3

To a stirred solution of methyl pyrimidin-5-ylacetate (2, 2.6 g, 17.08 mmol) in DMF (15 mL) was added 60% NaH (1.4 g, 34.16 mmol) portion wise at 0° C. and the resulting mixture was stirred at room temperature for 45 minutes. To the resulting mixture was then added 1,2-dibromoethane (4.4 mL, 51.26 mmol) drop wise at 0° C. over a period of 10 minutes and the reaction mixture was further stirred at room temperature for 2 hours. After completion (monitored by TLC, 50% EtOAc in hexanes, Rf 0.6), the residue was partitioned between water (50 mL) and ethyl acetate (200 mL). Organic part was separated and the aqueous part extracted with ethyl acetate (2×100 ml). Combined organic layers were washed with brine, dried over sodium sulfate and concentrated under vacuo. The crude residue was purified by column chromatography (100-200 mesh silica, gradient elution of 100% hexanes to 20% ethyl acetate in hexanes) to afford 1.2 g of methyl 1-(pyrimidin-5-yl)cyclopropanecarboxylate (3) as light yellow liquid. Yield: 1.2 g (39.4%). $^1$H NMR (400 MHz, DMSO-$d_6$) δ 9.08 (s, 1H), 8.80 (s, 2H), 3.58 (s, 3H), 1.55 (m, 2H), 1.37 (m, 2H). LCMS [M+H]$^+$: 179.2

Step 3:

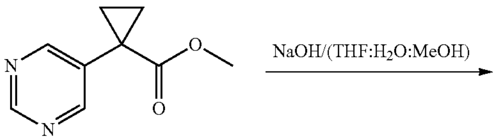

3

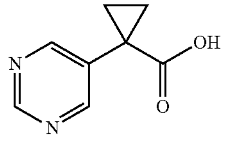

4

To a stirred solution of methyl 1-(pyrimidin-5-yl)cyclopropanecarboxylate (3, 1.2 g, 6.73 mmol) in THF:MeOH:$H_2O$ [1:1:1; 30 mL] was added NaOH (540 mg, 13.47 mmol) at 0° C. and the resulting mixture was stirred at room temperature for 2 hours. After completion (monitored by TLC, 50% EtOAc in hexanes, Rf=0.1), the reaction mixture was concentrated under reduced pressure. The residue was diluted with water (10 mL) and the resulting solution was neutralized with 2N HCl solution. Excess water was evaporated under vacuo 10% MeOH/DCM (50 mL) was added to the resulting semi-solid mass. The resulting slurry was stirred for 30 minutes and filtered. The filtrate was concentrated under vacuo and the resulting mass was azeotroped with toluene (2×20 mL) to afford 1-(pyrimidin-5-yl)cyclopropanecarboxylic acid (4) as an off-white solid. This material was used for the next step without further purification.

Yield: 900 mg (81.4%). $^1$H NMR (400 MHz, DMSO-$d_6$) δ 9.00 (s, 1H), 8.71 (s, 2H), 1.40 (m, 2H), 1.12 (m, 2H). LCMS $[M+H]^+$: 163.0

Step 4:

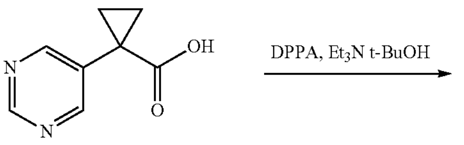

4

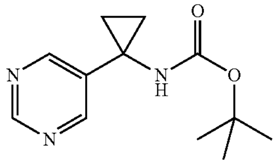

5

To a stirred solution of 1-(pyrimidin-5-yl)cyclopropanecarboxylic acid (4, 900 mg, 5.48 mmol) in toluene (25 mL) were added triethylamine (0.9 mL, 6.57 mmol) and diphenyl phosphoryl azide (1.3 mL, 5.92 mmol) drop wise. The resulting mixture was stirred at room temperature for 1 hour. Tert-butanol (2.6 mL, 26.86 mmol) was then added to the reaction mixture and it was heated at 90° C. for 3 hours. After completion (monitored by TLC, 50% EtOAc in hexanes, Rf 0.4), the reaction mixture was partitioned between water (50 mL) and ethyl acetate (200 mL). Organic part was separated and the aqueous part was further extracted with ethyl acetate (2×50 mL). Combined organic layer was washed with brine, dried over sodium sulfate and concentrated under vacuo. The crude residue was purified by column chromatography (100-200 mesh silica, gradient elution of 100% hexanes to 20% ethyl acetate in hexanes) to afford tert-butyl [1-(pyrimidin-5-yl)cyclopropyl]carbamate (5) as yellow sticky gum. Yield: 550 mg (42.6%). $^1$H NMR (400 MHz, DMSO-$d_6$) δ 8.99 (br s, 1H), 8.54 (br s, 2H), 7.84 (s, 1H), 1.37 (s, 9H), 1.35-1.05 (m, 4H). LCMS $[M+H]^+$: 236.1

Step 5:

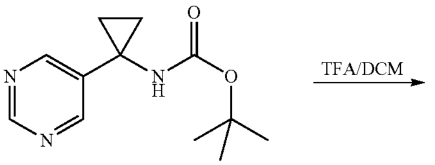

5

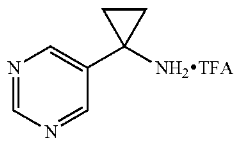

6

To a stirred solution of tert-butyl [1-(pyrimidin-5-yl)cyclopropyl]carbamate (5, 550 mg, 2.34 mmol) in DCM (5 mL) was added TFA (1.8 mL, 23.37 mmol) drop-wise at 0° C. and the resulting mixture was stirred at room temperature for 2 hours. After completion (monitored by TLC, 5% MeOH in DCM, Rf 0.1), the reaction mixture was concentrated under reduced pressure. The residue was triturated with diethyl ether and concentrated under vacuo to afford 1-(pyrimidin-5-yl)cyclopropanamine trifluoroacetate (6) as an off-white solid. Yield: 250 mg (43%). $^1$H NMR (400 MHz, DMSO-$d_6$) δ 9.17 (s, 1H), 8.93-8.84 (m, 5H), 1.37 (m, 4H). LCMS $[M+H]^+$: 136.0

Step 6:

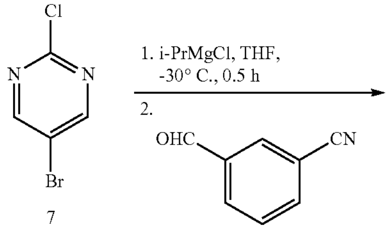

7

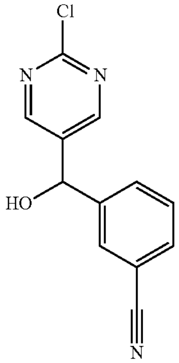

8

5-Bromo-2-chloropyrimidine (7, 19.3 g, 1 eq, 0.1 mol) was dissolved in 500 mL of dry THF and cooled at −40° C. under nitrogen. To this solution was added i-PrMgCl solution in THF (75 mL, 0.15 mol) at −30° C. over 15 minutes, then stirred at −30° C. for more 30 minutes. To the resulting mixture was added 3-formylbenzonitrile (16.4 g, 0.125 mol). The mixture was stirred at −30° C. for an additional hour. The reaction was quenched by addition of saturated $NH_4Cl$ (250 mL) and extracted with ethyl acetate (1 L). Combined organic extracts were washed with brine, dried over $Na_2SO_4$, filtered and concentrated under reduced pressure to give the crude product, which was purified by column chromatography on silica gel (eluting with petroleum ether/ethyl acetate, from 95/5 to 60/40) to yield 8.0 g of desired 3-[(2-chloropyrimidin-5-yl)(hydroxy)methyl]benzonitrile (8) (yield: 32.6%). LCMS: $[M+H]^+$: 245.9. $^1$H NMR (400 MHz, CDCl3) δ 8.60 (s, 2H), 7.72 (s, 1H), 7.64 (d, 1H), 7.59 (d, 1H), 7.53 (t, 1H), 5.94 (d, 1H), 3.14 (d, 1H).

Step 7:

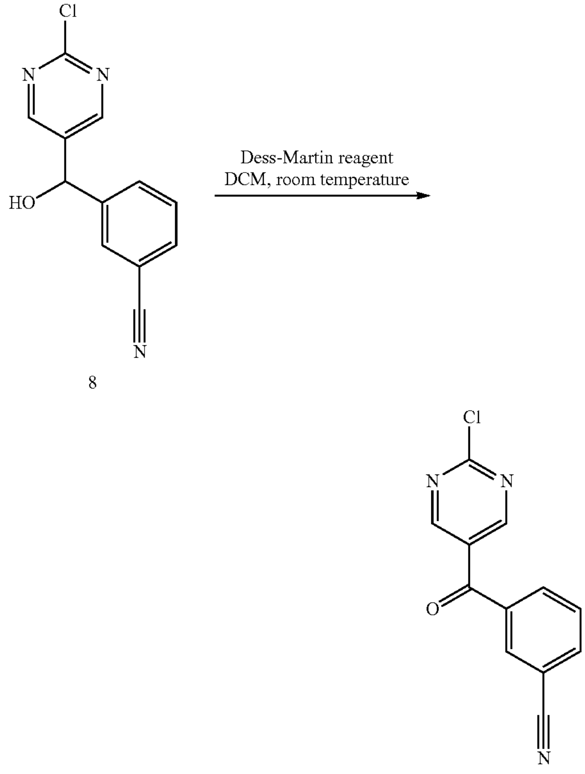

8

9

To a solution of 3-[(2-chloropyrimidin-5-yl)(hydroxy)methyl]benzonitrile (8, 2.0 g, 8.163 mmol, 1 eq.) in dry DCM (30 mL), was added Dess-Martin periodinane (6.92 g, 16.33 mmol, 2 eq.). The mixture was stirred at room temperature for 1.5 hours. TLC showed compound 8 was consumed. The mixture was washed in turn with aqueous $Na_2S_2O_3$ (20% w.t., 15 mL) and brine, dried over $Na_2SO_4$, filtered and concentrated under reduced pressure to give the crude product, which was purified by column chromatography on silica gel (eluting with petroleum ether/ethyl acetate, from 10/1 to 2/1) to give 3-[(2-chloropyrimidin-5-yl)carbonyl]benzonitrile (9) as a white solid. Yield: 1.1 g (55%). $^1$H NMR (400 MHz, DMSO-$d_6$) δ 9.11 (s, 2H), 8.35 (d, 1H), 8.34-8.18 (m, 2H), 7.83 (t, 1H). LCMS: $[M+H]^+$: 243.9.

Step 8:

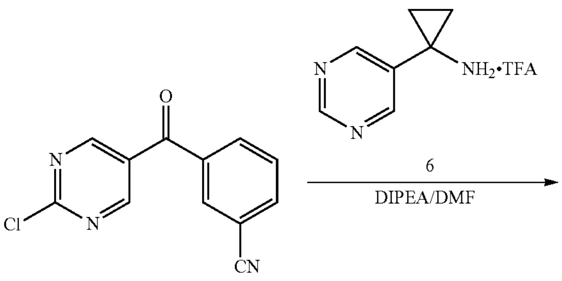

9

-continued

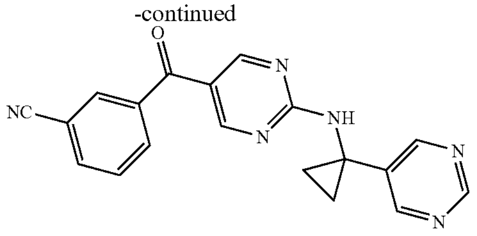

To a stirred solution of 3-(2-chloro-pyrimidine-5-carbonyl)-benzonitrile (9, 6.5 g, 26.7 mmol) and 1-(pyrimidin-5-yl)cyclopropanamine trifluoroacetate (6, 7.5 g, 30.9 mmol) in dry THF (120 mL) was added drop-wise DIEA (33 g, 258 mmol) at room temperature. After the addition, the reaction mixture was stirred at 60° C. for 4 hours after which time the reaction was completed. The reaction mixture was concentrated to give residue, which was dissolved in ethyl acetate (150 mL), washed with brine (80 mL×2), dried over $Na_2SO_4$ and concentrated in vacuo to give the crude product. The crude was purified by column chromatography (eluted with petroleum ether/THF from 3/1 to 1/1) to give the title compound (7.2 g) with 85% purity, which was further purified by prep-HPLC to afford 3-[(2-{[1-(pyrimidin-5-yl)cyclopropyl]amino}pyrimidin-5-yl)carbonyl]benzonitrile as an off-white solid. Yield: 5 g (54%) as a light yellow solid.

Prep-HPLC condition:

The raw material was dissolved in THF.

Column: LUNA 250 mm×50 mm, 10 μm

Mobile phase: A: $H_2O$+0.25% FA, B: ACN

Gradient: B from 15% to 40% in 25 min

Flow rate: 90 mL/min

Detective Wavelength: 220 nm/254 nm

The desired product was also obtained through the following stepwise purification. The crude product (8 g) after workup was purified by silica gel column chromatography eluting with DCM: ethyl acetate (100:0 to 2:1). Further purification by sequential trituration first with ethyl acetate (150 mL) and then with DCM (500 ml) afforded the title compound as a yellow solid. Yield: 5.0 g, (49%)

$^1$H NMR (400 MHz, DMSO-$d_6$) δ 9.13 (br s, 1H), 8.99 (s, 1H), 8.75-8.65 (m, 2H), 8.61 (s, 2H), 8.16 (br s, 1H), 8.10 (d, 1H), 8.02 (d, 1H), 7.74 (t, 1H), 1.60-1.50 (m, 2H), 1.40-1.30 (m, 2H). LCMS $[M+H]^+$: 343. HPLC: 98.30% (method 6, retention time=3.36 min).

Example 2: Preparation of 3-[(2-{[1-(pyridin-3-yl)cyclopropyl]amino}pyrimidin-5-yl)carbonyl]benzonitrile

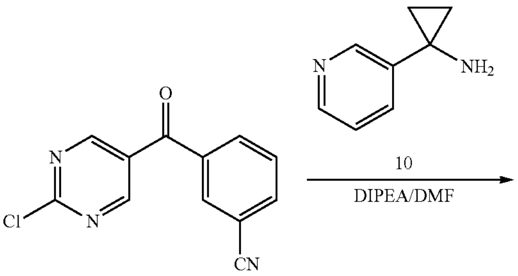

9

-continued

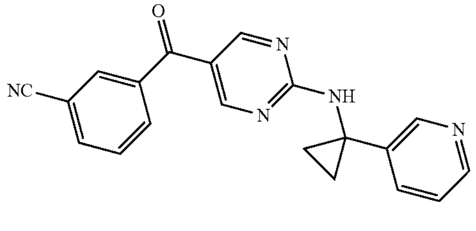

The desired product was prepared according to the method described in example 1 step 8 using 3-[(2-chloropyrimidin-5-yl)carbonyl]benzonitrile (9) and commercially available 1-(pyridin-3-yl)cyclopropanamine (10). The purification by prep HPLC (column: phenomenex gemini C18 250×21.2 mm×8 um; mobile phase: from 23% MeCN in water (Ammonia, pH=10) to 33% MeCN in water (Ammonia, pH=10) afforded 3-[(2-{[1-(pyridin-3-yl)cyclopropyl]amino}pyrimidin-5-yl)carbonyl]benzonitrile as an off-white solid. Yield: 10.2 mg (7%). $^1H$ NMR (400 MHz, MeOH-$d_4$) δ 8.71 (s, 1H), 8.63 (s, 1H), 8.44 (s, 1H), 8.30-8.29 (d, 1H), 8.04 (s, 1H), 7.97-7.92 (m, 2H), 7.70-7.65 (m, 2H), 7.32-7.29 (m, 1H), 1.40-1.38 (d, 4H). LCMS: $[M+H]^+$:342, HPLC 98.79% (method 1, retention time=2.23 min).

Example 3: Preparation of 3-({2-[(2-phenylpropan-2-yl)amino]pyrimidin-5-yl}carbonyl)benzonitrile

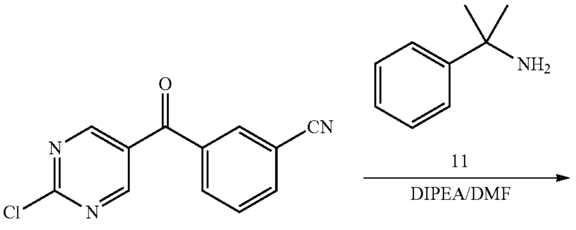

9

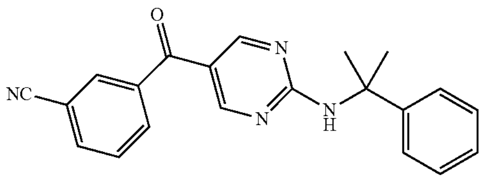

The desired product was prepared according to the method described in example 1 step 8 using compound 9 and commercially available 2-phenylpropan-2-amine (II). The purification by prep HPLC (column: boston symmetrix ODS-H 150×30 mm×5 um; mobile phase: from 46% MeCN in water (0.225% FA) to 56% MeCN in water (0.225% FA); Wavelength: 220 nm) afforded 3-({2-[(2-phenylpropan-2-yl)amino]pyrimidin-5-yl}carbonyl)benzonitrile as a white solid. Yield: 50 mg (24%). $^1H$ NMR (400 MHz, MeOH-$d_4$) δ 8.71 (s, 1H), 8.47 (s, 1H), 8.04 (d, 1H), 7.98-7.96 (m, 2H), 7.71 (t, 1H), 7.44-7.42 (m, 2H), 7.30-7.26 (m, 2H), 7.18 (t, 1H), 1.81 (s, 6H). LCMS: $[M+H]^+$:343.1, HPLC 98.91% (method 1, retention time=3.95 min)

Example 4: Preparation of 3-[(2-{[(2-aminopyrimidin-5-yl)methyl]amino}pyrimidin-5-yl)carbonyl]benzonitrile Step 1:

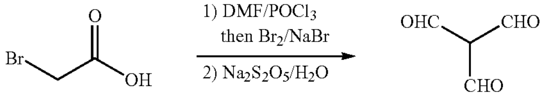

13

14

To a stirred solution of bromoacetic acid (13, 5 g, 35.98 mmol) in DMF (11.1 mL, 143.92 mmol) was added a $POCl_3$ (10 mL, 107.94 mmol) drop-wise over 30 minutes while maintaining the reaction temperature at 15° C. The resulting mixture was stirred at room temperature for another 30 minutes. The reaction mixture was then heated at 90° C. for 2 hours and then at 110° C. for further 7 hours. The reaction mixture was then cooled to room temperature and poured in crushed ice (500 g) with stirring. A solution of bromine (3.7 mL, 71.96 mmol) and NaBr (11.1 g, 107.94 mmol) in water (25 mL) was then added to the reaction mixture and stirring was continued for another 1 hour at 10° C. The resulting orange precipitate was filtered, washed with cold water (2×25 mL) and dried under vacuo. To a suspension of this crude solid in water (45 mL) was added solid $N_2S_2O_5$ (6.85 g, 36 mmol) in portions and the resulting mixture was stirred for 15 minutes at room temperature. The pale yellow solution was then made strongly alkaline by gradual addition of excess solid NaOH (8.5 g, 212.5 mmol) at 20° C. After 45 minutes of stirring the mixture was cooled with an ice bath and DCM (120 mL) and concentrated HCl (24 mL, 288 mmol) were added. Small portions of solid salts were removed by filtration. Organic part was separated and the aqueous part was extracted with DCM (2×250 mL). Combined organic layers were washed with brine, dried over sodium sulfate and concentrated under vacuo to afford methanetricarbaldehyde (14) as a yellowish solid. Yield: 2 g (55%). $^1H$ NMR (400 MHz, $CDCl_3$) δ 9.49 (s, 1H), 9.01 (br s, 3H).

Step 2:

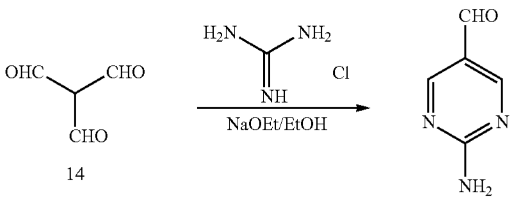

14

15

Sodium (1.2 g, 52 mmol) was dissolved in anhydrous ethanol (45 mL). To this freshly prepared solution was added methanetricarbaldehyde (14, 4.8 g, 47.96 mmol) and guanidine hydrochloride (5.5 g, 57.55 mmol). The resulting solution was stirred at room temperature for 1 hour and then refluxed for 20 hours. The solvent was evaporated and the residue was taken up in water (100 mL) and acidified to pH 1 by slow addition of 2N HCl. The acidic aqueous solution was neutralized by drop-wise addition of saturated aqueous sodium bicarbonate and was extracted by ethyl acetate (3×50 mL) Combined organic layers were washed with water, brine, dried over sodium sulfate and concentrated under vacuo to afford 2-aminopyrimidine-5-carbaldehyde (15) as a yellowish solid. Yield: 2 g (34%). $^1$H NMR (400 MHz, DMSO-$d_6$) δ 9.71 (s, 1H), 8.69 (s, 2H), 7.77 (br s, 2H). GCMS [m/z]: 123.0

Step 3:

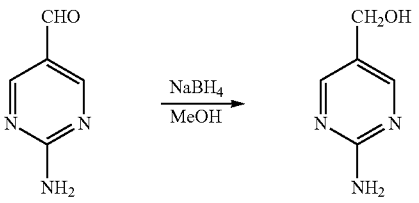

15 16

To a stirred solution of 2-aminopyrimidine-5-carbaldehyde (15, 500 mg, 4.06 mmol) in methanol (6 mL) was added sodium borohydride (200 mg, 5.28 mmol) in portions at 0° C. The resulting solution was slowly warmed to room temperature and was further stirred for 3 hours. After completion (monitored by TLC, 5% MeOH in DCM, Rf 0.3), the reaction mixture was quenched by addition of saturated aqueous $NH_4Cl$ solution and the resulting reaction mixture was concentrated under vacuo. The residue was directly loaded over a short column of silica gel (100-200 mesh) and eluted with gradient elution of 100% DCM to 7.5% MeOH in DCM. Concentration of fractions containing desired product afforded (2-aminopyrimidin-5-yl)methanol (16) as a light yellow solid. Yield: 340 mg (67%). $^1$H NMR (400 MHz, DMSO-$d_6$) δ 8.16 (s, 2H), 6.50 (br s, 2H), 4.99 (t, 1H), 4.26 (d, 2H). GCMS [m/z]: 125.0

Step 4:

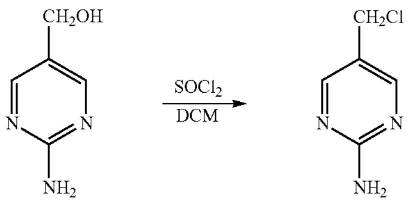

16 17

To a stirred solution of (2-aminopyrimidin-5-yl)methanol (16, 340 mg, 2.72 mmol) in DCM (5 mL) was added thionyl chloride (0.6 mL, 8.16 mmol) at 0° C. The resulting solution was slowly warmed to room temperature and was stirred for 16 hours. After complete consumption of compound 16 (monitored by TLC, 5% MeOH in DCM, Rf 0.3), the reaction mixture was concentrated under vacuo. The residue was triturated with acetone to afford the hydrochloride salt of 5-(chloromethyl)pyrimidin-2-amine (17) as an off-white solid. Yield: 340 mg (70%).

$^1$H NMR (400 MHz, DMSO-$d_6$) δ 8.57 (s, 2H), 7.90 (br s, 3H), 4.71 (s, 2H).

Step 5:

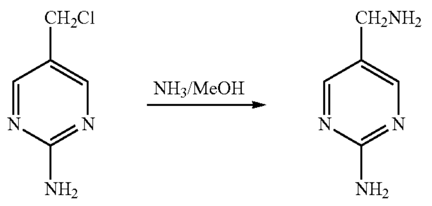

17 18

5-(Chloromethyl)pyrimidin-2-amine hydrochloride salt (17, 340 mg, 1.90 mmol) was added to a methanolic ammonia solution (~7 M, 10 mL, 7 mmol) in a sealed tube and the resulting solution was stirred at room temperature for 48 hours. After completion (monitored by TLC, 5% MeOH in DCM, Rf 0.2), the reaction mixture was concentrated under vacuo. The residue was triturated with petroleum ether and DCM to afford crude hydrochloride salt of 5-(aminomethyl)pyrimidin-2-amine (18) as an off-white solid. This material has been used in the next step without further purification. Yield: 300 mg (99%). $^1$H NMR (400 MHz, DMSO-$d_6$) δ 8.32 (s, 2H), 7.37 (br s, 4H), 6.77 (br s, 2H), 3.80 (s, 2H). GCMS [m/z]: 124.0

Step 6:

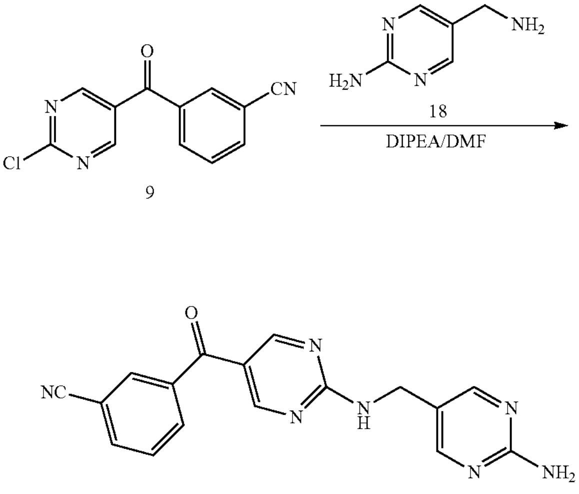

18

9

The desired product was prepared according to the method described in example 1 step 8 using 3-[(2-chloropyrimidin-5-yl)carbonyl]benzonitrile (9) and 5-(aminomethyl)pyrimidin-2-amine(18). The purification by preparative TLC preparation (TLC Silica gel 60 F254, 20×20 cm plates; mobile phase: 4% MeOH in DCM) afforded 3-[(2-{[(2-aminopyrimidin-5-yl)methyl]amino}pyrimidin-5-yl)carbonyl]benzonitrile as a light yellow solid. Yield: 12 mg (17%). $^1$H NMR (400 MHz, DMSO-$d_6$) δ 8.75-8.62 (m, 3H), 8.22 (s, 2H), 8.16 (s, 1H), 8.10 (d, 1H), 8.02 (d, 1H), 7.75 (t, 1H), 6.55 (br s, 2H), 4.37 (d, 2H). LCMS [M−H]$^-$: 332.0 HPLC: 94.28% (method 3, retention time=5.211 min).

Example 5: Preparation of 3-[(2-{[1-(pyrazin-2-yl)cyclopropyl]amino}pyrimidin-5-yl)carbonyl]benzonitrile Step 1:

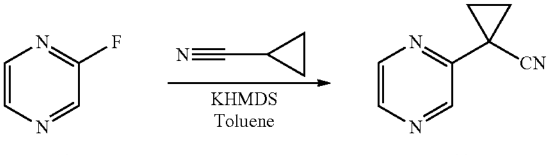

19 20

To a stirred solution of 2-fluoropyrazine (19, 4 g, 40.78 mmol) and cyclopropanecarbonitrile (2.75 g, 40.98 mmol) in dry toluene (50 mL) was added a THF solution of KHMDS (1 M, 40.98 mL, 40.98 mmol) drop-wise at 0° C. The resulting dark brown suspension was slowly brought to room temperature and stirred for further 4 hours. After completion (monitored by TLC, 30% EtOAc in hexanes, Rf 0.3), the reaction mixture was partitioned between water (200 mL) and ethyl acetate (200 mL). Organic part was separated and the aqueous part was extracted with ethyl acetate (2×500 ml). The combined organic extracts were dried over sodium sulfate and concentrated under vacuo. The crude residue was purified by column chromatography (100-200 mesh silica, gradient elution of 10% to 30% EtOAc in hexanes) to give 1-(pyrazin-2-yl)cyclopropanecarbonitrile (20) as a yellow solid. Yield: 600 mg (10%). $^1$H NMR (400 MHz, MeOH-$d_4$) δ 8.86 (d, 1H), 8.45-8.55 (m, 2H), 1.75-1.90 (m, 4H). GCMS [m/z]: 145

Step 2:

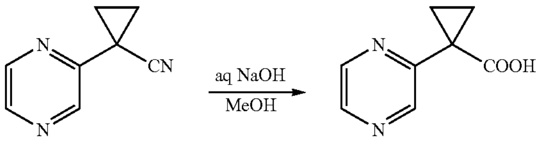

20 21

To a stirred solution of 1-(pyrazin-2-yl)cyclopropanecarbonitrile (20, 597 mg, 4.10 mmol) in methanol (12 mL) was added a 20% aqueous solution of NaOH (4.7 mL) drop-wise and the resulting solution was heated at 75° C. for 22 hours. After completion (monitored by TLC, 50% EtOAc in hexanes, Rf 0.1), the pH of the reaction was slowly brought to 2-3 by slow addition of 6N aqueous HCl. The reaction mixture was concentrated under reduced pressure and the residue was slurried in 10% methanol in DCM (100 mL). The reaction mixture was then filtered and the filtrate was concentrated under vacuo to afford 1-(pyrazin-2-yl)cyclopropanecarboxylic acid (21) as a brown solid. This material was used directly for the next step without further purification. Yield: 370 mg (55%). $^1$H NMR (400 MHz, DMSO-$d_6$) δ 8.86 (br s, 1H), 8.47-8.55 (m, 2H), 1.50-1.65 (m, 2H), 1.35-1.45 (m, 2H). LCMS $[M+H]^+$: 165.2

Step 3:

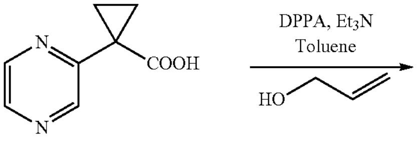

21

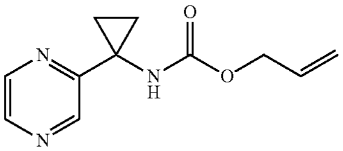

22

To a stirred solution of 1-(pyrazin-2-yl)cyclopropanecarboxylic acid (21, 460 mg, 2.802 mmol) and $Et_3N$ (0.47 mL, 3.362 mmol) in toluene (150 mL) was added DPPA (0.65 mL, 3.026 mmol) drop-wise. The resulting solution was stirred at the room temperature for 1 hour. Allyl alcohol (0.9 mL, 13.73 mmol) was then added and the resulting reaction mixture was heated at 90° C. for 3 hours. After completion (monitored by TLC, 50% EtOAc in hexanes, Rf 0.5) the reaction mixture was partitioned between water (200 mL) and ethyl acetate (250 mL). Organic layer was separated and the aqueous part was extracted with ethyl acetate (100 ml). Combined organic layers were washed with brine, dried over sodium sulfate and concentrated under vacuo. The crude residue was purified by column chromatography (100-200 mesh silica, gradient elution of 20% to 30% ethyl acetate in hexanes) to afford prop-2-en-1-yl [1-(pyrazin-2-yl)cyclopropyl]carbamate (22) as a gummy solid. Yield: 230 mg (37%). $^1$H NMR (400 MHz, MeOH-$d_4$) δ 8.86 (br s, 1H), 8.45-8.50 (m, 1H), 8.30-8.35 (m, 1H), 5.90-6.05 (m, 1H), 5.34 (d, 1H), 5.21 (d, 1H), 4.57 (d, 2H), 1.50-1.65 (m, 2H), 1.25-1.40 (m, 2H). LCMS $[M+H]^+$: 220.4

Step 4:

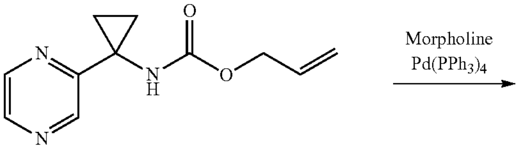

22

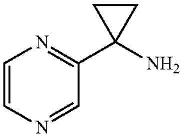

23

To a stirred degassed solution of prop-2-en-1-yl [1-(pyrazin-2-yl)cyclopropyl]carbamate (22, 230 mg, 1.045 mmol) and morpholine (0.9 mL, 10.45 mmol) in THF (10 mL) was added $Pd(Ph_3)_4$(72 mg, 0.0627 mmol) and the resulting yellow reaction mixture was stirred at 50° C. for 3 hours. After completion (monitored by TLC, 50% EtOAc in hexanes, Rf 0.5), the reaction mixture was concentrated under reduced pressure and the crude residue was purified by column chromatography (100-200 mesh silica, gradient elution of 100% DCM to 5% MeOH in DCM) followed by preparative TLC (TLC Silica gel 60 F254, 20×20 cm plates;

mobile phase: 1.5% MeOH in DCM) to afford 1-(pyrazin-2-yl)cyclopropanamine (23) as light yellow liquid. Yield: 50 mg (35%). $^1$H NMR (400 MHz, MeOH-$d_4$) δ 8.82 (d, 1H), 8.46 (d, 1H), 8.33 (d, 1H), 1.31-1.37 (m, 2H), 1.12-1.17 (q, 2H). LCMS $[M+H]^+$: 136.0

Step 5:

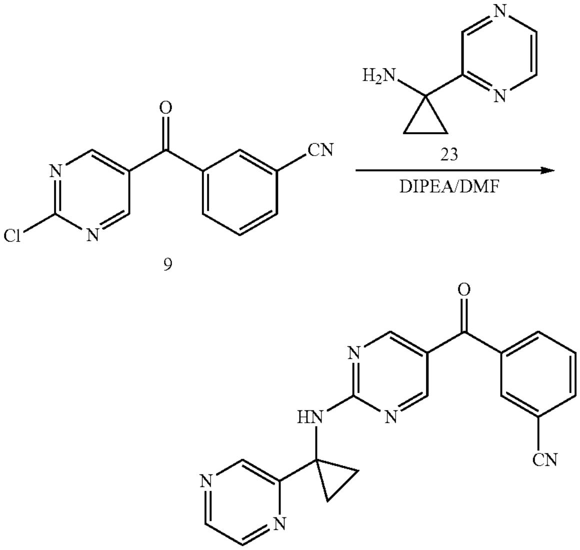

23

9

The desired product was prepared according to the method described in example 1 step 8 using 3-[(2-chloropyrimidin-5-yl)carbonyl]benzonitrile (9) and 1-(pyrazin-2-yl)cyclopropanamine (23). The purification by preparative TLC preparation (TLC Silica gel 60 F254, 20×20 cm plates; mobile phase: 3% MeOH in DCM) afforded 3-[(2-{[1-(pyrazin-2-yl)cyclopropyl]amino}pyrimidin-5-yl)carbonyl] benzonitrile as an off-white solid. Yield: 30 mg (43%). $^1$H NMR (400 MHz, DMSO-$d_6$) δ 9.16 (br s, 1H), 8.79-8.76 (m, 1H), 8.70-8.76 (m, 1H), 8.49-8.53 (m, 2H), 8.41 (d, 1H), 8.16 (br s, 1H), 8.09 (d, 1H), 8.02 (d, 1H), 7.75 (t, 1H), 1.70-1.55 (m, 2H), 1.40-1.30 (m, 2H). LCMS $[M+H]^+$: 343 HPLC: 99.70% (method 2, retention time=6.42 min).

Example 6: Preparation of 3-[(2-{[(6-aminopyridin-3-yl)methyl]amino}pyrimidin-5-yl)carbonyl]benzonitrile Step 1:

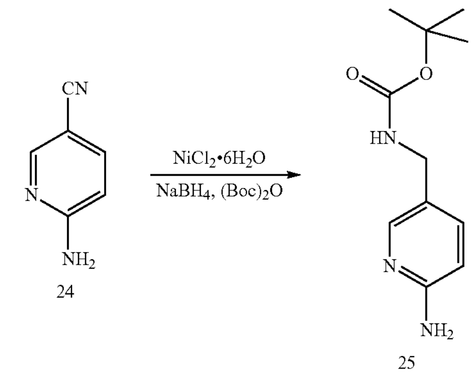 [SMILES: N#Cc1ccc(N)nc1 ; CC(C)(C)OC(=O)NCc1ccc(N)nc1]

24

25

To a stirred solution of 6-aminopyridine-3-carbonitrile (24, 500 mg, 4.2 mmol), ditert-butyl dicarbonate (1.92 mL, 8.4 mmol) and $NiCl_2.6H_2O$ (100 mg, 0.42 mmol) in methanol (25 mL) was added sodium borohydride (1.11 g, 29.4 mmol) at 0° C. in portions. The resulting solution was then slowly warmed to room temperature and then stirred for 1 hour. Di-ethylene triamine (0.45 mL, 4.2 mmol) was then added to the reaction mixture and stirred for further 1 hour. After completion (monitored by TLC, 5% MeOH in DCM, Rf 0.5), the reaction mixture was concentrated under vacuo and the residue was partitioned between saturated aq. $NaHCO_3$ (50 mL) and ethyl acetate (100 mL). Organic part was separated and washed with brine, dried over sodium sulfate and concentrated under vacuo. The crude residue was purified by column chromatography (100-200 mesh silica, gradient elution of 100% DCM to 2% MeOH in DCM) to afford tert-butyl [(6-aminopyridin-3-yl)methyl]carbamate (25) as a gum. Yield: 180 mg (19%). $^1$H NMR (400 MHz, DMSO-$d_6$) δ 7.75 (br s, 1H), 7.24 (dd, 1H), 7.20 (t, 1H), 6.37 (d, 1H), 5.76 (br s, 2H), 3.89 (d, 2H), 1.37 (s, 9H), LCMS $[M+H]^+$: 224.0

Step 2:

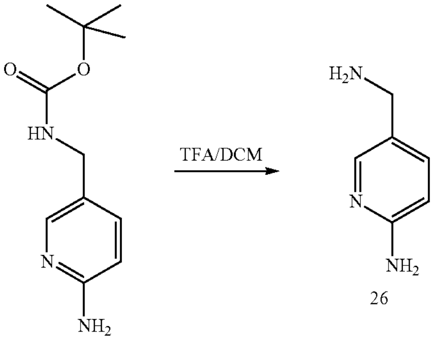

25

26

To a stirred solution of tert-butyl [(6-aminopyridin-3-yl)methyl]carbamate (25, 180 mg, 0.81 mmol) in DCM (5 mL) was added trifluoroacetic acid (0.6 mL, 8.1 mmol) at 0° C. drop-wise. The resulting solution was then slowly warmed up to room temperature and the stirring was continued for 2 hours. After completion (monitored by TLC, 10% MeOH in DCM, Rf 0.1), the reaction mixture was concentrated under vacuo and the residue was triturated with dry ether to afford trifluroacetic acid salt of 5-(aminomethyl)pyridin-2-amine (26) as brown sticky solid. Yield: 120 mg (63%). $^1$H NMR (400 MHz, DMSO-$d_6$) b 8.35 (br s, 2H), 8.18 (br s, 2H), 8.01 (br s, 1H), 7.94 (dd, 1H), 7.01 (d, 1H), 3.95 (d, 2H), LCMS $[M+H]^+$: 124.0

Step 3:

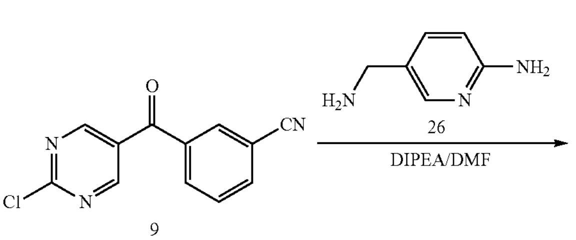

26

9

-continued

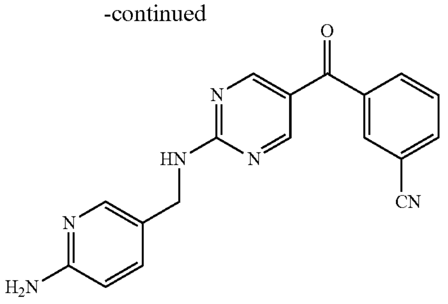

The desired product was prepared according to the method described in example 1 step 8 using 3-[(2-chloropyrimidin-5-yl)carbonyl]benzonitrile (9) and 5-(aminomethyl)pyridin-2-amine (26). The purification by preparative TLC purification (TLC Silica gel 60 F254, 20×20 cm plates; mobile phase: 4% MeOH in DCM) afforded 3-[(2-{[(6-aminopyridin-3-yl)methyl]amino}pyrimidin-5-yl)carbonyl]benzonitrile as a light yellow solid. Yield: 15 mg (22%). $^{1}$H NMR (400 MHz, DMSO-$d_6$) δ 8.74-8.65 (m, 3H), 8.16 (s, 1H), 8.10 (d, 1H), 8.02 (d, 1H), 7.88 (d, 1H), 7.75 (t, 1H), 7.35 (dd, 1H), 6.39 (d, 1H), 5.82 (br s, 2H), 4.40 (d, 2H). LCMS [M−H]$^-$: 329.4, HPLC: 96.18% (method 2, retention time=4.15 min)

Example 7: Preparation of 3-[(2-{[1-(pyridin-3-yl)ethyl]amino}pyrimidin-5-yl)carbonyl]benzonitrile

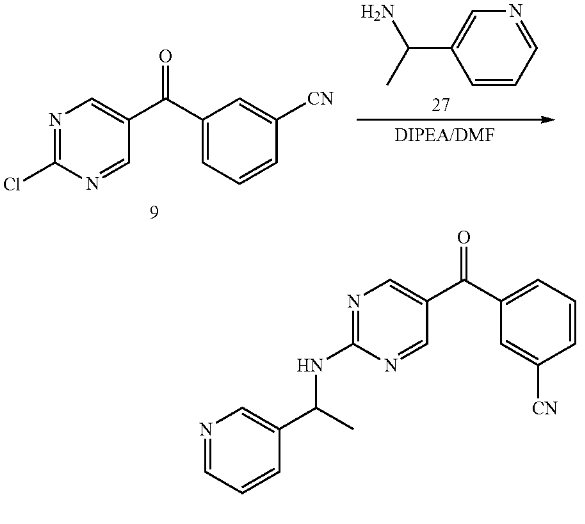

The desired product was prepared according to the method described in example 1 step 8 using 3-[(2-chloropyrimidin-5-yl)carbonyl]benzonitrile (9) and commercial available 1-(pyridin-3-yl)ethanamine (27). The purification by preparative TLC purification (TLC Silica gel 60 F254, 20×20 cm plates; mobile phase: 4% MeOH in DCM) afforded 3-[(2-{[1-(pyridin-3-yl)ethyl]amino}pyrimidin-5-yl)carbonyl]benzonitrile as a white solid. Yield: 8 mg (12%). $^{1}$H NMR (400 MHz, DMSO-$d_6$) δ 8.89 (d, 1H), 8.70-8.60 (m, 3H), 8.43 (d, 1H), 8.14 (s, 1H), 8.09 (d, 1H), 8.00 (d, 1H), 7.80 (d, 1H), 7.74 (t, 1H), 7.35 (dd, 1H), 5.36-5.23 (m, 1H), 1.52 (d, 3H). LCMS [M+H]: 330.0 HPLC: 99.71% (method 2, retention time=3.89 min)

Example 8: Preparation of 4-(1-{[5-(3-cyanobenzoyl)pyrimidin-2-yl]amino}ethyl)benzamide Step 1:

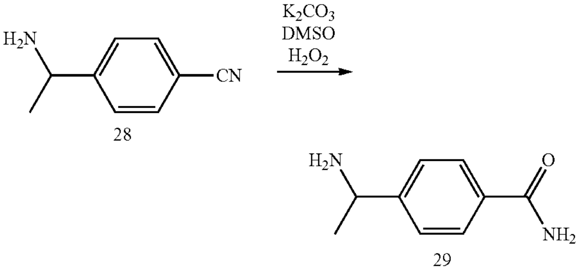

To the stirred solution of 4-(1-aminoethyl)benzonitrile (28, 500 mg, 3.420 mmol) in DMSO (4 mL) was added $K_2CO_3$ (1.9 g, 13.68 mmol) and the resulting mixture was allowed to stir at room temperature for 10 minutes. Then the reaction mixture was cooled to 5° C. followed by addition of aqueous $H_2O_2$(30%, 2.7 mL, 23.94 mmol) and allowed to stir at room temperature for 2 hours. After completion (monitored by TLC 10% MeOH in DCM, Rf-0.1) the reaction mixture was partitioned between water (10 mL) and 20% IPA in DCM (40 mL). Organic layer was separated and the aqueous layer was further extracted with 20% IPA in DCM (4×40 mL). The combined organic layers were dried over sodium sulfate and concentrated under vacuo. The crude residue thus obtained was purified by column chromatography (using silica gel 100-200 and gradient elution of 5-12% MeOH in DCM) to afford 4-(1-aminoethyl)benzamide (29) as an off-white solid. Yield: 400 mg (71%). $^{1}$H NMR (400 MHz, DMSO-$d_6$) δ 7.87 (br s, 1H), 7.79 (d, 2H), 7.41 (d, 2H), 7.24 (br s, 1H), 4.00 (q, 1H), 1.95 (br s, 2H), 1.23 (d, 3H). LCMS [M+H]$^+$: 165 HPLC: 99.11% (method 3, retention time=2.22 min).

Step 2:

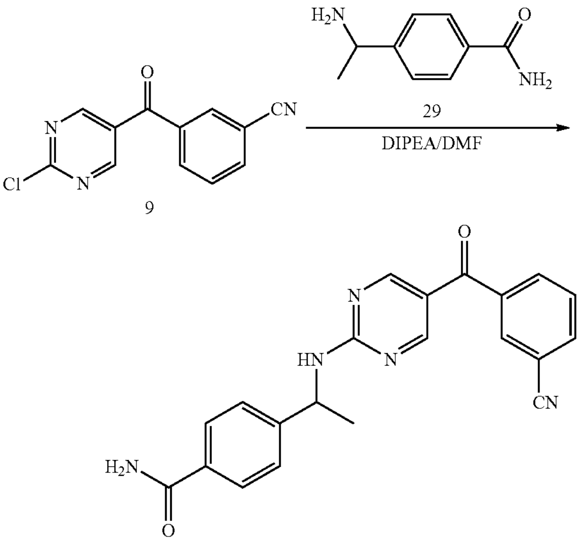

The desired product was prepared according to the method described in example 1 step 8 using 3-[(2-chloropyrimidin-5-yl)carbonyl]benzonitrile (9) and 4-(1-aminoethyl)benzamide (29). The purification by preparative TLC purification (TLC silica gel 60 F254, 20×20 cm plates; mobile phase: 4% MeOH in DCM) afforded 4-(1-{[5-(3-cyanobenzoyl)pyrimidin-2-yl]amino}ethyl)benzamide as a brown solid. Yield: 65 mg (42%). $^1$H NMR (400 MHz, DMSO-$d_6$) δ 8.89 (d, 1H), 8.71-8.62 (m, 2H), 8.14 (s, 1H), 8.08 (d, 1H), 7.99 (d, 1H), 7.88 (br s, 1H), 7.80 (d, 2H), 7.73 (t, 1H), 7.45 (d, 2H), 7.28 (br s, 1H), 5.26-5.32 (m, 1H), 1.50 (d, 3H). LCMS [M+H]$^+$: 372.4, HPLC: 99.77% (method 4, retention time=7.40 min).

Example 9: (−)-4-(1-{[5-(3-cyanobenzoyl)pyrimidin-2-yl]amino}ethyl)benzamide and Example 10: (+)-4-(1-{[5-(3-cyanobenzoyl)pyrimidin-2-yl]amino}ethyl)benzamide 4-(1-{[5-(3-cyanobenzoyl)pyrimidin-2-yl]amino}ethyl)benzamide (50 mg) was resolved using preparative chiral HPLC to obtain two enantiomers peak-1 (example 10, 14 mg, retention time=14.34 min) and peak-2 (example 9, 16 mg, retention time=27.84 min).

Details of preparative HPLC separation conditions are given below:

CHIRAL HPLC Parameters-PREP

Column: CHIRALPAK-IA (20×250 mm) 5p,

Mobile Phase: MeOH/DEA: 100/0.1; v/v

Flow rate: 18.0 ml/min,

U.V wavelength: 310 nm,

Solubility: DCM:MeOH.

Run Time: 50 min.

(−)-4-(1-{[5-(3-cyanobenzoyl)pyrimidin-2-yl]amino}ethyl)benzamide (example 9, peak 2)

Analytica data: $^1$H NMR (400 MHz, DMSO-$d_6$) δ 8.89 (d, 1H), 8.71-8.62 (m, 2H), 8.14 (s, 1H), 8.08 (d, 1H), 7.99 (d, 1H), 7.88 (br s, 1H), 7.80 (d, 2H), 7.73 (t, 1H), 7.45 (d, 2H), 7.28 (br s, 1H), 5.26-5.32 (m, 1H), 1.50 (d, 3H). LCMS [M+H]$^+$: 372

HPLC=99.40% (method 3, retention time=3.50 min); Specific rotation: [−170°] at =25° C., (c=0.2% sol in MeOH)

(+)-4-(1-{[5-(3-cyanobenzoyl)pyrimidin-2-yl]amino}ethyl)benzamide (example 10, peak 1): analytical data: $^1$H NMR (400 MHz, DMSO-$d_6$) δ 8.89 (d, 1H), 8.71-8.62 (m, 2H), 8.14 (s, 1H), 8.08 (d, 1H), 7.99 (d, 1H), 7.88 (br s, 1H), 7.80 (d, 2H), 7.73 (t, 1H), 7.45 (d, 2H), 7.28 (br s, 1H), 5.26-5.32 (m, 1H), 1.50 (d, 3H). LCMS [M+H]$^+$: 372.4

HPLC=99.31% (method 3, retention time=3.50 min); Specific rotation: [+212° ] at 25° C. (c=0.21% in MeOH)

Example 11: Preparation of {2-[(pyrazin-2-ylmethyl)amino]pyrimidin-5-yl}[3-(trifluoromethyl)phenyl]methanone Step 1:

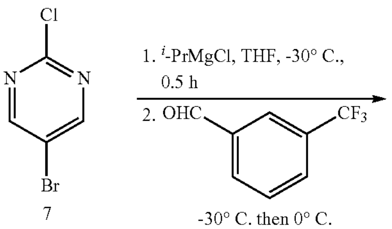

7

-continued

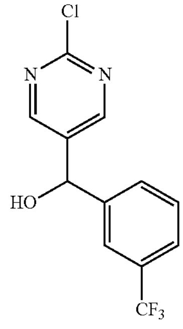

30

(2-Chloropyrimidin-5-yl)[3-(trifluoromethyl)phenyl]methanol (30) was prepared according to the method described in example 1 step 6 using 5-bromo-2-chloropyrimidine (7, 10 g, 51.6 mmol) and commercially available 3-(trifluoromethyl)benzaldehyde (6.92 mL, 51.6 mmol). The purification by column chromatography purification (silica gel gradient using petroleum ether/ethyl acetate, from 90/10 to 60/40) afforded (2-chloropyrimidin-5-yl)[3-(trifluoromethyl)phenyl]methanol (9.0 g, 60%) as a pale yellow liquid. $^1$HNMR (DMSO-$d_6$) 5 8.80 (s, 2H), 7.84 (s, 1H), 7.81-7.73 (m, 1H), 7.71-7.55 (m, 2H), 6.59 (br s, 1H), 6.01 (s, 1H). LCMS [M+H]$^+$: 288.9.

Step 2:

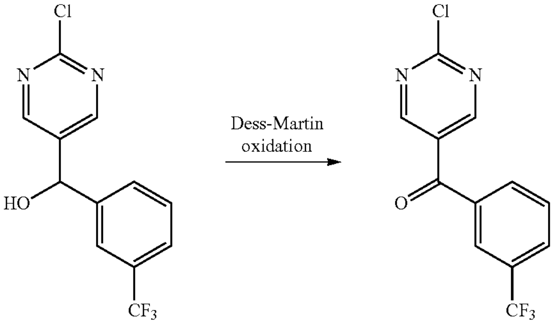

30 31

(2-Chloropyrimidin-5-yl)[3-(trifluoromethyl)phenyl]methanone (31) was prepared according to the method described in example 1 step 7 with (2-chloropyrimidin-5-yl)[3-(trifluoromethyl)phenyl]methanol (30, 3.5 g). The purification by column chromatography purification (silica gel, gradient using petroleum ether/ethyl acetate, from 90/10 to 50/50) afforded (2-chloropyrimidin-5-yl)[3-(trifluoromethyl)phenyl]methanone as a white solid. Yield: 3.1 g (63%). $^1$H NMR (400 MHz, DMSO-$d_6$) δ 9.10 (s, 2H), 8.18-8.13 (m, 3H), 7.85-7.83 (m, 1H). LCMS [M+H]$^+$: 286.8.

Step 3:

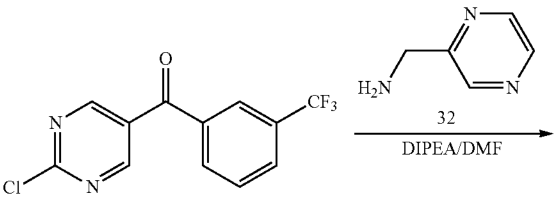

31

32

-continued

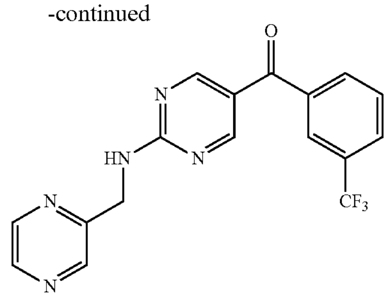

The desired product was prepared according to the method described in example 1 step 8 using (2-chloropyrimidin-5-yl)[3-(trifluoromethyl)phenyl]methanone (31) and commercially available 1-(pyrazin-2-yl)methanamine (32). The purification by prep HPLC (column: Boston Symmetrix ODS-H 150×30 mm×5 um; mobile phase: from 33% MeCN in water (0.225% FA) to 53% MeCN in water (0.225% FA), wavelength: 220 nm) afforded {2-[(pyrazin-2-ylmethyl)amino]pyrimidin-5-yl}[3-(trifluoromethyl)phenyl]methanone as white solid. Yield: 39 mg (32%). $^1$H NMR (400 MHz, MeOH-$d_4$) δ 8.76 (d, 2H), 8.68 (d, 1H), 8.60 (t, 1H), 8.52 (d, 1H), 8.05-7.96 (m, 3H), 7.80-7.73 (m, 1H), 4.89 (s, 2H). LCMS [M+H]$^+$: 360.0. HPLC=96.52% (method 1, retention time=3.04 min).

Example 12 preparation of {2-[(pyridin-3-ylmethyl)amino]pyrimidin-5-yl}[3-(trifluoromethyl)phenyl]methanone

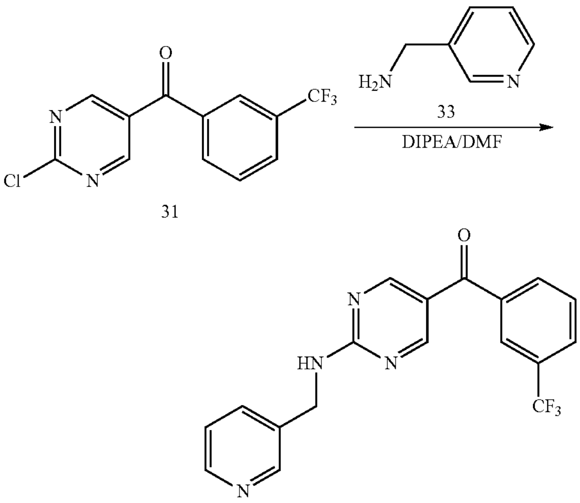

31

33

The desired product was prepared according to the method described in example 1 step 8 using (2-chloropyrimidin-5-yl)[3-(trifluoromethyl)phenyl]methanone (31) and commercially available 1-(pyridin-3-yl)methanamine (33). The purification by prep HPLC [Column: Agella venusil ASB C18 150×21.2 mm×5 um; mobile phase: from 26% MeCN in water (0.225% FA) to 48% MeCN in water (0.225% FA); wavelength: 220 nm] afforded {2-[(pyridin-3-ylmethyl)amino]pyrimidin-5-yl}[3-(trifluoromethyl)phenyl]methanone as light yellow solid. Yield: 201.4 mg (40%). $^1$H NMR (400 MHz, DMSO-$d_6$) δ 8.87 (t, 1H), 8.69 (s, 2H), 8.60 (s, 1H), 8.46 (d, 1H), 8.02-8.00 (m, 3H), 7.80-7.70 (m, 2H), 7.40-7.30 (m, 1H), 4.63 (d, 2H). LCMS [M+H]$^+$: 358.8. HPLC=97.07% (method 1, retention time=2.40 min)

Example 13: Preparation of [3-(methylsulfonyl)phenyl]{2-[(pyridin-3-ylmethyl)amino]pyrimidin-5-yl}methanone Step 1:

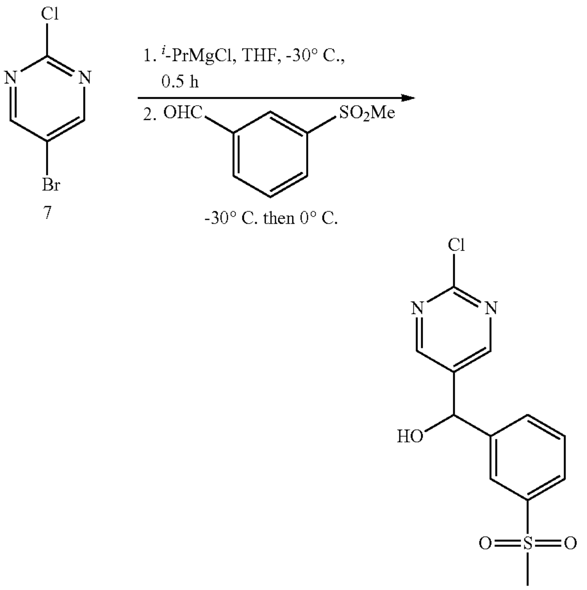

7

34

(2-Chloropyrimidin-5-yl)[3-(methylsulfonyl)phenyl]methanol (34) was prepared according to the method described in example 1 step 6 using 5-bromo-2-chloropyrimidine (7, 5 g, 25.8 mmol) and commercially available 3-(methylsulfonyl)benzaldehyde (4.7 g, 25.8 mmol). Purification using column chromatography (TLC condition: Rf: 0.2 in 20% EtOAc/petroleum ether) afforded (2-chloropyrimidin-5-yl)[3-(methylsulfonyl)phenyl]methanol as an off-white solid (2.5 g, 32%). $^1$HNMR (DMSO-$d_6$) δ 8.80 (s, 2H), 8.03 (s, 1H), 7.86-7.82 (m, 1H), 7.78-7.76 (m, 1H), 7.64-7.61 (m, 1H), 6.60 (s, 1H), 6.03-6.02 (m, 1H), 3.2 (s, 3H). LCMS [M+H]$^+$: 299. LCMS Purity: 97%

Step 2:

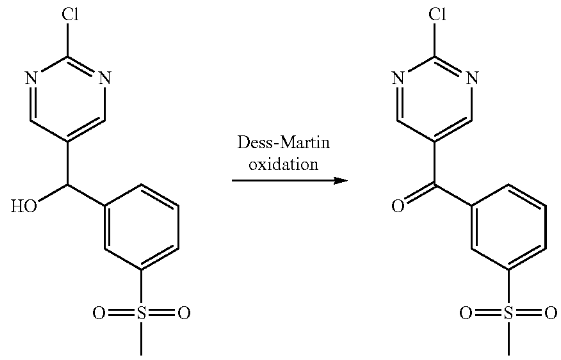

34

35

(2-Chloropyrimidin-5-yl)[3-(methylsulfonyl)phenyl] methanone (35) was prepared according to the method described in example 1 step 6 using (2-chloropyrimidin-5-yl)[3-(methylsulfonyl)phenyl]methanol (34). The purification by column chromatography (TLC condition: Rf: 0.8 at 20% EtOAc/petroleum ether) afforded the desired (2-chloropyrimidin-5-yl)[3-(methylsulfonyl)phenyl]methanone as an off-white solid. Yield: 1.5 g (62%). $^1$H NMR (400 MHz, $CDCl_3$) δ 9.10 (s, 2H), 8.32 (s, 1H), 8.30-8.26 (m, 1H), 8.22-8.18 (m, 1H), 7.94-7.87 (m, 1H), 3.32 (s, 3H); LCMS $[M+H]^+$: 297.2

Step 3:

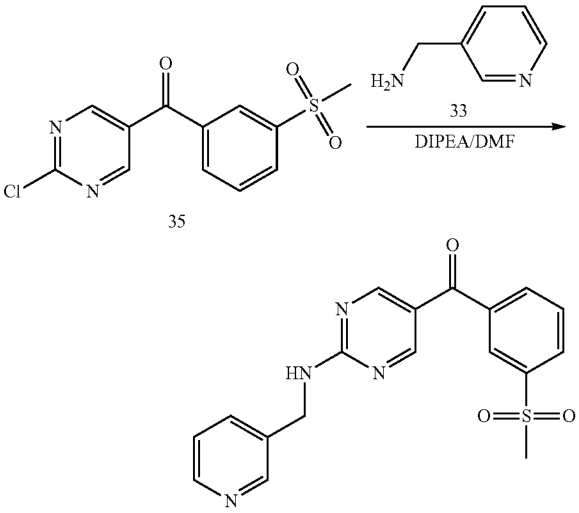

35

The desired product was prepared according to the method described in example 1 step 6 using (2-chloropyrimidin-5-yl)[3-(methylsulfonyl)phenyl]methanone (35) and commercially available 1-(pyridin-3-yl)methanamine (33). The purification by the column chromatography (silica gel, Rf: 0.1 at 60% EtOAc/petroleum ether) afforded [3-(methylsulfonyl)phenyl]{2-[(pyridin-3-ylmethyl)amino]pyrimidin-5-yl}methanone as an off-white solid. Yield: 23 mg (18%). $^1$HNMR (DMSO-$d_6$) δ 8.88-8.83 (m, 1H), 8.73 (s, 2H), 8.58-8.56 (m, 1H), 8.48-8.45 (m, 1H), 8.21-8.18 (m, 2H), 8.07-8.05 (m, 1H), 7.85-7.82 (m, 1H), 7.76-7.73 (m, 1H), 7.38-7.34 (m, 1H), 4.64 (d, 2H), 3.32 (s, 3H). LCMS $[M+H]^+$: 368.9, HPLC 97.8% (method 7, retention time=1.353 min)

Example 14 preparation of (3-methylphenyl){2-[(pyridin-3-ylmethyl)amino]pyrimidin-5-yl}methanone Step 1:

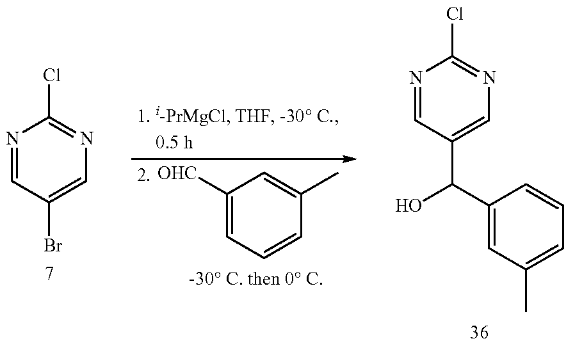

7

36

(2-Chloropyrimidin-5-yl)(3-methylphenyl)methanol (36) was prepared according to the method described in example 1 step 6 using 5-bromo-2-chloropyrimidine (7) and commercially available 3-methylbenzaldehyde. The purification by column chromatography (Rf: 0.6 at 40% EtOAc/petroleum ether) afforded the desired (2-chloropyrimidin-5-yl)(3-methylphenyl)methanol (36) as an off-white solid (2.8 g, 46%). $^1$HNMR (DMSO-$d_6$) δ 8.74 (s, 2H), 7.25-7.19 (m, 3H), 7.08-7.03 (m, 1H), 6.30 (s, 1H), 5.82 (s, 1H), 2.28 (s, 3H). LCMS $[M+H]^+$: 235; LCMS 96.06%

Step 2:

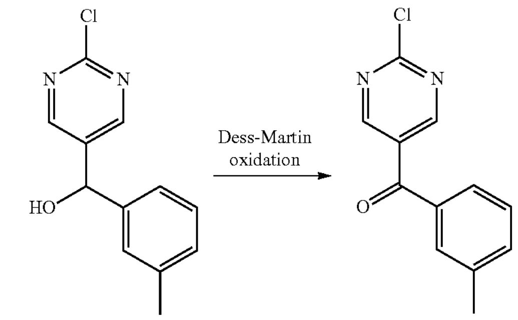

36 37

(2-Chloropyrimidin-5-yl)(3-methylphenyl)methanone (37) was prepared according to the method described in example 1 step 7 using (2-chloropyrimidin-5-yl)(3-methylphenyl)methanol (36). The purification by column chromatography (silica gel, Rf: 0.76 at 40% EtOAc/petroleum ether) afforded (2-chloropyrimidin-5-yl)(3-methylphenyl) methanone (37) as an off-white solid. Yield: 2.1 g, (75.8%. $^1$HNMR (DMSO-$d_6$) δ 9.04 (s, 2H), 7.71-7.63 (m, 2H), 7.59-7.55 (m, 1H), 7.52-7.46 (m, 1H). LCMS $[M+H]^+$: 233, LCMS 98.85%

Step 3:

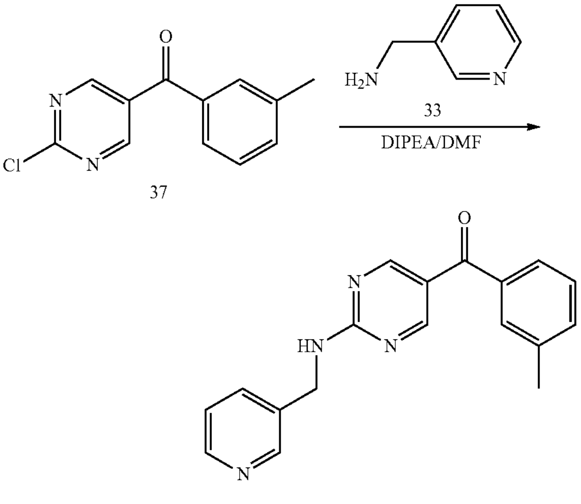

37

The desired product was prepared according to the method described in example 1 step 8 using (2-chloropyrimidin-5-yl)(3-methylphenyl)methanone (37) and commercially available 1-(pyridin-3-yl)methanamine (33).

The purification by prep HPLC [column: Kromasil Eternity-5-C18 150x30 mmx5 um; mobile phase: from 15% MeCN in water (0.225% formic acid) to 32% MeCN in water (0.225% formic acid); wavelength: 220 nm] afforded (3-methylphenyl){2-[(pyridin-3-ylmethyl)amino]pyrimidin-5-yl}methanone (0.5 mole equivalent formic acid) as an off-white solid. Yield: 405 mg (62%). $^1$H NMR (400 MHz, MeOH-$d_4$) δ 8.74 (s, 2H), 8.59 (s, 1H), 8.46-8.45 (m, 1H), 7.90 (d, 1H), 7.56 (s, 1H), 7.53 (d, 1H), 7.49 (d, 1H), 7.46-7.42 (m, 2H), 4.75 (s, 2H), 2.45 (s, 3H). LCMS $[M+H]^+$: 305. HPLC 98.00% (method 1, retention time=2.36 min).

Example 15 preparation of (2-fluorophenyl){2-[(pyridin-3-ylmethyl)amino]pyrimidin-5-yl}methanone Step 1:

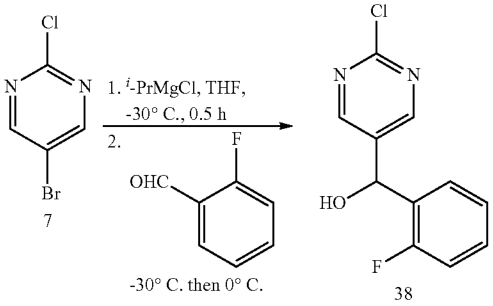 [SMILES: Clc1ncc(Br)cn1 ; O=Cc1ccccc1F ; OC(c1cnc(Cl)nc1)c1ccccc1F]

(2-Chloropyrimidin-5-yl)(2-fluorophenyl)methanol (38) was prepared according to the method described in example 1 step 6 using 5-bromo-2-chloropyrimidine (7) and commercially available 2-fluorobenzaldehyde. The purification by column chromatography (EtOAc and hexane) afforded (2-chloropyrimidin-5-yl)(2-fluorophenyl)methanol (38). Yield: 1.7 g (34%).

Step 2:

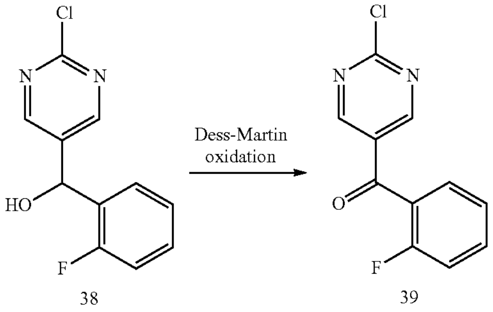 [SMILES: OC(c1cnc(Cl)nc1)c1ccccc1F ; O=C(c1cnc(Cl)nc1)c1ccccc1F]

(2-Chloropyrimidin-5-yl)(2-fluorophenyl)methanone (39) was prepared according to the method described in example 1 step 7 using (2-chloropyrimidin-5-yl)(2-fluorophenyl)methanol (38). The purification by column chromatography (silica gel) afforded (2-chloropyrimidin-5-yl)(2-fluorophenyl)methanone (39) as an off-white solid. Yield: 591 mg (35%). $^1$H NMR (400 MHz, DMSO-$d_6$) δ 9.09 (d, 2H), 7.81-7.75 (m, 2H), 7.48-7.43 (m, 2H). LC-MS $[M+H]^+$: 236.8. HPLC=96.49% (method 1, retention time=2.32 min).

Step 3:

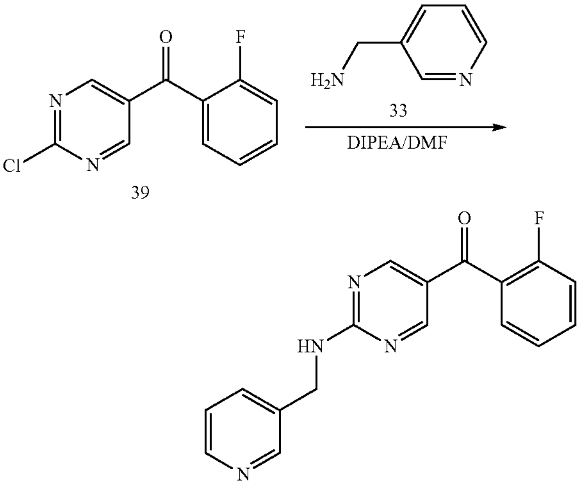

The desired product was prepared according to the method described in example 1 step 8 using (2-chloropyrimidin-5-yl)(2-fluorophenyl)methanone (39) and commercially available 1-(pyridin-3-yl)methanamine (33). The purification by prep HPLC [column: Kromasil Eternity-5-C18 150x30 mmx5 um; mobile phase: from 7% MeCN in water (0.1% TFA) to 37% MeCN in water (0.1% TFA); wavelength: 220 nm] afforded (2-fluorophenyl){2-[(pyridin-3-ylmethyl)amino]pyrimidin-5-yl}methanone (1.00 mol equivalent of TFA) as an off-yellow solid. Yield: 32 mg (13%).

$^1$H NMR (400 MHz, DMSO-$d_6$) δ 8.94 (t, 1H), 8.76 (s, 1H), 8.69-8.61 (m, 3H), 8.20 (d, 1H), 7.78-7.74 (m, 1H), 7.68-7.66 (m, 1H), 7.59-7.55 (m, 1H), 7.40-7.34 (m, 2H), 4.72 (d, 2H). LCMS $[M+H]^+$: 308.9. HPLC=98.67% (method 1, retention time=2.61 min)

Example 16 preparation of (2-{[1-(pyrimidin-5-yl)cyclopropyl]amino}pyrimidin-5-yl)[3-(trifluoromethyl)phenyl]methanone

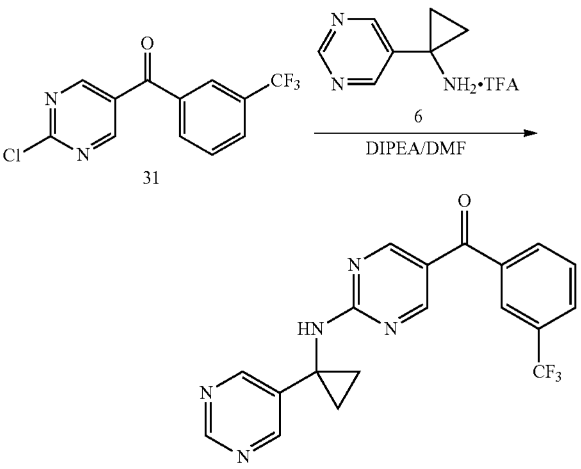

The desired product was prepared according to the method described in example 1 step 8 using (2-chloropyrimidin-5-yl)[3-(trifluoromethyl)phenyl]methanone (31) and 1-(pyrimidin-5-yl)cyclopropanamine (6). The purification by preparative TLC (TLC Silica gel 60 F254, 20×20 cm plates; mobile phase: 3% MeOH in DCM) afforded (2-{[1-(pyrimidin-5-yl)cyclopropyl]amino}pyrimidin-5-yl)[3-(trifluoromethyl)phenyl]methanone as an off-white solid. Yield: 21.6 mg (16%). $^1$H NMR (400 MHz, DMSO-$d_6$) δ 9.13 (s, 1H), 9.00 (s, 1H), 8.74-8.67 (m, 2H), 8.62 (s, 2H), 8.03-8.00 (m, 3H), 7.78 (t, 1H), 1.53-1.48 (m, 2H), 1.38-1.33 (m, 2H). LCMS [M+H]$^+$: 386.0, HPLC: 94.03% (method 2, retention time=3.828 min).

Example 17 preparation of [3-(methylsulfonyl)phenyl](2-{[1-(pyrimidin-5-yl)cyclopropyl]amino}pyrimidin-5-yl)methanone

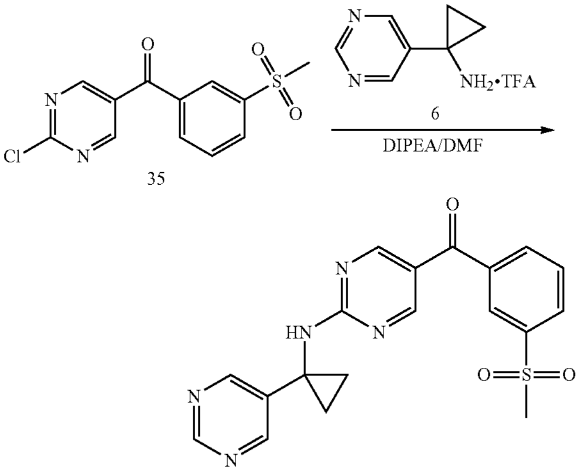

The desired product was prepared according to the method described in example 1 step 8 using (2-chloropyrimidin-5-yl)[3-(methylsulfonyl)phenyl]methanone (35) and 1-(pyrimidin-5-yl)cyclopropanamine (6). The purification by preparative TLC (TLC Silica gel 60 F254, 20×20 cm plates; mobile phase: 3% MeOH in DCM) afforded [3-(methylsulfonyl)phenyl](2-{[1-(pyrimidin-5-yl)cyclopropyl]amino}pyrimidin-5-yl)methanone as an off-white solid. Yield: 20 mg (15%). $^1$H NMR (400 MHz, DMSO-$d_6$) b 9.13 (s, 1H) 9.00 (s, 1H), 8.77-8.69 (m, 2H), 8.62 (s, 2H), 8.20-8.17 (m, 2H), 8.06 (d, 1H), 7.82 (t, 1H), 3.30 (s, 3H), 1.53-1.49 (m, 2H), 1.38-1.36 (m, 2H). LCMS [M+H]$^+$: 396.2. HPLC: 95.84% (method 2, retention time=3.123 min)

Example 18 preparation of (3-methoxyphenyl)(2-{[1-(pyrimidin-5-yl)cyclopropyl]amino}pyrimidin-5-yl)methanone Step 1:

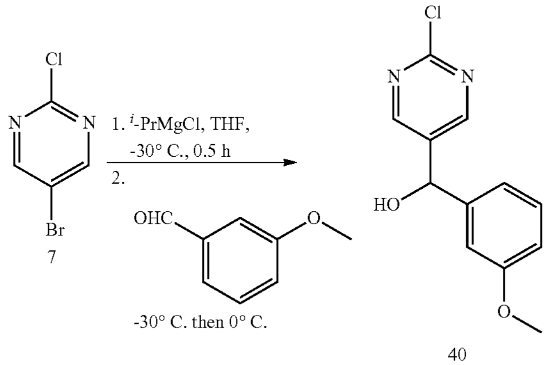

(2-Chloropyrimidin-5-yl)(3-methoxyphenyl)methanol (40) was prepared according to the method described in example 1 step 6 using 5-bromo-2-chloropyrimidine (7) and commercially available 3-methoxybenzaldehyde. The purification by column chromatography (product Rf 0.4 at 30% EtOAc in hexanes, 100-200 mesh silica, gradient elution of 100% hexanes to 15% ethyl acetate in hexanes) afforded (2-chloropyrimidin-5-yl)(3-methoxyphenyl)methanol (40) as a yellow solid. Yield: 1.5 g (58%), $^1$H NMR (400 MHz, DMSO-$d_6$) δ 8.74 (s, 2H), 7.28 (t, 1H), 7.00 (s, 1H), 6.97 (d, 1H), 6.83 (d, 1H), 6.34 (d, 1H), 5.83 (d, 1H), 3.74 (s, 3H). GCMS [M+H]: 251

Step 2:

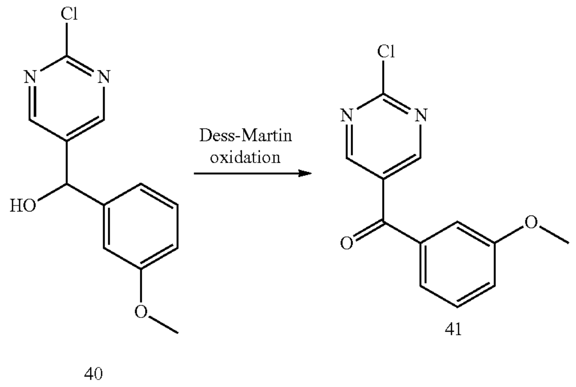 [SMILES: COc1cccc(C(O)c2cnc(Cl)nc2)c1 ; COc1cccc(C(=O)c2cnc(Cl)nc2)c1]

The desired compound was prepared according to the method described in example 1 step 7 with (2-chloropyrimidin-5-yl)(3-methoxyphenyl)methanol (40). The purification by column chromatography (100-200 mesh silica, gradient elution of 100% hexanes to 10% EtOAc in hexanes) afforded (2-chloropyrimidin-5-yl)(3-methoxyphenyl)methanone (41) as an off-white solid. Yield: 900 mg (60%). $^1$H NMR (400 MHz, DMSO-$d_6$) δ 9.05 (s, 2H), 7.54 (t, 1H), 7.42 (d, 1H), 7.36 (s, 1H) 7.33 (dd, 1H), 3.83 (s, 3H). LCMS [M+H]$^+$: 248.8

Step 3:

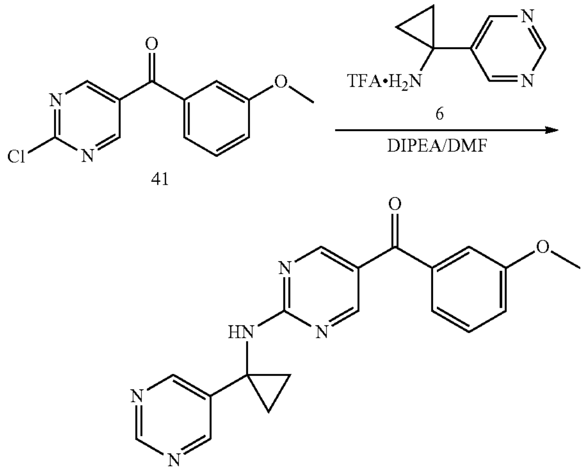

The desired product was prepared according to the method described in example 1 step 8 using (2-chloropyrimidin-5-yl)(3-methoxyphenyl)methanone (41) and 1-(pyrimidin-5-yl)cyclopropanamine (6). The purification by prep TLC [TLC Silica gel 60 F254, 20×20 cm plates; mobile phase: 3% MeOH in DCM] afforded (3-methoxyphenyl)(2-{[1-(pyrimidin-5-yl)cyclopropyl]amino}pyrimidin-5-yl) methanone as light yellow solid. Yield: 25 mg (19%). $^1$H NMR (400 MHz, DMSO-$d_6$) δ 9.05 (s, 1H), 9.00 (s, 1H), 8.69-8.61 (m, 4H), 7.44 (t, 1H), 7.30-7.22 (m, 3H), 3.81 (s, 3H), 1.51-1.45 (m, 2H), 1.39-1.33 (m, 2H). LCMS $[M+H]^+$: 348.2. HPLC: 97.75% (method 2, retention time=3.478 min)

Example 19 preparation of [3-(methylsulfonyl)phenyl]{6-[(pyrimidin-5-ylmethyl)amino]pyridin-3-yl}methanone Step 1:

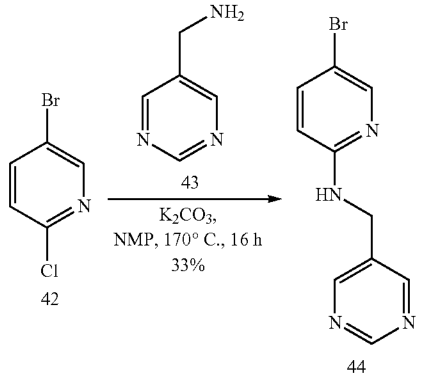 [SMILES: Clc1ccc(Br)cn1 ; NCc1cncnc1 ; Brc1ccc(NCc2cncnc2)nc1]

To a stirred solution of 5-bromo-2-chloropyridine (42, 200 mg, 1.04 mmol) and 1-(pyrimidin-5-yl)methanamine (43, 170 mg, 1.56 mmol] in NMP (2 mL) was added powdered $K_2CO_3$ (574 mg, 4.16 mmol) and the resulting solution was heated at 170° C. for 16 hours in a sealed tube. After completion (monitored by TLC, 5% MeOH in DCM, Rf 0.2) the reaction mixture was partitioned between water (70 mL) and ethyl acetate (100 mL). Organic layer was separated and the aqueous part was further extracted with ethyl acetate (2×50 mL). Combined organic layers were washed with brine, dried over sodium sulfate and concentrated under vacuo. The purification by column chromatography (using silica gel 100-200 and gradient elution of 0-2% MeOH in DCM) afforded 5-bromo-N-(pyrimidin-5-ylmethyl)pyridin-2-amine (43) as light yellow solid. Yield: 90 mg (33%). $^1$H NMR (400 MHz, $CDCl_3$) δ 9.13 (s, 1H), 8.74 (s, 2H), 8.13 (d, 1H), 7.50 (dt, 1H), 6.36 (d, 1H), 5.01 (s, 1H), 4.58 (d, 2H). LCMS $[M-H]^-$: 265.2

Step 2:

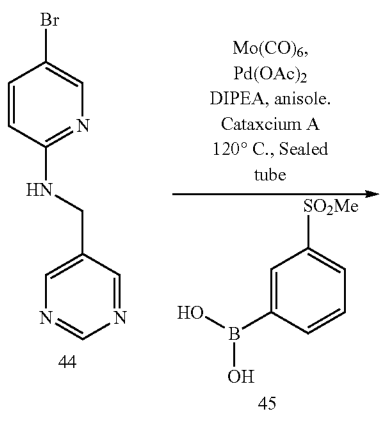

-continued

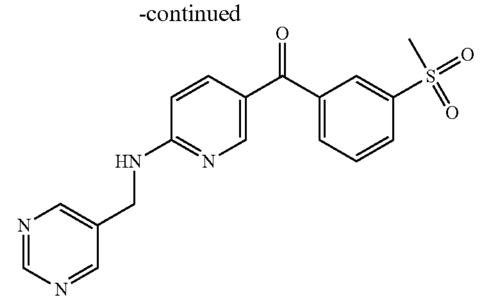

A stirred solution of 5-bromo-N-(pyrimidin-5-ylmethyl) pyridin-2-amine (44, 290 mg, 1.09 mmol), cataCXium A (49 mg, 0.14 mmol) and DIPEA (0.94 mL, 5.45 mmol) in anisole: toluene (1:1, 10 mL) was degassed with argon for 5 minutes and then sonicated for 5 minutes. This process was repeated three times, then [3-(methylsulfonyl)phenyl]boronic acid (45, 2.23 mmol), $Mo(CO)_6$ (489 mg, 1.85 mmol) and a mixture of $Pd(OAc)_2$ (0.025 M, 2.70 mL, 0.067 mmol) in degassed anisole was added to the reaction mixture and the reaction mixture was allowed to stir at 120° C. for 18 hours in a sealed tube. After completion (monitored by TLC 5% MeOH in DCM, Rf ~0.2) reaction mixture was partitioned between EtOAc (100 mL) and water (70 mL). Organic layer was separated and aqueous layer was further extracted with EtOAc (50 mL). Combined organic layer was washed with brine (50 mL) dried over sodium sulfate and concentrated under vacuo. The purification by preparative TLC (TLC Silica gel 60 F254, 20×20 cm plates; mobile phase: 4% MeOH in DCM) afforded [3-(methylsulfonyl) phenyl]{6-[(pyrimidin-5-ylmethyl)amino]pyridin-3-yl}methanone as an off-white solid. $^1$H NMR (400 MHz, DMSO-$d_6$) δ 9.08 (s, 1H), 8.79 (s, 2H), 8.42 (d, 1H), 8.24 (t, 1H), 8.18-8.14 (m, 1H), 8.14-8.12 (m, 1H), 8.03-7.99 (m, 1H), 7.87 (dd, 1H), 7.81 (t, 1H), 6.70 (d, 1H), 4.64 (d, 2H), 3.29 (s, 3H). LCMS $[M+H]^+$: 369.2, HPLC: 98.42% (method 3, retention time=2.892 min)

Example 20 preparation of [3-(methylsulfonyl)phenyl]{2-[(pyrimidin-5-ylmethyl)amino]pyrimidin-5-yl}methanone Step 1:

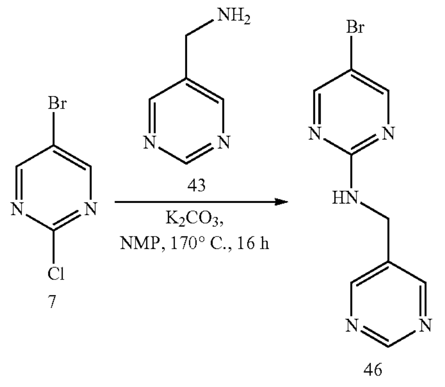 [SMILES: Clc1ncc(Br)cn1 ; NCc1cncnc1 ; Brc1cnc(NCc2cncnc2)nc1]

5-Bromo-N-(pyrimidin-5-ylmethyl)pyrimidin-2-amine (46) was prepared according to the method described in example 19 step 1 using 5-bromo-2-chloropyrimidine (7) and 1-(pyrimidin-5-yl)methanamine (43). $^1$H NMR (400

MHz, $CDCl_3$ with a couple of drops of MeOH-$d_4$) 5 9.06 (s, 1H), 8.71 (s, 2H), 8.26 (s, 2H), 4.56 (s, 2H). LCMS $[M-H]^-$: 264

Step 2:

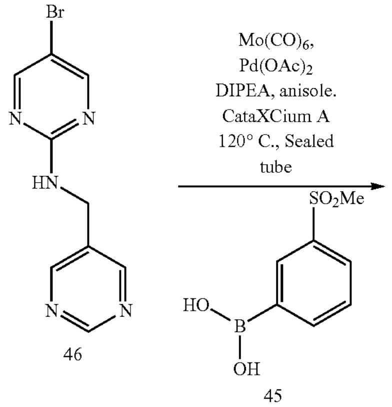

46
45

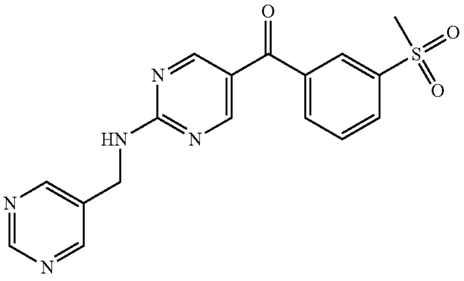

The desired example was prepared according to the method described in example 19 step 2 using [3-(methylsulfonyl)phenyl]boronic acid (45) and 5-bromo-N-(pyrimidin-5-ylmethyl)pyrimidin-2-amine (46). The purification by preparative TLC (TLC Silica gel 60 F254, 20×20 cm plates; mobile phase: 4% MeOH in DCM) afforded [3-(methylsulfonyl)phenyl]{2-[(pyrimidin-5-ylmethyl)amino]pyrimidin-5-yl}methanone as an off-white solid. Yield: 10 mg (6%). $^1H$ NMR (400 MHz, DMSO-$d_6$) δ 9.10 (s, 1H), 8.86 (t, 1H), 8.79 (s, 2H), 8.73 (s, 2H), 8.23-8.18 (m, 2H), 8.07 (d, 1H), 7.83 (t, 1H), 4.65 (d, 2H), 3.30 (s, 3H). LCMS $[M+H]^+$: 370.0. HPLC: 98.64% (method 2, retention time=3.55 min).

Example 21 preparation of [3-(methylsulfonyl)phenyl]{2-[(pyridazin-3-ylmethyl)amino]pyrimidin-5-yl}methanone

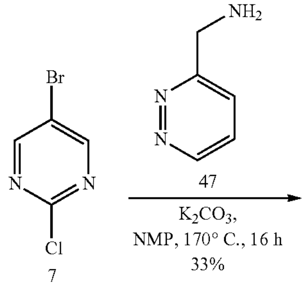

7
47

-continued

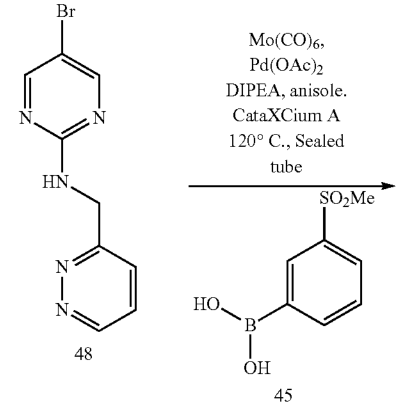

48
45

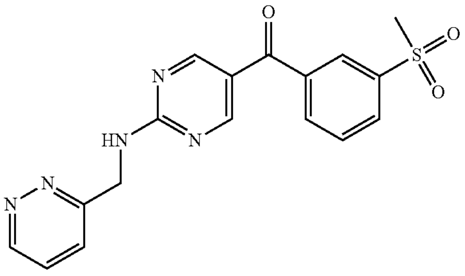

The desired example was prepared according to the method described in example 19 steps 1 and 2 using 1-(pyridazin-3-yl)methanamine (47), 5-bromo-2-chloropyrimidine (7) and [3-(methylsulfonyl)phenyl]boronic acid (45). The purification by preparative TLC (TLC silica gel 60 F254, 20×20 cm plates; mobile phase: 4% MeOH in DCM) afforded [3-(methylsulfonyl)phenyl]{2-[(pyridazin-3-ylmethyl)amino]pyrimidin-5-yl}methanone as off-white solid. $^1H$ NMR (400 MHz, MeOH-$d_4$) δ 9.08 (d, 1H), 8.65-8.85 (m, 2H), 8.27 (s, 1H), 8.23-8.18 (m, 1H), 8.08-8.05 (m, 1H), 7.81 (t, 1H), 7.76-7.73 (m, 1H), 7.70-7.66 (m, 1H), 5.00 (s, 2H), 3.17 (s, 3H). LCMS $[M+H]^+$: 370.0. HPLC: 98.64% (method 5, retention time=13.025 min).

Examples 22-161 were prepared by methods related to those described herein. Synthetic method A refers to the methods described in Scheme 1 and Scheme 3. Synthetic method B refers to the method described in Scheme 2.

| Eg # | Structure | IUPAC Name | MS data | NMR data | Synthetic method |
|---|---|---|---|---|---|
| 22 | 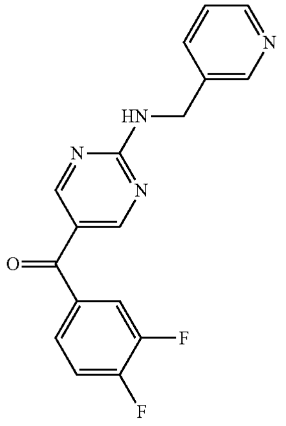 [SMILES: O=C(c1cnc(NCc2cccnc2)nc1)c1ccc(F)c(F)c1] | (3,4-difluorophenyl){2-[(pyridin-3-ylmethyl)amino] pyrimidin-5-yl}methanone | $[M + H]^+$: 327.1 | $^1H$ NMR (300 MHz, DMSO-d6): δ 8.81 (t, 1H), 8.69 (s, 2H), 8.56 (m, 1H), 8.45 (m, 1H), 7.9-7.75 (m, 1H), 7.75-7.7 (m, 1H), 7.65-7.55 (m, 2H), 7.4-7.3 (m, 1H), 4.63 (d, 2H) | A |
| 23 | 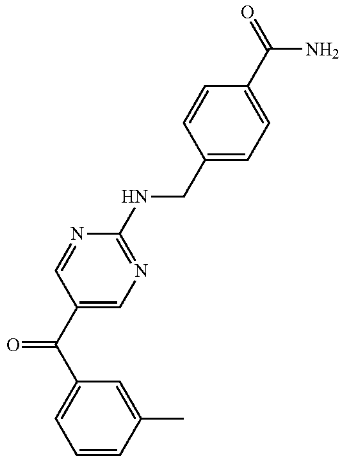 [SMILES: Cc1cccc(C(=O)c2cnc(NCc3ccc(C(N)=O)cc3)nc2)c1] | 4-({[5-(3-methylbenzoyl) pyrimidin-2-yl]amino}methyl) benzamide | $[M + H]^+$: 347.2 | $^1H$ NMR (300 MHz, DMSO-d6): δ 8.74 (t, 1H), 8.66 (d, 2H), 7.9 (s, 1H), 7.8 (d, 2H), 7.55-7.4 (m, 4H), 7.35 (d, 2H), 7.3 (s, 1H), 4.66 (d, 2H), 2.39 (s, 3H) | A |
| 24 | 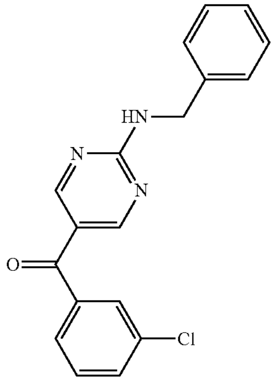 [SMILES: O=C(c1cnc(NCc2ccccc2)nc1)c1cccc(Cl)c1] | [2-(benzylamino) pyrimidin-5-yl](3-chlorophenyl) methanone | $[M + H]^+$: 322, 324 | $^1H$ NMR (400 MHz, CDCl3): δ 8.8 (br s, 1H), 8.7 (br s, 1H), 7.75 (m, 1H), 7.65-7.55 (m, 2H), 7.45 (t, 1H), 7.35-7.25 (m, 5H), 6.1 (br t, 1H), 4.75 (d, 2H) | A |

-continued

| Eg # | Structure | IUPAC Name | MS data | NMR data | Synthetic method |
|---|---|---|---|---|---|
| 25 | 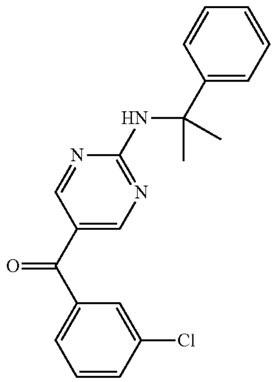 [SMILES: CC(C)(Nc1ncc(C(=O)c2cccc(Cl)c2)cn1)c1ccccc1] | (3-chlorophenyl){2-[(2-phenylpropan-2-yl)amino]pyrimidin-5-yl}methanone | $[M+H]^+$: 352/354 | $^1H$ NMR (400 MHz, CDCl3): δ 8.75 (br s, 1H), 8.55 (br s, 1H), 7.65 (m, 1H), 7.6-7.5 (m, 2H), 7.45-7.35 (m, 3H), 7.35-7.25 (m, 2H), 7.25-7.15 (m, 1H), 6.2 (br s, 1H), 1.85 (s, 6H | A |
| 26 | 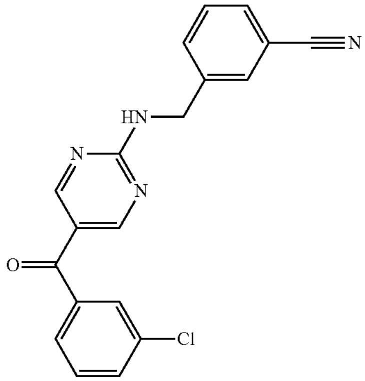 [SMILES: N#Cc1cccc(CNc2ncc(C(=O)c3cccc(Cl)c3)cn2)c1] | 3-({[5-(3-chlorobenzoyl) pyrimidin-2-yl]amino}methyl) benzonitrile | $[M+H]^+$: 347/349 | $^1H$ NMR (400 MHz, DMSO d6): δ 8.85 (br t, 1H), 8.7-8.6 (m, 2H), 7.8-7.65 (m, 6H), 7.6-7.5 (m, 2H), 4.65 (d, 2H | A |
| 27 | 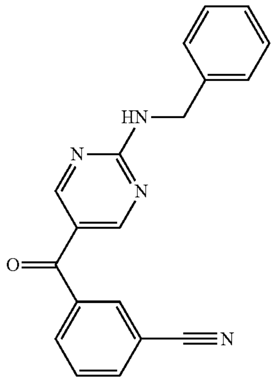 [SMILES: N#Cc1cccc(C(=O)c2cnc(NCc3ccccc3)nc2)c1] | 3-{[2-(benzylamino) pyrimidin-5-yl]carbonyl} benzonitrile | $[M+H]^+$: 315.1 | $^1H$ NMR (300 MHz, DMSO-d6): δ 8.82 (t, 1H), 8.68 (s, 2H), 8.2-8.0 (m, 3H), 7.8-7.7 (m, 1H), 7.4-7.2 (m, 5H), 4.65 (d, 2H | A |

-continued

| Eg # | Structure | IUPAC Name | MS data | NMR data | Synthetic method |
|---|---|---|---|---|---|
| 28 | 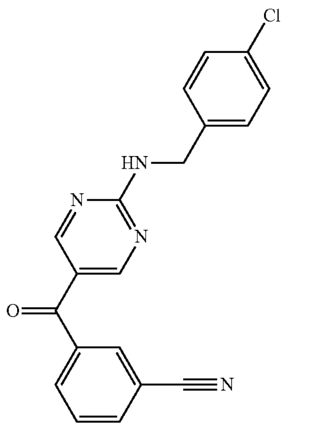 [SMILES: N#Cc1cccc(C(=O)c2cnc(NCc3ccc(Cl)cc3)nc2)c1] | 3-({2-[(4-chlorobenzyl)amino] pyrimidin-5-yl}carbonyl) benzonitrile | $[M + H]^+$: 349.1 | $^1H$ NMR (300 MHz, DMSO-d6): δ 8.84 (t, 1H), 8.68 (m, 2H), 8.15 (s, 1H), 8.10 (d, 1H), 8.02 (d, 1H), 7.74 (t, 1H), 7.4-7.3 (m, 4H), 4.6 (d, 2H | A |
| 29 | 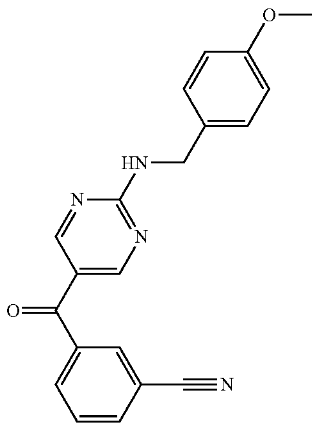 [SMILES: COc1ccc(CNc2ncc(C(=O)c3cccc(C#N)c3)cn2)cc1] | 3-({2-[(4-methoxybenzyl) amino]pyrimidin-5-yl}carbonyl) benzonitrile | $[M + H]^+$: 345.2 | $^1H$ NMR (300 MHz, DMSO-d6): δ 8.77 (t, 1H), 8.68 (s, 2H), 8.15 (s, 1H), 8.09 (d, 1H), 8.01 (d, 1H), 7.74 (m, 1H), 7.25 (d, 2H), 6.88 (d, 2H), 4.54 (d, 2H), 3.71 (s, 3H) | A |
| 30 | 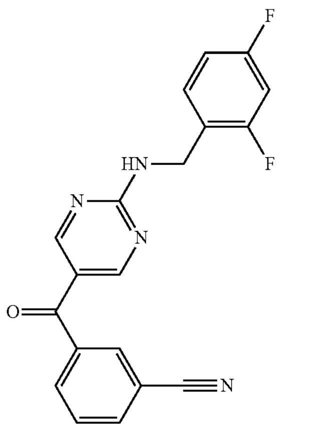 [SMILES: N#Cc1cccc(C(=O)c2cnc(NCc3ccc(F)cc3F)nc2)c1] | 3-({2-[(2,4-difluorobenzyl) amino]pyrimidin-5-yl}carbonyl) benzonitrile | $[M + H]^+$: 351.2 | $^1H$ NMR (300 MHz, DMSO-d6): δ 8.79 (t, 1H), 8.7 (s, 2H), 8.15 (s, 1H), 8.09 (d, 1H), 8.02 (d, 1H), 7.75 (t, 1H), 7.41 (m, 1H), 7.22 (m, 1H), 7.05 (m, 1H), 4.62 (d, 2H) | A |

-continued

| Eg # | Structure | IUPAC Name | MS data | NMR data | Synthetic method |
|---|---|---|---|---|---|
| 31 | 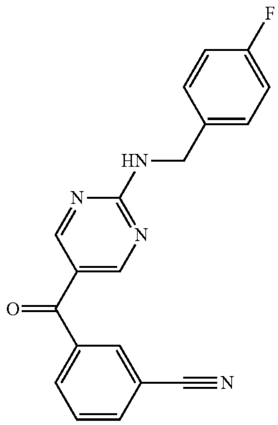 [SMILES: N#Cc1cccc(C(=O)c2cnc(NCc3ccc(F)cc3)nc2)c1] | 3-({2-[(4-fluorobenzyl)amino]pyrimidin-5-yl}carbonyl)benzonitrile | $[M + H]^+$: 333.2 | $^1$H NMR (300 MHz, DMSO-d6): δ 8.83 (t, 1H), 8.69 (s, 2H), 8.15 (s, 1H), 8.1 (d, 1H), 8.02 (d, 1H), 7.74 (t, 1H), 7.36 (m, 2H), 7.14 (m, 2H), 4.6 (d, 2H) | A |
| 32 | 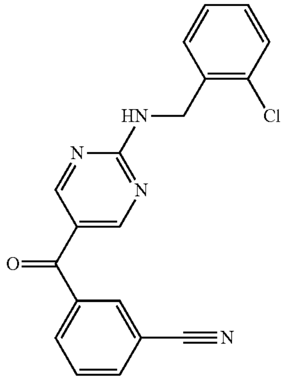 [SMILES: N#Cc1cccc(C(=O)c2cnc(NCc3ccccc3Cl)nc2)c1] | 3-({2-[(2-chlorobenzyl)amino]pyrimidin-5-yl}carbonyl)benzonitrile | $[M + H]^+$: 349.1 | $^1$H NMR (300 MHz, DMSO-d6): δ 8.81 (t, 1H), 8.75-8.65 (m, 2H), 8.16 (s, 1H), 8.1 (d, 1H), 8.05 (d, 1H), 7.8-7.7 (m, 1H), 7.5-7.4 (m, 1H), 7.4-7.2 (m, 3H), 4.65 (d, 2H | A |
| 33 | 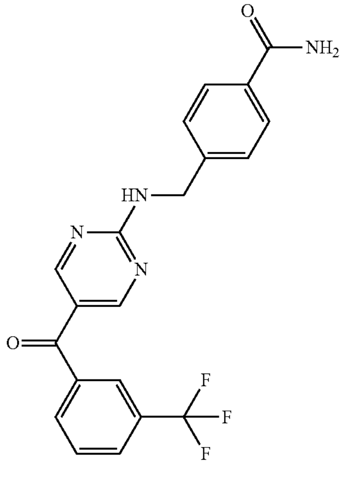 [SMILES: NC(=O)c1ccc(CNc2ncc(C(=O)c3cccc(C(F)(F)F)c3)cn2)cc1] | 4-[({5-[3-(trifluoromethyl)benzoyl]pyrimidin-2-yl}amino)methyl]benzamide | $[M + H]^+$: 400.8 | $^1$H NMR (400 MHz, DMSO-d6): δ 8.88-8.84 (t, 1H), 8.70-8.66 (m, 2H), 8.02-8.00 (m, 3H), 7.92 (s, 1H), 7.82-7.76 (m, 3H), 7.38-7.36 (m, 2H), 7.32 (s, 1H), 4.67-4.65 (d, 2H) | A |

-continued

| Eg # | Structure | IUPAC Name | MS data | NMR data | Synthetic method |
|---|---|---|---|---|---|
| 34 | 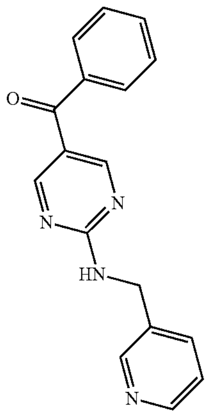 [SMILES: O=C(c1ccccc1)c1cnc(NCc2cccnc2)nc1] | phenyl{2-[(pyridin-3-ylmethyl)amino]pyrimidin-5-yl}methanone | $[M + H]^+$: 291 | $^1$H NMR (400 MHz, MeOD-d3): δ 8.74 (s, 2H), 8.58 (s, 1H), 8.45 (d, 1H), 8.12 (br s, 1H), 7.89 (d, 2H), 7.75 (d, 2H), 7.67-7.64 (m, 1H), 7.57-7.53 (m, 2H), 7.44-7.41 (m, 1H), 4.74 (s, 2H) | A |
| 35 | 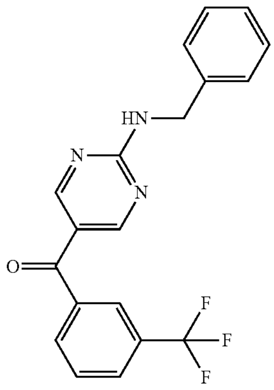 [SMILES: O=C(c1cnc(NCc2ccccc2)nc1)c1cccc(C(F)(F)F)c1] | [2-(benzylamino)pyrimidin-5-yl][3-(trifluoromethyl)phenyl]methanone | $[M - H]^-$: 356 | $^1$H NMR (400 MHz, DMSO-d6): δ 8.85 (t, 1H), 8.7 (s, 2H), 8.05 (m, 3H), 7.85 (t, 1H), 7.35-7.15 (m, 5H), 4.65 (d, 2H) | A |
| 36 | 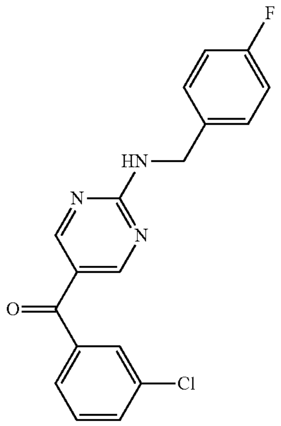 [SMILES: O=C(c1cnc(NCc2ccc(F)cc2)nc1)c1cccc(Cl)c1] | (3-chlorophenyl){2-[(4-fluorobenzyl)amino]pyrimidin-5-yl}methanone | $[M + H]^+$: 342, 344 | $^1$H NMR (400 MHz, CDCl3): δ 8.8 (br s, 1H), 8.7 (br s, 1H), 7.7 (m, 1H), 7.6 (m, 2H), 7.4 (t, 1H), 7.35 (m, 2H), 7.05 (m, 2H), 6.1 (br t, 1 H), 4.7 (d, 2H) | A |

-continued

| Eg # | Structure | IUPAC Name | MS data | NMR data | Syn-thetic method |
|---|---|---|---|---|---|
| 37 | 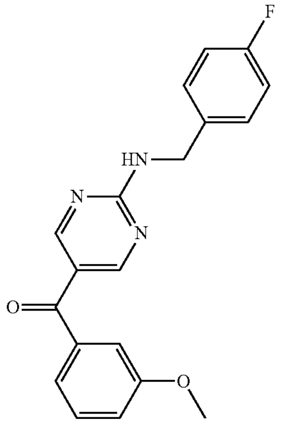 [SMILES: COc1cccc(C(=O)c2cnc(NCc3ccc(F)cc3)nc2)c1] | {2-[(4-fluorobenzyl) amino]pyrimidin-5-yl}(3-methoxyphenyl) methanone | $[M-H]^-$: 336 | $^1H$ NMR (400 MHz, DMSO-d6): δ 8.75 (t, 1H), 8.65 (s, 2H), 7.45 (m, 1H), 7.35 (m, 2H), 7.3-7.1 (m, 5H), 4.6 (d, 2H), 3.8 (s, 3H) | A |
| 38 | 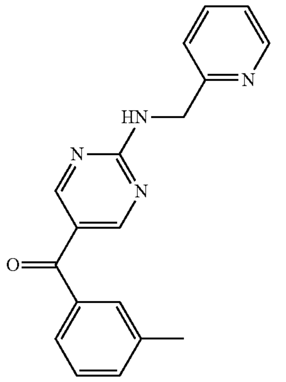 [SMILES: Cc1cccc(C(=O)c2cnc(NCc3ccccn3)nc2)c1] | (3-methylphenyl){2-[(pyridin-2-ylmethyl)amino] pyrimidin-5-yl}methanone | $[M+H]^+$: 305 | $^1H$ NMR (300 MHz, DMSO-d6): δ 8.8-8.6 (m, 3H), 8.5 (m, 1H), 7.75 (t, 1H), 7.6-7.4 (m, 4H), 7.35-7.2 (m, 2H), 4.7 (d, 2H), 2.4 (s, 3H) | A |
| 39 | 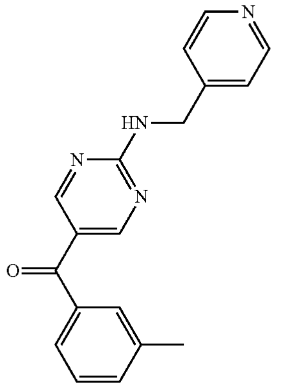 [SMILES: Cc1cccc(C(=O)c2cnc(NCc3ccncc3)nc2)c1] | (3-methylphenyl){2-[(pyridin-4-ylmethyl)amino] pyrimidin-5-yl}methanone | $[M+H]^+$: 305 | $^1H$ NMR (300 MHz, DMSO-d6): δ 8.75 (t, 1H), 8.7 (m, 2H), 8.5 (m, 2H), 7.6-7.4 (m, 4H), 7.3 (m, 2H), 4.65 (d, 2H), 2.35 (s, 3H | A |

-continued

| Eg # | Structure | IUPAC Name | MS data | NMR data | Synthetic method |
|---|---|---|---|---|---|
| 40 | 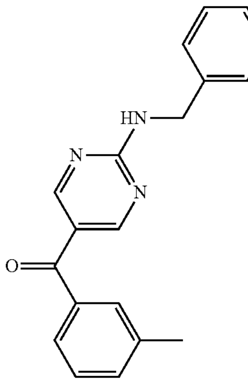 | [2-(benzylamino) pyrimidin-5-yl](3-methylphenyl) methanone | $[M + H]^+$: 304 | $^1H$ NMR (300 MHz, DMSO-d6): δ 8.75 (t, 1H), 8.65 (s, 2H), 7.6-7.4 (m, 4H), 7.35-7.2 (m, 5H), 4.6 (d, 2H), 2.35 (s, 3H) | A |
| 41 | 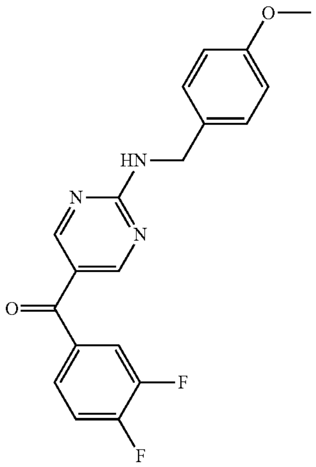 [SMILES: COc1ccc(CNc2ncc(C(=O)c3ccc(F)c(F)c3)cn2)cc1] | (3,4-difluorophenyl){2-[(4-methoxybenzyl) amino]pyrimidin-5-yl}methanone | $[M + H]^+$: 356 | $^1H$ NMR (300 MHz, DMSO-d6): δ 8.75 (t, 1H), 8.65 (s, 2H), 7.6-7.4 (m, 4H), 7.35-7.2 (m, 5H), 4.6 (d, 2H), 2.35 (s, 3H | A |
| 42 | 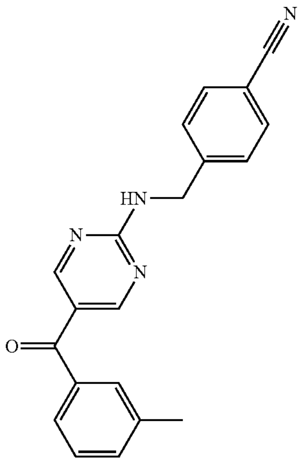 [SMILES: Cc1cccc(C(=O)c2cnc(NCc3ccc(C#N)cc3)nc2)c1] | 4-({[5-(3-methylbenzoyl) pyrimidin-2-yl]amino}methyl) benzonitrile | $[M + H]^+$: 329 | $^1H$ NMR (300 MHz, DMSO-d6): δ 8.8 (t, 1H), 8.65 (m, 2H), 7.8 (d, 2H), 7.6-7.4 (m, 6H), 4.65 (d, 2H), 2.4 (s, 3H) | A |

-continued

| Eg # | Structure | IUPAC Name | MS data | NMR data | Synthetic method |
| --- | --- | --- | --- | --- | --- |
| 43 | 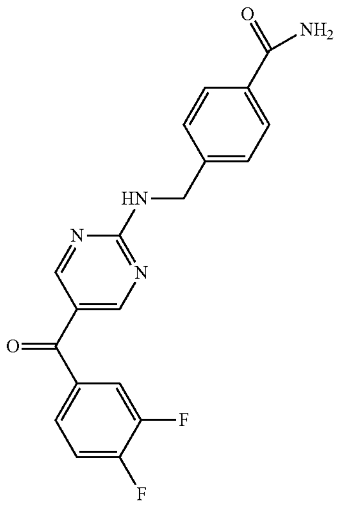 [SMILES: NC(=O)c1ccc(CNc2ncc(C(=O)c3ccc(F)c(F)c3)cn2)cc1] | 4-({[5-(3,4-difluorobenzoyl) pyrimidin-2-yl]amino}methyl) benzamide | $[M + H]^+$: 369 | $^1$H NMR (300 MHz, DMSO-d6): δ 8.8 (t, 1H), 8.65 (m, 2H), 8.0-7.8 (m, 4H), 7.6 (m, 2H), 7.45-7.2 (m, 3H), 4.65 (d, 2H) | A |
| 44 | 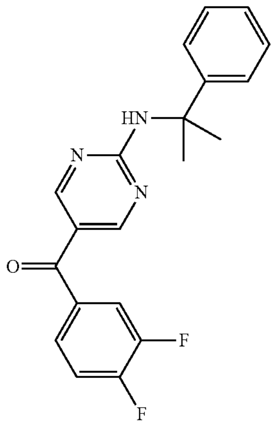 [SMILES: CC(C)(Nc1ncc(C(=O)c2ccc(F)c(F)c2)cn1)c1ccccc1] | (3,4-difluorophenyl){2-[(2-phenylpropan-2-yl)amino]pyrimidin-5-yl}methanone | $[M + H]^+$: 354 | $^1$H NMR (300 MHz, DMSO-d6): δ 8.7 (t, 1H), 8.65 (m, 2H), 8.0-7.8 (m, 4H), 7.6 (m, 2H), 7.45-7.2 (m, 3H), 4.65 (d, 2H | A |
| 45 | 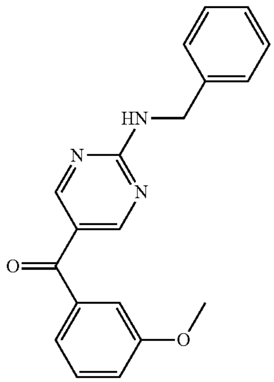 [SMILES: COc1cccc(C(=O)c2cnc(NCc3ccccc3)nc2)c1] | [2-(benzylamino) pyrimidin-5-yl](3-methoxyphenyl) methanone | $[M - H]^-$: 318.3 | $^1$H NMR (400 MHz, CDCl3): δ 8.85 (br s, 1H), 8.55 (br s, 1H), 7.45-7.25 (m, 8H), 7.15 (m, 1H), 6.35 (br t, 1 H), 4.75 (d, 2H), 3.75 (s, 3H) | A |

-continued

| Eg # | Structure | IUPAC Name | MS data | NMR data | Synthetic method |
|---|---|---|---|---|---|
| 46 | 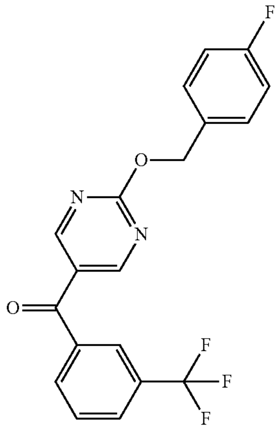 [SMILES: O=C(c1cnc(OCc2ccc(F)cc2)nc1)c1cccc(C(F)(F)F)c1] | {2-[(4-fluorobenzyl)oxy]pyrimidin-5-yl}[3-(trifluoromethyl)phenyl]methanone | $[M + H]^+$: 377 | $^1H$ NMR (400 MHz, DMSO-$d_6$): δ 8.98 (s, 2H), 8.1 (t, 3H), 7.83 (t, 1H), 7.57 (t, 2H), 7.24 (t, 2H), 5.51 (s, 2H) | A |
| 47 | 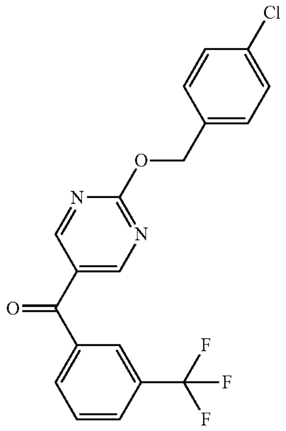 [SMILES: O=C(c1cnc(OCc2ccc(Cl)cc2)nc1)c1cccc(C(F)(F)F)c1] | {2-[(4-chlorobenzyl)oxy]pyrimidin-5-yl}[3-(trifluoromethyl)phenyl]methanone | $[M + H]^+$: 393 | $^1H$ NMR (400 MHz, DMSO-$d_6$): δ 8.98 (s, 2H), 8.09 (t, 3H), 7.83 (t, 1H), 7.51 (q, 4H), 5.55 (s, 2H) | A |
| 48 | 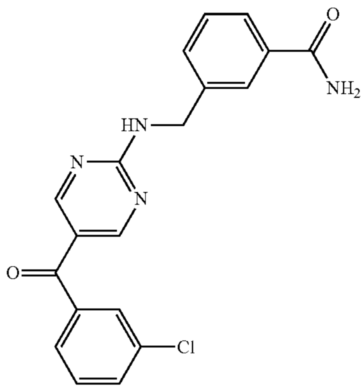 [SMILES: NC(=O)c1cccc(CNc2ncc(C(=O)c3cccc(Cl)c3)cn2)c1] | 3-({[5-(3-chlorobenzoyl)pyrimidin-2-yl]amino}methyl)benzamide | $[M + H]^+$: 367 | $^1H$ NMR (400 MHz, DMSO-$d_6$): δ 8.81 (t, 1H), 8.67 (br s, 2H), 7.93 (br s, 1H), 7.85 (s, 1H), 7.64-7.77 (m, 4H), 7.57 (t, 1H), 7.47 (d, 1H), 7.36-7.42 (m, 1H), 7.32 (br s, 1H), 4.66 (d, 2H) | A |

-continued

| Eg # | Structure | IUPAC Name | MS data | NMR data | Syn-thetic method |
|---|---|---|---|---|---|
| 49 | 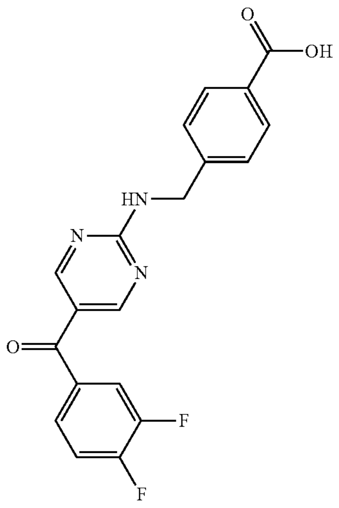 [SMILES: O=C(O)c1ccc(CNc2ncc(C(=O)c3ccc(F)c(F)c3)cn2)cc1] | 4-({[5-(3,4-difluorobenzoyl)pyrimidin-2-yl]amino}methyl)benzoic acid | [M + H]$^+$: 370 | $^1$H NMR (400 MHz, DMSO-$d_6$): δ 12.9 (s, 1H), 8.84 (t, 1H), 8.68 (d, 2H), 7.9 (d, 2H), 7.81 (m, 1H), 7.6 (m, 2H), 7.42 (d, 2H), 4.66 (d, 2H) | A |
| 50 | 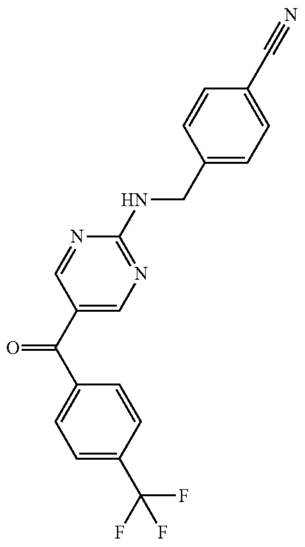 [SMILES: N#Cc1ccc(CNc2ncc(C(=O)c3ccc(C(F)(F)F)cc3)cn2)cc1] | 4-[({5-[4-(trifluoromethyl)benzoyl]pyrimidin-2-yl}amino)methyl]benzonitrile | LCMS [M + H]$^+$: 383. * | * HPLC Method SP3126, Retention Time 1.73 min. | A |
| 51 | 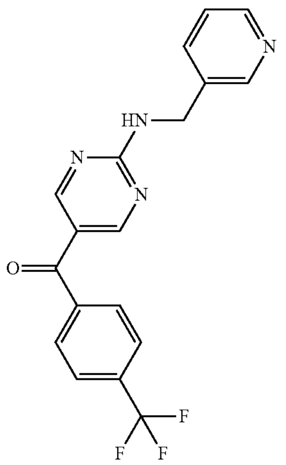 [SMILES: O=C(c1ccc(C(F)(F)F)cc1)c1cnc(NCc2cccnc2)nc1] | {2-[(pyridin-3-ylmethyl)amino]pyrimidin-5-yl}[4-(trifluoromethyl)phenyl]methanone | LCMS [M + H]$^+$: 359. * | *HPLC Method SP3126, Retention Time 1.45 min. | A |

-continued

| Eg # | Structure | IUPAC Name | MS data | NMR data | Synthetic method |
|---|---|---|---|---|---|
| 52 | 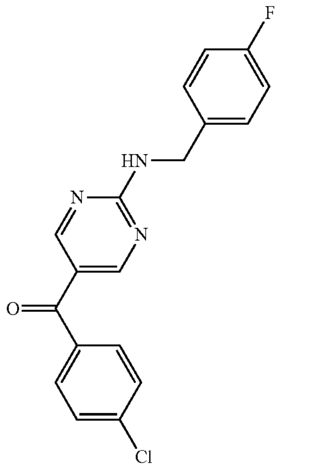 [SMILES: O=C(c1ccc(Cl)cc1)c1cnc(NCc2ccc(F)cc2)nc1] | (4-chlorophenyl){2-[(4-fluorobenzyl)amino]pyrimidin-5-yl}methanone | LCMS $[M + H]^+$: 342.* | * HPLC Method SP3126, Retention Time 1.76 min. | A |
| 53 | 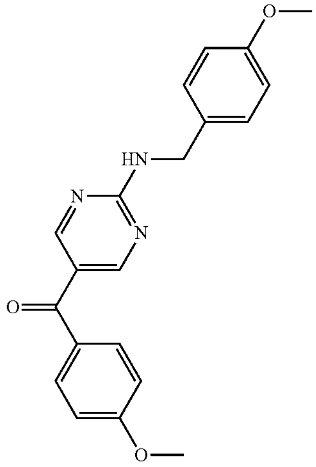 [SMILES: COc1ccc(CNc2ncc(C(=O)c3ccc(OC)cc3)cn2)cc1] | {2-[(4-methoxybenzyl)amino]pyrimidin-5-yl}(4-methoxyphenyl)methanone | LCMS $[M + H]^+$: 350.* | *HPLC Method SP3126, Retention Time 1.68 min. | A |
| 54 | 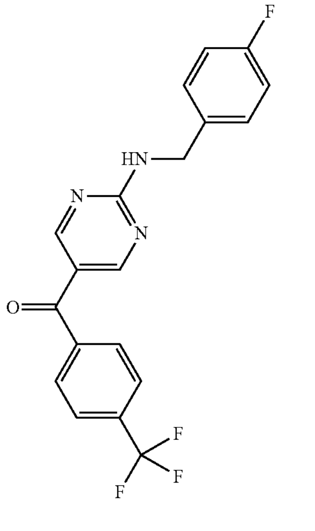 [SMILES: O=C(c1ccc(C(F)(F)F)cc1)c1cnc(NCc2ccc(F)cc2)nc1] | {2-[(4-fluorobenzyl)amino]pyrimidin-5-yl}[4-(trifluoromethyl)phenyl]methanone | LCMS $[M + H]^+$: 376.* | * HPLC Method SP3126, Retention Time 1.77 min. | A |

-continued

| Eg # | Structure | IUPAC Name | MS data | NMR data | Synthetic method |
|---|---|---|---|---|---|
| 55 | 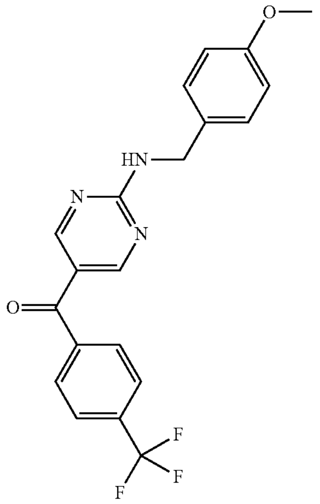 [SMILES: COc1ccc(CNc2ncc(C(=O)c3ccc(C(F)(F)F)cc3)cn2)cc1] | {2-[(4-methoxybenzyl) amino]pyrimidin-5-yl}[4-(trifluoromethyl) phenyl]methanone | LCMS [M + H]+: 388.* | | A |
| 56 | 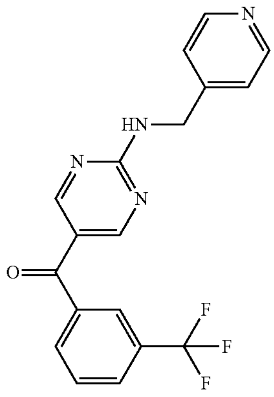 [SMILES: O=C(c1cnc(NCc2ccncc2)nc1)c1cccc(C(F)(F)F)c1] | {2-[(pyridin-4-ylmethyl)amino] pyrimidin-5-yl}[3-(trifluoromethyl) phenyl]methanone | LCMS [M + H]+: 359. | * HPLC Method SP3126, Retention Time 1.76 min. | A |
| 57 | 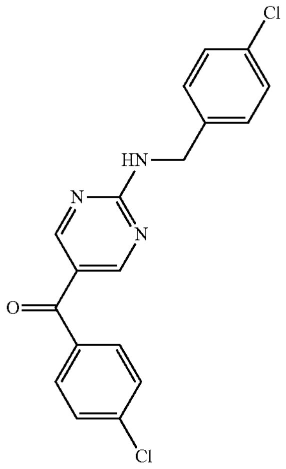 [SMILES: O=C(c1ccc(Cl)cc1)c1cnc(NCc2ccc(Cl)cc2)nc1] | {2-[(4-chlorobenzyl) amino]pyrimidin-5-yl}(4-chlorophenyl) methanone | LCMS [M + H]+: 358.* | HPLC Method SP3126, Retention Time 1.81 min. | A |

-continued

| Eg # | Structure | IUPAC Name | MS data | NMR data | Synthetic method |
|---|---|---|---|---|---|
| 58 | 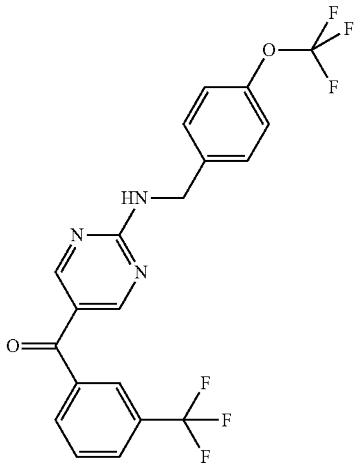 [SMILES: O=C(c1cnc(NCc2ccc(OC(F)(F)F)cc2)nc1)c1cccc(C(F)(F)F)c1] | (2-{[4-(trifluoromethoxy)benzyl]amino}pyrimidin-5-yl)[3-(trifluoromethyl)phenyl]methanone | LCMS [M + H]$^+$: 442. * | * HPLC Method SP3126, Retention Time 1.82 min. | A |
| 59 | 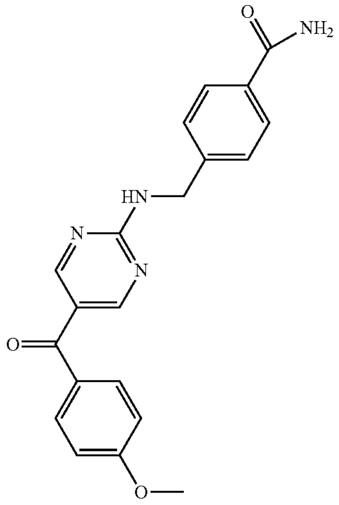 [SMILES: COc1ccc(C(=O)c2cnc(NCc3ccc(C(N)=O)cc3)nc2)cc1] | 4-({[5-(4-methoxybenzoyl)pyrimidin-2-yl]amino}methyl)benzamide | [M + Na]$^+$: 385 | $^1$H NMR (400 MHz, MeOH-$d_4$): δ 8.94 (br s, 1H), 8.83 (br s, 1H), 7.90 (d, 2H), 7.85 (d, 2H), 7.53 (d, 2H), 7.12 (d, 2H), 4.88 (s, 2H), 3.93 (s, 3H) | A |
| 60 | 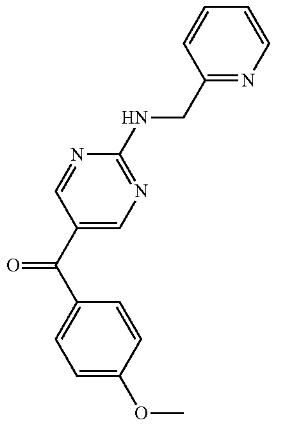 [SMILES: COc1ccc(C(=O)c2cnc(NCc3ccccn3)nc2)cc1] | (4-methoxyphenyl){2-[(pyridin-2-ylmethyl)amino]pyrimidin-5-yl}methanone | [M + H]$^+$: 321. * | * HPLC Method SP3126, Retention Time 1.45 min. | A |

-continued

| Eg # | Structure | IUPAC Name | MS data | NMR data | Synthetic method |
|---|---|---|---|---|---|
| 61 | 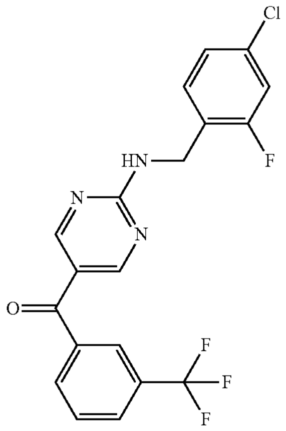 [SMILES: O=C(c1cnc(NCc2ccc(Cl)cc2F)nc1)c1cccc(C(F)(F)F)c1] | {2-[(4-chloro-2-fluorobenzyl) amino]pyrimidin-5-yl}[3-(trifluoromethyl) phenyl]methanone | LCMS $[M + H]^+$: 410.* | *HPLC Method SP3126, Retention Time 1.82 min. | A |
| 62 | 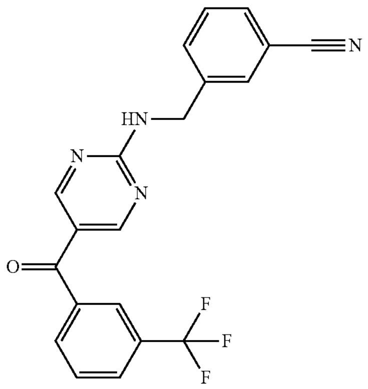 [SMILES: N#Cc1cccc(CNc2ncc(C(=O)c3cccc(C(F)(F)F)c3)cn2)c1] | 3-[({5-[3-(trifluoromethyl) benzoyl]pyrimidin-2-yl}amino)methyl] benzonitrile | LCMS $[M + H]^+$: 383. * | * HPLC Method SP3126, Retention Time 1.72 min. | A |
| 63 | 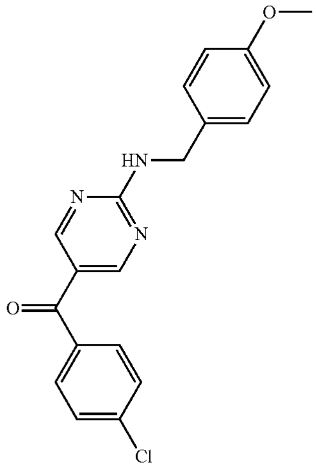 [SMILES: COc1ccc(CNc2ncc(C(=O)c3ccc(Cl)cc3)cn2)cc1] | (4-chlorophenyl){2-[(4-methoxybenzyl) amino]pyrimidin-5-yl}methanone | LCMS $[M + H]^+$: 354.* | * HPLC Method SP3126, Retention Time 1.75 min. | A |

-continued

| Eg # | Structure | IUPAC Name | MS data | NMR data | Synthetic method |
|---|---|---|---|---|---|
| 64 | 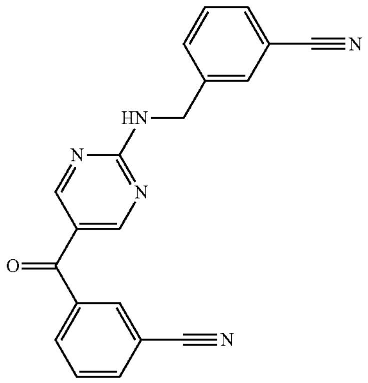 [SMILES: N#Cc1cccc(CNc2ncc(C(=O)c3cccc(C#N)c3)cn2)c1] | 3-({[5-(3-cyanobenzoyl) pyrimidin-2-yl]amino}methyl) benzonitrile | $[M + H]^+$: 340 | $^1H$ NMR (400 MHz, MeOH-$d_4$): δ 8.74 (s, 2H), 8.11 (s, 1H), 8.04-7.98 (m, 2H), 7.75-7.69 (m, 3H), 7.63 (d, 1H), 7.52 (t, 1H), 4.75 (s, 2H) | A |
| 65 | 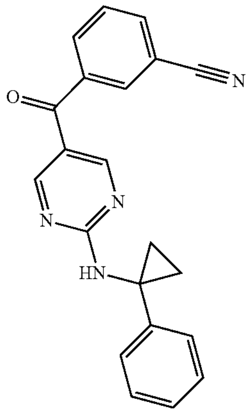 [SMILES: N#Cc1cccc(C(=O)c2cnc(NC3(c4ccccc4)CC3)nc2)c1] | 3-({2-[(1-phenylcyclopropyl) amino]pyrimidin-5-yl}carbonyl) benzonitrile | $[M + H]^+$: 341 | $^1H$ NMR (400 MHz, MeOH-$d_4$): δ 8.58 (d, 1H), 8.48 (d, 1H), 7.92 (s, 1H), 7.85-7.79 (m, 2H), 7.55 (t, 1H), 7.09-7.07 (m, 4H), 6.99-6.96 (m, 1H), 1.20 (d, 4H) | A |
| 66 | 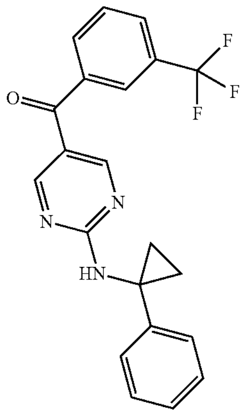 [SMILES: O=C(c1cnc(NC2(c3ccccc3)CC2)nc1)c1cccc(C(F)(F)F)c1] | {2-[(1-phenylcyclopropyl) amino]pyrimidin-5-yl}[3-(trifluoromethyl) phenyl]methanone | $[M + H]^+$: 384 | $^1H$ NMR (400 MHz, DMSO-$d_6$): δ 9.12 (s, 1H), 8.71 (s, 1H), 8.673 (s, 1H), 8.03-8.01 (m, 3H), 7.81-7.79 (m, 1H), 7.29-7.25 (m, 2H), 7.20-7.15 (m, 3H), 1.32 (d, 4H) | A |

-continued

| Eg # | Structure | IUPAC Name | MS data | NMR data | Synthetic method |
|---|---|---|---|---|---|
| 67 | 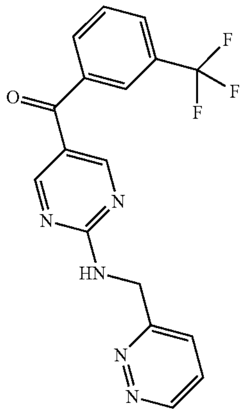 [SMILES: O=C(c1cnc(NCc2cccnn2)nc1)c1cccc(C(F)(F)F)c1] | {2-[(pyridazin-3-ylmethyl)amino]pyrimidin-5-yl}[3-(trifluoromethyl)phenyl]methanone | $[M + H]^+$: 360 | $^1H$ NMR (400 MHz, DMSO-$d_6$): δ 9.16 (d, 1H), 8.90 (t, 1H), 8.74 (d, 1H), 8.69 (s, 1H), 8.05-8.02 (m, 3H), 7.81 (t, 1H). 7.69-7.66 (m, 2H), 4.93 (d, 2H) | A |
| 68 | 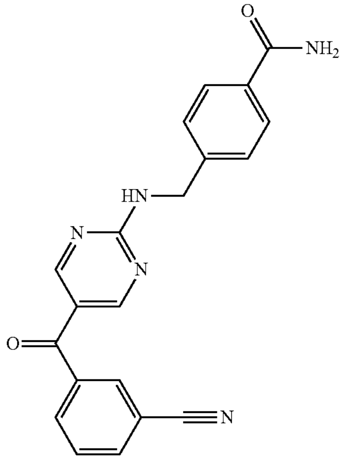 [SMILES: N#Cc1cccc(C(=O)c2cnc(NCc3ccc(C(N)=O)cc3)nc2)c1] | 4-({[5-(3-cyanobenzoyl)pyrimidin-2-yl]amino}methyl)benzamide | $[M + Na]^+$: 380 | $^1H$ NMR (400 MHz, DMSO-$d_6$): δ 8.90 (t, 1H), 8.71 (d, 2H), 8.18 (s, 1H), 8.12 (d, 1H), 8.04 (d, 1H), 7.94 (s, 1H), 7.84 (d, 2H), 7.77 (t, 1H), 7.39 (d, 2H), 7.34 (s, 1H), 4.68 (d, 2H) | A |
| 69 | 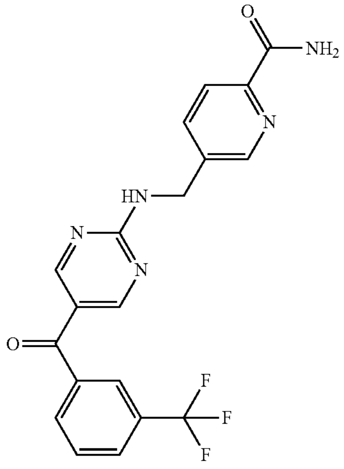 [SMILES: NC(=O)c1ccc(CNc2ncc(C(=O)c3cccc(C(F)(F)F)c3)cn2)cn1] | 5-[({5-[3-(trifluoromethyl)benzoyl]pyrimidin-2-yl}amino)methyl]pyridine-2-carboxamide | $[M + H]^+$: 402 | $^1H$ NMR (400 MHz, DMSO-$d_6$): δ 8.85 (t, 1H), 8.72 (s, 2H), 8.62 (s, 1H), 8.04-8.01 (m, 5H), 7.91(d, 1H), 7.81 (t, 1H), 7.56 (s, 1H), 4.74 (d, 2H) | A |

-continued

| Eg # | Structure | IUPAC Name | MS data | NMR data | Synthetic method |
|---|---|---|---|---|---|
| 70 | 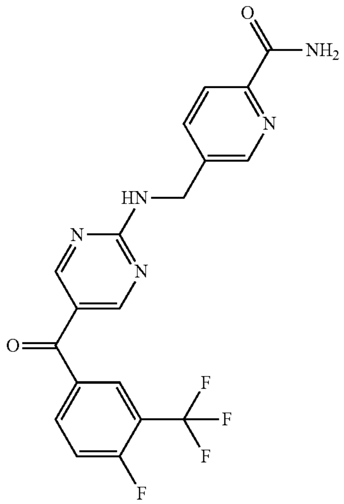 [SMILES: NC(=O)c1ccc(CNc2ncc(C(=O)c3ccc(F)c(C(F)(F)F)c3)cn2)cn1] | 5-[({5-[4-fluoro-3-(trifluoromethyl) benzoyl]pyrimidin-2-yl}amino)methyl] pyridine-2-carboxamide | [M + H]+: 420 | $^1$H NMR (400 MHz, DMSO-$d_6$): δ 8.93-8.90 (m, 1H), 8.73-8.72 (m, 2H), 8.62 (s, 1H), 8.15-8.07 (m, 3H), 8.02 (d, 1H), 7.92 (d, 1H), 7.71 (t, 1H), 7.63 (s, 1H), 4.73 (d, 2H) | A |
| 71 | 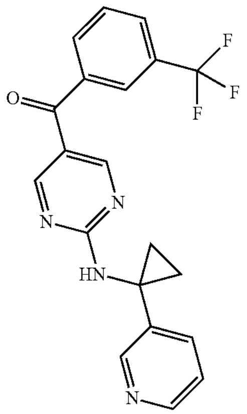 [SMILES: O=C(c1cnc(NC2(c3cccnc3)CC2)nc1)c1cccc(C(F)(F)F)c1] | (2-{[1-(pyridin-3-yl)cyclopropyl] amino}pyrimidin-5-yl)[3-(trifluoromethyl) phenyl]methanone | [M + H]+: 385 | $^1$H NMR (400 MHz, DMSO-$d_6$): δ 8.78-8.77 (m, 2H), 8.73-8.73 (m, 1H), 8.41 (d, 1H), 8.07-8.05 (m, 3H), 7.84 (t, 1H), 7.64 (d, 1H), 7.12-7.20 (m, 1H), 5.73-5.69 (m, 1H), 3.30-2.82 (m, 3H), 2.10-2.00 (m, 1H) | A |
| 72 | 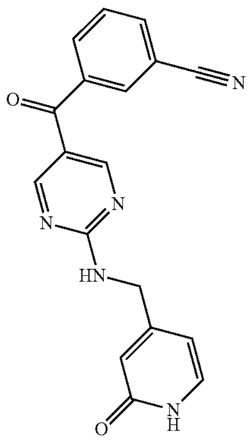 [SMILES: N#Cc1cccc(C(=O)c2cnc(NCc3cc[nH]c(=O)c3)nc2)c1] | 3-[(2-{[(2-oxo-1,2-dihydropyridin-4-yl)methyl]amino} pyrimidin-5-yl)carbonyl] benzonitrile | [M + H]+: 332 | $^1$H NMR (400 MHz, DMSO-$d_6$): δ 11.41 (br s, 1H), 8.76 (t, 1H), 8.70 (d, 2H), 8.16 (s, 1H), 8.10 (d, 1H), 8.02 (d, 1H), 7.74 (t, 1H), 7.29 (d, 1H), 6.20-6.10 (m, 2H), 4.42 (d, 2H) | A |

-continued

| Eg # | Structure | IUPAC Name | MS data | NMR data | Synthetic method |
|---|---|---|---|---|---|
| 73 | 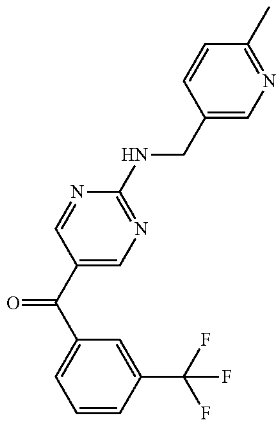 [SMILES: Cc1ccc(CNc2ncc(C(=O)c3cccc(C(F)(F)F)c3)cn2)cn1] | (2-{[(6-methylpyridin-3-yl)methyl]amino}pyrimidin-5-yl)[3-(trifluoromethyl)phenyl]methanone | $[M-H]^-$: 371 | $^1$H NMR (400 MHz, $CDCl_3$): δ 8.78 (br s, 1H), 8.68 (br s, 1H), 8.51 (d, 1H), 8.00 (s, 1H), 7.89 (d. 1H), 7.86 (d, 1H), 7.65 (t, 1H), 7.58 (dd, 1H), 7.13 (d, 1H), 6.53-6.47 (m, 1H), 4.72 (d, 2H), 2.54 (s, 3H) | A |
| 74 | 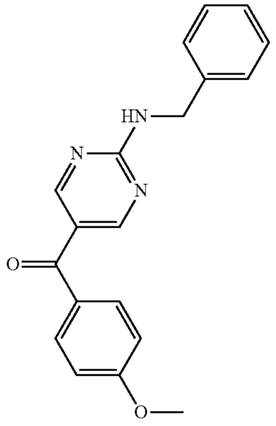 | [2-(benzylamino)pyrimidin-5-yl](4-methoxyphenyl)methanone | LCMS $[M+H]^+$: 320.* | * HPLC methodSP3126, Retention Time 1.69 min. | A |
| 75 | 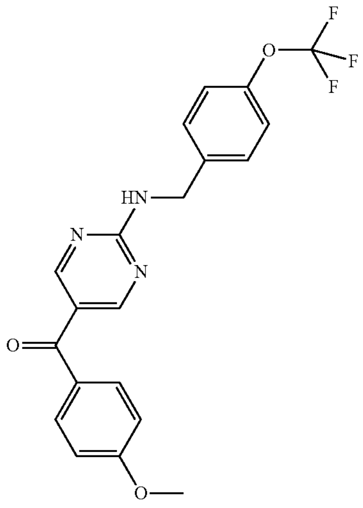 [SMILES: COc1ccc(C(=O)c2cnc(NCc3ccc(OC(F)(F)F)cc3)nc2)cc1] | (4-methoxyphenyl)(2-{[4-(trifluoromethoxy)benzyl]amino}pyrimidin-5-yl)methanone | LCMS $[M+H]^+$: 404. * | HPLC methodSP3126, Retention Time 1.77 min. | A |

-continued

| Eg # | Structure | IUPAC Name | MS data | NMR data | Synthetic method |
|---|---|---|---|---|---|
| 76 | 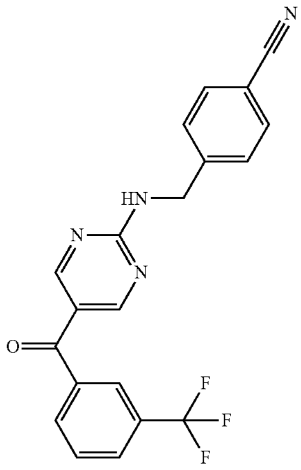 [SMILES: N#Cc1ccc(CNc2ncc(C(=O)c3cccc(C(F)(F)F)c3)cn2)cc1] | 4-[({5-[3-(trifluoromethyl) benzoyl]pyrimidin-2-yl}amino)methyl] benzonitrile | LCMS [M + H]+: 383. * | * HPLC methodSP3126, Retention Time 1.72 min. | A |
| 77 | 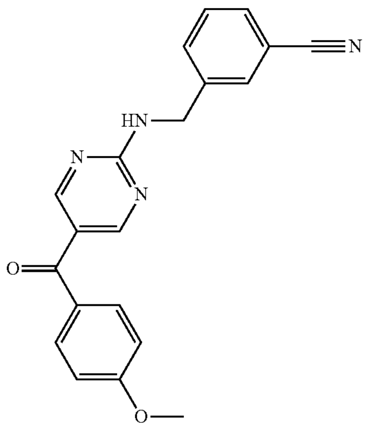 [SMILES: COc1ccc(C(=O)c2cnc(NCc3cccc(C#N)c3)nc2)cc1] | 3-({[5-(4-methoxybenzoyl) pyrimidin-2-yl]amino}methyl) benzonitrile | LCMS [M + H]+: 345. * | * HPLC methodSP3126, Retention Time 1.65 min. | A |
| 78 | 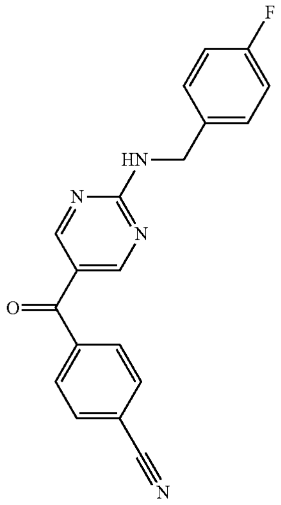 [SMILES: N#Cc1ccc(C(=O)c2cnc(NCc3ccc(F)cc3)nc2)cc1] | 4-({2-[(4-fluorobenzyl) amino]pyrimidin-5-yl}carbonyl) benzonitrile | [M + H]+: 333 | $^{1}$H NMR (400 MHz, DMSO-$d_6$): δ 8.83 (t, 1H), 8.69 (s, 2H), 8.15 (s, 1H), 8.10 (d, 1H), 8.02 (d, 1H), 7.74 (t, 1H), 7.44-7.31 (m, 2H), 7.14 (t, 2H), 4.60 (d, 2H) | A |

-continued

| Eg # | Structure | IUPAC Name | MS data | NMR data | Synthetic method |
|---|---|---|---|---|---|
| 79 | 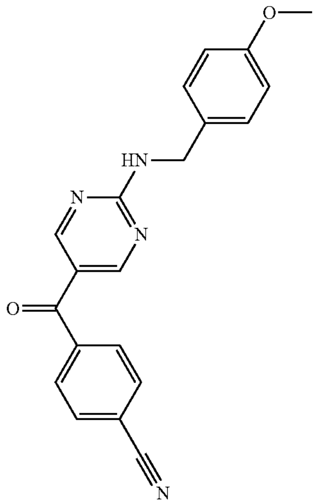 [SMILES: COc1ccc(CNc2ncc(C(=O)c3ccc(C#N)cc3)cn2)cc1] | 4-({2-[(4-methoxybenzyl)amino]pyrimidin-5-yl}carbonyl)benzonitrile | $[M + H]^+$: 345 | $^1H$ NMR (400 MHz, DMSO-$d_6$): δ 8.77 (t, 1H), 8.68 (s, 2H), 8.15 (s, 1H), 8.09 (d, 1H), 8.01 (d, 1H), 7.74 (t, 1H), 7.25 (d, 2H), 6.88 (d, 2H), 4.54 (d, 2H), 3.71 (s, 3H) | A |
| 80 | 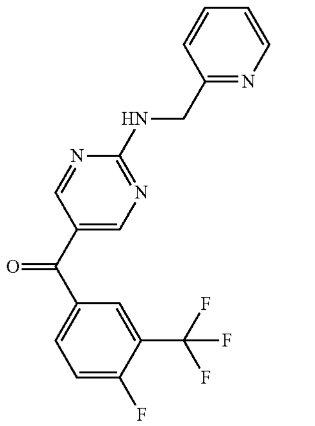 [SMILES: O=C(c1cnc(NCc2ccccn2)nc1)c1ccc(F)c(C(F)(F)F)c1] | [4-fluoro-3-(trifluoromethyl)phenyl]{2-[(pyridin-2-ylmethyl)amino]pyrimidin-5-yl}methanone | $[M + H]^+$: 377 | $^1H$ NMR (400 MHz, DMSO-$d_6$): δ 8.80 (br s, 1H), 8.75-8.65 (d, 2H), 8.51 (s, 1H), 8.17-8.02 (m, 2H), 7.79-7.63 (m, 2H), 7.35-7.22 (m, 2H), 4.72 (d, 2H) | A |
| 81 | 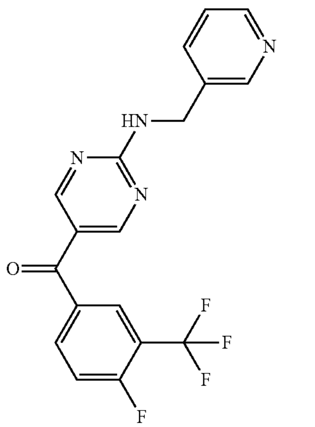 [SMILES: O=C(c1cnc(NCc2cccnc2)nc1)c1ccc(F)c(C(F)(F)F)c1] | [4-fluoro-3-(trifluoromethyl)phenyl]{2-[(pyridin-3-ylmethyl)amino]pyrimidin-5-yl}methanone | $[M + H]^+$: 377 | $^1H$ NMR (400 MHz, DMSO-$d_6$): δ 8.84 (t, 1H), 8.70 (s, 2H), 8.56 (d, 1H), 8.46 (dd, 1H), 8.15-8.11 (m, 1H), 8.09-8.04 (m, 1H), 7.77-7.67 (m, 2H), 7.35 (dd, 1H), 4.63 (d, 2H) | A |

-continued

| Eg # | Structure | IUPAC Name | MS data | NMR data | Synthetic method |
|---|---|---|---|---|---|
| 82 | 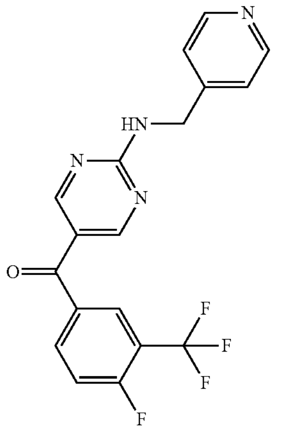 [SMILES: O=C(c1cnc(NCc2ccncc2)nc1)c1ccc(F)c(C(F)(F)F)c1] | [4-fluoro-3-(trifluoromethyl)phenyl]{2-[(pyridin-4-ylmethyl)amino]pyrimidin-5-yl}methanone | $[M + H]^+$ 377 | $^1H$ NMR (400 MHz, DMSO-$d_6$): δ 8.85 (t, 1H), 8.74-8.67 (m, 2H), 8.49 (d, 2H), 8.14-8.10 (m, 1H), 8.07-8.02 (m, 1H), 7.73-7.64 (m, 1H), 7.3 (d, 2H), 4.64 (d, 2H) | A |
| 83 | 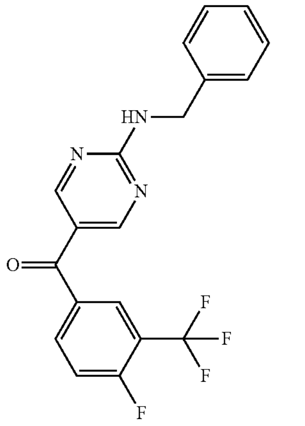 | [2-(benzylamino)pyrimidin-5-yl][4-fluoro-3-(trifluoromethyl)phenyl]methanone | $[M + H]^+$: 376 | $^1H$ NMR (400 MHz, DMSO-$d_6$): δ 8.81 (t, 1H), 8.69 (s, 2H), 8.17-8.12 (m, 1H), 8.09-8.05 (m, 1H), 7.75-7.65 (m, 1H), 7.37-7.30 (m, 4H), 7.27-7.20 (m, 1H), 4.62(d, 2H) | A |
| 84 | 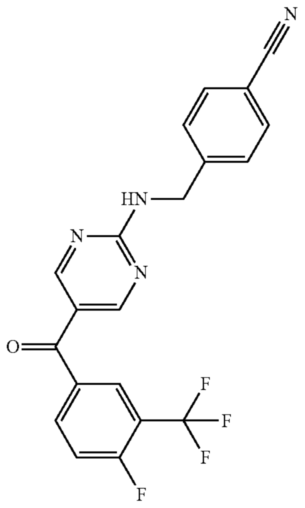 [SMILES: N#Cc1ccc(CNc2ncc(C(=O)c3ccc(F)c(C(F)(F)F)c3)cn2)cc1] | 4-[({5-[4-fluoro-3-(trifluoromethyl)benzoyl]pyrimidin-2-yl}amino)methyl]benzonitrile | $[M + H]^+$: 401 | $^1H$ NMR (400 MHz, DMSO-$d_6$): δ 8.88 (t, 1H), 8.74-8.64 (m, 2H), 8.15-8.03 (m, 2H), 7.80 (d, 2H), 7.72-7.64 (m, 1H), 7.50 (d, 2H), 4.69 (d, 2H) | A |

-continued

| Eg # | Structure | IUPAC Name | MS data | NMR data | Synthetic method |
|---|---|---|---|---|---|
| 85 | 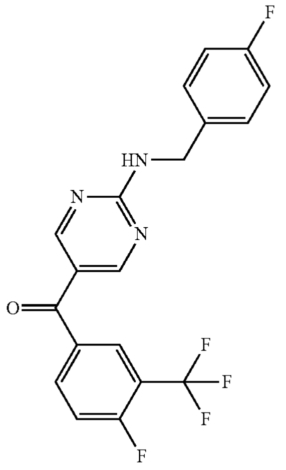 [SMILES: O=C(c1cnc(NCc2ccc(F)cc2)nc1)c1ccc(F)c(C(F)(F)F)c1] | {2-[(4-fluorobenzyl) amino]pyrimidin-5-yl}[4-fluoro-3-(trifluoromethyl) phenyl]methanone | $[M + H]^+$: 394 | $^1$H NMR (400 MHz, DMSO-$d_6$): δ 8.81 (t, 1H), 8.70 (s, 2H), 8.15-8.11 (m, 1H), 8.08-8.04 (m, 1H), 7.73-7.66 (m, 1H), 7.40-7.32 (m, 2H), 7.19-7.09 (m, 2H), 4.6 (d, 2H) | A |
| 86 | 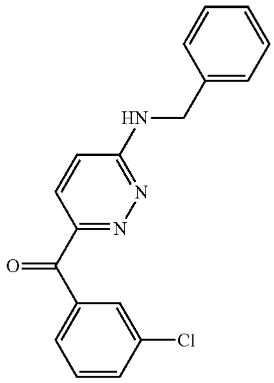 [SMILES: O=C(c1cccc(Cl)c1)c1ccc(NCc2ccccc2)nn1] | [6-(benzylamino) pyridazin-3-yl](3-chlorophenyl) methanone | $[M + H]^+$: 324 | $^1$H NMR (400 MHz, DMSO-$d_6$): δ 8.29 (br s, 1H), 8.01 (s, 1H), 7.97-7.87 (m, 2H), 7.70 (br d, 1H), 7.57 (t, 1H), 7.42-7.21 (m, 5H), 7.10 (d, 1H), 4.80 (s, 2H) | A |
| 87 | 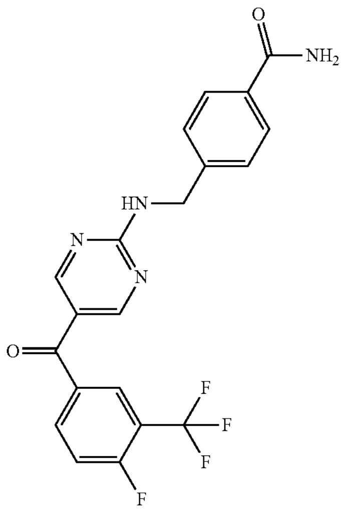 [SMILES: NC(=O)c1ccc(CNc2ncc(C(=O)c3ccc(F)c(C(F)(F)F)c3)cn2)cc1] | 4-[({5-[4-fluoro-3-(trifluoromethyl) benzoyl]pyrimidin-2-yl}amino)methyl] benzamide | $[M + H]^+$: 419 | $^1$H NMR (400 MHz, DMSO-$d_6$): δ 8.85 (t, 1H), 8.71 (s, 1H), 8.69 (s, 1H), 8.14-8.09 (m, 1H), 8.08-8.03 (m, 1H), 7.90 (br s, 1H), 7.82 (d, 2H), 7.71-7.64 (m, 1H), 7.37 (d, 2H), 7.30 (br s, 1H), 4.67 (d, 2H) | A |

-continued

| Eg # | Structure | IUPAC Name | MS data | NMR data | Synthetic method |
|---|---|---|---|---|---|
| 88 | 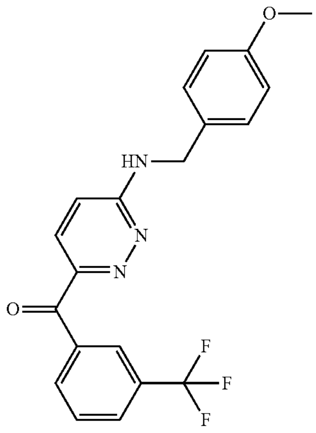 [SMILES: COc1ccc(CNc2ccc(C(=O)c3cccc(C(F)(F)F)c3)nn2)cc1] | {6-[(4-methoxybenzyl)amino]pyridazin-3-yl}[3-(trifluoromethyl)phenyl]methanone | $[M + H]^+$: 388 | $^1H$ NMR (400 MHz, DMSO-$d_6$): δ 8.31-8.18 (m, 3H), 8.04 (d, 1H), 7.92 (d, 1H), 7.78 (t, 1H), 7.30 (d, 2H), 7.10 (d, 1H), 6.90 (d, 2H), 4.80 (d, 2H), 3.77 (s, 3H) | A |
| 89 | 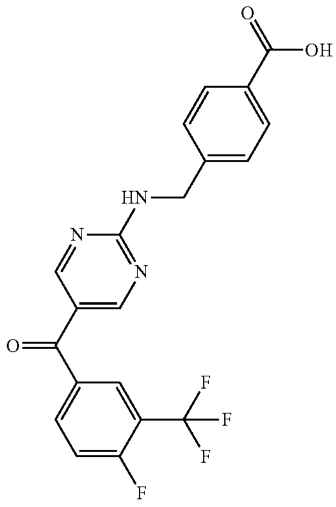 [SMILES: O=C(O)c1ccc(CNc2ncc(C(=O)c3ccc(F)c(C(F)(F)F)c3)cn2)cc1] | 4-[({5-[4-fluoro-3-(trifluoromethyl)benzoyl]pyrimidin-2-yl}amino)methyl]benzoic acid | $[M + H]^+$: 420 | $^1H$ NMR (400 MHz, DMSO-$d_6$): δ 8.80 (t, 1H), 8.69 (s, 2H), 8.14-8.09 (m, 1H), 8.06 (d, 1H), 7.80 (d, 2H), 7.67 (t, 1H), 7.21 (d, 2H), 4.62 (d, 2H) | A |
| 90 | 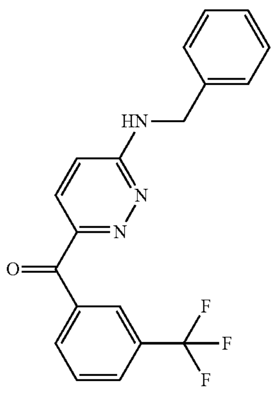 [SMILES: O=C(c1cccc(C(F)(F)F)c1)c1ccc(NCc2ccccc2)nn1] | [6-(benzylamino)pyridazin-3-yl][3-(trifluoromethyl)phenyl]methanone | $[M + H]^+$: 358 | $^1H$ NMR (400 MHz, DMSO-$d_6$): δ 8.38-8.26 (m, 3H), 8.01 (d, 1H), 7.93 (d, 1H), 7.77 (t, 1H), 7.40-7.32 (m, 4H), 7.28-7.23 (m, 1H), 7.04 (d, 1H), 4.76 (d, 2H) | A |

-continued

| Eg # | Structure | IUPAC Name | MS data | NMR data | Synthetic method |
|---|---|---|---|---|---|
| 91 | 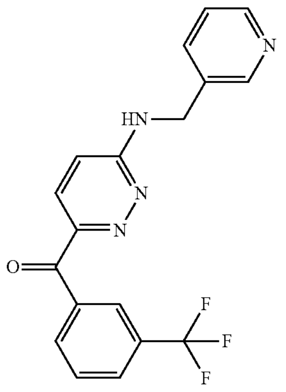 [SMILES: O=C(c1cccc(C(F)(F)F)c1)c1ccc(NCc2cccnc2)nn1] | {6-[(pyridin-3-ylmethyl)amino] pyridazin-3-yl}[3-(trifluoromethyl) phenyl]methanone | $[M + H]^+$: 359 | $^1H$ NMR (400 MHz, DMSO-$d_6$): δ 8.65 (s, 1H), 8.47 (d, 1H), 8.34 (br s, 1H), 8.31-8.26 (m, 2H), 8.02 (d, 1H), 7.94 (d, 1H), 7.81-7.76 (m, 2H), 7.39-7.34 (m, 1H), 7.06 (d, 1H), 4.76 (d, 2H) | A |
| 92 | 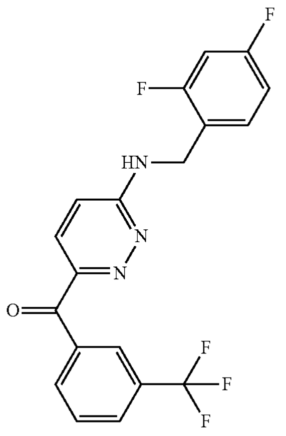 [SMILES: O=C(c1cccc(C(F)(F)F)c1)c1ccc(NCc2ccc(F)cc2F)nn1] | {6-[(2,4-difluorobenzyl) amino]pyridazin-3-yl}[3-(trifluoromethyl) phenyl]methanone | $[M + H]^+$: 394 | $^1H$ NMR (400 MHz, DMSO-$d_6$): δ 8.29-8.22 (m, 3H), 8.09 (d, 1H), 7.94 (d, 1H), 7.78 (t, 1H), 7.48 (q, 1H), 7.30-7.21 (m, 1H), 7.11-7.02 (m, 2H), 4.75 (d, 2H) | A |
| 93 | 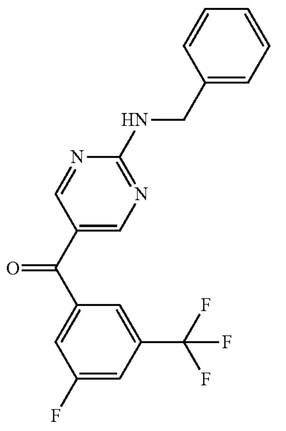 [SMILES: O=C(c1cnc(NCc2ccccc2)nc1)c1cc(F)cc(C(F)(F)F)c1] | [2-(benzylamino) pyrimidin-5-yl][3-fluoro-5-(trifluoromethyl) phenyl]methanone | $[M + H]^+$: 376 | $^1H$ NMR (400 MHz, DMSO-$d_6$): δ 8.86 (t, 1H), 8.70 (s, 2H), 8.00 (d, 1H), 7.89 (d, 1H), 7.84 (s, 1H), 7.35-7.31 (m, 4H), 7.27-7.21 (m, 1H), 4.63 (d, 2H) | A |

-continued

| Eg # | Structure | IUPAC Name | MS data | NMR data | Synthetic method |
|---|---|---|---|---|---|
| 94 | 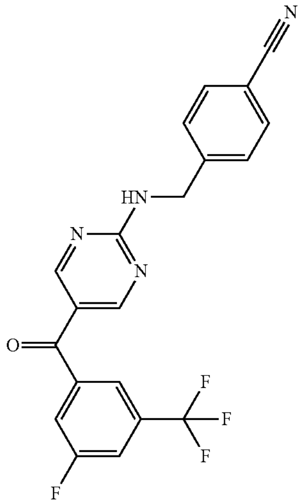 [SMILES: N#Cc1ccc(CNc2ncc(C(=O)c3cc(F)cc(C(F)(F)F)c3)cn2)cc1] | 4-[({5-[3-fluoro-5-(trifluoromethyl) benzoyl]pyrimidin-2-yl}amino)methyl] benzonitrile | $[M + H]^+$: 401 | $^1H$ NMR (400 MHz, DMSO-$d_6$): δ 8.92 (t, 1H), 7.72 (s, 1H), 7.68 (s, 1H), 8.01 (d, 1H), 7.88 (d, 1H), 7.86 (s, 1H), 7.80 (d, 2H), 7.50 (d, 2H), 4.71 (d, 2H) | A |
| 95 | 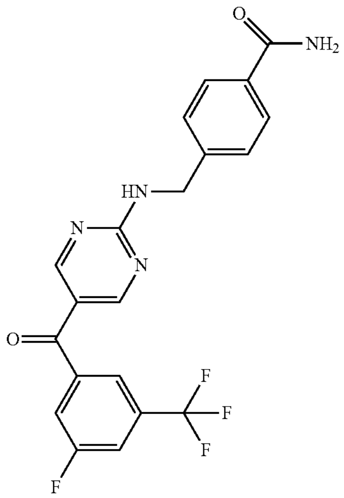 [SMILES: NC(=O)c1ccc(CNc2ncc(C(=O)c3cc(F)cc(C(F)(F)F)c3)cn2)cc1] | 4-[({5-[3-fluoro-5-(trifluoromethyl) benzoyl]pyrimidin-2-yl}amino)methyl] benzamide | $[M + H]^+$: 419 | $^1H$ NMR (400 MHz, DMSO-$d_6$): δ 8.89 (t, 1H), 8.72-8.68 (m, 2H), 8.00 (d, 1H), 7.93-7.80 (m, 5H), 7.39 (d, 2H), 7.30 (br s, 1H), 4.67 (d, 2H) | A |
| 96 | 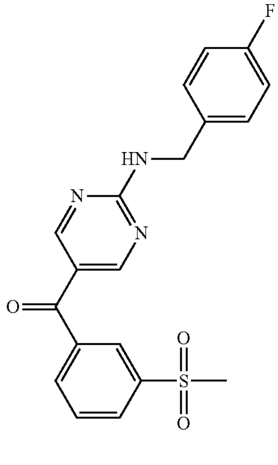 [SMILES: CS(=O)(=O)c1cccc(C(=O)c2cnc(NCc3ccc(F)cc3)nc2)c1] | {2-[(4-fluorobenzyl) amino]pyrimidin-5-yl}[3-(methylsulfonyl) phenyl]methanone | $[M + H]^+$: 386 | $^1H$ NMR (400 MHz, DMSO-$d_6$): δ 8.82 (t, 1H), 8.70 (s, 2H), 8.21-8.18 (m, 2H), 8.05 (d, 1H), 7.82 (t, 1H), 7.40-7.35 (m, 2H), 7.19-7.11 (m, 2H), 4.60 (d, 2H) | A |

-continued

| Eg # | Structure | IUPAC Name | MS data | NMR data | Synthetic method |
|---|---|---|---|---|---|
| 97 | 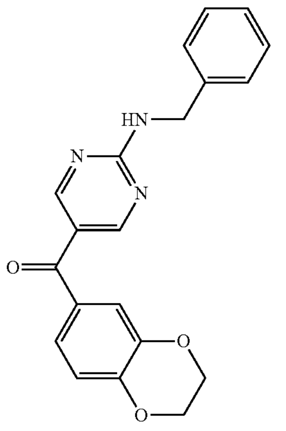 [SMILES: O=C(c1cnc(NCc2ccccc2)nc1)c1ccc2c(c1)OCCO2] | [2-(benzylamino) pyrimidin-5-yl](2,3-dihydro-1,4-benzodioxin-6-yl)methanone | $[M + H]^+$: 348 | $^1H$ NMR (400 MHz, DMSO-$d_6$): δ 8.69-8.60 (m, 3H), 7.32 (d, 4H), 7.29-7.21 (m, 3H), 6.99 (d, 1H), 4.61 (d, 2H), 4.37-4.25 (m, 4H) | A |
| 98 | 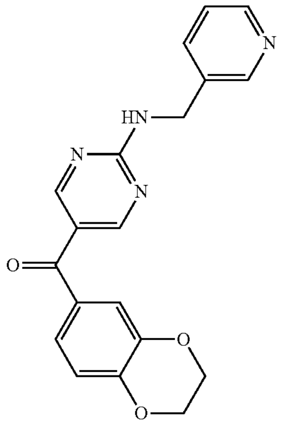 [SMILES: O=C(c1cnc(NCc2cccnc2)nc1)c1ccc2c(c1)OCCO2] | 2,3-dihydro-1,4-benzodioxin-6-yl{2-[(pyridin-3-ylmethyl)amino] pyrimidin-5-yl}methanone | $[M + H]^+$: 349 | $^1H$ NMR (400 MHz, DMSO-$d_6$): δ 8.72-8.61 (m, 3H), 8.56 (d, 1H), 8.47-8.43 (m, 1H), 7.76-7.71 (m, 1H), 7.38-7.33 (m, 1H), 7.27-7.22 (m, 2H), 7.01 (d, 1H), 4.62 (d, 2H), 4.38-4.26 (m, 4H) | A |
| 99 | 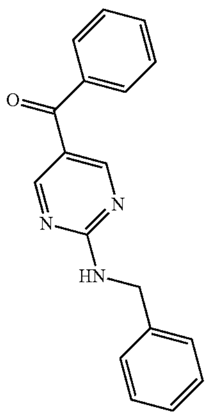 | [2-(benzylamino) pyrimidin-5-yl](phenyl) methanone | $[M + H]^+$: 290 | $^1H$ NMR (400 MHz, DMSO-$d_6$): δ 8.73 (t, 1H), 8.67 (s, 2H), 7.72 (d, 2H), 7.62-7.68 (m, 1H), 7.51-7.57 (m, 2H), 7.33 (d, 4H), 7.21-7.27 (m, 1H), 4.62 (d, 2H) | A |

-continued

| Eg # | Structure | IUPAC Name | MS data | NMR data | Synthetic method |
|---|---|---|---|---|---|
| 100 | 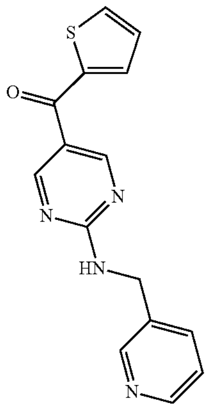 [SMILES: O=C(c1cnc(NCc2cccnc2)nc1)c1cccs1] | {2-[(pyridin-3-ylmethyl)amino]pyrimidin-5-yl}(thiophen-2-yl)methanone | $[M + H]^+$: 297 | $^1H$ NMR (400 MHz, DMSO-$d_6$): δ ppm 8.80 (d, 1H), 8.71 (t, 1H), 8.57 (s, 1H), 8.46 (d, 1H), 8.07 (d, 1H), 7.84 (d, 1H), 7.74 (d, 1H), 7.33-7.38 (m, 1 H), 7.27 (t, 1H), 4.64 (d, 2H) | A |
| 101 | 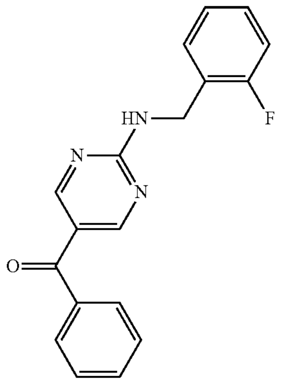 [SMILES: O=C(c1ccccc1)c1cnc(NCc2ccccc2F)nc1] | {2-[(2-fluorobenzyl)amino]pyrimidin-5-yl}(phenyl)methanone | $[M + H]^+$: 308 | $^1H$ NMR (400 MHz, DMSO-$d_6$): δ ppm 8.64-8.73 (m, 1H), 7.73 (d, 1H), 7.62-7.69 (m, 1H), 7.52-7.58 (m, 2H), 7.27-7.40 (m, 2H), 7.13-7.22 (m, 2H), 4.66 (d, 2 H) | A |
| 102 | 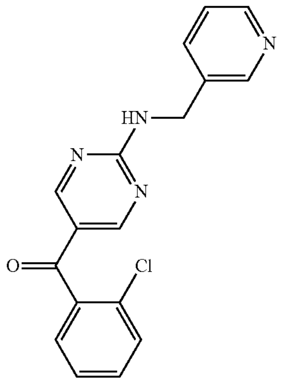 [SMILES: O=C(c1cnc(NCc2cccnc2)nc1)c1ccccc1Cl] | (2-chlorophenyl){2-[(pyridin-3-ylmethyl)amino]pyrimidin-5-yl}methanone | $[M + H]^+$: 324.7 | $^1H$ NMR (400 MHz, DMSO-d6): δ 9.03-8.99 (t, 1H), 8.76(s, 1H), 8.69-8.67(d, 1H), 8.61-8.60 (m, 1H), 8.56-8.55(m, 1H), 8.19-8.17 (d, 1H), 7.76-7.73 (m, 1H) , 7.62-7.49 (m, 4H), 4.73-4.71 (d, 2H) | A |

-continued

| Eg # | Structure | IUPAC Name | MS data | NMR data | Syn-thetic method |
|---|---|---|---|---|---|
| 103 | 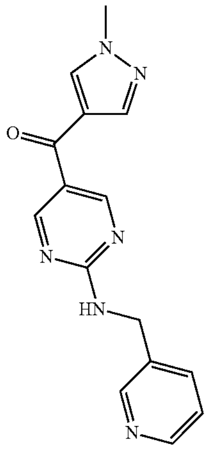 [SMILES: Cn1cc(C(=O)c2cnc(NCc3cccnc3)nc2)cn1] | (1-methyl-1H-pyrazol-4-yl){2-[(pyridin-3-ylmethyl)amino] pyrimidin-5-yl}methanone | [M + H]$^+$: 294.9 | $^1$H NMR (400 MHz, MeOH-d4): δ 8.96-8.92 (m, 3H), 8.82-8.80 (d, 1H), 8.73-8.71 (d, 1H), 8.32 (s, 1H), 8.13-8.09 (m, 1H), 8.00 (s, 1H), 4.97 (m, 2H), 3.98 (s, 3H) | A |
| 104 | 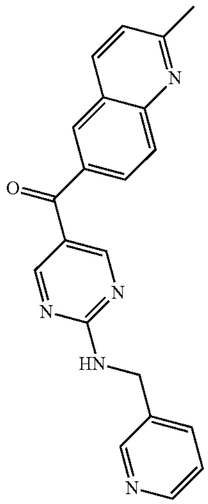 [SMILES: Cc1ccc2cc(C(=O)c3cnc(NCc4cccnc4)nc3)ccc2n1] | (2-methylquinolin-6-yl){2-[(pyridin-3-ylmethyl)amino] pyrimidin-5-yl}methanone | [M + H]$^+$: 356.0 | $^1$H NMR (400 MHz, Methanol-d4): δ 8.81 (s, 2H), 8.59 (s, 1H), 8.45 (d, 1H), 8.39 (d, 1H), 8.33(s, 1H), 8.09 (s, 2H), 7.90 (d, 1H), 7.55 (d, 1H), 7.43 (dd, 1H), 4.75 (s, 2H), 2.78 (s, 3H) | A |
| 105 | 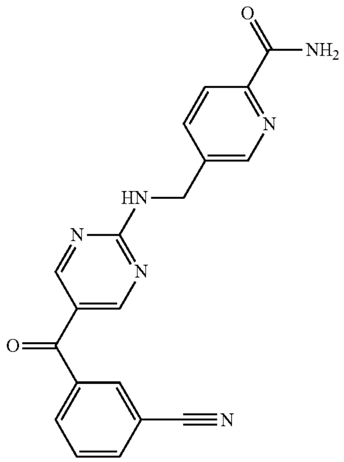 [SMILES: N#Cc1cccc(C(=O)c2cnc(NCc3ccc(C(N)=O)nc3)nc2)c1] | 5-({[5-(3-cyanobenzoyl) pyrimidin-2-yl]amino}methyl) pyridine-2-carboxamide | [M + Na]$^+$: 380.9 | $^1$H NMR (400 MHz, CDCl3): δ 8.74-8.70 (m, 2H), 8.52 (s, 1H), 8.12 (d, 1H), 7.95 (s, 1H), 7.89 (d, 1H), 7.82-7.71(m, 3H), 7.60-7.56 (m, 1H), 6.05 (s, 1H), 5.47 (s, 1H), 4.77(d, 2H) | A |

-continued

| Eg # | Structure | IUPAC Name | MS data | NMR data | Synthetic method |
|---|---|---|---|---|---|
| 106 | 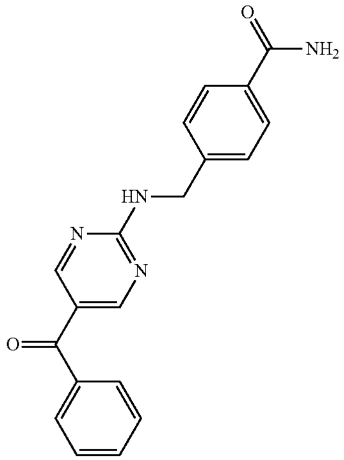 | 4-{[(5-benzoylpyrimidin-2-yl)amino]methyl}benzamide | [M + Na]$^+$: 354.9 | $^1$H NMR (400 MHz, Methanol-d4): δ 8.73 (s, 2H), 7.85 (d, 2H), 7.75 (d, 2H), 7.70-7.63 (m, 1H), 7.61-7.55 (m, 2H), 7.47 (d, 2H), 4.76 (s, 2H) | A |
| 107 | 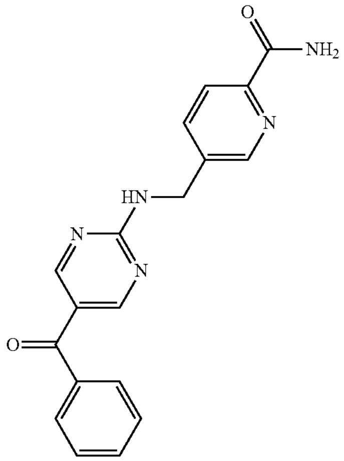 [SMILES: NC(=O)c1ccc(CNc2ncc(C(=O)c3ccccc3)cn2)cn1] | 5-{[(5-benzoylpyrimidin-2-yl)amino]methyl}pyridine-2-carboxamide | [M + Na]$^+$: 356.1 | $^1$H NMR (400 MHz, DMSO): δ 8.80 (m, 1H), 8.67 (d, 2H), 8.59 (s, 1H), 8.07 (s, 1H), 8.00-7.98 (m, 1H), 7.90-7.88 (m, 1H), 7.73-7.70 (m, 2H), 7.65-7.56 (m, 4H), 4.69 (d, 2H) | A |
| 108 | 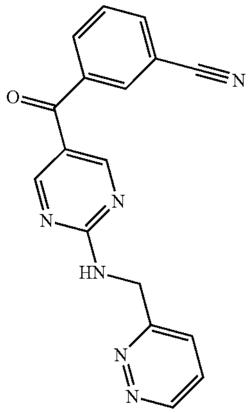 [SMILES: N#Cc1cccc(C(=O)c2cnc(NCc3cccnn3)nc2)c1] | 3-({2-[(pyridazin-3-ylmethyl)amino]pyrimidin-5-yl}carbonyl)benzonitrile | [M + H]$^+$: 316.8 | $^1$H NMR (400 MHz, Methanol-d4): δ 9.11 (d, 1H), 8.78 (s, 1H), 8.73 (s, 1H), 8.11 (s, 1H), 8.05-7.99 (m, 2H), 7.78-7.69 (m, 3H), 5.02 (s, 2H) | A |

-continued

| Eg # | Structure | IUPAC Name | MS data | NMR data | Synthetic method |
|---|---|---|---|---|---|
| 109 | 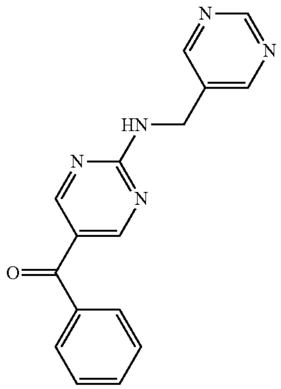 [SMILES: O=C(c1ccccc1)c1cnc(NCc2cncnc2)nc1] | phenyl{2-[(pyrimidin-5-ylmethyl)amino]pyrimidin-5-yl}methanone | $[M+H]^+$: 291.9 | $^1$H NMR (400 MHz, Methanol-d4): δ 9.06 (s, 1H), 8.84 (s, 2H), 8.74 (s, 2H), 7.75 (d, 2H), 7.65-7.63 (m, 1H), 7.55 (t, 2H), 4.73 (s, 2H) | A |
| 110 | 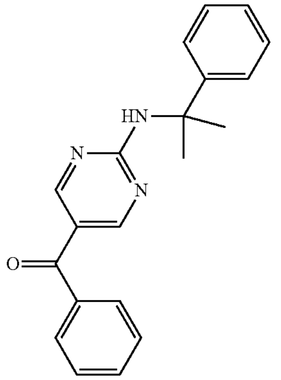 [SMILES: CC(C)(Nc1ncc(C(=O)c2ccccc2)cn1)c1ccccc1] | phenyl{2-[(2-phenylpropan-2-yl)amino]pyrimidin-5-yl}methanone | $[M+H]^+$: 318.0 | $^1$H NMR (400 MHz, Methanol-d4): δ 8.68 (brs, 2H), 8.64 (brs, 1H), 7.71 (d, 2H), 7.64 (t, 1H), 7.53 (t, 7.2Hz, 2H), 7.43 (d, 2H), 7.29 (t, 2H), 7.19 (t, 1H), 1.81 (s, 6H) | A |
| 111 | 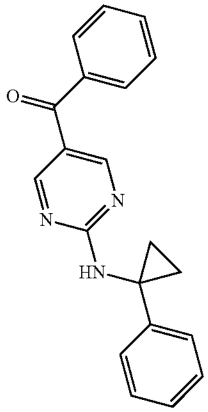 [SMILES: O=C(c1ccccc1)c1cnc(NC2(c3ccccc3)CC2)nc1] | phenyl{2-[(1-phenylcyclopropyl)amino]pyrimidin-5-yl}methanone | $[M+H]^+$: 315.9 | $^1$H NMR (400 MHz, DMSO-d6): δ 8.75 (s, 1H), 8.65 (s, 1H), 7.74 (d, 2H), 7.64-7.62 (m, 1H), 7.54 (t, 2H), 7.26-7.25 (m, 4H), 7.17-7.14 (m, 1H), 1.38 (d, 4H) | A |

-continued

| Eg # | Structure | IUPAC Name | MS data | NMR data | Synthetic method |
|---|---|---|---|---|---|
| 112 | 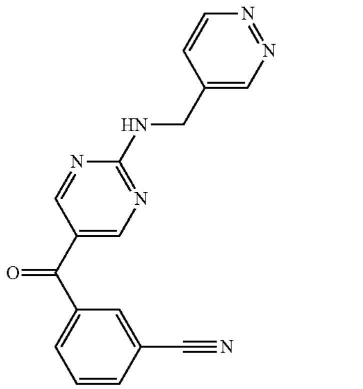 [SMILES: N#Cc1cccc(C(=O)c2cnc(NCc3ccnnc3)nc2)c1] | 3-({2-[(pyridazin-4-ylmethyl)amino]pyrimidin-5-yl}carbonyl)benzonitrile | [M + H]+: 316.9 | $^1$H NMR (400 MHz, Methanol-d4): δ 9.24 (s, 1H), 9.13 (d, 1H), 8.78 (s, 1H), 8.71 (s, 1H), 8.10 (s, 1H), 8.038-7.98 (m, 2H), 7.75-7.71 (m, 2H), 4.80 (s, 2H) | A |
| 113 | 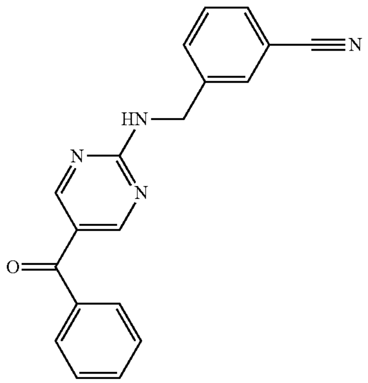 [SMILES: N#Cc1cccc(CNc2ncc(C(=O)c3ccccc3)cn2)c1] | 3-{[(5-benzoylpyrimidin-2-yl)amino]methyl}benzonitrile | [M + H]+: 315.0 | $^1$H NMR (400 MHz, Methanol-d4): δ 8.73 (s, 2H), 7.76-7.73 (m, 3H), 7.71-7.69 (m, 1H), 7.67-7.62 (m, 2H), 7.57-7.50 (m, 3H), 4.74 (s, 2H) | A |
| 114 | 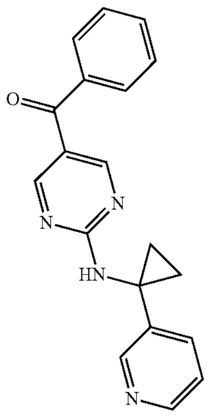 [SMILES: O=C(c1ccccc1)c1cnc(NC2(c3cccnc3)CC2)nc1] | phenyl(2-{[1-(pyridin-3-yl)cyclopropyl]amino}pyrimidin-5-yl)methanone | [M + H]+: 317.0 | $^1$H NMR (400 MHz, Methanol-d4): δ 8.78 (d, 2H), 8.39 (d, 1H), 7.79 (d, 3H), 7.67-7.66(m, 1H), 7.58 (t, 2H), 7.28-7.25 (m, 1H), 5.82 (t, 1H), 3.15-3.13 (m, 1H), 3.08-3.02 (m, 1H), 2.74-2.70 (m, 1H), 2.14-2.09 (m, 1H) | A |

-continued

| Eg # | Structure | IUPAC Name | MS data | NMR data | Synthetic method |
|---|---|---|---|---|---|
| 115 | 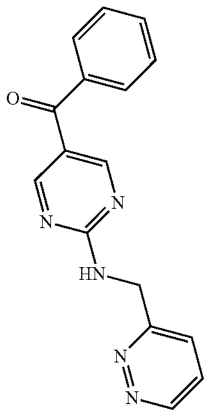 | phenyl{2-[(pyridazin-3-ylmethyl)amino]pyrimidin-5-yl}methanone | $[M+H]^+$: 291.9 | $^1H$ NMR (400 MHz, Methanol-d4): δ 9.00 (d, 1H), 8.63 (d, 2H), 7.66-7.63 (m, 3H), 7.61-7.53 (m, 2H), 7.44 (d, 2H), 4.90 (s, 2H) | A |
| 116 | 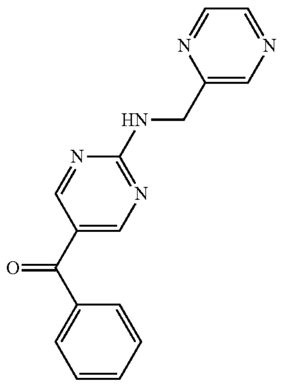 [SMILES: O=C(c1ccccc1)c1cnc(NCc2cnccn2)nc1] | phenyl{2-[(pyrazin-2-ylmethyl)amino]pyrimidin-5-yl}methanone | $[M+H]^+$: 291.9 | $^1H$ NMR (400 MHz, Methanol-d4): δ 8.90 (brs, 2H), 8.77 (s, 1H), 8.68 (s, 1H), 8.60 (d, 1H), 7.82 (d, 2H), 7.70 (t, 1H), 7.58 (t, 2H), 5.00 (s, 2H) | A |
| 117 | 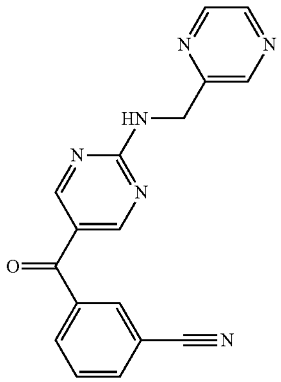 [SMILES: N#Cc1cccc(C(=O)c2cnc(NCc3cnccn3)nc2)c1] | 3-({2-[(pyrazin-2-ylmethyl)amino]pyrimidin-5-yl}carbonyl)benzonitrile | $[M+H]^+$: 316.9 | $^1H$ NMR (400 MHz, Methanol-d4): δ 8.77 (s, 2H), 8.73 (s, 1H), 8.67 (d, 1H), 8.60-8.58 (m, 1H), 8.52 (d, 1H), 8.120 (d, 1H), 8.05-7.99 (m, 2H), 7.74 (t, 1H), 4.88 (s, 2H) | A |
| 118 | 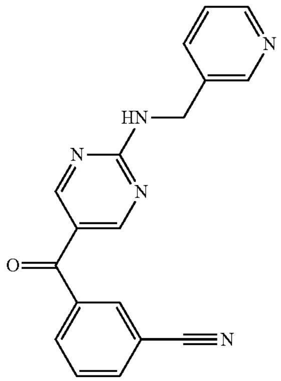 [SMILES: N#Cc1cccc(C(=O)c2cnc(NCc3cccnc3)nc2)c1] | 3-({2-[(pyridin-3-ylmethyl)amino]pyrimidin-5-yl}carbonyl)benzonitrile | $[M+H]^+$: 316.0 | $^1H$ NMR (400 MHz, Methanol-d4): δ 8.75 (s, 2H), 8.60 (d, 1H), 8.46 (d, 1H), 8.11 (d, 1H), 8.05-7.99 (m, 2H), 7.93 (d, 1H), 7.74 (t, 1H), 7.47-7.44 (m, 1H), 4.76 (s, 2H) | A |

-continued

| Eg # | Structure | IUPAC Name | MS data | NMR data | Synthetic method |
|---|---|---|---|---|---|
| 119 | 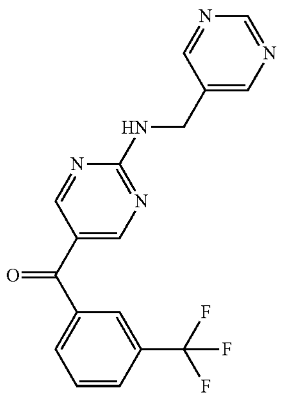 [SMILES: O=C(c1cnc(NCc2cncnc2)nc1)c1cccc(C(F)(F)F)c1] | {2-[(pyrimidin-5-ylmethyl)amino]pyrimidin-5-yl}[3-(trifluoromethyl)phenyl]methanone | $[M + H]^+$: 360.0 | $^1$H NMR (400 MHz, Methanol-d4): δ 9.06 (s, 1H), 8.84 (s, 1H), 8.75 (s, 1H), 8.03 (s, 1H), 8.00 (d, 1H), 7.95 (d, 1H), 7.76 (t, 1H), 4.74 (s, 2H) | A |
| 120 | 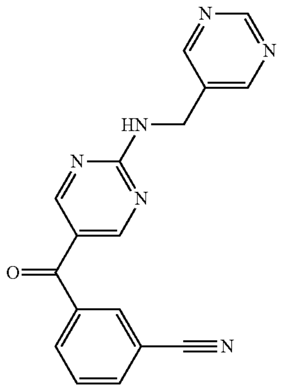 [SMILES: N#Cc1cccc(C(=O)c2cnc(NCc3cncnc3)nc2)c1] | 3-({2-[(pyrimidin-5-ylmethyl)amino]pyrimidin-5-yl}carbonyl)benzonitrile | $[M + H]^+$: 316.9 | $^1$H NMR (400 MHz, Methanol-d4): δ 9.07 (s, 1H), 8.85 (s, 2H), 8.76 (s, 2H), 8.12 (s, 1H), 8.05-7.99 (m, 2H), 7.74 (t, 1H), 4.75 (s, 2H) | A |
| 121 | 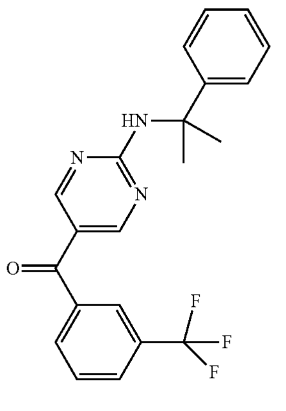 [SMILES: CC(C)(Nc1ncc(C(=O)c2cccc(C(F)(F)F)c2)cn1)c1ccccc1] | {2-[(2-phenylpropan-2-yl)amino]pyrimidin-5-yl}[3-(trifluoromethyl)phenyl]methanone | $[M + H]^+$: 386.1 | $^1$H NMR (400 MHz, Methanol-d4): δ 8.70 (s, 1H), 8.48 (s, 1H), 7.97 (s, 1H), 7.93 (d, 2H), 7.73 (t, 8 Hz, 1H), 7.43 (d, 2H), 7.28 (t, 2H), 7.19-7.18 (m, 1H), 1.80 (s, 6H) | A |

-continued

| Eg # | Structure | IUPAC Name | MS data | NMR data | Synthetic method |
|---|---|---|---|---|---|
| 122 | 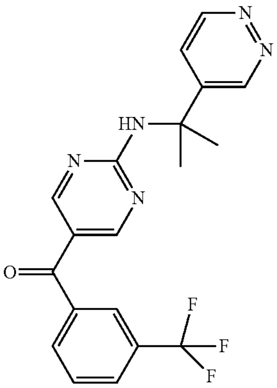 | {2-[(pyridazin-4-ylmethyl)amino] pyrimidin-5-yl}[3-(trifluoromethyl) phenyl]methanone | $[M + H]^+$: 359.9 | $^1$H NMR (400 MHz, DMSO-d6): δ 9.32 (s, 1H), 9.26 (d, 1H), 8.91 (t, 1H), 8.737 (d, 1H), 8.65-8.64 (m, 1H), 8.02-8.00 (m, 3H), 7.79 (d, 2H), 4.74 (d, 2H) | A |
| 123 | 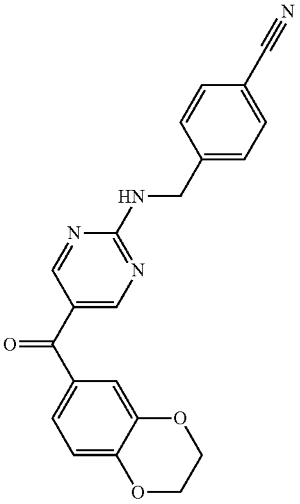 [SMILES: N#Cc1ccc(CNc2ncc(C(=O)c3ccc4c(c3)OCCO4)cn2)cc1] | 3-({[5-(2,3-dihydro-1,4-benzodioxin-6-ylcarbonyl)pyrimidin-2-yl]amino}methyl) benzonitrile | $[M + H]^+$ 373.0 | $^1$HNMR (DMSO-d6): δ 8.65 (m, 3H), 7.71 (m, 3H), 7.54 (t, 1H), 7.26 (m, 2H), 7.01(d, 1H), 4.61 (d, 2H), 4.33 (m, 4H) | A |
| 124 | 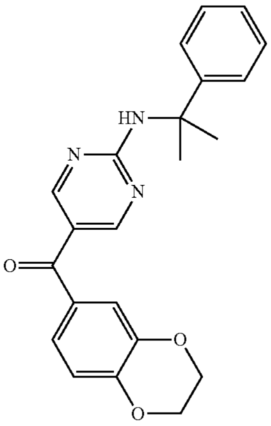 [SMILES: CC(C)(Nc1ncc(C(=O)c2ccc3c(c2)OCCO3)cn1)c1ccccc1] | 2,3-dihydro-1,4-benzodioxin-6-yl{2-[(2-phenylpropan-2-yl)amino]pyrimidin-5-yl}methanone | $[M + H]^+$: 376.1 | $^1$HNMR (DMSO-d6): δ 8.61 (bs, 1H), 8.48 (S, 1H), 8.36 (bs, 1H), 7.36 (d, 2H), 7.26(t, 2H), 7.16 (m, 3H), 6.98 (d, 1H), 4.31 (m, 4H), 1.70 (s, 6H) | A |

-continued

| Eg # | Structure | IUPAC Name | MS data | NMR data | Synthetic method |
|---|---|---|---|---|---|
| 125 | 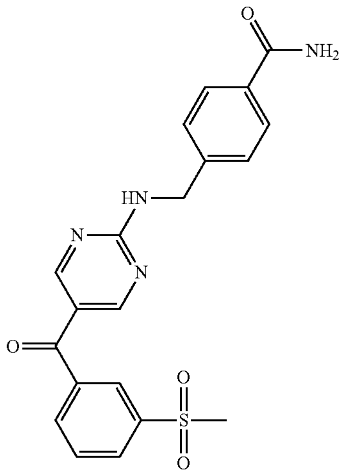 [SMILES: CS(=O)(=O)c1cccc(C(=O)c2cnc(NCc3ccc(C(N)=O)cc3)nc2)c1] | 4-[({5-[3-(methylsulfonyl) benzoyl]pyrimidin-2-yl}amino)methyl] benzamide | $[M + H]^+$: 411.0 | $^1$HNMR (DMSO-d6): δ 8.86 (t, 1H), 8.7 (m, 2H), 8.19(m, 2H), 8.06 (m, 1H), 7.9 (bs, 1H), 7.83 (m, 3H), 7.38 (d, 2H), 7.3 (bs, 1H), 4.64 (d, 2H), 3.30 (s, 3H) | A |
| 126 | 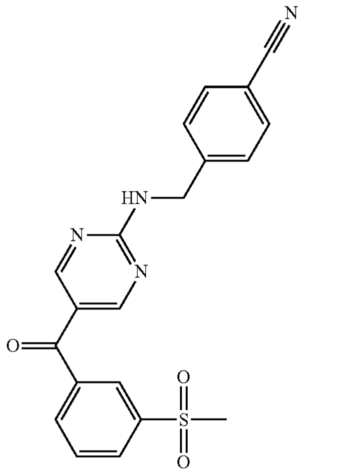 [SMILES: CS(=O)(=O)c1cccc(C(=O)c2cnc(NCc3ccc(C#N)cc3)nc2)c1] | 4-[({5-[3-(methylsulfonyl) benzoyl]pyrimidin-2-yl}amino)methyl] benzonitrile | $[M + H]^+$: 393.0 | $^1$HNMR (DMSO-d6): δ 8.89 (t, 1H), 8.70 (m, 2H), 8.19(m, 2H), 8.07 (m, 1H), 7.82 (m, 3H), 7.50 (d, 2H), 4.64 (d, 2H), 3.3 (s, 3H) | A |
| 127 | 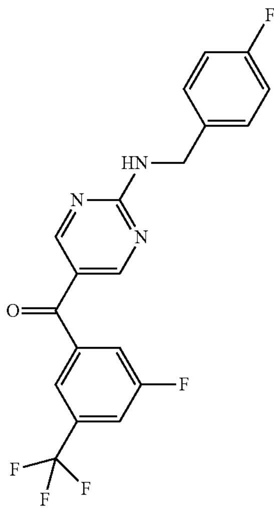 [SMILES: O=C(c1cnc(NCc2ccc(F)cc2)nc1)c1cc(F)cc(C(F)(F)F)c1] | {2-[(4-fluorobenzyl) amino]pyrimidin-5-yl}[3-fluoro-5-(trifluoromethyl) phenyl]methanone | $[M + H]^+$: 394.0 | $^1$HNMR (DMSO-d6): δ 8.86 (t, 1H), 8.70 (s, 2H), 8.00 (d, 1H), 7.8 (m, 2H), 7.36 (m, 2H), 7.14 (m, 2H), 4.71 (d, 2H) | A |

-continued

| Eg # | Structure | IUPAC Name | MS data | NMR data | Synthetic method |
|---|---|---|---|---|---|
| 128 | 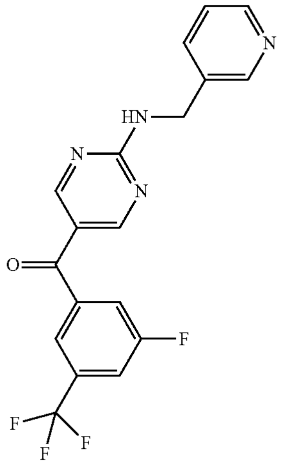 [SMILES: O=C(c1cnc(NCc2cccnc2)nc1)c1cc(F)cc(C(F)(F)F)c1] | [3-fluoro-5-(trifluoromethyl) phenyl]{2-[(pyridin-3-ylmethyl)amino] pyrimidin-5-yl}methanone | [M + H]+: 376.9 | $^1$HNMR (DMSO-d6): δ 8.88 (t, 1H), 8.71 (s, 2H), 8.56 (d, 1H), 8.46 (dd, 1H), 8.08 (d, 1H), 7.8 (m, 2H), 7.73 (d, 1H), 7.35 (m, 1H), 4.70 (d, 2H) | A |
| 129 | 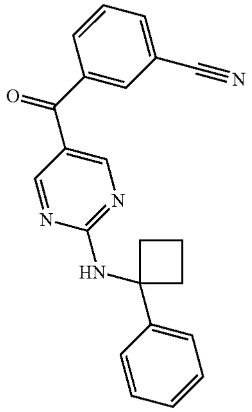 [SMILES: N#Cc1cccc(C(=O)c2cnc(NC3(c4ccccc4)CCC3)nc2)c1] | 3-({2-[(1-phenylcyclobutyl) amino]pyrimidin-5-yl}carbonyl) benzonitrile | [M + H]+: 355.4 | $^1$H NMR (400 MHz, DMSO-$d_6$): δ 9.16 (s, 1H), 8.65 (d, 1H), 8.49 (d, 1H), 8.10 (s, 1H), 8.07 (d, 1H), 7.96 (d, 1H), 7.71 (t, 1H), 7.47 (d, 2H), 7.29 (t, 2H), 7.17 (t, 1H), 2.70-2.50 (m, 4H), 2.15-1.95 (m, 1H), 1.95-1.75 (m, 1H) | A |
| 130 | 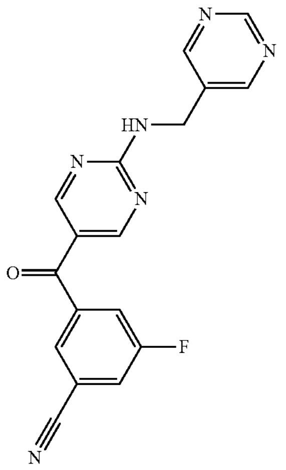 [SMILES: N#Cc1cc(F)cc(C(=O)c2cnc(NCc3cncnc3)nc2)c1] | 3-fluoro-5-({2-[(pyrimidin-5-ylmethyl)amino] pyrimidin-5-yl}carbonyl) benzonitrile | [M + H]+: 335.2 | $^1$H NMR (400 MHz, DMSO-$d_6$): δ 9.09 (s, 1H), 8.88 (t, 1H), 8.78 (s, 2H), 8.72 (s, 2H), 8.14 (d, 1H), 8.04 (s, 1H), 7.91 (d, 1H), 4.64 (d, 2H). | A |

-continued

| Eg # | Structure | IUPAC Name | MS data | NMR data | Synthetic method |
|---|---|---|---|---|---|
| 131 | 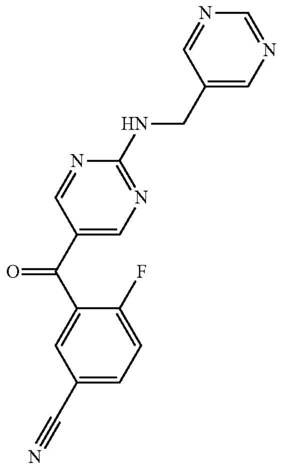 [SMILES: N#Cc1ccc(F)c(C(=O)c2cnc(NCc3cncnc3)nc2)c1] | 4-fluoro-3-({2-[(pyrimidin-5-ylmethyl)amino]pyrimidin-5-yl}carbonyl)benzonitrile | $[M + H]^+$: 335.2 | $^1H$ NMR (400 MHz, DMSO-$d_6$): δ 9.08 (s, 1H), 8.97 (t, 1H), 8.77 (s, 2H), 8.69 (bs, 2H), 8.10-8.20 (m, 2H), 7.62 (t, 1H), 4.63 (d, 2H). | A |
| 132 | 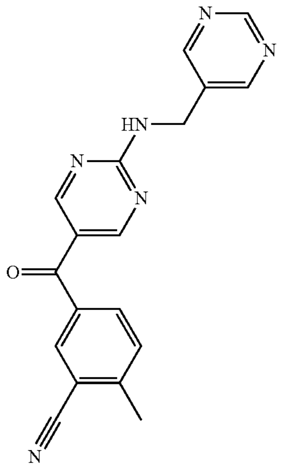 [SMILES: Cc1ccc(C(=O)c2cnc(NCc3cncnc3)nc2)cc1C#N] | 2-methyl-5-({2-[(pyrimidin-5-ylmethyl)amino]pyrimidin-5-yl}carbonyl)benzonitrile | $[M + H]^+$: 331.4 | $^1H$ NMR (400 MHz, DMSO-$d_6$): δ 9.09 (s, 1H), 8.83-8.76 (m, 3H), 8.70 (s, 2H), 8.11 (d, 1H), 7.93 (dd, 1H), 7.64 (d, 1H), 2.57 (d, 2H). | A |
| 133 | 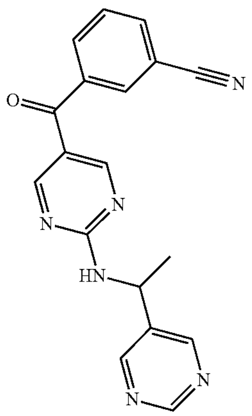 [SMILES: CC(Nc1ncc(C(=O)c2cccc(C#N)c2)cn1)c1cncnc1] | 3-[(2-{[1-(pyrimidin-5-yl)ethyl]amino}pyrimidin-5-yl)carbonyl]benzonitrile | $[M + H]^+$: 331.2 | $^1H$ NMR (400 MHz, $CDCl_3$): δ 9.13 (s, 1H), 8.77 (s, 2H), 8.80-8.65 (m, 2H), 7.99 (br s, 1H), 7.92 (d, 1H), 7.86 (d, 1H), 7.63 (t, 1H), 6.03 (d, 1H, NH), 5.35-5.20 (m, 1H), 1.69 (d, 3H). | A |

-continued

| Eg # | Structure | IUPAC Name | MS data | NMR data | Syn-thetic method |
|---|---|---|---|---|---|
| 134 | 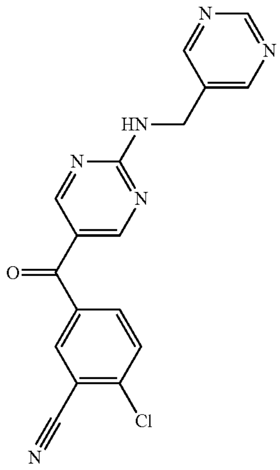 [SMILES: N#Cc1cc(C(=O)c2cnc(NCc3cncnc3)nc2)ccc1Cl] | 2-chloro-5-({2-[(pyrimidin-5-ylmethyl)amino]pyrimidin-5-yl}carbonyl)benzonitrile | $[M+H]^+$ 351.2 | $^1$H NMR (400 MHz, DMSO-$d_6$): δ 9.09 (s, 1H), 8.86 (t, 1H), 8.79 (s, 2H), 8.73 (s, 2H), 8.31 (d, 1H), 8.02 (dd, 1H), 7.91 (d, 1H), 4.64 (d, 2H). | A |
| 135 | 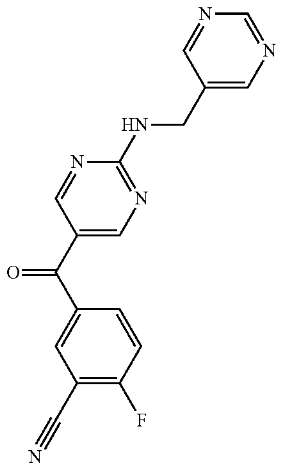 [SMILES: N#Cc1cc(C(=O)c2cnc(NCc3cncnc3)nc2)ccc1F] | 2-fluoro-5-({2-[(pyrimidin-5-ylmethyl)amino]pyrimidin-5-yl}carbonyl)benzonitrile | $[M+H]^+$: 335.2 | $^1$H NMR (400 MHz, DMSO-$d_6$): δ 9.09 (s, 1H), 8.84 (t, 1H), 8.79 (s, 2H), 8.72 (br s, 2H), 8.31 (dd, 1H), 8.02-8.15 (m, 1H), 7.69 (t, 1H), 4.64 (d, 2H). | A |
| 136 | 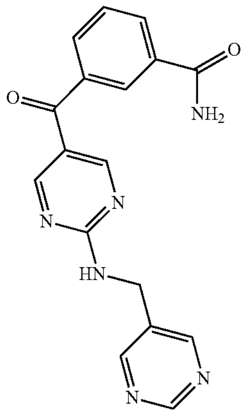 [SMILES: NC(=O)c1cccc(C(=O)c2cnc(NCc3cncnc3)nc2)c1] | 3-({2-[(pyrimidin-5-ylmethyl)amino]pyrimidin-5-yl}carbonyl)benzamide | $[M-H]^-$: 335.0 | $^1$H NMR (400 MHz, DMSO-$d_6$): δ 9.09 (s, 1H), 8.79 (s, 2H), 8.82-8.72 (m, 1H), 8.70 (s, 2H), 8.19 (s, 1H), 8.18-8.12 (m, 2H), 7.87 (d, 1H), 7.63 (t, 1H), 7.51 (br s, 1H), 4.64 (d, 2H). | A |

-continued

| Eg # | Structure | IUPAC Name | MS data | NMR data | Synthetic method |
|---|---|---|---|---|---|
| 137 | 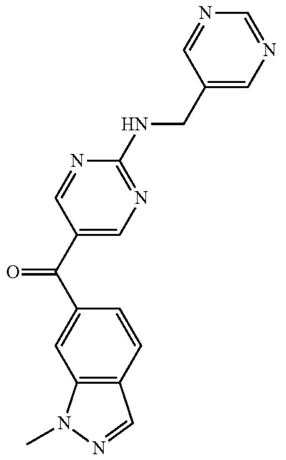 [SMILES: Cn1ncc2ccc(C(=O)c3cnc(NCc4cncnc4)nc3)cc21] | (1-methyl-1H-indazol-6-yl){2-[(pyrimidin-5-ylmethyl)amino]pyrimidin-5-yl}methanone | $[M + H]^+$: 346.0 | $^1$H NMR (400 MHz, DMSO-$d_6$): δ 9.10 (s, 1H), 8.80 (s, 2H), 8.72-8.67 (m, 3H), 8.24 (d, 2H), 7.80 (q, 2H), 4.64 (d, 2H), 4.10 (s, 3H). | B |
| 138 | 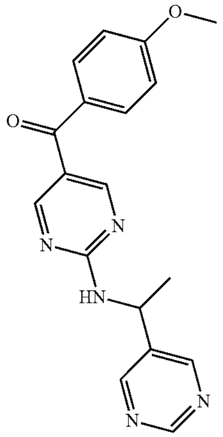 [SMILES: COc1ccc(C(=O)c2cnc(NC(C)c3cncnc3)nc2)cc1] | (4-methoxyphenyl)(2-{[1-(pyrimidin-5-yl)ethyl]amino}pyrimidin-5-yl)methanone | $[M - H]^-$: 336.0 | $^1$H NMR (400 MHz, DMSO-$d_6$): δ 9.08 (s, 1H), 8.85 (s, 2H), 8.73 (d, 1H), 8.62 (d, 2H), 7.73 (d, 2H), 7.07 (d, 2H), 5.20-5.40 (m, 1H), 3.85 (s, 3H), 1.55 (d, 3H). | A |
| 139 | 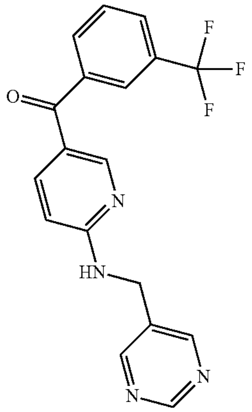 [SMILES: O=C(c1ccc(NCc2cncnc2)nc1)c1cccc(C(F)(F)F)c1] | {6-[(pyrimidin-5-ylmethyl)amino]pyridin-3-yl}[3-(trifluoromethyl)phenyl]methanone | $[M + H]^+$: 359.2 | $^1$H NMR (400 MHz, DMSO-$d_6$): δ 9.08 (s, 1H), 8.78 (s, 2H), 8.39 (d, 1H), 8.26-8.21 (m, 1H), 8.01-7.92 (m, 3H), 7.86 (dd, 1H), 7.77 (t, 1H), 6.69 (d, 1H), 4.62 (d, 2H). | B |

-continued

| Eg # | Structure | IUPAC Name | MS data | NMR data | Synthetic method |
|---|---|---|---|---|---|
| 140 | 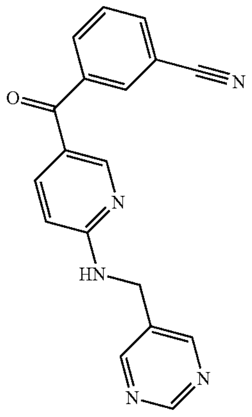 [SMILES: N#Cc1cccc(C(=O)c2ccc(NCc3cncnc3)nc2)c1] | 3-({6-[(pyrimidin-5-ylmethyl)amino]pyridin-3-yl}carbonyl)benzonitrile | [M + H]+: 316.2 | $^1$H NMR (400 MHz, DMSO-$d_6$): δ 9.08 (s, 1H), 8.78 (s, 2H), 8.40 (s, 1H), 8.24 (t, 1H), 8.10-8.05 (m, 2H), 7.96 (d, 1H), 7.86 (dd, 1H), 7.73 (t, 1H), 6.69 (d, 1H), 4.63 (d, 2H). | B |
| 141 | 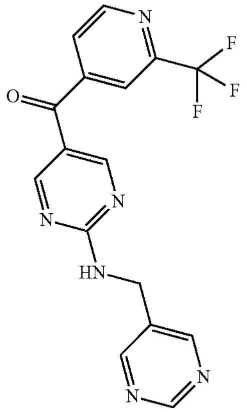 [SMILES: O=C(c1cnc(NCc2cncnc2)nc1)c1ccnc(C(F)(F)F)c1] | {2-[(pyrimidin-5-ylmethyl)amino]pyrimidin-5-yl}[2-(trifluoromethyl)pyridin-4-yl]methanone | [M + H]+: 361.0 | $^1$H NMR (400 MHz, DMSO-$d_6$): δ 9.09 (s, 1H), 8.97-8.92 (m, 2H), 8.78 (s, 2H), 8.73 (s, 2H), 8.07 (s, 1H), 7.95 (d, 1H), 4.64 (d, 2H). | B |
| 142 | 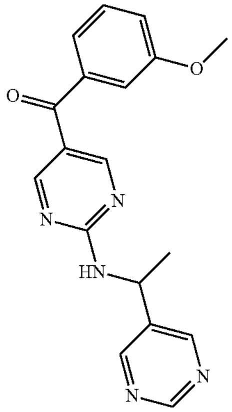 [SMILES: COc1cccc(C(=O)c2cnc(NC(C)c3cncnc3)nc2)c1] | (3-methoxyphenyl)(2-{[1-(pyrimidin-5-yl)ethyl]amino}pyrimidin-5-yl)methanone | [M + H]+: 336.2 | $^1$H NMR (400 MHz, DMSO-$d_6$): δ 9.07 (s, 1H), 8.84-8.80 (m, 3H), 8.65 (d, 2H), 7.45 (t, 1H), 7.28-7.19 (m, 3H), 5.29 (t, 1H), 3.81 (s, 3H), 1.55 (d, 3H) | B |

-continued

| Eg # | Structure | IUPAC Name | MS data | NMR data | Synthetic method |
|---|---|---|---|---|---|
| 143 | 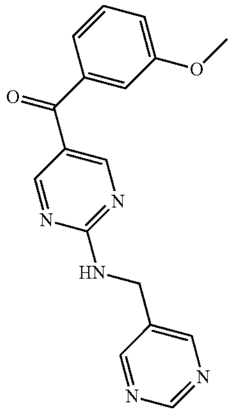 [SMILES: COc1cccc(C(=O)c2cnc(NCc3cncnc3)nc2)c1] | (3-methoxyphenyl){2-[(pyrimidin-5-ylmethyl)amino]pyrimidin-5-yl}methanone | $[M + H]^+$: 322.2 | $^1H$ NMR (400 MHz, DMSO-$d_6$): δ 9.08 (s, 1H), 8.78 (s, 2H), 8.74 (t, 1H), 8.68 (s, 2H), 7.46 (t, 3H), 7.27 (d, 1H), 7.20-7.25 (m, 2H), 4.65-4.60 (m, 2H), 3.80 (s, 3H) | B |
| 144 | 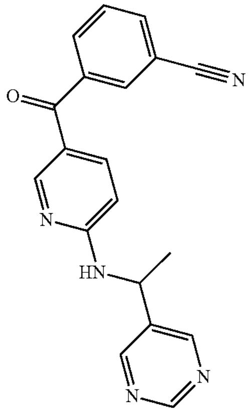 [SMILES: CC(Nc1ccc(C(=O)c2cccc(C#N)c2)cn1)c1cncnc1] | 3-[(6-{[1-(pyrimidin-5-yl)ethyl]amino}pyridin-3-yl)carbonyl]benzonitrile | $[M + H]^+$: 330.0 | 1H NMR (400 MHz, DMSO-d6): δ ppm 9.06 (s, 1H), 8.81 (s, 2H), 8.33 (s, 1H), 8.20-8.25 (m, 1H), 8.05 (bs, 2H), 7.93 (d, 1H), 7.84 (d, 1H), 7.71 (t, 1H), 6.69 (d, 1H), 5.15-5.35 (m, 1H), 1.54 (d, 3H) | B |
| 145 | 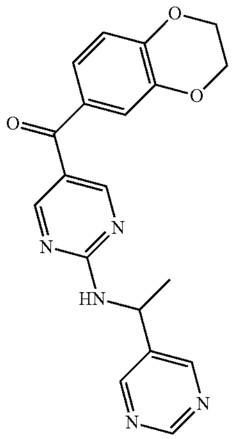 | 2,3-dihydro-1,4-benzodioxin-6-yl{2-[(pyrimidin-5-ylmethyl)amino]pyrimidin-5-yl}methanone | $[M + H]^+$: 350.1 | $^1H$ NMR (400 MHz, DMSO-$d_6$): δ 9.08 (s, 1H), 8.78 (s, 2H), 8.64-8.70 (m, 3H), 7.24-7.26 (m, 2H), 7.00 (d, 1H), 4.62 (d, 2H), 4.30-4.35 (m, 4H). | B |

-continued

| Eg # | Structure | IUPAC Name | MS data | NMR data | Synthetic method |
|---|---|---|---|---|---|
| 146 | 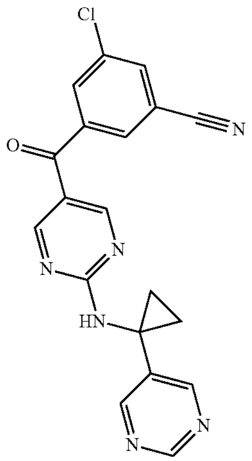 [SMILES: N#Cc1cc(Cl)cc(C(=O)c2cnc(NC3(c4cncnc4)CC3)nc2)c1] | 3-chloro-5-[(2-{[1-(pyrimidin-5-yl)cyclopropyl]amino}pyrimidin-5-yl)carbonyl]benzonitrile | $[M + H]^+$: 377.0 | $^1H$ NMR (400 MHz, MeOH-$d_4$): δ 8.96 (s, 1H), 8.80-8.63 (m, 4H), 8.17 (d, 1H), 7.99 (dd, 1H), 7.79 (d, 1H), 1.56-1.40 (m, 4H). | A |
| 147 | 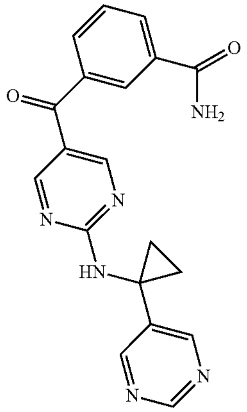 [SMILES: NC(=O)c1cccc(C(=O)c2cnc(NC3(c4cncnc4)CC3)nc2)c1] | 3-[(2-{[1-(pyrazin-2-yl)cyclopropyl]amino}pyrimidin-5-yl)carbonyl]benzamide | $[M + H]^+$: 360.9 | $^1H$ NMR (400 MHz, $CDCl_3$): δ 8.85 (s, 1H), 8.76 (s, 1H), 8.61 (s, 1H), 8.44 (s, 1H), 8.36 (d, 1H), 8.16 (s, 1H), 8.08 (d, 1H), 7.90 (d, 1H), 7.61 (t, 1H), 6.48 (s, 1H), 6.17 (s, 1H), 5.72 (s, 1H), 1.89-1.78 (m, 2H), 1.44 (q, 2H). | A |
| 148 | 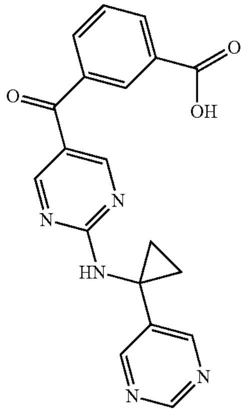 [SMILES: O=C(O)c1cccc(C(=O)c2cnc(NC3(c4cncnc4)CC3)nc2)c1] | 3-[(2-{[1-(pyrimidin-5-yl)cyclopropyl]amino}pyrimidin-5-yl)carbonyl]benzoic acid | $[M + H]^+$: 362.0 | $^1H$ NMR (400 MHz, DMSO-$d_6$): δ 13.29 (s, 1H), 9.09 (s, 1H), 8.99 (s, 1H), 8.71 (s, 1H), 8.68 (s, 1H), 8.62 (s, 2H), 8.19 (d, 2H), 7.97 (d, 1H), 7.68 (t, 1H), 1.50 (t, 2H), 1.36 (t, 2H). | A |

-continued

| Eg # | Structure | IUPAC Name | MS data | NMR data | Synthetic method |
|---|---|---|---|---|---|
| 149 | 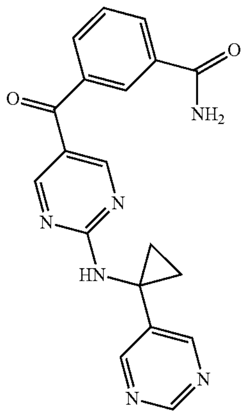 | 3-[(2-{[1-(pyrimidin-5-yl)cyclopropyl]amino}pyrimidin-5-yl)carbonyl]benzamide | $[M + H]^+$: 361.0 | $^1$H NMR (400 MHz, DMSO-$d_6$): δ 9.09 (s, 1H), 8.99 (s, 1H), 8.70 (d, 2H), 8.62 (s, 2H), 8.20 (s, 1H), 8.17 (s, 1H), 8.13 (d, 1H), 7.87 (d, 1H), 7.63 (t, 1H), 7.52 (s, 1H), 1.50 (t, 2H), 1.36 (t, 2H). | A |
| 150 | 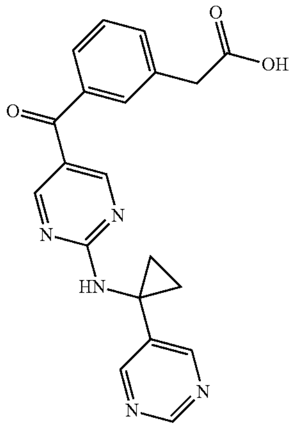 [SMILES: O=C(O)Cc1cccc(C(=O)c2cnc(NC3(c4cncnc4)CC3)nc2)c1] | {3-[(2-{[1-(pyrimidin-5-yl)cyclopropyl]amino}pyrimidin-5-yl)carbonyl]phenyl}acetic acid | $[M + H]^+$: 376.2 | $^1$H NMR (400 MHz, DMSO-$d_6$): δ 12.42 (s, 1H), 9.05 (s, 1H), 8.99 (s, 1H), 8.68 (d, 2H), 8.62 (s, 2H), 7.64 (s, 1H), 7.61 (d, 1H), 7.54 (d, 1H), 7.49 (t, 1H), 3.70 (s, 2H), 1.50 (t, 2H), 1.36 (d, 2H). | A |
| 151 | 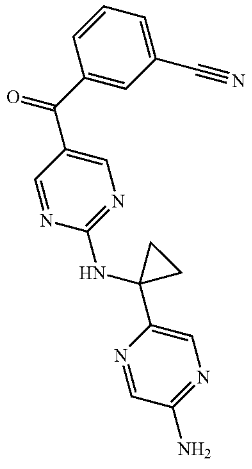 [SMILES: N#Cc1cccc(C(=O)c2cnc(NC3(c4cnc(N)cn4)CC3)nc2)c1] | 3-[(2-{[1-(5-aminopyrazin-2-yl)cyclopropyl]amino}pyrimidin-5-yl)carbonyl]benzonitrile | $[M + H]^+$: 358.0 | $^1$H NMR (400 MHz, MeOH-$d_4$): δ 8.77 (s, 1H), 8.67 (s, 1H), 8.10 (s, 1H), 8.02 (d, 1H), 7.98 (d, 1H), 7.88 (s, 1H), 7.85 (s, 1H), 7.72 (t, 1H), 1.57-1.52 (m, 2H), 1.25 (q, 2H). | A |

-continued

| Eg # | Structure | IUPAC Name | MS data | NMR data | Synthetic method |
|---|---|---|---|---|---|
| 152 | 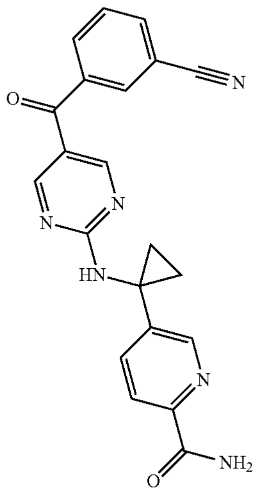 [SMILES: N#Cc1cccc(C(=O)c2cnc(NC3(c4ccc(C(N)=O)nc4)CC3)nc2)c1] | 5-(1-{[5-(3-cyanobenzoyl) pyrimidin-2-yl]amino}cyclopropyl)pyridine-2-carboxamide | $[M + H]^+$: 384.9 | $^1H$ NMR (400 MHz, $CDCl_3$): δ 8.79 (s, 1H), 8.74 (s, 1H), 8.49 (d, 1H), 8.11 (d, 1H), 8.01 (s, 1H), 7.96 (d, 1H), 7.87 (d, 1H), 7.76 (s, 1H), 7.70-7.65 (m, 1H), 7.63 (d, 1H), 6.62 (s, 1H), 5.64 (s, 1H), 1.57-1.46 (m, 4H). | A |
| 153 | 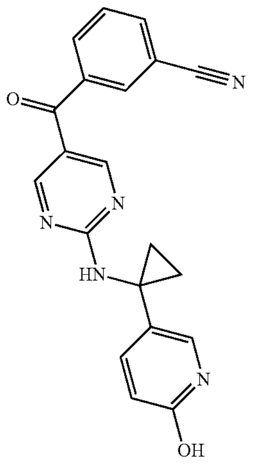 [SMILES: N#Cc1cccc(C(=O)c2cnc(NC3(c4ccc(O)nc4)CC3)nc2)c1] | 3-[(2-{[1-(6-hydroxypyridin-3-yl)cyclopropyl] amino}pyrimidin-5-yl)carbonyl] benzonitrile | $[M + H]^+$: 357.6 | $^1H$ NMR (400 MHz, $CDCl_3$): δ 12.55 (s, 1H), 8.77 (s, 1H), 8.74 (s, 1H), 8.02 (s, 1H), 7.96 (d, 1H), 7.88 (d, 1H), 7.65 (t1H), 7.54-7.47 (m, 2H), 6.58-6.50 (m, 2H), 1.25 (d, 4H). | A |
| 154 | 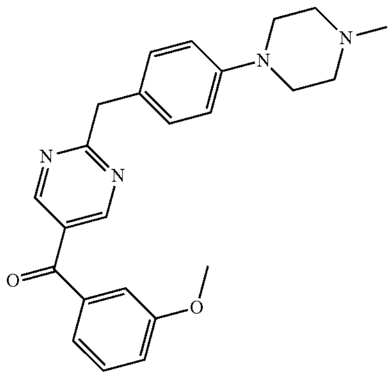 | (3-methoxyphenyl) (2-{[4-(4-methylpiperazin-1-yl)benzyl]amino} pyrimidin-5-yl)methanone | $[M + H]^+$: 418.4 | $^1H$ NMR (400 MHz, DMSO-d6): δ 8.64 (dd, 3H), 7.50-7.42 (m, 1H), 7.26 (d, 1H), 7.24-7.20 (m, 2H), 7.18 (d, 2H), 6.88 (d, 2H), 4.50 (d, 2H), 3.82 (s, 3H), 3.13-3.02 (m, 4H), 2.44 (s, 4H), 2.21 (s, 3H). | A |

-continued

| Eg # | Structure | IUPAC Name | MS data | NMR data | Synthetic method |
|---|---|---|---|---|---|
| 155 | 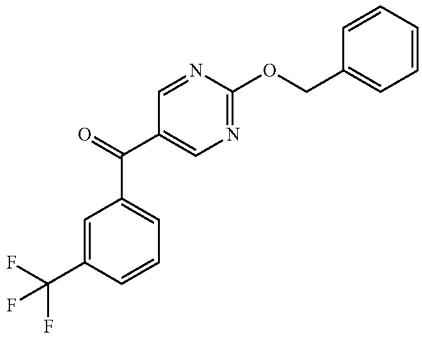 [SMILES: O=C(c1cnc(OCc2ccccc2)nc1)c1cccc(C(F)(F)F)c1] | [2-(benzyloxy) pyrimidin-5-yl][3-(trifluoromethyl) phenyl]methanone | [M + H]$^+$: 359.1 | $^1$H HMR (400 MHz, DMSO-d6): δ 8.98 (s, 2H), 8.10 (t, 3H), 7.84 (t, 1H), 7.50 (d, 2H), 7.40 (q, 3H), 5.53 (s, 2H) | A |
| 156 | 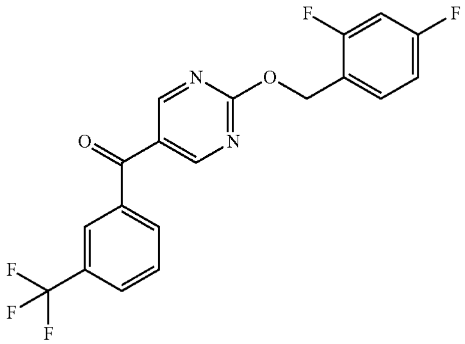 [SMILES: O=C(c1cnc(OCc2ccc(F)cc2F)nc1)c1cccc(C(F)(F)F)c1] | {2-[(2,4-difluorobenzyl)oxy] pyrimidin-5-yl}[3-(trifluoromethyl) phenyl]methanone | [M + H]$^+$: 395.1 | $^1$H HMR (400 MHz, DMSO-d6): δ 8.98 (s, 2H), 8.10 (t, 3H), 7.83 (t, 1H), 7.68 (q, 1H), 7.34 (dd, 1H), 7.16 (dd, 1H), 5.54 (s, 2H) | A |
| 157 | 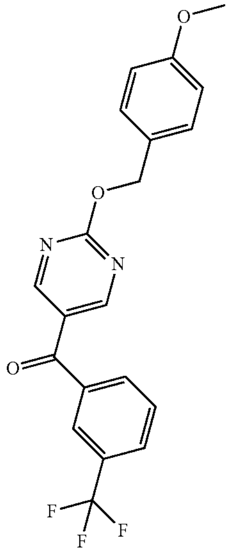 [SMILES: COc1ccc(COc2ncc(C(=O)c3cccc(C(F)(F)F)c3)cn2)cc1] | {2-[(4-methoxybenzyl) oxy]pyrimidin-5-yl}[3-(trifluoromethyl) phenyl]methanone | [M + H]$^+$: 389.1 | $^1$H HMR (400 MHz, DMSO-d6): δ 8.97 (s, 2H), 8.09 (t, 3H), 7.83 (t, 1H), 7.44 (d, 2H), 6.96 (d, 2H), 5.45 (s, 2H), 3.77 (s, 3H) | A |

-continued

| Eg # | Structure | IUPAC Name | MS data | NMR data | Synthetic method |
|---|---|---|---|---|---|
| 158 | 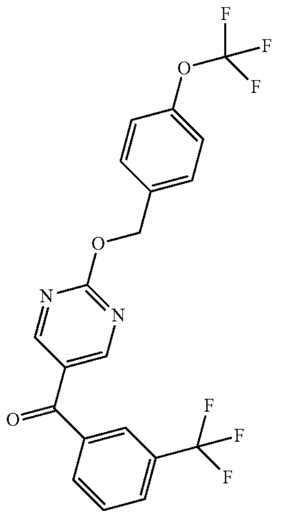 [SMILES: O=C(c1cnc(OCc2ccc(OC(F)(F)F)cc2)nc1)c1cccc(C(F)(F)F)c1] | (2-{[4-(trifluoromethoxy) benzyl]oxy} pyrimidin-5-yl)[3-(trifluoromethyl) phenyl]methanone | [M + H]$^+$: 443.1 | $^1$H HMR (400 MHz, DMSO-d6): δ 8.99 (s, 2H), 8.10 (t, 3H), 7.83 (t, 1H), 7.64 (d, 2H), 7.41 (d, 2H), 5.54 (s, 2H) | A |
| 159 | 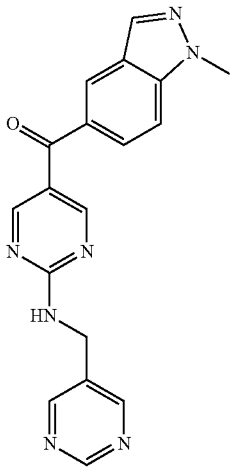 [SMILES: Cn1ncc2cc(C(=O)c3cnc(NCc4cncnc4)nc3)ccc21] | (1-methyl-1H-indazol-5-yl){2-[(pyrimidin-5-ylmethyl)amino] pyrimidin-5-yl}methanone | [M + H]$^+$: 346.0 | $^1$H HMR (400 MHz, DMSO-d6): δ 9.09 (s, 1H), 8.79 (s, 2H), 8.72-8.67 (m, 3H), 8.24 (d, 2H), 7.80 (q, 2H), 4.64 (d, 2H), 4.10 (s, 3H) | A |
| 160 | 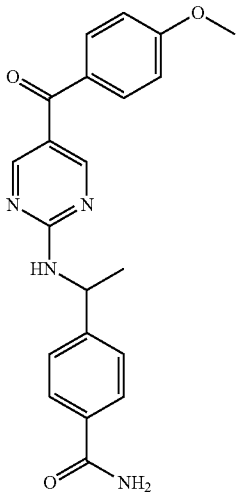 [SMILES: COc1ccc(C(=O)c2cnc(NC(C)c3ccc(C(N)=O)cc3)nc2)cc1] | 4-(1-{[5-(4-methoxybenzoyl) pyrimidin-2-yl]amino}ethyl) benzamide | [M + H]$^+$: 377.4 | $^1$H HMR (400 MHz, DMSO-d6): δ 8.70 (d, 1H), 8.63 (br s, 1H), 8.57 (br s, 1H), 7.88 (brs, 1H), 7.80 (d, 2H), 7.71 (d, 2H), 7.45 (d, 2H), 7.28 (br s, 1H), 7.06 (d, 2H), 5.15-5.35 (m, 1H), 3.84 (s, 3H), 1.48 (d, 1H) | A |

-continued

| Eg # | Structure | IUPAC Name | MS data | NMR data | Synthetic method |
|---|---|---|---|---|---|
| 161 | 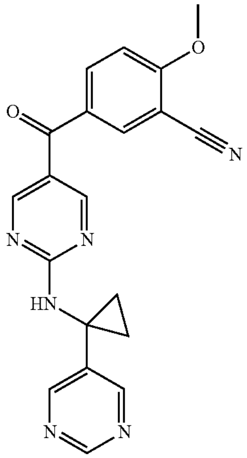 [SMILES: COc1ccc(C(=O)c2cnc(NC3(c4cncnc4)CC3)nc2)cc1C#N] | 2-methoxy-5-[(2-{[1-(pyrimidin-5-yl)cyclopropyl]amino}pyrimidin-5-yl)carbonyl]benzonitrile | $[M + H]^+$: 372.9 | $^1H$ HMR (400 MHz, Methanol-d4): δ 8.97 (s, 1H), 8.73 (s, 4H), 8.09-8.03 (m, 2H), 7.33 (d, J = 8.6 Hz, 1H), 4.06 (s, 3H), 1.55-1.50 (m, 2H), 1.49-1.44 (m, 2H) | A |
| 162 | 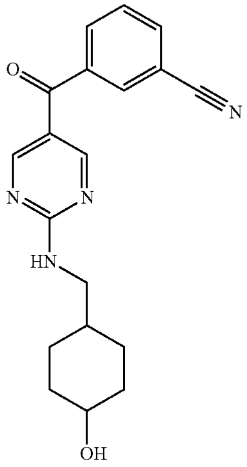 [SMILES: N#Cc1cccc(C(=O)c2cnc(NCC3CCC(O)CC3)nc2)c1] | 3-[(2-{[(4-hydroxycyclohexyl)methyl]amino}pyrimidin-5-yl)carbonyl]benzonitrile | $[M + H]^+$: 337.2 | $^1H$ NMR (400 MHz, MeOH-$d_4$) δ 8.69 (d, 2H), 8.09 (s, 1H), 8.00 (dd, 2H), 7.73 (t, 1H), 3.51 (d, 1H), 1.97 (d, 2H), 1.85 (d, 2H), 1.62 (s, 1H), 1.32-1.18 (m, 2H), 1.15-1.02 (m, 2H). | A |
| 163 | 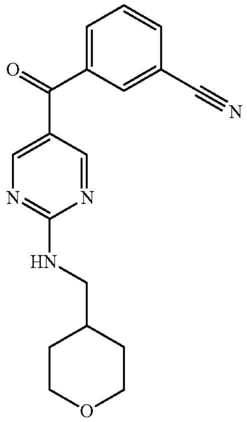 [SMILES: N#Cc1cccc(C(=O)c2cnc(NCC3CCOCC3)nc2)c1] | 3-({2-[(tetrahydro-2H-pyran-4-ylmethyl)amino]pyrimidin-5-yl}carbonyl)benzonitrile | $[M + H]^+$: 323.4 | $^1H$ NMR (400 MHz, DMSO-d6) δ 8.68 (d, 1H), 8.64 (d, 1H), 8.41 (t, 1H), 8.15 (s, 1H), 8.09 (d, 1H), 8.01 (d, 1H), 7.75 (t, 1H), 3.83 (d, 2H), 3.35-3.20 (m, 4H), 1.90-1.80(m, 1H), 1.60 (bd, 2H), 1.25-1.15 (m, 2H). | A |

-continued
| Eg # | Structure | IUPAC Name | MS data | NMR data | Synthetic method |
|---|---|---|---|---|---|
| 164 | 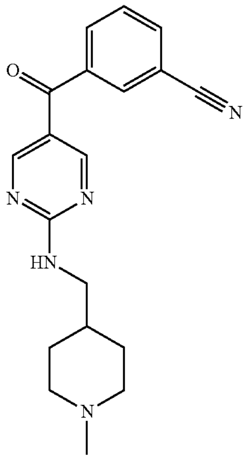 [SMILES: CN1CCC(CNc2ncc(C(=O)c3cccc(C#N)c3)cn2)CC1] | 3-[(2-{[(1-methylpiperidin-4-yl)methyl]amino}pyrimidin-5-yl)carbonyl]benzonitrile | $[M + H]^+$: 336.2 | $^1$H NMR (400 MHz, CDCl3) δ 8.72 (d, 2H), 8.00 (s, 1H), 7.95 (d, 1H), 7.86 (d, 1H), 7.64 (t, 1H), 5.84 (bs, 1H), 3.44 (t, 2H), 2.93 (d, 2H), 2.31 (s, 3H), 2.01 (t, 2H), 1.78 (d, 2H), 1.50-1.35 (m, 3H). | A |
| 165 | 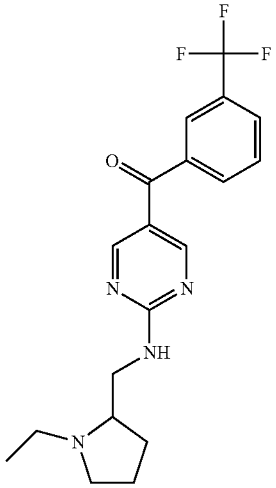 [SMILES: CCN1CCCC1CNc1ncc(C(=O)c2cccc(C(F)(F)F)c2)cn1] | (2-{[(1-ethylpyrrolidin-2-yl)methyl]amino}pyrimidin-5-yl)[3-(trifluoromethyl)phenyl]methanone | $[M + H]^+$: 379.4 | $^1$H NMR (400 MHz, DMSO-d6) δ 8.71-8.61 (m, 2H), 8.15 (t, 1H), 8.05-7.96 (m, 3H), 7.79 (t, 1H), 3.56 (ddd, 1H), 3.25-3.15 (m, 1H), 3.03 (dd, 1H), 2.91-2.79 (m, 1H), 2.65-2.56 (m, 1H), 2.26 (dq, 1H), 2.12 (q, 1H), 1.85-1.75 (m, 1H), 1.62 (dtt, 3H), 1.03 (t, 3H). | A |

Summary of Biological Assays and Data

Human Vanin-1 Enzyme Assay 1.

The in vitro assay measures enzymatic cleavage of the fluorescently-labeled vanin substrate, pantetheine 7-amino-4-trifluoromethylcoumarin, by human vanin-1.

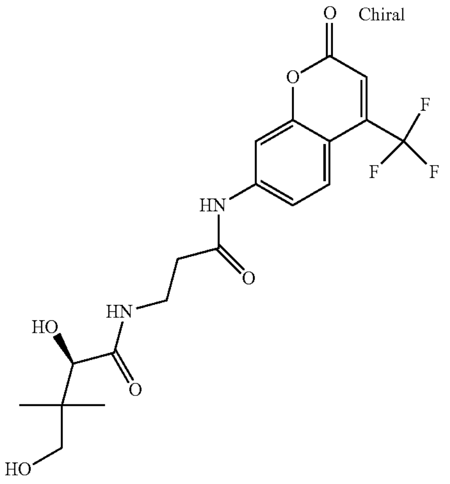 [SMILES: CC(C)(CO)[C@@H](O)C(=O)NCCC(=O)Nc1ccc2c(C(F)(F)F)cc(=O)oc2c1]

The vanin-1 protein was prepared in-house from a construct expressing the extracellular domain of human vanin-1 (GenBank ID NM_004666) preceded N-terminally by the honey bee melittin signal peptide, a GSG linker sequence, a His6X tag and a FLAG tag. The secreted, soluble enzyme was purified from the conditioned medium from a CHO cell line stably expressing the resulting protein. Enzyme purification was performed through sequential Ni NTA and size-exclusion chromatography steps.

The test inhibitors were solubilized in DMSO to a stock concentration of 30 mM. On the day of the assay, dose response plates were prepared by diluting the inhibitors in DMSO at compound concentration 200-fold the final in-assay concentration. Intermediate concentrations were prepared by diluting in DMSO in a four-fold series for a total of 11 data points.

To prepare a working solution of human vanin-1, the enzyme was diluted to 33.3 pM in the assay buffer consisting of 50 mM Tris-HCl pH=8.0, 50 mM KCl, 0.005% Brij-35 and 1.6 mM cysteamine. To begin the assay 100 nL was transferred from the compound plate to the assay plate. Next, 15 μL of the vanin-1 working solution were transferred to the assay plate. The inhibitor and enzyme were incubated at room temperature for 30 minutes. The enzyme reaction was then initiated by the addition of 5 μL of 200 μM pantetheine 7-amino-4-trifluoromethylcoumarin prepared in assay buffer. The final concentrations in the assay were 25 pM human vanin-1 and 50 uM substrate. The final concentration of DMSO was 0.5%. The assay plates were incubated for 60 minutes and before they were read on a Perkin Elmer EnVision Model 2103 using a 405 nm excitation wavelength and a 510 nm emission wavelength for detection.

Human Vanin-1 Enzyme Assay 2.

The in vitro assay measures enzymatic cleavage of the fluorescently-labeled vanin substrate, pantetheine 7-amino-4-trifluoromethylcoumarin, by human vanin-1.

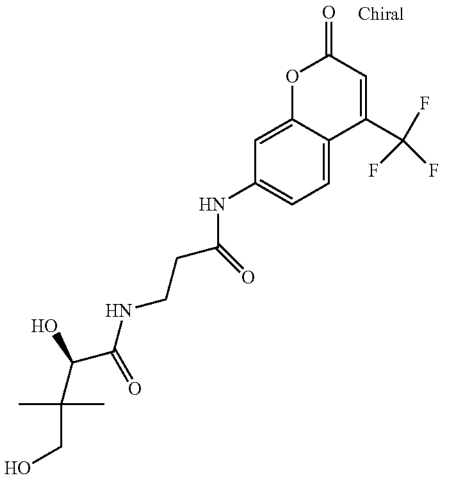 [SMILES: CC(C)(CO)[C@@H](O)C(=O)NCCC(=O)Nc1ccc2c(C(F)(F)F)cc(=O)oc2c1]

The vanin-1 protein was prepared in-house from a construct expressing the extracellular domain of human vanin-1 (GenBank ID NM_004666) preceded N-terminally by the honey bee melittin signal peptide, a GSG linker sequence, a His6X tag and a FLAG tag. The secreted, soluble enzyme was purified from the conditioned medium from a CHO cell line stably expressing the resulting protein. Enzyme purification was performed through sequential Ni NTA and size-exclusion chromatography steps.

On the day of the assay, dose response plates were prepared by diluting the inhibitors in DMSO at compound concentration 100-fold the final in-assay concentration. Concentration series were prepared by serially diluting in DMSO in a half-log series for a total of 11 data points. Intermediate compound plates containing compound in 10% DMSO were then created by diluting the compounds 10-fold in assay buffer consisting of 50 mM Tris-HCl pH=8.0, 50 mM KCl, 0.005% Brij-35 and 1.5 mM cysteamine. To begin the assay 3 μL were transferred from the intermediate compound plate to the assay plate.

A working solution of human vanin-1 was prepared by diluting the enzyme stock to 1.25 nM in assay buffer. Next, 24 μL of the vanin-1 working solution were transferred to the assay plate. The enzyme reaction was then initiated by the addition of 3 μL of 100 μM pantetheine 7-amino-4-trifluoromethylcoumarin prepared in assay buffer. The final concentrations in the assay were 1 nM human vanin-1 and 10 uM substrate. The final concentration of DMSO was 1%. The assay plates were incubated for 45 minutes and before they were read on a Spectramax M5 using a 405 nm excitation wavelength and a 505 nm emission wavelength for detection.

Human Vanin-1 Enzyme Assay 3.

The in vitro assay measures enzymatic cleavage of the fluorescently-labeled vanin substrate, pantetheine 7-amino-4-trifluoromethylcoumarin, by human vanin-1.

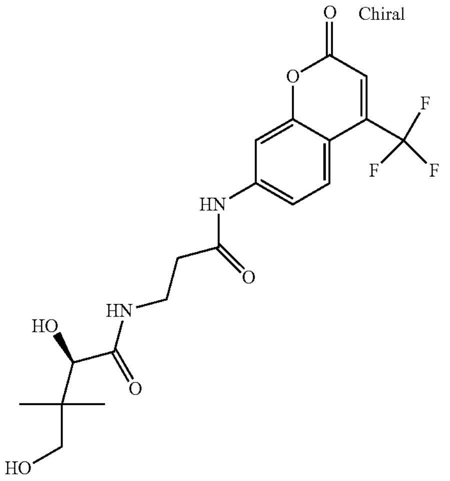 [SMILES: CC(C)(CO)[C@@H](O)C(=O)NCCC(=O)Nc1ccc2c(C(F)(F)F)cc(=O)oc2c1]

The vanin-1 protein was prepared in-house from a construct expressing the extracellular domain of human vanin-1 (GenBank ID NM_004666) preceded N-terminally by the honey bee melittin signal peptide, a GSG linker sequence, a His6X tag and a FLAG tag. The secreted, soluble enzyme was purified from the conditioned medium from a CHO cell line stably expressing the resulting protein. Enzyme purification was performed through sequential Ni NTA and size-exclusion chromatography steps.

On the day of the assay, dose response plates were prepared by diluting the inhibitors in DMSO at compound concentration 100-fold the final in-assay concentration. Concentration series were prepared by serially diluting in DMSO in a two-fold series for a total of 11 data points. Intermediate compound plates containing compound in 10% DMSO were then created by diluting the compounds 10-fold in assay buffer consisting of 50 mM Tris-HCl pH=8.0, 50 mM KCl, 0.005% Brij-35 and 1.5 mM cysteamine. To begin the assay 3 μL were transferred from the intermediate compound plate to the assay plate.

A working solution of human vanin-1 was prepared by diluting the enzyme stock to 2.5 nM in assay buffer. Next, 24 μL of the vanin-1 working solution were transferred to the assay plate. The enzyme reaction was then initiated by the addition of 3 μL of 100 μM pantetheine 7-amino-4-trifluoromethylcoumarin prepared in 5 uM acetic acid. The final concentrations in the assay were 2 nM human vanin-1 and 10 uM substrate. The final concentration of DMSO was 1%. The assay plates were incubated at room temperature for 15 minutes and before they were read on a Tecan Safire using a 405 nm excitation wavelength and a 505 nm emission wavelength for detection.

The biological activity of certain compounds of the invention was tested in one or more of the assays described above. The results are shown in Table 1.

TABLE 1

| Example number | Human Vanin-1 Assay 1 IC50 (nM) | Human Vanin-1 Assay 2 IC50 (nM) | Human Vanin-1 Assay 3 IC50 (nM) |
|---|---|---|---|
| 1 | 4.1 | 7.0 | — |
| 2 | — | — | 2.1 |
| 3 | 13.6 | 15.3 | 75.0 |
| 4 | 22.4 | 21.0 | — |
| 5 | 3.4 | 9.8 | — |

TABLE 1-continued

| Example number | Human Vanin-1 Assay 1 IC50 (nM) | Human Vanin-1 Assay 2 IC50 (nM) | Human Vanin-1 Assay 3 IC50 (nM) |
|---|---|---|---|
| 6 | 37.3 | 24.8 | — |
| 7 | — | 3.9 | — |
| 8 | — | 91.4 | — |
| 9 | 10.3 | 41.3 | — |
| 10 | >20000.0 | >10000.0 | — |
| 11 | 6.4 | 9.0 | <6.2 |
| 12 | 1.9 | 2.9 | 0.5 |
| 13 | — | 2.0 | >26.1 |
| 14 | 47.8 | 31.5 | <13.0 |
| 15 | 329.2 | 92.4 | 169.7 |
| 16 | 1.7 | 2.6 | — |
| 17 | 0.8 | 1.8 | — |
| 18 | 26.5 | 12.3 | — |
| 19 | 1442.5 | 28.8 | — |
| 20 | 9.4 | 17.0 | — |
| 21 | — | 63.0 | — |
| 22 | 93.3 | — | 43.7 |
| 23 | 178.2 | 98.7 | 159.5 |
| 24 | 1243.0 | 316.7 | 273.8 |
| 25 | 74.1 | 64.5 | 11.5 |
| 26 | 4169.6 | — | 63.2 |
| 27 | 79.7 | 40.4 | 52.2 |
| 28 | 38.2 | 21.8 | 8.4 |
| 29 | 121.6 | 72.7 | 106.9 |
| 30 | 36.4 | 35.5 | 16.8 |
| 31 | 101.8 | 57.2 | 14.0 |
| 32 | 95.3 | 71.3 | 14.3 |
| 33 | 7.3 | 55.9 | 206.1 |
| 34 | 53.7 | 107.5 | 69.3 |
| 35 | 241.5 | — | 20.5 |
| 36 | — | — | 31.0 |
| 37 | — | 226.4 | 77.2 |
| 38 | 857.4 | 867.7 | 734.6 |
| 39 | 467.1 | — | 659.6 |
| 40 | 1739.7 | 170.4 | 543.2 |
| 41 | 4267.9 | — | 808.1 |
| 42 | 1063.5 | — | 709.3 |
| 43 | 2219.1 | — | 489.8 |
| 44 | 507.6 | — | 104.8 |
| 45 | 793.6 | 187.9 | 143.7 |
| 46 | >20000.0 | — | >212.8 |
| 47 | >5132.7 | — | >729.2 |
| 48 | 218.5 | 357.3 | 397.7 |
| 49 | 5690.9 | >7622.3 | 112.1 |
| 50 | — | — | 204.5 |
| 51 | — | — | 44.9 |
| 52 | — | — | 170.2 |
| 53 | — | — | 637.4 |
| 54 | — | — | 35.4 |
| 55 | — | — | <16.5 |
| 56 | — | — | 36.2 |
| 57 | — | — | 889.0 |
| 58 | — | — | 133.0 |
| 59 | 2276.2 | 624.0 | 192.3 |
| 60 | — | — | 89.5 |
| 61 | — | — | 24.9 |
| 62 | 150.4 | — | >122.9 |
| 63 | — | — | 569.4 |
| 64 | 99.2 | — | 74.4 |
| 65 | 18.8 | 22.1 | 12.0 |
| 66 | 21.3 | 44.8 | 10.6 |
| 67 | — | 47.9 | 81.6 |
| 68 | 106.8 | 73.1 | 78.8 |
| 69 | 29.4 | — | 46.8 |
| 70 | 139.9 | — | 77.8 |
| 71 | — | — | 23.8 |
| 72 | 187.9 | 86.2 | — |
| 73 | 1.7 | 10.6 | 1.2 |
| 74 | — | — | 736.4 |
| 75 | — | — | 617.2 |
| 76 | — | — | 111.5 |
| 77 | — | — | 998.1 |
| 78 | >20000.0 | — | 687.0 |
| 79 | 15130.4 | — | 347.7 |
| 80 | 384.3 | — | 30.1 |
| 81 | 3.4 | — | >16.9 |

TABLE 1-continued

| Example number | Human Vanin-1 Assay 1 IC50 (nM) | Human Vanin-1 Assay 2 IC50 (nM) | Human Vanin-1 Assay 3 IC50 (nM) |
|---|---|---|---|
| 82 | 111.1 | — | 55.5 |
| 83 | 1048.0 | — | 84.4 |
| 84 | 503.4 | — | 110.7 |
| 85 | 1127.2 | — | 52.8 |
| 86 | 14664.2 | — | 758.3 |
| 87 | 67.1 | 45.2 | 25.9 |
| 88 | 18568.2 | — | 9.3 |
| 89 | 1001.5 | — | 614.6 |
| 90 | 7426.2 | — | 86.4 |
| 91 | 789.0 | 783.4 | 91.3 |
| 92 | >20000.0 | — | 565.9 |
| 93 | 2149.1 | — | 154.1 |
| 94 | 2199.2 | — | 987.4 |
| 95 | 91.9 | 241.9 | 166.3 |
| 96 | 14.2 | — | 414.9 |
| 97 | 4847.8 | — | 873.3 |
| 98 | 101.8 | 148.9 | 55.5 |
| 99 | 1684.4 | — | 536.6 |
| 100 | 161.9 | 122.4 | 145.0 |
| 101 | 803.9 | — | 150.4 |
| 102 | 858.0 | 549.1 | 722.4 |
| 103 | — | 563.1 | 380.6 |
| 104 | 195.5 | 116.5 | 200.3 |
| 105 | 145.9 | 195.0 | 173.2 |
| 106 | 387.4 | 990.5 | 422.7 |
| 107 | 906.4 | — | 751.1 |
| 108 | 110.9 | 110.3 | 96.7 |
| 109 | 143.4 | 144.8 | 95.3 |
| 110 | 421.7 | 238.2 | 63.5 |
| 111 | 366.6 | 202.2 | 182.0 |
| 112 | 5571.6 | 856.4 | 1869.3 |
| 113 | 871.7 | 333.8 | 258.7 |
| 114 | 379.9 | 254.5 | 169.7 |
| 115 | 1400.5 | 1511.4 | 806.0 |
| 116 | 419.2 | 560.6 | 321.0 |
| 117 | 50.5 | 31.8 | 18.1 |
| 118 | 4.0 | 11.2 | 4.6 |
| 119 | — | 11.3 | 6.1 |
| 120 | 36.0 | 37.8 | 16.6 |
| 121 | 32.3 | 50.4 | 9.1 |
| 122 | — | — | 600.9 |
| 123 | 5247.3 | 1320.7 | 437.5 |
| 124 | 525.7 | 798.4 | 222.9 |
| 125 | — | 21.9 | >1250.0 |
| 126 | 28.2 | 44.0 | 40.6 |
| 127 | 3945.1 | — | 36.2 |
| 128 | 38.1 | 38.9 | 43.5 |
| 129 | 9.9 | 12.4 | — |
| 130 | 481.7 | 288.6 | — |
| 131 | 541.4 | 370.2 | — |
| 132 | 125.7 | 98.2 | — |
| 133 | — | 15.5 | — |
| 134 | 259.1 | 100.3 | — |
| 135 | 48.4 | 68.3 | — |
| 136 | 187.4 | 137.1 | — |
| 137 | 501.0 | 1012.4 | — |
| 138 | 194.4 | 437.0 | — |
| 139 | — | 31.5 | — |
| 140 | 143.9 | 64.4 | — |
| 141 | — | 280.0 | — |
| 142 | 17.1 | 34.3 | — |
| 143 | 81.5 | 109.9 | — |
| 144 | 12.5 | 19.8 | — |
| 145 | 329.4 | 485.5 | — |
| 146 | 26.0 | — | — |
| 147 | 55.7 | — | — |
| 148 | 259.5 | — | — |
| 149 | 25.6 | — | — |
| 150 | 23.9 | — | — |
| 151 | 27.8 | — | — |
| 152 | 77.7 | — | — |
| 153 | 307.4 | — | — |
| 154 | — | 6410.3 | 3791.0 |
| 155 | >20000.0 | — | >1112.8 |
| 156 | >20000.0 | — | >1132.5 |
| 157 | — | — | >2335.3 |

TABLE 1-continued

| Example number | Human Vanin-1 Assay 1 IC50 (nM) | Human Vanin-1 Assay 2 IC50 (nM) | Human Vanin-1 Assay 3 IC50 (nM) |
|---|---|---|---|
| 158 | — | — | >2886.4 |
| 159 | 2747.1 | 3084.1 | — |
| 160 | 3437.9 | 7154.6 | — |
| 161 | 1846.8 | — | — |
| 162 | 72.6 | — | — |
| 163 | 2875.7 | 2225.2 | — |
| 164 | 1805.3 | 8569 | — |
| 165 | 11924.1 | — | 6896 |

Induced Colitis Mouse Model

Methods

Example 1 along with sulfasalazine was evaluated in DSS (Dextran Sodium Sulfate) —induced colitis mouse model of IBD. Experimental colitis was induced in healthy young female BALB/C mice by providing 4% DSS; molecular weight 36,000-50,000 (wt/vol) in drinking water ad-libitium for seven days followed by water alone for another seven days. At the commencement of the study, mice were between 7-8 weeks of age, weighing 18-20 g. All the mice were obtained from The Jackson Laboratory, Bar Harbor, Me. 04609 USA. The test articles Example 1 and vehicle were administered subcutaneously (sc) once a day beginning day −1 and continued till day 14. The positive control, Sulfasalazine was dosed orally (po) once a day beginning day 5 and continued till day 14 (Table 2). The body weights were recorded prior to dosing and daily thereafter for fourteen days. Clinical assessments of the mice were performed every other day beginning day 5. The clinical assessment includes body weight, stool consistency and the presence of blood in the stools and scored accordingly to the Table-3. At the end of the study mice were sacrificed using CO2 asphyxiation and colon from the colocecal junction to the anus was removed, washed and cleaned of all fecal matter using PBS, measured and weighed. The data are presented as the mean±standard error (SEM). Data were analyzed using two-way ANOVA using Bonferroni post-test. groups were considered significant at $p<0.05$.

Results

Administration of DSS led to development of colitis in the vehicle treated mice based on percentage change in body weights, disease activity index and colon length. The decrease in body weight gains were observed from day 6 till day 11 and then started recovering. Subcutaneous administration of Example 1 at 50 mg/kg body weight showed mark improvement in all of the parameters examined including loss of body weight, Disease Activity Index (DAI) and colon length.

TABLE 2

Experimental design

| Group | Description | N | ROA | Dose Conc. | Dosing Volume/ mouse | Dosing Frequency |
|---|---|---|---|---|---|---|
| 1 | Naive (No DSS Control) | 8 | sc | xxxx | 200 µl | QD Days −1-14 |
| 2 | Vehicle (DSS Control) | 12 | sc | xxxx | 200 µl | QD Days −1-14 |

TABLE 2-continued

| Experimental design | | | | | | |
|---|---|---|---|---|---|---|
| Group | Description | N | ROA | Dose Conc. | Dosing Volume/ mouse | Dosing Frequency |
| 3 | Sulfasalazine | 12 | po | 100 mg/kg | 200 μl | QD Days 5-14 |
| 4 | Example 1 | 12 | sc | 50 mg/kg | 200 μl | QD Days -1-14 |

TABLE 3

| Disease activity index | | | |
|---|---|---|---|
| Score | Weight Loss (%) | Stool Consistency | Occult/Gross bleeding |
| 0 | No Loss | Normal | Normal |
| 1 | 1-5 | | |
| 2 | 5-10 | Loose | Occult |
| 3 | 10-15 | | |
| 4 | >15 | Diarrhea | Gross Bleeding |

Figure 2:
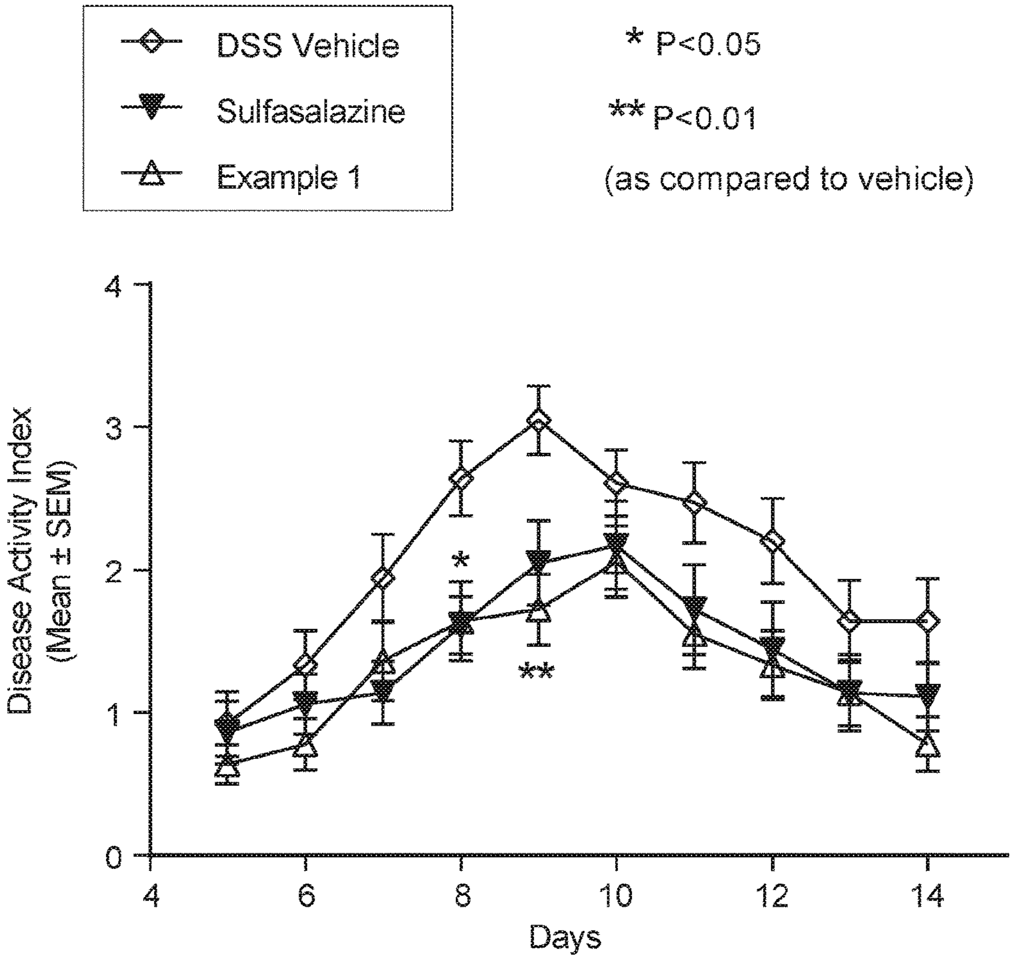
FIG. 2 shows the disease activity index of the mice in the induced colitis mouse model of Inflammatory Bowel Disease following exposure to 4% dextran sulfate sodium, including results obtained with the test compound. Disease activity index reflects a combination of percent weight loss, stool consistency and occult/gross bleeding scores.
Figure 3:
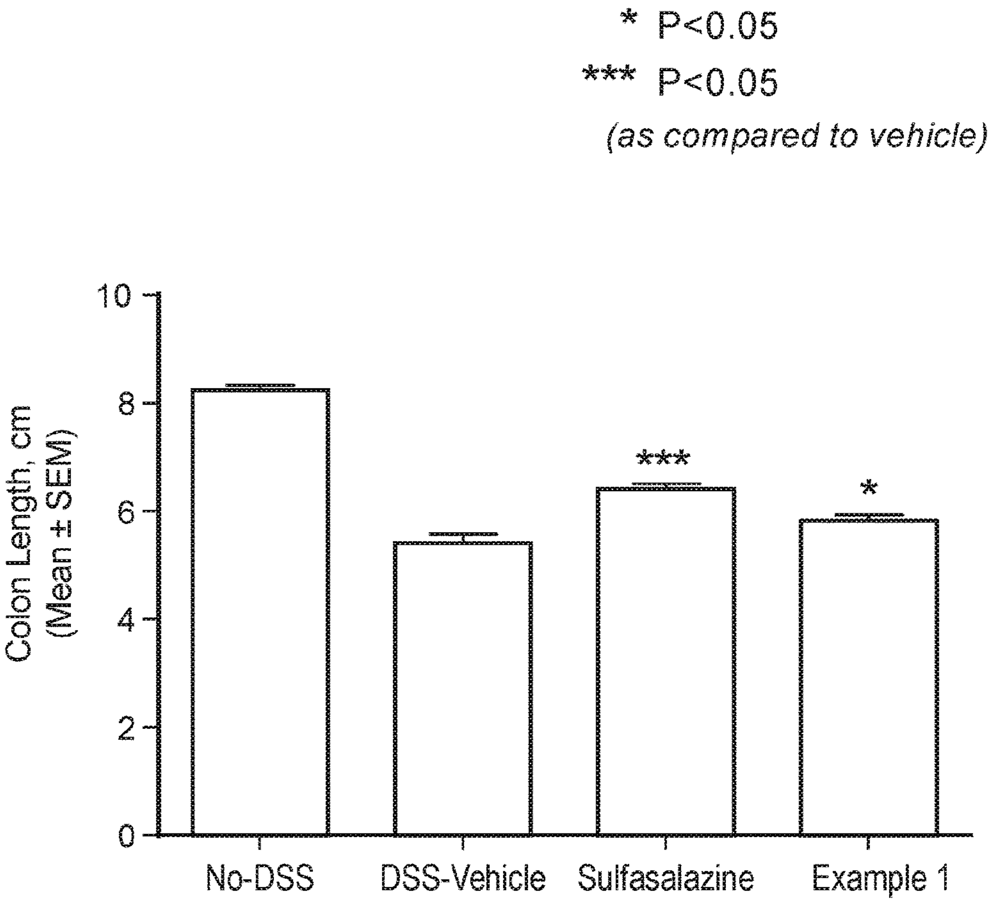
FIG. 3 shows the colon length (cm) of the mice in the induced colitis mouse model of Inflammatory Bowel Disease following exposure to 4% dextran sulfate sodium, including results obtained with the test compound.

The results demonstrate that the compound of Example 1 showed similar improvement in the colitis to oral administration of Sulfasalazine at 100 mg/kg (FIG. 1-3).

Variations, modifications, and other implementations of what is described herein will occur to those skilled in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

Each of the printed publications, including but not limited to patents, patent applications, books, technical papers, trade publications and journal articles described or referenced in this specification are herein incorporated by reference in their entirety and for all purposes.

The invention claimed is:

1. A compound of Formula I:

Formula I

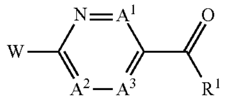

or a pharmaceutically acceptable salt thereof, wherein $A^1$ is $C(R^3)$, $A^2$ is N and $A^3$ is $C(R^3)$;

$R^1$ is selected from the group consisting of:

(i) 6 to 10 membered aryl optionally substituted with one, two, three or four E; and (ii) 5 to 11 membered heteroaryl optionally substituted with one, two, three or four E, wherein said 5 to 11 membered heteroaryl (a) comprises one, two or three heteroatoms independently selected for each occurrence from the group consisting of —N═, —N(J)-, —O—, and —S— and (b) is not bound to the carbonyl of Formula (I) through a nitrogen;

W is selected from the group consisting of:

(i) $—NHCG_2\text{-}R^2$;

(ii) $—NHCG_2CG_2\text{-}R^2$;

(iii) $—OCG_2\text{-}R^2$;

(iv) $—OCG_2CG_2\text{-}R^2$;

$R^2$ is selected from the group consisting of:

(i) phenyl optionally substituted with one, two, three or four E; and (ii) 5 to 6 membered heteroaryl optionally substituted with one, two, three or four E, wherein said 5 to 6 membered heteroaryl comprises one or two heteroatoms independently selected for each occurrence from the group consisting of —N═, —N(J)-, —O—, and —S—;

(iii) $—C_3\text{-}C_7$ carbocyclyl optionally substituted with one, two, three, four, five or six E;

(iv) 4 to 7 membered heterocyclyl optionally substituted with one, two, three, four, five or six E, wherein said 4 to 7 membered heterocyclyl comprises one or two heteroatoms independently selected for each occurrence from the group consisting of —N(J)-, —O— and —S—; and (v) 4 to 7 membered heterocyclyl optionally substituted with one, two, three, four, five or six E, wherein said 4 to 7 membered heterocyclyl is (i) bound to W through a first heterocyclyl ring heteroatom —N— and (ii) which optionally comprises a second ring heteroatom independently selected from the group consisting of —N(J)-, —O—, and —S—;

$R^3$ is independently selected for each occurrence from the group consisting of —H, —F, —Cl, —CN, $—CH_3$, $—CH_2CH_3$, $—CH_2F$, $—CHF_2$, $—CF_3$, $—CF_2CF_3$, $—OCH_3$, $—OCH_2F$, $—OCHF_2$, $—OCF_3$, $—SCH_3$, $—SCH_2F$, $—SCHF_2$, and $—SCF_3$;

E is independently selected for each occurrence from the group consisting of:

(i) —H;

(ii) —halo;

(iii) —CN;

(iv) —OH;

(v) $—CO_2H$;

(vi) $—C_1\text{-}C_6$alkyl optionally substituted with one, two, three, four, five or six K;

(vii) $—OC_1\text{-}C_6$alkyl optionally substituted with one, two, three, four, five or six K;

(viii) $—SC_1\text{-}C_6$alkyl optionally substituted with one, two, three, four, five or six K;

(ix) $—C_3\text{-}C_5$cycloalkyl optionally substituted with one, two, three, four, five or six K;

(x) $—OC_3\text{-}C_5$cycloalkyl optionally substituted with one, two, three, four, five or six K;

(xi) $—SC_3\text{-}C_5$cycloalkyl optionally substituted with one, two, three, four, five or six K;

(xii) $—C_1\text{-}C_6$alkyl($C_3\text{-}C_5$cycloalkyl) optionally substituted with one, two, three, four, five or six K;

(xiii) 4 to 7 membered heterocyclyl optionally substituted with one, two, three, four, five or six K, wherein said 4 to 7 membered heterocyclyl comprises one or two heteroatoms independently selected for each occurrence from the group consisting of —N(J)-, —O— or —S—;

(xiv) $—NH_2$;

(xv) $—NH(C_1\text{-}C_6$alkyl), which $C_1\text{-}C_6$alkyl is optionally substituted with one, two, three, four, five or six K;

(xvi) —$N(C_1$-$C_6alkyl)_2$, which $C_1$-$C_6$alkyl is, independently for each occurrence, optionally substituted with one, two, three, four, five or six K;

(xvii) —$C(O)NH_2$;

(xviii) —$C(O)NH(C_1$-$C_6$alkyl), which $C_1$-$C_6$alkyl is optionally substituted with one, two, three, four, five or six K;

(xix) —$C(O)N(C_1$-$C_6alkyl)_2$, which $C_1$-$C_6$alkyl is, independently for each occurrence, optionally substituted with one, two, three, four, five or six K;

(xx) —$NHC(O)(C_1$-$C_6$alkyl), which $C_1$-$C_6$alkyl is optionally substituted with one, two, three, four, five or six K;

(xxi) —$N(C_1$-$C_6$alkyl)$C(O)(C_1$-$C_6$alkyl), which $C_1$-$C_6$alkyl is, independently for each occurrence, optionally substituted with one, two, three, four, five or six K;

(xxii) —$SO_2(C_1$-$C_6$alkyl), which $C_1$-$C_6$alkyl is optionally substituted with one, two, three, four, five or six K;

(xxiii) —$SO_2NH_2$;

(xxiv) —$SO_2NH(C_1$-$C_6$alkyl), which $C_1$-$C_6$alkyl is optionally substituted with one, two, three, four, five or six K;

(xxv) —$SO_2N(C_1$-$C_6alkyl)_2$, which $C_1$-$C_6$alkyl is, independently for each occurrence optionally substituted with one, two, three, four, five or six K;

(xxvi) —$NHSO_2(C_0$-$C_6$alkyl), which $C_1$-$C_6$alkyl is optionally substituted with one, two, three, four, five or six K; and (xxvii) —$N(C_1$-$C_6$alkyl)$SO_2(C_1$-$C_6$alkyl), which $C_1$-$C_6$alkyl is, independently for each occurrence, optionally substituted with one, two, three, four, five or six K;

G is independently selected for each occurrence from the group consisting of:

(i) —H;

(ii) —halo;

(iii) —OH;

(iv) —$C_1$-$C_6$alkyl optionally substituted optionally substituted with one, two, three, four, five or six K;

(v) —$OC_1$-$C_6$alkyl optionally substituted with one, two, three, four, five or six K;

(vi) —$SC_1$-$C_6$alkyl optionally substituted with one, two, three, four, five or six K;

(vii) —$NH(C_1$-$C_6$alkyl), which $C_1$-$C_6$alkyl is optionally substituted with one, two, three, four, five or six K;

(viii) —$N(C_1$-$C_6alkyl)_2$, which $C_1$-$C_6$alkyl is, independently for each occurrence, optionally substituted with one, two, three, four, five or six K;

(ix) —$C_3$-$C_5$cycloalkyl optionally substituted with one, two, three, four, five or six K; and (x) 4 to 5 membered heterocyclyl optionally substituted with one, two, three, four, five or six K, which said 4 to 5 membered heterocyclyl comprises one or two heteroatoms independently selected for each occurrence from the group consisting of —N(J)-, —O— or —S—;

or two geminal G may, together with the carbon to which they are bound, form a —$C_3$-$C_5$cycloalkylene optionally substituted with one, two, three, four, five or six K or a 4 to 5 membered heterocyclylene optionally substituted with one, two, three, four, five or six K, wherein said 4 to 5 membered heterocyclylene comprises one heteroatom independently selected from the group consisting of —N(J)-, —O—, or —S—;

J is independently selected, for each occurrence, from the group consisting of:

(i) —H;

(ii) —$C_1$-$C_6$alkyl optionally substituted with one, two, three, four, five or six K;

(iii) —$C(O)NH_2$;

(iv) —$C(O)NH(C_1$-$C_6$alkyl), which $C_1$-$C_6$alkyl is optionally substituted with one, two, three, four, five or six K;

(v) —$C(O)N(C_1$-$C_6alkyl)_2$, which $C_1$-$C_6$alkyl is, independently for each occurrence, optionally substituted with one, two, three, four, five or six K; and (vi) —$SO_2(C_1$-$C_6$alkyl), which $C_1$-$C_6$alkyl is optionally substituted with one, two, three, four, five or six halo; and K is independently selected, for each occurrence, from the group consisting of —H, —F, —Cl, —OH, —CN, —$CO_2H$, —$CH_3$, —$CH_2CH_3$, —$CH_2F$, —$CHF_2$, —$CF_3$, —$CF_2CF_3$, —$OCH_3$, —$OCH_2F$, —$OCHF_2$, —$OCF_3$, —$SCH_3$, —$SCH_2F$, —$SCHF_2$, —$SCF_3$— $NH_2$, —$NH(CH_3)$, —$N(CH_3)_2$, and —$CONH_2$.

2. A compound according to claim 1, or a pharmaceutically acceptable salt thereof, wherein $R^3$ is selected from the group consisting of —H, —F, —$CH_3$, —$CH_2F$, —$CHF_2$, —$CF_3$, —$OCH_3$, —$OCH_2F$, —$OCHF_2$, and —$OCF_3$.

3. A compound according to claim 2, or a pharmaceutically acceptable salt thereof, wherein $R^1$ is selected from the group consisting of phenyl, thiophenyl, 1,4-dioxochromanyl, quinolinyl, pyrazolyl, indazolyl, pyridinyl, N-methylindazolyl and N-methyl-pyrazolyl.

4. A compound according to claim 3, or a pharmaceutically acceptable salt thereof, wherein W is selected from the group consisting of —$NHCG_2$-$R^2$ and —$OCG_2$-$R^2$.

5. A compound according to claim 4, or a pharmaceutically acceptable salt thereof, wherein G is selected from the group consisting of —H; —$C_1$-$C_6$alkyl; methyl; —$OC_1$-$C_6$alkyl; and —$C_3$-$C_5$cycloalkyl; or two geminal G may, together with the carbon to which they are bound, form a —$C_3$-$C_5$cycloalkylene, cyclopropylene or cyclobutylene.

6. A compound selected from the group consisting of:

3-[(2-{[1-(pyrimidin-5-yl)cyclopropyl]amino}pyrimidin-5-yl)carbonyl]benzonitrile;

3-[(2-{[1-(pyridin-3-yl)cyclopropyl]amino}pyrimidin-5-yl)carbonyl]benzonitrile;

3-({2-[(2-phenylpropan-2-yl)amino]pyrimidin-5-yl}carbonyl)benzonitrile;

3-[(2-{[(2-aminopyrimidin-5-yl)methyl]amino}pyrimidin-5-yl)carbonyl]benzonitrile;

3-[(2-{[1-(pyrazin-2-yl)cyclopropyl]amino}pyrimidin-5-yl)carbonyl]benzonitrile;

3-[(2-{[(6-aminopyridin-3-yl)methyl]amino}pyrimidin-5-yl)carbonyl]benzonitrile;

3-[(2-{[1-(pyridin-3-yl)ethyl]amino}pyrimidin-5-yl)carbonyl]benzonitrile;

4-(1-{[5-(3-cyanobenzoyl)pyrimidin-2-yl]amino}ethyl)benzamide;

(−)-4-(1-{[5-(3-cyanobenzoyl)pyrimidin-2-yl]amino}ethyl)benzamide;

(+)-4-(1-{[5-(3-cyanobenzoyl)pyrimidin-2-yl]amino}ethyl)benzamide;

{2-[(pyrazin-2-ylmethyl)amino]pyrimidin-5-yl}[3-(trifluoromethyl)phenyl]methanone;

{2-[(pyridin-3-ylmethyl)amino]pyrimidin-5-yl}[3-(trifluoromethyl)phenyl]methanone;

[3-(methylsulfonyl)phenyl]{2-[(pyridin-3-ylmethyl)amino]pyrimidin-5-yl}methanone;

(3-methylphenyl){2-[(pyridin-3-ylmethyl)amino]pyrimidin-5-yl}methanone;

(2-fluorophenyl){2-[(pyridin-3-ylmethyl)amino]pyrimidin-5-yl}methanone;

(2-{[1-(pyrimidin-5-yl)cyclopropyl]amino}pyrimidin-5-yl)[3-(trifluoromethyl)phenyl]methanone;

[3-(methylsulfonyl)phenyl](2-{[1-(pyrimidin-5-yl)cyclopropyl]amino}pyrimidin-5-yl)methanone;

(3-methoxyphenyl)(2-{[1-(pyrimidin-5-yl)cyclopropyl]amino}pyrimidin-5-yl)methanone;

[3-(methylsulfonyl)phenyl]{2-[(pyrimidin-5-ylmethyl)amino]pyrimidin-5-yl}methanone;

[3-(methylsulfonyl)phenyl]{2-[(pyridazin-3-ylmethyl)amino]pyrimidin-5-yl}methanone;

(3,4-difluorophenyl){2-[(pyridin-3-ylmethyl)amino]pyrimidin-5-yl}methanone;

4-({[5-(3-methylbenzoyl)pyrimidin-2-yl]amino}methyl)benzamide;

[2-(benzylamino)pyrimidin-5-yl](3-chlorophenyl)methanone;

(3-chlorophenyl){2-[(2-phenylpropan-2-yl)amino]pyrimidin-5-yl}methanone;

3-({[5-(3-chlorobenzoyl)pyrimidin-2-yl]amino}methyl)benzonitrile;

3-{[2-(benzylamino)pyrimidin-5-yl]carbonyl}benzonitrile;

3-({2-[(4-chlorobenzyl)amino]pyrimidin-5-yl}carbonyl)benzonitrile;

3-({2-[(4-methoxybenzyl)amino]pyrimidin-5-yl}carbonyl)benzonitrile;

3-({2-[(2,4-difluorobenzyl)amino]pyrimidin-5-yl}carbonyl)benzonitrile;

3-({2-[(4-fluorobenzyl)amino]pyrimidin-5-yl}carbonyl)benzonitrile;

3-({2-[(2-chlorobenzyl)amino]pyrimidin-5-yl}carbonyl)benzonitrile;

4-[({5-[3-(trifluoromethyl)benzoyl]pyrimidin-2-yl}amino)methyl]benzamide;

phenyl{2-[(pyridin-3-ylmethyl)amino]pyrimidin-5-yl}methanone;

[2-(benzylamino)pyrimidin-5-yl][3-(trifluoromethyl)phenyl]methanone;

(3-chlorophenyl){2-[(4-fluorobenzyl)amino]pyrimidin-5-yl}methanone;

{2-[(4-fluorobenzyl)amino]pyrimidin-5-yl}(3-methoxyphenyl)methanone;

(3-methylphenyl){2-[(pyridin-2-ylmethyl)amino]pyrimidin-5-yl}methanone;

(3-methylphenyl){2-[(pyridin-4-ylmethyl)amino]pyrimidin-5-yl}methanone;

[2-(benzylamino)pyrimidin-5-yl](3-methylphenyl)methanone;

(3,4-difluorophenyl){2-[(4-methoxybenzyl)amino]pyrimidin-5-yl}methanone;

4-({[5-(3-methylbenzoyl)pyrimidin-2-yl]amino}methyl)benzonitrile;

4-({[5-(3,4-difluorobenzoyl)pyrimidin-2-yl]amino}methyl)benzamide;

(3,4-difluorophenyl){2-[(2-phenylpropan-2-yl)amino]pyrimidin-5-yl}methanone;

[2-(benzylamino)pyrimidin-5-yl](3-methoxyphenyl)methanone;

{2-[(4-fluorobenzyl)oxy]pyrimidin-5-yl}[3-(trifluoromethyl)phenyl]methanone;

{2-[(4-chlorobenzyl)oxy]pyrimidin-5-yl}[3-(trifluoromethyl)phenyl]methanone;

3-({[5-(3-chlorobenzoyl)pyrimidin-2-yl]amino}methyl)benzamide;

4-({[5-(3,4-difluorobenzoyl)pyrimidin-2-yl]amino}methyl)benzoic acid;

4-[({5-[4-(trifluoromethyl)benzoyl]pyrimidin-2-yl}amino)methyl]benzonitrile;

{2-[(pyridin-3-ylmethyl)amino]pyrimidin-5-yl}[4-(trifluoromethyl)phenyl]methanone;

(4-chlorophenyl){2-[(4-fluorobenzyl)amino]pyrimidin-5-yl}methanone;

{2-[(4-methoxybenzyl)amino]pyrimidin-5-yl}(4-methoxyphenyl)methanone;

{2-[(4-fluorobenzyl)amino]pyrimidin-5-yl}[4-(trifluoromethyl)phenyl]methanone;

{2-[(4-methoxybenzyl)amino]pyrimidin-5-yl}[4-(trifluoromethyl) phenyl]methanone;

{2-[(pyridin-4-ylmethyl)amino]pyrimidin-5-yl}[3-(trifluoromethyl) phenyl]methanone;

{2-[(4-chlorobenzyl)amino]pyrimidin-5-yl}(4-chlorophenyl)methanone;

(2-{[4-(trifluoromethoxy)benzyl]amino}pyrimidin-5-yl)[3-(trifluoromethyl)phenyl]methanone;

4-({[5-(4-methoxybenzoyl)pyrimidin-2-yl]amino}methyl)benzamide;

(4-methoxyphenyl){2-[(pyridin-2-ylmethyl)amino]pyrimidin-5-yl}methanone;

{2-[(4-chloro-2-fluorobenzyl)amino]pyrimidin-5-yl}[3-(trifluoromethyl)phenyl]methanone;

3-[({5-[3-(trifluoromethyl)benzoyl]pyrimidin-2-yl}amino)methyl]benzonitrile;

(4-chlorophenyl){2-[(4-methoxybenzyl)amino]pyrimidin-5-yl}methanone;

3-({[5-(3-cyanobenzoyl)pyrimidin-2-yl]amino}methyl)benzonitrile;

3-({2-[(1-phenylcyclopropyl)amino]pyrimidin-5-yl}carbonyl)benzonitrile;

{2-[(1-phenylcyclopropyl)amino]pyrimidin-5-yl}[3-(trifluoromethyl)phenyl]methanone;

{2-[(pyridazin-3-ylmethyl)amino]pyrimidin-5-yl}[3-(trifluoromethyl)phenyl]methanone;

4-({[5-(3-cyanobenzoyl)pyrimidin-2-yl]amino}methyl)benzamide;

5-[({5-[3-(trifluoromethyl)benzoyl]pyrimidin-2-yl}amino)methyl]pyridine-2-carboxamide;

5-[({5-[4-fluoro-3-(trifluoromethyl)benzoyl]pyrimidin-2-yl}amino)methyl]pyridine-2-carboxamide;

(2-{[1-(pyridin-3-yl)cyclopropyl]amino}pyrimidin-5-yl)[3-(trifluoromethyl)phenyl]methanone;

3-[(2-{[(2-oxo-1,2-dihydropyridin-4-yl)methyl]amino}pyrimidin-5-yl)carbonyl]benzonitrile;

(2-{[(6-methylpyridin-3-yl)methyl]amino}pyrimidin-5-yl)[3-(trifluoromethyl)phenyl]methanone;

[2-(benzylamino)pyrimidin-5-yl](4-methoxyphenyl)methanone;

(4-methoxyphenyl)(2-{[4-(trifluoromethoxy)benzyl]amino}pyrimidin-5-yl)methanone;

4-[({5-[3-(trifluoromethyl)benzoyl]pyrimidin-2-yl}amino)methyl]benzonitrile;

3-({[5-(4-methoxybenzoyl)pyrimidin-2-yl]amino}methyl)benzonitrile;

4-({2-[(4-fluorobenzyl)amino]pyrimidin-5-yl}carbonyl)benzonitrile;

4-({2-[(4-methoxybenzyl)amino]pyrimidin-5-yl}carbonyl)benzonitrile;

[4-fluoro-3-(trifluoromethyl) phenyl]{2-[(pyridin-2-ylmethyl)amino]pyrimidin-5-yl}methanone;

[4-fluoro-3-(trifluoromethyl) phenyl]{2-[(pyridin-3-ylmethyl)amino]pyrimidin-5-yl}methanone;

[4-fluoro-3-(trifluoromethyl) phenyl]{2-[(pyridin-4-ylmethyl)amino]pyrimidin-5-yl}methanone;

[2-(benzylamino)pyrimidin-5-yl][4-fluoro-3-(trifluoromethyl)phenyl]methanone;

4-[({5-[4-fluoro-3-(trifluoromethyl)benzoyl]pyrimidin-2-yl}amino)methyl]benzonitrile;

{2-[(4-fluorobenzyl)amino]pyrimidin-5-yl}[4-fluoro-3-(trifluoromethyl)phenyl]methanone;

4-[({5-[4-fluoro-3-(trifluoromethyl)benzoyl]pyrimidin-2-yl}amino)methyl]benzamide;

4-[({5-[4-fluoro-3-(trifluoromethyl)benzoyl]pyrimidin-2-yl}amino)methyl]benzoic acid;

[2-(benzylamino)pyrimidin-5-yl][3-fluoro-5-(trifluoromethyl)phenyl]methanone;

4-[({5-[3-fluoro-5-(trifluoromethyl)benzoyl]pyrimidin-2-yl}amino)methyl]benzonitrile;

4-[({5-[3-fluoro-5-(trifluoromethyl)benzoyl]pyrimidin-2-yl}amino)methyl]benzamide;

{2-[(4-fluorobenzyl)amino]pyrimidin-5-yl}[3-(methyl sulfonyl)phenyl]methanone;

[2-(benzylamino)pyrimidin-5-yl](2,3-dihydro-1,4-benzodioxin-6-yl)methanone;

2,3-dihydro-1,4-benzodioxin-6-yl{2-[(pyridin-3-ylmethyl)amino]pyrimidin-5-yl}methanone;

[2-(benzylamino)pyrimidin-5-yl](phenyl)methanone;

{2-[(pyridin-3-ylmethyl)amino]pyrimidin-5-yl}(thiophen-2-yl)methanone;

{2-[(2-fluorobenzyl)amino]pyrimidin-5-yl}(phenyl) methanone;

(2-chlorophenyl){2-[(pyridin-3-ylmethyl)amino]pyrimidin-5-yl}methanone;

(1-methyl-1H-pyrazol-4-yl){2-[(pyridin-3-ylmethyl) amino]pyrimidin-5-yl}methanone;

(2-methylquinolin-6-yl){2-[(pyridin-3-ylmethyl)amino] pyrimidin-5-yl}methanone;

5-({[5-(3-cyanobenzoyl)pyrimidin-2-yl]amino}methyl) pyridine-2-carboxamide;

4-{[(5-benzoylpyrimidin-2-yl)amino]methyl}benzamide;

5-{[(5-benzoylpyrimidin-2-yl)amino]methyl}pyridine-2-carboxamide;

3-({2-[(pyridazin-3-ylmethyl)amino]pyrimidin-5-yl}carbonyl)benzonitrile;

phenyl{2-[(pyrimidin-5-ylmethyl)amino]pyrimidin-5-yl}methanone;

phenyl{2-[(2-phenylpropan-2-yl)amino]pyrimidin-5-yl}methanone;

phenyl{2-[(1-phenylcyclopropyl)amino]pyrimidin-5-yl}methanone;

3-({2-[(pyridazin-4-ylmethyl)amino]pyrimidin-5-yl}carbonyl)benzonitrile;

3-{[(5-benzoylpyrimidin-2-yl)amino] methyl}benzonitrile;

phenyl(2-{[1-(pyridin-3-yl)cyclopropyl] amino}pyrimidin-5-yl)methanone;

phenyl{2-[(pyridazin-3-ylmethyl)amino]pyrimidin-5-yl}methanone;

phenyl{2-[(pyrazin-2-ylmethyl)amino]pyrimidin-5-yl}methanone;

3-({2-[(pyrazin-2-ylmethyl)amino]pyrimidin-5-yl}carbonyl)benzonitrile;

3-({2-[(pyridin-3-ylmethyl)amino]pyrimidin-5-yl}carbonyl)benzonitrile;

{2-[(pyrimidin-5-ylmethyl)amino]pyrimidin-5-yl}[3-(trifluoromethyl)phenyl]methanone;

3-({2-[(pyrimidin-5-ylmethyl)amino]pyrimidin-5-yl}carbonyl)benzonitrile;

{2-[(2-phenylpropan-2-yl)amino]pyrimidin-5-yl}[3-(trifluoromethyl)phenyl]methanone;

{2-[(pyridazin-4-ylmethyl)amino]pyrimidin-5-yl}[3-(trifluoromethyl)phenyl]methanone;

3-({[5-(2,3-dihydro-1,4-benzodioxin-6-ylcarbonyl)pyrimidin-2-yl]amino}methyl)benzonitrile;

2,3-dihydro-1,4-benzodioxin-6-yl{2-[(2-phenylpropan-2-yl)amino]pyrimidin-5-yl}methanone;

4-[({5-[3-(methylsulfonyl)benzoyl]pyrimidin-2-yl}amino)methyl]benzamide;

4-[({5-[3-(methylsulfonyl)benzoyl]pyrimidin-2-yl}amino)methyl]benzonitrile;

{2-[(4-fluorobenzyl)amino]pyrimidin-5-yl}[3-fluoro-5-(trifluoromethyl)phenyl]methanone;

[3-fluoro-5-(trifluoromethyl) phenyl]{2-[(pyridin-3-ylmethyl)amino]pyrimidin-5-yl}methanone;

3-({2-[(1-phenylcyclobutyl)amino]pyrimidin-5-yl}carbonyl)benzonitrile;

3-fluoro-5-({2-[(pyrimidin-5-ylmethyl)amino]pyrimidin-5-yl}carbonyl)benzonitrile;

4-fluoro-3-({2-[(pyrimidin-5-ylmethyl)amino]pyrimidin-5-yl}carbonyl)benzonitrile;

2-methyl-5-({2-[(pyrimidin-5-ylmethyl)amino]pyrimidin-5-yl}carbonyl)benzonitrile;

3-[(2-{[1-(pyrimidin-5-yl)ethyl]amino}pyrimidin-5-yl) carbonyl]benzonitrile;

2-chloro-5-({2-[(pyrimidin-5-ylmethyl)amino]pyrimidin-5-yl}carbonyl)benzonitrile;

2-fluoro-5-({2-[(pyrimidin-5-ylmethyl)amino]pyrimidin-5-yl}carbonyl)benzonitrile;

3-({2-[(pyrimidin-5-ylmethyl)amino]pyrimidin-5-yl}carbonyl)benzamide;

(1-methyl-1H-indazol-6-yl){2-[(pyrimidin-5-ylmethyl) amino]pyrimidin-5-yl}methanone;

(4-methoxyphenyl)(2-{[1-(pyrimidin-5-yl)ethyl] amino}pyrimidin-5-yl)methanone;

{2-[(pyrimidin-5-ylmethyl)amino]pyrimidin-5-yl}[2-(trifluoromethyl)pyridin-4-yl]methanone;

(3-methoxyphenyl)(2-{[1-(pyrimidin-5-yl)ethyl] amino}pyrimidin-5-yl)methanone;

(3-methoxyphenyl){2-[(pyrimidin-5-ylmethyl)amino]pyrimidin-5-yl}methanone;

2,3-dihydro-1,4-benzodioxin-6-yl{2-[(pyrimidin-5-ylmethyl)amino]pyrimidin-5-yl}methanone;

3-chloro-5-[(2-{[1-(pyrimidin-5-yl)cyclopropyl] amino}pyrimidin-5-yl)carbonyl]benzonitrile;

3-[(2-{[1-(pyrazin-2-yl)cyclopropyl]amino}pyrimidin-5-yl)carbonyl]benzamide;

3-[(2-{[1-(pyrimidin-5-yl)cyclopropyl]amino}pyrimidin-5-yl)carbonyl]benzoic acid;

3-[(2-{[1-(pyrimidin-5-yl)cyclopropyl]amino}pyrimidin-5-yl)carbonyl]benzamide;

{3-[(2-{[1-(pyrimidin-5-yl)cyclopropyl] amino}pyrimidin-5-yl)carbonyl]phenyl}acetic acid;

3-[(2-{[1-(5-aminopyrazin-2-yl)cyclopropyl] amino}pyrimidin-5-yl)carbonyl]benzonitrile;

5-(1-{[5-(3-cyanobenzoyl)pyrimidin-2-yl] amino}cyclopropyl)pyridine-2-carboxamide;

3-[(2-{[1-(6-hydroxypyridin-3-yl)cyclopropyl] amino}pyrimidin-5-yl)carbonyl]benzonitrile;

(3-methoxyphenyl)(2-{[4-(4-methylpiperazin-1-yl)benzyl]amino}pyrimidin-5-yl)methanone;

[2-(benzyloxy)pyrimidin-5-yl][3-(trifluoromethyl)phenyl]methanone;

{2-[(2,4-difluorobenzyl)oxy]pyrimidin-5-yl}[3-(trifluoromethyl)phenyl]methanone;

{2-[(4-methoxybenzyl)oxy]pyrimidin-5-yl}[3-(trifluoromethyl)phenyl]methanone;

(2-{[4-(trifluoromethoxy)benzyl]oxy}pyrimidin-5-yl)[3-(trifluoromethyl)phenyl]methanone;

(1-methyl-1H-indazol-5-yl){2-[(pyrimidin-5-ylmethyl)amino]pyrimidin-5-yl}methanone;

4-(1-{[5-(4-methoxybenzoyl)pyrimidin-2-yl]amino}ethyl)benzamide;

2-methoxy-5-[(2-{[1-(pyrimidin-5-yl)cyclopropyl]amino}pyrimidin-5-yl)carbonyl]benzonitrile;

3-[(2-{[(4-hydroxycyclohexyl)methyl]amino}pyrimidin-5-yl)carbonyl]benzonitrile;

3-({2-[(tetrahydro-2H-pyran-4-ylmethyl)amino]pyrimidin-5-yl}carbonyl)benzonitrile;

3-[(2-{[(1-methylpiperidin-4-yl)methyl]amino}pyrimidin-5-yl)carbonyl]benzonitrile; and (2-{[(1-ethylpyrrolidin-2-yl)methyl]amino}pyrimidin-5-yl)[3-(trifluoromethyl)phenyl]methanone;

or a pharmaceutically acceptable salt thereof.

7. A compound selected from the group consisting of:

3-[(2-{[1-(pyrimidin-5-yl)cyclopropyl]amino}pyrimidin-5-yl)carbonyl]benzonitrile;

3-[(2-{[1-(pyridin-3-yl)cyclopropyl]amino}pyrimidin-5-yl)carbonyl]benzonitrile;

3-[(2-{[1-(pyrazin-2-yl)cyclopropyl]amino}pyrimidin-5-yl)carbonyl]benzonitrile;

{2-[(pyrazin-2-ylmethyl)amino]pyrimidin-5-yl}[3-(trifluoromethyl)phenyl]methanone;

{2-[(pyridin-3-ylmethyl)amino]pyrimidin-5-yl}[3-(trifluoromethyl)phenyl]methanone;

(2-{[1-(pyrimidin-5-yl)cyclopropyl]amino}pyrimidin-5-yl)[3-(trifluoromethyl)phenyl]methanone;

[3-(methylsulfonyl)phenyl](2-{[1-(pyrimidin-5-yl)cyclopropyl]amino}pyrimidin-5-yl)methanone;

[3-(methylsulfonyl)phenyl]{2-[(pyrimidin-5-ylmethyl)amino]pyrimidin-5-yl}methanone;

4-[({5-[3-(trifluoromethyl)benzoyl]pyrimidin-2-yl}amino)methyl]benzamide;

(2-{[(6-methylpyridin-3-yl)methyl]amino}pyrimidin-5-yl)[3-(trifluoromethyl)phenyl]methanone;

[4-fluoro-3-(trifluoromethyl)phenyl]{2-[(pyridin-3-ylmethyl)amino]pyrimidin-5-yl}methanone;

3-({2-[(pyridin-3-ylmethyl)amino]pyrimidin-5-yl}carbonyl)benzonitrile; and 3-({2-[(1-phenylcyclobutyl)amino]pyrimidin-5-yl}carbonyl)benzonitrile;

or a pharmaceutically acceptable salt thereof.

8. A pharmaceutical composition comprising a compound according to claim 1, or a pharmaceutically acceptable salt thereof, and a pharmaceutically acceptable excipient.

* * * * *